US007897747B2

(12) United States Patent
Mindrinos et al.

(10) Patent No.: US 7,897,747 B2

(45) Date of Patent: Mar. 1, 2011

(54) METHOD TO PRODUCE SINGLE STRANDED DNA OF DEFINED LENGTH AND SEQUENCE AND DNA PROBES PRODUCED THEREBY

(75) Inventors: Michael Mindrinos, Menlo Park, CA (US); Sujatha Krishnakumar, Cupertino, CA (US); Ronald W. Davis, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 141 days.

(21) Appl. No.: 11/805,676

(22) Filed: May 24, 2007

(65) Prior Publication Data

US 2008/0026393 A1 Jan. 31, 2008

Related U.S. Application Data

(60) Provisional application No. 60/808,490, filed on May 25, 2006.

(51) Int. Cl.

*C07H 21/04* (2006.01)
*C12Q 1/68* (2006.01)
*C12P 19/34* (2006.01)

(52) U.S. Cl. .......................... 536/24.3; 435/6; 435/91.2

(58) Field of Classification Search ....................... None
See application file for complete search history.

(56) References Cited

U.S. PATENT DOCUMENTS

| | | | | |
|---|---|---|---|---|
| 4,683,195 | A | 7/1987 | Mullis et al. | |
| 4,683,202 | A | 7/1987 | Mullis et al. | |
| 4,883,750 | A | 11/1989 | Whiteley et al. | |
| 4,965,188 | A | 10/1990 | Mullis et al. | |
| 5,066,584 | A | 11/1991 | Gyllensten et al. | |
| 5,130,238 | A | 7/1992 | Malek et al. | |
| 5,455,166 | A | 10/1995 | Walker | |
| 5,518,900 | A | 5/1996 | Nikiforov et al. | |
| 5,854,033 | A * | 12/1998 | Lizardi | 435/91.2 |
| 6,221,603 | B1 * | 4/2001 | Mahtani | 435/6 |
| 6,235,472 | B1 | 5/2001 | Landegren et al. | |
| 6,558,928 | B1 | 5/2003 | Landegren et al. | |
| 6,812,005 | B2 * | 11/2004 | Fan et al. | 435/91.2 |
| 6,815,167 | B2 | 11/2004 | Crothers et al. | |
| 6,858,412 | B2 | 2/2005 | Willis et al. | |
| 6,955,901 | B2 | 10/2005 | Schouten | |
| 2002/0012902 | A1 | 1/2002 | Fuchs et al. | |
| 2004/0067511 | A1 * | 4/2004 | Thomas | 435/6 |
| 2004/0171047 | A1 * | 9/2004 | Dahl et al. | 435/6 |
| 2005/0026204 | A1 * | 2/2005 | Landegren | 435/6 |
| 2005/0255477 | A1 | 11/2005 | Carr et al. | |

OTHER PUBLICATIONS

Sambrook et al., "Ch.10 Preparation of Radiolabeled DNA and RNA probes," (selected pages) in Molecular Cloning: A Laboratory Manual, Second Edition, Cold Spring Harbor Laboratory Press, 1989, pp. 10.4-10.5, and 10.29.*

Padgett et al., "Creating seamless junctions independent of restriction sites in PCR cloning," Gene, 1996, vol. 168, pp. 31-35.*

Russell G. Higuchi, et al., "Production of singled-stranded DNA templates by exonuclease digestion following the polymerase chain reaction," *Nucleic Acids Research*, 1989, vol. 17, No. 14, 5865.

Jan P. Schouten, et al., "Relative quantification of 40 nucleic acid sequences by multiplex ligation-dependent probe amplification," *Nucleic Acids Research*, 2002, vol. 30, No. 12, e57.

Johan Banér, et al., "Parallel gene analysis with allele-specific padlock probes and tag microarrays," *Nucleic Acids Research*, 2003, vol. 31, No. 17, e103.

J. Aquiles Sanchez, et al., "Linear-After-The-Exponential (LATE)-PCR: An advanced method of asymmetric PCR and its uses in quantitative real-time analysis," PNAS, Feb. 17, 2004, vol. 101, No. 7, 1933-1938.

Brock F. Binkowski, et al., "Correcting errors in synthetic DNA through consensus shuffling," *Nucleic Acids Research*, 2005, 33(6), e55.

Fredrik Dahl, et al., "Multiplex amplification enabled by selective circularization of large sets of genomic DNA fragments," *Nucleic Acids Research*, 2005, vol. 33, No. 8, e71.

Marianna Szemes, et al., "Diagnostic application of padlock probes—multiplex detection of plant pathogens using universal microarrays," *Nucleic Acids Research*, Apr. 28, 2005, vol. 33, No. 8, e70.

* cited by examiner

*Primary Examiner*—Kenneth R Horlick
*Assistant Examiner*—David C Thomas
(74) *Attorney, Agent, or Firm*—David J. Aston; Peters Verny, LLP

(57) ABSTRACT

A method for producing a single stranded DNA (ssDNA) molecule of a defined length and sequence is disclosed. This method enables the preparation of, inter alia, probes of greater length than can be chemically synthesized. The method starts with a double stranded molecule, such as genomic, double stranded DNA (dsDNA) from any organism. A fragment of the starting molecule (dsDNA) is amplified by specific primers engineered to introduce cleavage sites on either side of the desired sequence. Cleavage steps on the amplified, engineered fragment are combined with a phosphate removal step, thereby creating a construct that can be digested with an exonuclease without damage to the desired ssDNA. Probes, which hybridize with large gaps between the ends of the probes, are also disclosed.

16 Claims, 4 Drawing Sheets

3A

3B

3C

4A

4B

METHOD TO PRODUCE SINGLE STRANDED DNA OF DEFINED LENGTH AND SEQUENCE AND DNA PROBES PRODUCED THEREBY

CROSS-REFERENCE TO RELATED APPLICATIONS

This application claims priority from U.S. Provisional Patent Application No. 60/808,490 filed on May 25, 2006, which is hereby incorporated by reference in its entirety.

STATEMENT OF GOVERNMENTAL SUPPORT

This invention was made with U.S. Government support under PO1HG000205 and US 54GM62119. The U.S. Government has certain rights in this invention.

REFERENCE TO SEQUENCE LISTING, COMPUTER PROGRAM, OR COMPACT DISK

The present application includes sequences to be included in a Sequence Listing in computer readable form found on an accompanying computer disk. The present application further includes a lengthy table submitted in electronic form on CD.

BACKGROUND OF THE INVENTION

1. Field of the Invention

The present invention relates to the field of nucleic acid synthesis and analysis, and particularly to the field of preparing single stranded DNA probes or primers of defined sequence and length.

2. Related Art

BACKGROUND

The generation of single-stranded DNA has a large number of applications in understanding biological functions of gene expression and function, treatment of diseases in plants and animals, and in applications to diagnostics and forensics. There are currently several applications that rely on the use of long oligonucleotides as probes. These include molecular inversion probes (Willis et al., 2000 U.S. Pat. No. 6,858,412), wherein probes termed "pre-circle" probes are hybridized at either end to a target, then circularized by filling the gap between the ends. It is said that the gap may be between 1 and 2000 nucleotides (Col. 14 1. 35), but the examples are directed to single nucleotide gaps. This method is based on the fact that the two targeting domains of a pre-circle probe can be preferentially ligated together, if they are hybridized to a target strand such that they abut and if perfect complementarity exists at the two bases being ligated together. Perfect complementarity at the termini allows the formation of a ligation substrate such that the two termini can be ligated together to form a closed circular probe. If this complementarity does not exist, no ligation substrate is formed and the probes are not ligated together to an appreciable degree. Once the precircle probes have been ligated, the unligated precircle probes and/or target sequences are optionally removed or inactivated. The closed circular probe is then linearized by cleavage at the cleavage site, resulting in a cleaved probe comprising the universal priming sites at the new termini of the cleaved probe. The patent further states that, due to the length of the precircle probes, it is preferred that each target domain range in size from about 5 bases to about 100 bases, with from about 5 to about 40 being especially preferred.

Padlock probes are described in Landegren et al., U.S. Pat. No. 6,235,472, and Landegren et al., 2001). The term "padlock probe" refers to a probe designed to be circularized in the presence of a target sequence, so that it may be caused to close around the target-containing nucleic acid strand such that the cyclic probe will interlock with and thereby be efficiently linked to the target nucleic acid to be detected. In other words, because of the helical nature of double-stranded nucleic acids, such as DNA, circularized probes will be wound around the target strand, topologically connecting probes to target molecules through catenation, in a manner similar to "padlocks". Such covalent catenation of probe molecules to target sequences results in the formation of a hybrid that resists extreme washing conditions, serving to reduce non-specific signals in genetic assays. Any probes hybridizing in a non-specific manner may therefore be efficiently removed by subjecting the target to non-hybridizing conditions and/or exonuclease activity. Further, the novel method may be performed with even very short synthetic probes since only part of the probe molecule needs to form a rigid double-stranded DNA molecule with the target molecule, whereas the rest of the probe molecule may be highly flexible, optionally branched single-stranded DNA or any other spacer material. In this system, a probe is hybridized to a target nucleic acid sequence, such as a DNA strand, via two end segments of the detecting reagent, designated Probe 1 and Probe 3, the latter being complementary to two respective non-contiguous sequences of the target molecule. An additional probe, designated Probe 2, is hybridized to the intermediate segment of the target molecule with the probe ends in juxtaposition to Probe 1 and Probe 3, respectively, and then ligated to the two ends.

Another application of single stranded DNA molecules is described in Fredriksson S., et al., "Protein detection using proximity-dependent DNA ligation assays," *Nat Biotechnol,* 2002 May; 20(5):473-7. This paper describes a technique for protein detection, in which the coordinated and proximal binding of a target protein by two DNA aptamers promotes ligation of oligonucleotides linked to each aptamer affinity probe. The ligation of two such proximity probes gives rise to an amplifiable DNA sequence that reflects the identity and amount of the target protein.

Another method for nucleic acid formation is strand displacement amplification (SDA), which is generally described in U.S. Pat. Nos. 5,455,166 and 5,130,238. A single stranded target nucleic acid, usually a DNA target sequence, is contacted with an SDA primer. An "SDA primer" generally has a length of 25-100 nucleotides and is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease", which is chosen to cleave a strand either at the recognition site, or either 3' or 5' to it, without cleaving the complementary sequence, either because the enzyme only cleaves one strand or because of the incorporation of the substituted nucleotides.

For many of the assays described above, single stranded DNA probes are synthesized chemically. Currently, these probes are very expensive to manufacture to the required specificity and purity that these applications demand.

Various attempts have been made to produce defined single-stranded DNA. Nikiforov and Knapp (U.S. Pat. No. 5,518,900) describe a method for producing single-stranded DNA from a PCR fragment where one of the primers used for amplification has a modification that makes that strand resistant to exonuclease digestion. This method suffers from the drawback that every probe requires the synthesis of oligonucleotides with chemically modified nucleotides, which is not economically feasible in large-scale genomic studies.

Higuchi et al., (1989) describe a method for producing single-stranded DNA from PCR fragments where one of the amplification primers is phosphorylated and the corresponding strand with the phosphorylated primers is a preferential substrate for nuclease digestion. The drawback of this method is that the non-phosphorylated strand from a blunt-end DNA molecule (as in a PCR product) acts as a substrate, though with reduced efficiency.

Binkowski, et al., "Correcting errors in synthetic DNA through consensus shuffling," *Nucleic Acids Res*, Mar. 30, 2005; 33(6): e55, describe a method termed consensus shuffling and demonstrate its use to significantly reduce random errors in synthetic DNA. In this method, errors are revealed as mismatches by re-hybridization of the population. The DNA is fragmented, and mismatched fragments are removed upon binding to an immobilized mismatch binding protein (MutS).

BRIEF SUMMARY OF THE INVENTION

The following brief summary is not intended to include all features and aspects of the present invention, nor does it imply that the invention must include all features and aspects discussed in this summary. The present methods are useful for producing any single stranded DNA molecule where sequence exactness, including exact beginning and ending of all molecules, is needed. The DNA thus produced need not therefore be a probe. In general, the present synthetic methods involving cleavage and digestion of dsDNA permit creation of ssDNA of greater lengths than previously possible, e.g., lengths of 100 to 1000 or even higher nt.

The present invention, in one aspect, comprises a polynucleic acid probe, having a defined length between two ends and a defined sequence, for hybridization to a target polynucleic acid sequence, comprising specified subsequences which are designed to allow the probe to hybridize to relatively widely spaced target regions, have the gap between the target regions filed, and then be circularized, and, finally, be amplified in circular form. The probe will contain the following subsequences: (a) a first target sequence, at one end of the probe, complementary to a first target region of the target polynucleic acid, for specifically binding thereto (the target region being, e.g., human genomic DNA); (b) a second target sequence, at an opposite end of the probe, complementary to a second target region of the target polynucleic acid for specifically binding thereto, where said first and second target regions are separated on the target polynucleic acid by a gap of at least 25-250 nt of target sequence, more preferably between 250 and 1000 nt; (c) at least one amplification primer site, adjacent the target sequence, and connected to a backbone sequence, for specifically binding a PCR primer, said primer oriented in a direction for amplification of target sequences only when nucleic acids are joined to the target sequences as complementary to the target polynucleic acid and further oriented to not amplify the backbone sequence; and (d) a backbone sequence of at least 25 nt, preferably 125-400 nt chosen to be non-complementary to the target polynucleic acid.

The probe will typically be DNA, but can include modified nucleic acids or hybrids. The probe may comprise two amplification primer sites, one adjacent the first target sequence and one adjacent the second target sequence, oriented towards each other, whereby the circularized probe is selectively amplified after linear nucleic acids are digested with an endonuclease. The probe is circularized by gap filling and ligating between the target sequences of the probe, thereby forming a circular probe.

The probe may be formed with different sizes, but contain the afore-mentioned sequences, wherein the backbone region is from a non-human organism and the target sequences hybridize to human genetic sequences.

In one aspect of the invention, the target sequences are adjacent to a 5' end and a 3' end of an exon of a eukaryotic gene, so that an entire exon sequence is obtained and amplified for further study. In certain aspects the invention comprises a primer for performing PCR amplification comprising a homology region for hybridization to a target under annealing conditions and a non-homologous restriction endonuclease recognition sequence. The probe may further comprise a non-homologous region for forming a primer-binding site to another primer.

DETAILED DESCRIPTION OF THE PREFERRED EMBODIMENT

Definitions

Figure 1:
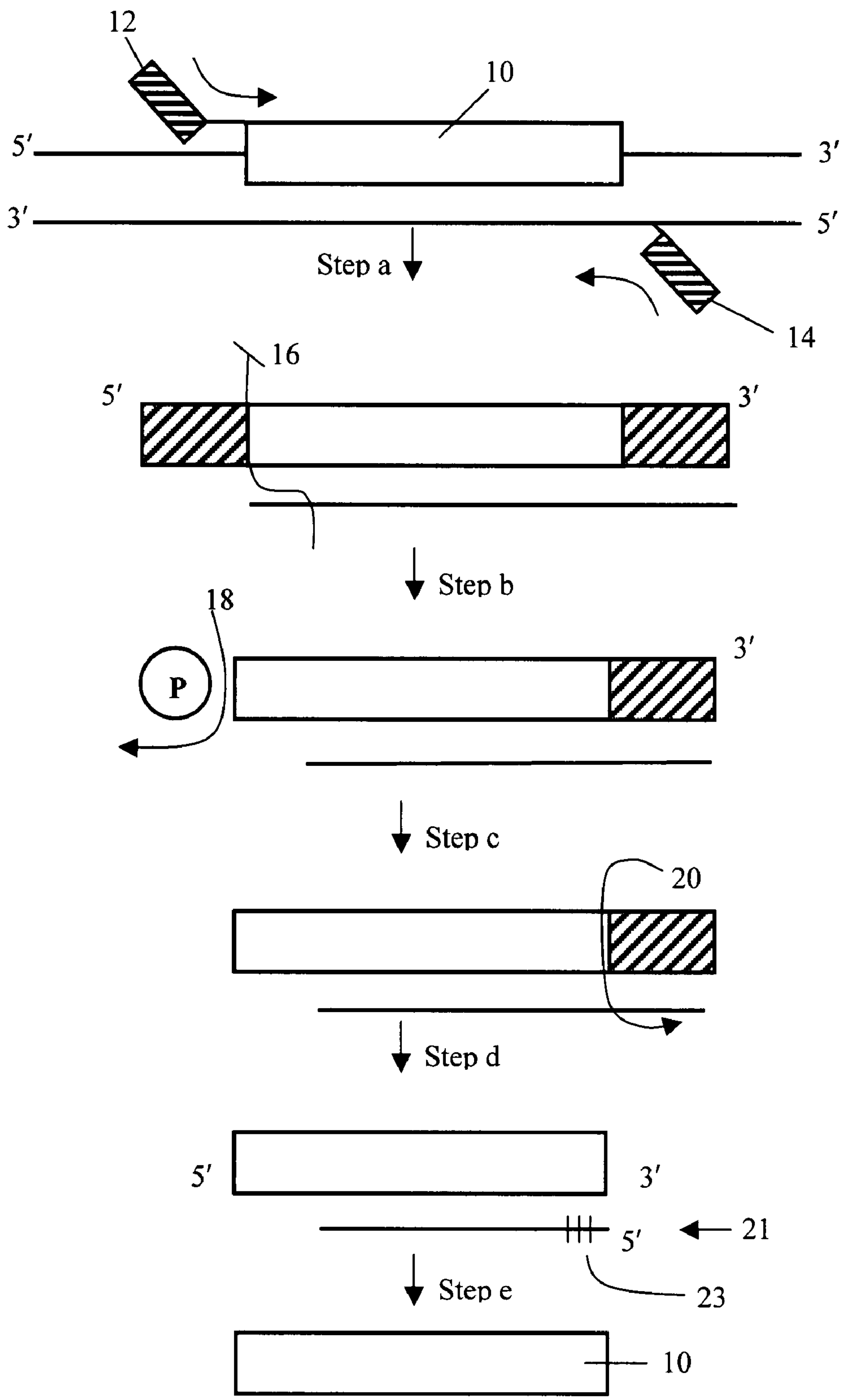
FIG. 1 is a diagram representing the creation of a single stranded polynucleotide (e.g., DNA) probe having a defined length and sequence.

The term "probe" refers to a polynucleic acid that contains target regions that specifically bind to a target, complementary thereto. As is known, in order to be specific the target region must be at least 10 bases long, and should be between 10 and 50, or even longer, bases long. The present probes preferably comprise two target regions, and the regions should be selected to be non-complementary, i.e. not bind to each other. The present probes include nucleic acid sequences that are used to detect identical, allelic or related nucleic acid sequences. The probes are isolated oligonucleotides or polynucleotides and may or may not be attached to a detectable label or reporter molecule. Typical labels include radioactive isotopes, ligands, chemiluminescent agents, and enzymes.

The term "target nucleic acid" refers to the polynucleic acids to be analyzed in the presently preferred method of using the probes to be synthesized. In most cases, the DNA will be human DNA, preferably genomic DNA. However, the present probes may be adapted for use with any sample, including bacteria, viruses, and, particularly in the case of viruses, may include RNA targets. Hybridization of DNA to RNA targets is described in Schwille et al., "Quantitative Hybridization Kinetics of DNA Probes to RNA in Solution Followed by Diffusional Fluorescence Correlation Analysis," *Biochemistry,* 1996, 35, 10182-10193. A polymerase may be used to extend the probe bound to the target nucleic acid by inserting bases complementary to the target.

The term "restriction enzyme" is used in its conventional sense. Restriction enzymes are traditionally classified into three types on the basis of subunit composition, cleavage position, sequence-specificity and cofactor-requirements. Of particular interest are Type II enzymes, which cut DNA at defined positions close to or within their recognition sequences. They produce discrete restriction fragments and distinct gel banding patterns, and they are the only class used in the laboratory for DNA analysis and gene cloning. Rather then forming a single family of related proteins, type II enzymes are a collection of unrelated proteins of many different sorts. Type II enzymes frequently differ so utterly in amino acid sequence from one another, and indeed from every other known protein, that they likely arose independently in the course of evolution rather than diverging from common ancestors.

The most common type II enzymes are those like Hha I, Hind III and Not I that cleave DNA within their recognition sequences. Enzymes of this kind are the principle ones available commercially. Most recognize DNA sequences that are symmetric because they bind to DNA as homodimers, but a few (e.g., BbvC I: CCTCAGC) (SEQ ID NO: 1) recognize asymmetric DNA sequences because they bind as heterodimers. Some enzymes recognize continuous sequences (e.g., EcoR I: GAATTC) (SEQ ID NO: 2) in which the two half-sites of the recognition sequence are adjacent, while others recognize discontinuous sequences (e.g., Bgl I: GCCNNNNNGGC) (SEQ ID NO: 3) in which the half-sites are separated. Cleavage leaves a 3'-hydroxyl on one side of each cut and a 5'-phosphate on the other. They require only magnesium for activity and the corresponding modification enzymes require only S-adenosylmethionine. They tend to be small, with subunits in the 200-350 amino acid range.

The next most common type II enzymes, usually referred to as "type IIs" are those like Fok I and Alw I that cleave outside of their recognition sequence to one side. These enzymes are intermediate in size, 400-650 amino acids in length, and they recognize sequences that are continuous and asymmetric. They comprise two distinct domains, one for DNA binding, and the other for DNA cleavage. They are thought to bind to DNA as monomers for the most part, but to cleave DNA cooperatively, through dimerization of the cleavage domains of adjacent enzyme molecules. For this reason, some type IIs enzymes are much more active on DNA molecules that contain multiple recognition sites.

The third major kind of type II enzyme, more properly referred to as "type IV" are large, combination restriction-and-modification enzymes, 850-1250 amino acids in length, in which the two enzymatic activities reside in the same protein chain. These enzymes cleave outside of their recognition sequences; those that recognize continuous sequences (e.g., Eco57 I: CTGAAG) (SEQ ID NO: 4) cleave on just one side; those that recognize discontinuous sequences (e.g., Bcg I: CGANNNNNNTGC) (SEQ ID NO: 5) cleave on both sides releasing a small fragment containing the recognition sequence. The amino acid sequences of these enzymes are varied but their organization is consistent. They comprise an N-terminal DNA-cleavage domain joined to a DNA-modification domain and one or two DNA sequence-specificity domains forming the C-terminus, or present as a separate subunit. When these enzymes bind to their substrates, they switch into either restriction mode to cleave the DNA, or modification mode to methylate it.

Type III enzymes are also large combination restriction-and-modification enzymes. They cleave outside of their recognition sequences and require two such sequences in opposite orientations within the same DNA molecule to accomplish cleavage; they rarely give complete digests. No laboratory uses have been devised for them, and none are available commercially.

The terms "complementary" and "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acid strands, in the design and use of peptide nucleic acid (PNA) molecules, and in the design of the present primers for adding restriction sites.

"Hybridization" refers to the process by which a polynucleotide strand anneals with a complementary strand through base pairing under defined hybridization conditions. Specific hybridization is an indication that two nucleic acid sequences share a high degree of identity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml denatured salmon sperm DNA.

Generally, stringency of hybridization is expressed, in part, with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook et al., 1989, Molecular Cloning: A Laboratory Manual, $2^{nd}$ ed., vol. 1 3, Cold Spring Harbor Press, Plainview N.Y.; specifically see volume 2, chapter 9. As described below, a primer that does not entirely match the target is used with appropriate stringency. The "stringency" here is achieved by varying the temperature, magnesium concentration, or both, in the annealing steps where primer and target bind to each other in PCR, or probe and target bind to each other in the SMART reaction. The important point here is that the annealing take place under the buffer conditions of the enzymatic reaction.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"PCR" refers to the polymerase chain reaction, as originally developed and covered by U.S. Pat. Nos. 4,683,195, 4,683,202 and 4,965,188, as well as variations on polymerase chain reaction. In this method, primers complementary to opposite end portions of the selected sequence(s) are used to promote, in conjunction with thermal cycling, successive rounds of primer-initiated replication. The amplified sequence(s) may be readily identified by a variety of techniques.

"Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 10 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Overview

1. Preparation of Probe Using Particular Restriction Endonuclease Reactions

The present method to produce single-stranded DNA molecules of defined length and sequence uses a double stranded DNA molecule as the template. To generate the desired single-stranded DNA molecule from the double stranded DNA template, we employ a series of enzymatic reactions that involves restriction endonucleases, a phosphatase, and an exonuclease. The DNA template can be either a PCR product or any other DNA molecule such as plasmid, viral, genomic DNA, or synthetic DNA.

Referring now to FIG. 1, the starting double stranded DNA is illustrated at the top. Within that molecule, the final, desired final strand is shown as box 10 on the top strand. In a PCR reaction, first shown as "step a," primers 12, 14 are hybridized to the strands and standard PCR amplification is carried out for the number of cycles desired, typically 10-30 cycles. The PCR products will have added sequences, shown with hatching, as non-complementary, containing restriction sites for yielding the defined ends. By using PCR primers having non-complementary portions, PCR products are obtained which have any predetermined 5' and 3' ends. This feature is exploited to engineer specific restriction enzyme sites where the cut site can precisely define any end of the final product. Furthermore, in the creation of SMART probes, as described below, the non-complementary portions of the PCR primers can be designed to include target sequences and primer sequences.

After the PCR product is obtained, in step b, shown in FIG. 1, the amplified double stranded material from step a is reacted with a first restriction endonuclease to create a cut 16 to create the desired sequence at the 5' end of desired top strand 10 of the molecule and create a 5' overhang whereby the desired 5' end overhangs the 3' complementary strand. The cut site should be at the nucleotide that is the desired 5' end, typically next to the first mismatch with the target sequence in the primer. That is, the desired 5' end is assumed to be present in the starting material, although it can be tailored by adding nucleotides in the primer.

After the step b digestion with the first restriction endonuclease (to create the desired 5' end), in step the phosphate group on the overhang is removed by a phosphatase (e.g., shrimp alkaline phosphatase) as shown at 18. Removal of this phosphate makes the top strand (containing the desired product) resistant to exonuclease digestion. After the phosphatase reaction, the double stranded DNA molecule is digested with the second restriction enzyme that creates the desired sequence at other end (3' end) of the molecule in step d.

The second restriction endonuclease is used as shown at 20 to create the desired sequence at the 3' end of the molecule. This should be a blunt end, but may also result in a 3' overhang of the desired strand, as shown at 23. We prefer to use restriction enzymes that generate a blunt-ended molecule in step d, but this is not the only option since there are other ways of generating a blunt end molecule that has a phosphate group. This series of digestions results in the generation a double-stranded DNA molecule with a blunt end that has a 5' phosphate group, and an overhang on the opposite end that has no phosphate group on the 5' end.

After restriction endonuclease and phosphatase treatment, the double-stranded molecule is converted to single strand by digestion with lambda exonuclease, as shown at 21. This generates the final 5' molecule 10, as shown in step e. The exonuclease (e.g., lambda exonuclease, exonucleases I-III from *E. coli*, nuclease Bal-31, exoribonucleases, and the exonuclease activities of DNA polymerases) will selectively degrade the strand with the phosphorylated 5' end and will keep the other strand intact. The method we have described requires the sequential digestions with restriction enzymes and a phosphatase step in between that allow the formation of a suitable substrate for an enzymatic exonuclease digestion. It does not rely on chemical modification of the primers to generate this molecule.

It is possible to carry out the above described steps with several different dsDNA starting materials and produce multiple, different ssDNAs. In this case the restriction enzymes used require a unique recognition site that is common to all the molecules. To achieve the goal to generating defined ends with shared restriction enzyme recognition sequences, the examples below describe two enzymes that cut in a sequence independent manner. That is, the cut site is outside of the recognition site. There are a few enzymes that have this flexibility of cutting in a sequence independent manner, and we chose two for purposes of illustration—BsaI and MlyI, discussed further below.

The order of the steps in certain respects is important. The amplification must be carried out first in order to generate a large number of final product molecules of the desired sequence, and to add the tailored ends for restriction cleavage. The first cleavage of step b must be done prior to phosphate removal in order to create the desired 5' nucleoside. The 3' cleavage of step d must follow this because a 5' phosphate on the bottom strand (to be removed) is needed for exonuclease digestion.

2. Selection of Restriction Enzymes

Restriction enzymes are chosen based on the desired 5' and 3' ends of the sequence. The most flexibility is obtained with restriction enzymes that cut outside the recognition site, and the recognition site is outside the desired sequence. Thus, there will be one enzyme where the cut is 5' of the recognition site, and one enzyme where the cut is 3' of the recognition site.

BsaI

Digestion with BsaI generates a 5' overhang five bases inward from the recognition site. The recognition site is GGTCTC, (SEQ ID NO: 6) however the cut site is outside the recognition sequence. It cuts in a sequence independent manner to generate a molecule with a 5' overhang that has a phosphate group.

```
Before Digestion:
5'GGTCTCN↓NNNNN...            (SEQ ID NO: 7)

3' CCAGAGNNNNN↑NNNNN...       (SEQ ID NO: 8)

After Digestion:
5'GGTCTCN P5'NNNNN...

3' CCAGAGNNNNN 3'NNNNN...     (SEQ ID NO: 603)
```

MlyI

The recognition sequence of MlyI is GAGTC, but the cut site is 5 bases inward, and it generates a blunt ended molecule with a 5' phosphate group. The cut site is not dependent on the sequence between the recognition site and the cut site. The cut site is marked with arrows.

```
Before Digestion
5'...GAGTCNNNNN↓NNNN...      (SEQ ID NO: 9)

3'...CTCACNNNNN↑NNNN...      (SEQ ID NO: 10)

After Digestion
5'...GAGTCNNNNN↓5'P NNNN...  (SEQ ID NO: 604)

3'...CTCACNNNNN↑3' NNNN...   (SEQ ID NO: 605)
```

The advantage of using restriction enzymes that digest a DNA molecule outside their recognition sequence is the fact that the restriction enzyme digests the DNA molecule in a position that is independent from the sequence constraints of the recognition site. In our methodology we have appropriately placed the position of the recognition sequences for the two restriction enzymes used in the method outside the sequence of the single stranded molecule we want to generate (see Table 1). For some applications, restriction enzymes that digest the DNA molecule within the recognition sequence of the enzyme also can be used. That is, if the desired end corresponds to the recognition/cut site of a restriction enzyme to be used. Also, the restriction enzyme used in the first digestion should produce a 5' overhang (recessed 3' hydroxyl end) even though this is not absolutely necessary.

Any restriction enzyme that produces a 5' overhang at the desired 5' end of the probe may be used (See FIG. 1, cut 16). Below is a representative list of suitable restriction enzymes. This information is adapted from information provided by New England BioLabs, Inc. at their web site. All recognition sequences are written 5' to 3' using the single letter code nomenclature with the point of cleavage indicated by a "/". Numbers in parentheses indicate point of cleavage for non-palindromic enzymes. Isoschizomers with alternative cleavage sites are indicated with a "^". Enzymes that are not currently commercially available are indicated with a "x". The New England BioLabs® Catalog number is shown in the center column.

TABLE 1

Restriction enzymes producing 5' overhang

| Enzyme | Sequence | NEB Enzyme | Catalog # | Sequence | Other Isoschizomers |
|---|---|---|---|---|---|
| Aar I | CACCTGC (4/8) SEQ ID NO: 11 | | | | |
| Acc36 I | ACCTGC (4/8) SEQ ID NO: 12 | BfuA I | R0701 | ACCTGC (4/8) SEQ ID NO: 12 | BfuA I, BspM I, Bve I |
| Ace IIIx | CAGCTC (7/11) SEQ ID NO: 13 | | | | |
| AclW I | GGATC (4/5) SEQ ID NO: 14 | Alw I | R0513 | GGATC (4/5) SEQ ID NO: 14 | Alw I, BspP I |
| Alw I | GGATC (4/5) SEQ ID NO: 14 | Alw I | R0513 | GGATC (4/5) SEQ ID NO: 14 | AclW I, BspP I |
| Alw26 I | GTCTC (1/5) SEQ ID NO: 15 | BsmA I | R0529 | GTCTC (1/5) SEQ ID NO: 15 | BsmA I, BsoMA I |
| Bbs I | GAAGAC (2/6) SEQ ID NO: 16 | Bbs I | R0539 | GAAGAC (2/6) SEQ ID NO: 16 | Bpi I, BpuA I, BstV2 I |
| Bbv I | GCAGC (8/12) SEQ ID NO: 17 | Bbv I | R0173 | GCAGC (8/12) SEQ ID NO: 17 | BseX I, BstV1 I |
| Bbv IIx | GAAGAC (2/6) SEQ ID NO: 18 | Bbs I | R0539 | GAAGAC (2/6) SEQ ID NO: 18 | Bbs I, Bpi I, BpuA I, BstV2 I |
| BceA I | ACGGC (12/14) SEQ ID NO: 19 | BceA I | R0623 | ACGGC (12/14) SEQ ID NO: 19 | |
| BfuA I | ACCTGC (4/8) SEQ ID NO: 12 | BfuA I | R0701 | ACCTGC (4/8) SEQ ID NO: 12 | Acc36 I, BspM I, Bve I |
| Bpi I | GAAGAC (2/6) SEQ ID NO: 20 | Bbs I | R0539 | GAAGAC (2/6) SEQ ID NO: 20 | Bbs I, BpuA I, BstV2 I |
| BpuA I | GAAGAC (2/6) SEQ ID NO: 20 | Bbs I | R0539 | GAAGAC (2/6) SEQ ID NO: 20 | Bbs I, Bpi I, BstV2 I |
| Bsa I | GGTCTC (1/5) SEQ ID NO: 21 | Bsa I | R0535 | GGTCTC (1/5) SEQ ID NO: 21 | Bso31 I, BspTN I, Eco31 I |
| BsmA I | GTCTC (1/5) SEQ ID NO: 15 | BsmA I | R0529 | GTCTC (1/5) SEQ ID NO: 15 | Alw26 I, BsoMA I |
| BsmB I | CGTCTC (1/5) SEQ ID NO: 22 | BsmB I | R0580 | CGTCTC (1/5) SEQ ID NO: 22 | Esp3 I |
| BsmF I | GGGAC (10/14) SEQ ID NO: 23 | BsmF I | R0572 | GGGAC (10/14) SEQ ID NO: 23 | BslF I |
| Bso31 I | GGTCTC (1/5) SEQ ID NO: 21 | Bsa I | R0535 | GGTCTC (1/5) SEQ ID NO: 21 | Bsa I, BspTN I, Eco31 I |

TABLE 1-continued

Restriction enzymes producing 5' overhang

| Enzyme | Sequence | NEB Enzyme | Catalog # | Sequence | Other Isoschizomers |
|---|---|---|---|---|---|
| BsoMA I | GTCTC (1/5) SEQ ID NO: 15 | BsmA I | R0529 | GTCTC (1/5) SEQ ID NO: 15 | Alw26 I, BsmA I |
| BspM I | ACCTGC (4/8) SEQ ID NO: 12 | BfuA I | R0701 | ACCTGC (4/8) SEQ ID NO: 12 | Acc36 I, BfuA I, Bve I |
| BspP I | GGATC (4/5) SEQ ID NO: 14 | Alw I | R0513 | GGATC (4/5) SEQ ID NO: 14 | AclW I, Alw I |
| BspTN I | GGTCTC (1/5) SEQ ID NO: 21 | Bsa I | R0535 | GGTCTC (1/5) SEQ ID NO: 21 | Bsa I, Bso31 I, Eco31 I |
| Bst6 I | CTCTTC (1/4) SEQ ID NO: 15 | Ear I | R0528 | CTCTTC (1/4) SEQ ID NO: 15 | Eam1104 I, Ear I, Ksp632 I |
| Eam1104 I | CTCTTC (1/4) SEQ ID NO: 15 | Ear I | R0528 | CTCTTC (1/4) SEQ ID NO: 15 | Bst6 I, Ear I, Ksp632 I |
| Ear I | CTCTTC (1/4) SEQ ID NO: 15 | Ear I | R0528 | CTCTTC (1/4) SEQ ID NO: 15 | Bst6 I, Eam1104 I, Ksp632 I |
| Eco31 I | GGTCTC (1/5) SEQ ID NO: 21 | Bsa I | R0535 | GGTCTC (1/5) SEQ ID NO: 21 | Bsa I, Bso31 I, BspTN I |
| Esp3 I | CGTCTC (1/5) SEQ ID NO: 22 | BsmB I | R0580 | CGTCTC (1/5) SEQ ID NO: 22 | BsmB I |
| Fau I | CCCGC (4/6) SEQ ID NO: 24 | Fau I | V0209 | CCCGC (4/6) SEQ ID NO: 24 | Smu I |
| Fok I | GGATG (9/13) SEQ ID NO: 25 | BstF5 I^ | V0031 | GGATG (2/0) SEQ ID NO: 25 | BseG I^, BstF5 I^ |
| Hga I | GACGC (5/10) SEQ ID NO: 26 | Hga I | R0154 | GACGC (5/10) SEQ ID NO: 26 | |
| Ksp632 I | CTCTTC (1/4) SEQ ID NO: 15 | Ear I | R0528 | CTCTTC (1/4) SEQ ID NO: 15 | Bst6 I, Eam1104 I, Ear I |
| Lwe I | GCATC (5/9) SEQ ID NO: 27 | SfaN I | R0172 | GCATC (5/9) SEQ ID NO: 27 | SfaN I |
| Ple I | GAGTC (4/5) SEQ ID NO: 28 | Mly I^ | R0610 | GAGTC (5/5) SEQ ID NO: 28 | Mly I^, Pps I, Sch I^ |
| Pps I | GAGTC (4/5) SEQ ID NO: 28 | Mly I^ | R0610 | GAGTC (5/5) SEQ ID NO: 28 | Mly I^, Ple I, Sch I^ |
| Sap I | GCTCTTC (1/4) SEQ ID NO: 29 | Sap I | R0569 | GCTCTTC (1/4) SEQ ID NO: 29 | |
| SfaN I | GCATC (5/9) SEQ ID NO: 27 | SfaN I | R0172 | GCATC (5/9) SEQ ID NO: 27 | Lwe I |
| Smu I | CCCGC (4/6) SEQ ID NO: 28 | Fau I | V0209 | CCCGC (4/6) SEQ ID NO: 28 | Fau I |
| Sth132 Ix | CCCG (4/8) SEQ ID NO: 29 | | | | |

TABLE 2

Restriction enzymes producing 3' overhang (see 23, step d, FIG. 1)

| Enzyme | Sequence | NEB Enzyme | Catalog # | Sequence | Other Isoschizomers | Enzyme |
|---|---|---|---|---|---|---|
| Acu I | CTGAAG (16/14) SEQ ID NO: 30 | Acu I | R0641 | CTGAAG (16/14) SEQ ID NO: 30 | Eco57 I | |
| AsuHP I | GGTGA (8/7) SEQ ID NO: 31 | Hph I | R0158 | GGTGA (8/7) SEQ ID NO: 31 | Hph I | |
| BciV I | GTATCC (6/5) SEQ ID NO: 32 | BciV I | R0596 | GTATCC (6/5) SEQ ID NO: 32 | Bfu I | |
| Bfi I | ACTGGG (5/4) SEQ ID NO: 33 | Bmr I | R0600 | ACTGGG (5/4) SEQ ID NO: 33 | Bmr I | |
| Bfu I | GTATCC (6/5) SEQ ID NO: 32 | BciV I | R0596 | GTATCC (6/5) SEQ ID NO: 32 | BciV I | |
| Bmr I | ACTGGG (5/4) SEQ ID NO: 33 | Bmr I | R0600 | ACTGGG (5/4) SEQ ID NO: 33 | Bfi I | |
| Bpm I | CTGGAG (16/14) SEQ ID NO: 34 | Bpm I | R0565 | CTGGAG (16/14) SEQ ID NO: 34 | Gsu I | |
| Bse3D I | GCAATG (2/0) SEQ ID NO: 35 | BsrD I | R0574 | GCAATG (2/0) SEQ ID NO: 35 | BseM I, BsrD I | |
| BseG I | GGATG (2/0) SEQ ID NO: 36 | BstF5 I | V0031 | GGATG (2/0) SEQ ID NO: 36 | BstF5 I, Fok I^ | |
| BseM I | GCAATG (2/0) SEQ ID NO: 35 | BsrD I | R0574 | GCAATG (2/0) SEQ ID NO: 35 | Bse3D I, BsrD I | |
| BseM II | CTCAG (10/8) SEQ ID NO: 37 | BspCN I^ | R0624 | CTCAG (9/7) SEQ ID NO: 37 | BspCN I^ | |

TABLE 2-continued

| Restriction enzymes producing 3' overhang (see 23, step d, FIG. 1) | | | | | | |
|---|---|---|---|---|---|---|
| Enzyme | Sequence | NEB Enzyme | Catalog # | Sequence | Other Isoschizomers | Enzyme |
| BseR I | GAGGAG (10/8) SEQ ID NO: 38 | BseR I | R0581 | GAGGAG (10/8) SEQ ID NO: 38 | | |
| BsrD I | GCAATG (2/0) SEQ ID NO: 39 | BsrD I | R0574 | GCAATG (2/0) SEQ ID NO: 39 | Bse3D I, BseM I | |
| BstF5 I | GGATG (2/0) SEQ ID NO: 40 | BstF5 I | V0031 | GGATG (2/0) SEQ ID NO: 40 | BtsC I, BseG I, Fok I^ | |
| Eci I | GGCGGA (11/9) SEQ ID NO: 41 | Eci I | R0590 | GGCGGA (11/9) SEQ ID NO: 41 | | |
| Eco57 I | CTGAAG (16/14) SEQ ID NO: 42 | Acu I | R0641 | CTGAAG (16/14) SEQ ID NO: 42 | Acu I | |
| Eco57M I | CTGRAG (16/14) SEQ ID NO: 43 | | | | | |
| Gsu I | CTGGAG (16/14) SEQ ID NO: 34 | Bpm I | R0565 | CTGGAG (16/14) SEQ ID NO: 34 | Bpm I | |
| Hph I | GGTGA (8/7) SEQ ID NO: 31 | Hph I | R0158 | GGTGA (8/7) SEQ ID NO: 31 | AsuHP I | |
| Mly I | GAGTC (5/5) SEQ ID NO: 28 | Mly I | R0610 | GAGTC (5/5) SEQ ID NO: 28 | Ple I^, Pps I^, Sch I | |
| Mme I | TCCRAC (20/18) SEQ ID NO: 44 | Mme I | R0637 | TCCRAC (20/18) SEQ ID NO: 44 | | |
| RleA Ix | CCCACA (12/9) SEQ ID NO: 45 | | | | | |
| Sch I | GAGTC (5/5) SEQ ID NO: 28 | Mly I | R0610 | GAGTC (5/5) SEQ ID NO: 28 | Mly I, Ple I^, Pps I^ | |
| TspDT I | ATGAA (11/9) SEQ ID NO: 46 | | | | | |
| TspGW I | ACGGA (11/9) SEQ ID NO: 46 | | | | | |
| Tth111 IIx | CAARCA (11/9) SEQ ID NO: 47 | | | | | |

The enzymes in Table 2 are useful if a recessed 5' end, which is also a suitable target for exonuclease digestion (as is a blunt end) is desired in the second digestion 3. Design of Probes for Multiplex Amplification (a) Introduction The polymerase chain reaction (PCR) is one of the most commonly used techniques in genomics. This method of amplifying DNA from a limited amount of template material has been used extensively in DNA sequencing, SNP genotyping, molecular diagnostics etc., and has become one of the most routine protocols in molecular biology. One of the challenges facing high-throughput genomics is expanding the scale of PCR while keeping costs low. Considerable efforts have been made during the past several years to increase the throughput of PCR by "multiplexing" the reactions. The goal of multiplex PCR is to amplify a large number of targets in the same reaction vessel. This has been a challenge because of the large number of spurious reaction products that arise when a mixture of oligonucleotides are used in the same PCR reaction. Cho et al., (1999) were successfully able to multiplex 50 primer pairs, but this is not the scale that is sufficient for high-throughput genomics.

The present methodology is useful for other "gap fill" techniques. For example, probe ligation methods have been reported. U.S. Pat. No. 4,883,750 to N. M. Whiteley, et al., D. Y. Wu, et al., *Genomics* 4:560 (1989), U. Landegren, et al., *Science* 241:1077 (1988), and E. Winn-Deen, et al., *Clin. Chem.* 37:1522 (1991). In one approach, known as oligonucleotide ligation assay ("OLA"), two probes or probe elements that span a target region of interest are hybridized to the target region. Where the probe element bases pair with adjacent target bases, the confronting ends of the probe elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of pairs of probe elements, the target sequence is amplified linearly, allowing very small amounts of target sequence to be detected and/or amplified. This approach is referred to as ligase detection reaction.

Another technique requiring "gap fill" is molecular inversion probe (MIP) technology (U.S. Pat. No. 6,858,412, described above). Using this technology, several thousand probes have been hybridized to genomic DNA in one reaction vessel. Both padlock probes and MIP technology use single-stranded "pre-circles" to hybridize to target DNA. These pre-circles contain sequences on the 3' and 5' ends that are complementary to the target DNA. The DNA in between the complementary target sequences in the probe does not hybridize with the target, and forms a loop between the two hybridized target sequences (HTS). In the presence of DNA polymerase and ligase, the molecule extends from the 3' end of the annealed probe and synthesizes a complement of the target until it reaches the 5' end of the annealed probe. This is the "gap-fill" reaction. The molecule is circularized at that point by DNA ligase. This molecule is then freed from genomic DNA by exonucleases. In the MIP protocol, the closed circle is linearized, and the target sequences amplified with primer sequences present in the loop. The circles are not opened in the padlock probes, and the sequences are amplified by the rolling circle method. Currently the MIP technology is extensively used in SNP genotyping where the hybridized target sequences are very close to each other with a gap length of just one base pair, and the "gap-fill" reaction is the polymerization of one nucleotide before the ligation reaction. The MIP technology can conceivably be used in multiplex PCR reactions where the HTS (hybridized target sequences) are far apart and the "gap-fill" reaction can involve the polymerization of several nucleotides.

Meng Li (2006) et al., have used the padlock probe method to perform a "gap-fill" reaction where the HTS were 20 bases apart, and rolling circle amplification was used to amplify the DNA.

In all of the above cases, as the distance between the HTS (hybridized target sequences) becomes farther apart, the "gap-fill" reactions are also longer. To our knowledge, there are no publications that perform these large gap-fill reactions extending hundreds of bases, and ligations using the padlock method. We hypothesize that the rate-limiting step to perform a padlock or MIP methodology where the HTS are few hundred base bases apart might reside in the physical constraints of the corresponding sequences present on the probe to find the appropriate target sequences in the template DNA. We hypothesize optimizing the length of the spacer molecule in the probe will improve the chances of the corresponding sequences on the probe of finding their counterparts on the template DNA more efficiently. Thus will facilitate a more efficient gap-fill reaction and the downstream steps of the MIP or padlock protocol.

The present gap filling protocols are similar to others in that the gap fill reaction mixture contains a polymerase and a mixture of all four deoxynucleoside-triphosphates (also called deoxynucleotides or dNTPs, i.e. dATP, dTTP, dCTP and dGTP) in a manner similar to the MIP reaction and other polymerizations. Suitable enzymes include the Stoffel fragment of Taq polymerase (Applied Biosystems) or T4 DNA polymerase or any other enzyme that has no strand displacement activity or 5' exonuclease activity. It is important that the gap fill reaction be carried out with an enzyme that has a lack of 5 prime exonuclease activity and a lack of strand displacement activity.

Modified or substituted dNTPs may be also used, such as 2'deoxyadenosine 5'-O-(1-thiotriphosphate), 5-methyldeoxycytidine 5'-triphosphate, 2'-deoxyuridine 5'-triphosphate, and 7-deaza-2'-deoxyguanosine 5'-triphosphate. In addition, the substitution of the dNTP may occur after incorporation into a newly synthesized strand; for example, a methylase may be used to add methyl groups to the synthesized strand. Peptide-nucleic acid residues may be incorporated, as described in US PGPUB 2005/0053944 "Methods and kit for hybridization analysis using peptide nucleic acid probes," hereby incorporated by reference.

(b) Design of Spacer Probes—Spacer Multiplex Amplification ReacTion (SMART)

A procedure which solves the problem of performing gap-fill reaction and ligation where the HTS (hybridized target sequences) are few hundred bases apart on the template DNA has been developed. We call the new methodology Spacer Multiplex Amplification ReacTion (SMART) because the success of the method is based on the optimization of the length of spacer backbone sequence on the probe. SMART probes are single-stranded molecules that have target (corresponding) sequences to genomic DNA or other target to be analyzed on either end of the of the probe sequence. An amplification primer AP1 and AP2 that was common to all the probes flanked each target. To test the hypothesis that the length of the spacer would determine the efficiency of longer extensions, we used probes where the length between the two common amplification primers was either 221 bases, or 38 bases as in conventional MIP probes. The SMART probes synthesized by the method we describe above, and the conventional MIP-size probes were synthesized chemically. The final configuration of the SMART probes, made according to FIG. 1, is shown in FIG. 2.

That is, the length of the spacer backbone should be at least 50% of the length of the HTS (hybridized target sequence) gap to be filled.

We reasoned that we could create molecules with varying spacer lengths by using the method of probe synthesis that we have developed and is described above. We designed smaller sized probes that approximated the conventional MIP sizes, and the larger probes for the corresponding targets to test our hypothesis.

Figure 2:
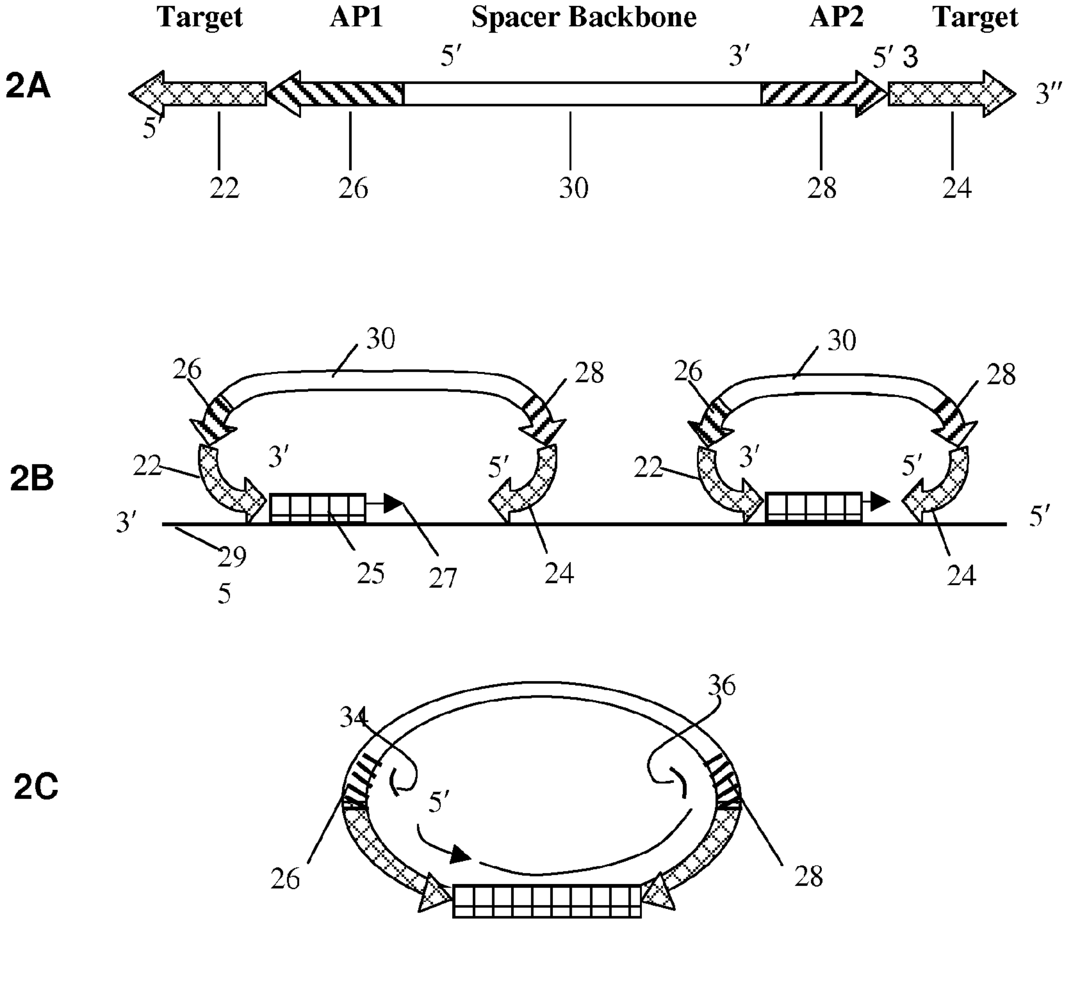
FIG. 2 is a diagram (2A) of a probe having common amplification primer regions and a spacer backbone, a diagram showing binding of a probe (2B) and a diagram of a circularized probe being amplified while still in a circle (2C)

As shown in FIG. 2, the present probes, as prepared by the present method, comprise target sequences 22, 24, which are exactly complementary to and bind to targets such as genomic DNA 29. The arrowheads 27 indicate the direction of polymerization on a single stranded target molecule 29 shown in 2B. As is conventionally known, all polymerases have 5' to 3, polymerization activity and require a template strand and either a DNA or RNA primer having a 3' end to which newly added bases are joined. AP1 and AP2 (26, 28) are common amplification primer sites for later amplification. Each probe comprises target sequences 22, 24, one on each end, primer sites 26, 28 next to each target sequence, and a spacer backbone 30 in between. The spacer backbones 30 are of variable length depending on the application. They are random DNA sequences that do not hybridize to target sequences. They may include peptide nucleic acids or other polymers.

As shown in FIG. 2B, multiple probes may be used on a target sequence, having unique target sequences 22, 24, but having common primer amplification sites 26, 28. Thus, in the amplification step shown in FIG. 2C, common primers binding to sites 26 and 28 will be used to amplify all hybridized, ligated probes. FIG. 2B shows one probe shown in FIG. 2A in contact with one region of single stranded target DNA 29 with a gap filling reaction catalyzed by DNA polymerase adding residues 25 and continuing as shown at 27 until the newly added region is complete up to the 5' end of probe target region 24. For purposes of illustration, another probe having a smaller spacer backbone and a smaller gap is targeted to a different sequence. The probes have different targeting regions, differing in size and sequence, but identical primer regions AP1 and AP2. This permits a high degree of multiplexing in the final amplification reaction. Gap filling reactions adding nucleotides 25 are carried out by DNA polymerase, preferably lacking 3'-5' exonuclease activity and the strand displacement activity, such as T4 polymerase, Taq, PolI (stofffel fragment). It is not necessary that the polymerase be thermostable.

Then, as shown in FIG. 2C, the probes are circularized by joining the newly added nucleotides to the end of the opposite target sequence. DNA ligase such as Ampligase, which functions at a high temperature, or any other DNA ligase such as T4 or *E. coli* DNA ligase may be used once the gap is filled. Then, an exonuclease is used to digest unreacted probes—which are linear—and target DNA. The circular probes that remain are then amplified as circles, as shown in 2C, using amplification primers 34, 36 targeted to primer sites AP1 and AP2. Multiple copies of the target sequences in the target DNA, including the filled in gaps, are then prepared for further analysis.

EXAMPLES

Example 1

Probe Synthesis

The desired single-stranded probe we want to create is 298 bp. and the sequence of the molecule is

SEQ ID NO: 48

5'TTGTTTTCTCCGTCGCCGTATCCCTTTAGTGAGGGTTAATAGTACGCT

TACTTCCGCGAAACGTCAGCGGAAGCACCACTATCTGGCGATCAAAAGGA

TGGTCATCGGTCACGGTGACAGTACGGGTACCTGACGGCCAGTCCACACT

GCTTTCACGCTGGCGCGGAAAAGCCGCGCTCG1CCGCCTTTACAATGTCC

CCGACGATTTTTTCCGCCCTCAGCGTACCGTTTATCGTACAGTTTTCAGC

TATCGTCACATTATTTAGGTGACACTATAGCCACAAATCAAGATCCGAAT

T3'

The underlined portions of the sequence represent the amplification primer sites described in Example 2, it being understood that the 5' primer is the reverse complement of the underlined sequence. The probe sequence of SEQ ID NO: 48 above is derived from a double stranded DNA product, and it may be present in any organism or vector, as part of a larger sequence, and is set forth below in double stranded form as

SEQ ID NO: 49

TTGTTTTCTCCGTCGCCGTATCCCTTTAGTGAGGGTTAATAGTACGCTTACTTCCGCGAA
AACAAAAGAGGCAGCGGCATAGGGAAATCACTCCCAATTATCATGCGAATGAAGGCGCTT

ACGTCAGCGGAAGCACCACTATCTGGCGATCAAAAGGATGGTCATCGGTCACGGTGACAG
TGCAGTCGCCTTCGTGGTGATAGACCGCTAGTTTTCCTACCAGTAGCCAGTGCCACTGTC

TACGGGTACCTGACGGCCAGTCCACACTGCTTTCACGCTGGCGCGGAAAAGCCGCGCTCG
ATGCCCATGGACTGCCGGTCAGGTGTGACGAAAGTGCGACCGCGCCTTTTCGGCGCGAGC

CCGCCTTTACAATGTCCCCGACGATTTTTTCCGCCCTCAGCGTACCGTTTATCGTACAGT
GGCGGAAATGTTACAGGGGCTGCTAAAAAAGGCGGGAGTCGCATGGCAAATAGCATGTCA

TTTCAGCTATCGTCACATTATTTAGGTGACACTATAGCCACAAATCAAGATCCGAATT
AAAGTCGATAGCAGTGTAATAAATCCACTGTGATATCGGTGTTTAGTTCTAGGCTTAA

STEP 1: Incorporation of restriction sites at the ends of double stranded template by PCR amplification with engineered primers:

The first step in the procedure is to incorporate the two restrictions sites at the appropriate position of the double stranded molecule. To achieve that, we amplified a double-stranded PCR product with PCR primers that had an MlyI sequence engineered into the one primer, and the BsaI sequence engineered into the other primer.

(SEQ ID NO: 50)

Reverse primer (MlyI_Target)

CATCGTGAGTCACTCGAATTCGGATCTTGATTTGTGG (SEQ ID NO: 51)

Forward primer (BsaI_Target)

GTACGAGGTCTCACTTGTTTTCTCCGTCGCCGTA

Thus, the reverse primer of SEQ ID NO: 50 and the forward primer SEQ ID NO: 51 do not hybridize completely to the target sequence of SEQ ID NO: 48. They will still function to prime a PCR amplification, and the amplification product will contain the engineered sequence shown in italics, which need not be complementary to the target sequence.

(SEQ ID NO: 52)

5' *GTACGAGGTCTCA*↓TTGTTTTCTCCGTCGCCGTA*TCCCTTTAGTGAGGGTTA*ATAGTACGC
3' CATGCT*CCAGAG*TAACA↑AAAGAGGCAGCGGCATAGGGAAATCACTCCCAATTATCATGCG

TTACTTCCGCGAAACGTCAGCGGAAGCACCACTATCTGGCGATCAAAAGGATGGTCATCG
AATGAAGGCGCTTTGCAGTCGCCTTCGTGGTGATAGACCGCTAGTTTTCCTACCAGTAGC

GTCACGGTGACAGTACGGGTACCTGACGGCCAGTCCACACTGCTTTCACGCTGGCGCGGA
CAGTGCCACTGTCATGCCCATGGACTGCCGGTCAGGTGTGACGAAAGTGCGACCGCGCCT

AAAGCCGCGCTCGCCGCCTTTACAATGTCCCCGACGATTTTTTCCGCCCTCAGCGTACCG
TTTCGGCGCGAGCGGCGGAAATGTTACAGGGGCTGCTAAAAAAGGCGGGAGTCGCATGGC

TTTATCGTACAGTTTTCAGCTATCGTCACATT*ATTTAGGTGACACTATAG*CCACAAATCA
AAATAGCATGTCAAAAGTCGATAGCAGTGTAATAAATCCACTGTGATATCGGTGTTTAGT

AGATCCGAATT⇓GAGT*GACTC*ACGATG 3'
TCTAGGCTTAA⇑*CTCACTGAGTGCTAC* 5' MlyI

STEP 2: Digestion at 5' End

The first digestion with BsaI generates a 5' overhang five bases inward from the recognition site on the top strand, and 1 base inward on the lower strand. This creates a molecule with a recessed 3' end and a protruding 5' end. The 5' end now has a phosphate group. The molecule will be as in SEQ ID NO: 52, with the portions 5' (top strand) and 3' (bottom strand) of the single bold arrow removed.

STEP 3: Phosphatase Treatment

The phosphate group on the 5' overhang of this molecule (shown as double underlined TTGT in SEQ ID NO: 52) is then cleaved with a phosphatase making it resistant to lambda exonuclease cleavage.

STEP 4: Second Digestion at 3' End to Create a Blunt End

The molecule is then digested with the enzyme MlyI that cuts 5 bases inward from the recognition site, and generates a blunt-end molecule that has a phosphate group at the 5' end. This can be seen in SEQ ID NO: 52 as removal of the portions 3' of the double arrow (top strand) and 5' of the double arrow (bottom strand). The 5' adenosine on the bottom strand will have a terminal phosphate group after the restriction enzyme cleavage.

STEP 5: Digestion of Second Strand

The molecule as shown in SEQ ID NO: 52 now has a 5' phosphate on the adenosine on the blunt end, and a non-phosphorylated 5' overhang (TTGT) on the other. As a result, when it is digested with Lambda exonuclease, the enzyme preferentially cleaves the phosphorylated strand, and generates the desired single-stranded molecule shown in SEQ ID NO: 48.

The desired ssDNA has now been formed. The target sequences, AP1 and AP2 are in bold and italic in SEQ ID NO: 52, above.

Example 2

Multiplex Probe Design

Enzymatic synthesis of the long single-stranded molecule was derived from a double-stranded PCR product following the procedure described above.

1) Generation of Double Stranded Templates Shown in FIG. 3A

Figure 3:
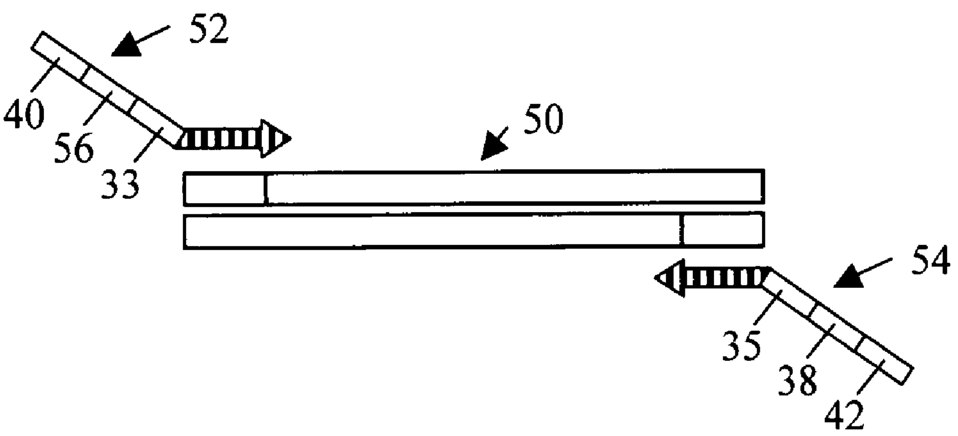
FIG. 3 is a diagram showing a technique for spacer multiplex detection, ("SMART," or Spacer Multiplex Amplification ReacTion) showing a target sequence and probe creation (3A), amplified sequence design (3B), and hybridization of the present probe (3C)
Figure 3:
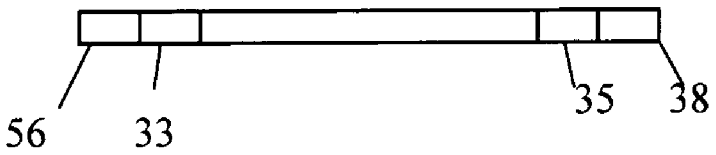
Figure 3:
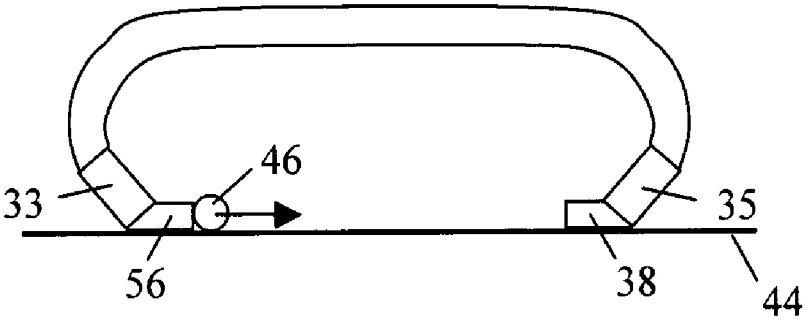

As shown in FIG. 3, double stranded DNA is first amplified using primers 52, 54. A 220 bp sequence from bacteriophage lambda, shown at 50, serves as starting point and a backbone for the probe. The phage was selected because its DNA would be non-hybridizable with human target DNA. The PCR amplification primers were synthesized with additional amplification primer 1 (AP1) sequence 33 on the forward primer and amplification primer 2 35 (AP2) sequence on the reverse amplification primers (FIG. 3A). These are common amplification primer targets for PCR using common primers for a multiple of probes in the downstream application. The molecule with the backbone and amplification primers was common for all the probes, except for the target sequences. The probes contain unique target sequences 56, 38.

The common lambda backbone was used as the template to make the template -specific probes (FIG. 3A). The forward primer had recognition sequences for MlyI (40) at the 5' end. The reverse primer had sequences complementary to the target on the genomic DNA that was the desired distance apart from first target, as well as the amplification primer 2 on the target and a BsaI recognition sequence 42 at the 5' end of the reverse primer. The resulting fragment has MlyI and BsaI adaptors flanking the two targets with the spacer DNA in between them (FIG. 3C) when the probe ends hybridize to the target.

2) Generation of Single Stranded Probe of FIG. 3B:

The PCR fragment generated as shown in FIG. 3A was digested with BsaI to generate the 5' overhang. The molecule was then dephosphorylated with Shrimp alkaline phosphatase to remove the 5' phosphate. It was then digested with MlyI to generate a specific 5' end opposite the specific end created with the BsaI digestion. This molecule then was digested with lambda exonuclease. The final probe configuration is shown in FIG. 3B, wherein the target sequences 56 and 38 were targeted to human genomic DNA 44. The single-stranded probe was subsequently phosphorylated with T4 polynucleotide kinase prior to being hybridized to the genomic DNA. Ligation requires a 5' phosphate group, added by this phoshporylation step, because it was removed earlier to protect from exonuclease digestion.

3. Amplification of Target 100 attomoles probe was annealed with 500 ng human genomic DNA. This was done by denaturation at 95° C. and annealing overnight at 58° C. As illustrated in FIG. 3C, the single stranded probe hybridized to the target, and was extended by polymerase as shown at 46. It was then ligated to form a circular probe.

The spacer backbone is illustrated in FIG. 3C as forming a loop between the hybridized targets. The DNA polymerase catalyzed the polymerization of DNA from the 3' end to fill the gap between the two targets. The ampligase enzyme closes the circle by ligating the two ends of the probe when the enzyme reaches the 5' end of the other target. The probes were extended and circularized using Stoffel polymerase and Ampligase in ampligase buffer (Epicenter). Following circularization, unreacted probe and genomic DNA were digested using Exonuclease I and III.

The exonuclease digestion freed the circles from genomic DNA. The circles were then amplified. It should be noted that, unlike the MIPS protocol, the molecules were not linearized, and amplification was performed using primer sequences present in the loop of probe that does not hybridize with the target. Specific amplification of probes that had hybridized was demonstrated by sequencing. The entire contents of the extension and ligation reactions were used for PCR amplification in a cocktail containing 10 mM tris-HCL (ph8.3), 50 mM Potassium Chloride, .2.5 mM Magnesium Chloride, and 2 units Amplitaq Gold. The primers used for amplification were done using the forward primer CGTCACATTATTTAG-GTGACACTATAG (SEQ ID NO: 606) and GCGTACTAT-TAACCCTCACTAAAGG (SEQ ID NO: 607) as the reverse primer. The cycling parameters were 10 mins of heat inactivation at 95° C. followed by 40 cycles of 95° C. for 30 sec, 63° C. for 30 sec, and 72° C. for 30 sec.

Example 3

Probe Target Annealing

We compared the ability of the conventional sized MIPS that were chemically synthesized, and the SMART probes that we generated, in their ability to extend from the annealed target. The SMART probes had a spacer of 280 nucleotides in between the target sequences and the MIPS probe had a spacer of 80 nucleotides. This would typically be part of an overall SMART probe of a length of about 320 nucleotides. We discovered that the SMART probes we tested were able to amplify target molecules with gaps up to about 400 nt long. These gaps are filled in as part of the present process, and the content of the filled gap provides analytical information. The longest extension tested in Table 1 was 330, with the longest success at 175, but it is expected, based on DNA polymerization in other techniques, that the present methods and materials would work for longer extensions by varying the size of the spacer. The MIPS probes on the other hand were unable to extend molecules in the ranges that we routinely observed with the SMART probes. (Table 3).

We have shown that the SMART probes synthesized by the method described above are able to function robustly by extending over larger distances than the conventional-sized MIP probes. We believe that the optimal backbone length will depend on the target size being amplified, and that having the ability to vary this spacer length will be important to be able to efficiently multiplex PCR from thousands of exons in a single reaction. These probes have application not only in multiplex PCR, but also to generate the constructs necessary for mismatch repair detection (MRD) assay.

TABLE 3

Comparison of MIP and SMART probes in amplification of identical genomic targets.

| Length of gap-fill (bases) | outcome of MIPS (80 base spacer) | outcome of SMARTS (280 base spacer) |
|---|---|---|
| 1 | successful | successful |
| 161 | successful | successful |
| 186 | successful | successful |
| 141 | successful | successful |
| 175 | successful | successful |
| 244 | failed | successful |
| 249 | failed | successful |
| 290 | failed | successful |
| 330 | failed | successful |

The above Table 3 shows that a MIPS probe with an 80 base space (region between target sequences) would not amplify when the gap between the ends of the probe was 244 nucleotides (nt). On the other hand, the SMART probes were successful at all gap distances tested, even those longer than the spacer. The SMART probes may be made to any length. It is very hard to synthesize a ss DNA molecule bigger than 120-140 base pair total and at the same time accurate and reliable for high through put molecular biology analysis. The present method enables the convenient synthesis of large ssDNA molecules and provides the opportunity for the discovery of novel methodologies, such as long-gapped circular probes.

Example 4

Preparation of Single Stranded Probe

Step 1: Creation of the Lambda Backbone Common to all Probes

The template used was Lambda DNA, shown at 30 in FIG. 3. Lambda DNA is commonly used as a substrate in restriction enzyme activity assays and for preparation of DNA molecular weight standards. The phage is isolated from a heat-inducible lysogenic *E. coli* W3110 (cI857 Sam7) strain. Primers (52 and 54 in FIG. 3) were prepared by the addition of Amplification 1 (AP1) and Amplification 2 (AP2) sequences to backbone from bacteriophage lambda.

Primer 1 (SK51 has AP1)

SEQ ID NO: 53

*TGTCTATAGTGTCACCTAAAT*TAATGTGACGATAGCTG

Primer 2 (SK52 has AP2seq)

SEQ ID NO: 54

*TGTCCCTTTAGTGAGGGTTAAT*AGTACGCTTACTTCCGCG

The sequence after amplification is

SEQ ID NO: 55

5' *TGTCTATAGTGTCACCTAAAT*TAAATTAATGTGACGATAGCTGAAAACT

GTACGATAAACGGTACGCTGAGGGCGGAAAAAATCGTCGGGGACATTGTA

AAGGCGGCGAGCGCGGCTTTTCCGCGCCAGCGTGAAAGCAGTGTGGACTG

GCCGTCAGGTACCCGTACTGTCACCGTGACCGATGACCATCCTTTTGATC

GCCAGATAGTGGTGCTTCCGCTGACGTTTCGCGGAAGTAAGCGTACT

*ATTAACCCTCACTAAAGGGACA*

The added sequences, from the primers, are bold and italicized.

Reaction Conditions

- 2.5 μl PCRII 10× buffer (ABI)
- 2.5 μl 25 mM $MgCl_2$
- 2.5 μl 1.25 mM dNTP
- 1.25 μl 5 uM SK51
- 1.25 μl 5 uMSK52
- 2.5 μl 10 ng/μl Bacteriophage lambda DNA
- 12.5 μl $dH_2O$
- 1.25 units amplitaq Gold (Applied Biosystems)

TABLE 4

PCR conditions

| | |
|---|---|
| Hold: | 94° C. 10 mins |
| Cycle | 94° C. 20 secs, 64° C. 30 sec 72° C. 30 sec. |
| Touch down in 0.5° C. decrements 14 cycles. | |
| Cycle | 94° C. 20 sec, 56° C. 30 sec 72° C. 30 sec |
| 25 cycles | |
| Hold | 72° C. 5 mins |
| Hold | 4° C. o/n |

STEP 2: Addition of MLYI and BSAI Adaptor Sequences and Probe Specific Sequences to Backbone SK302_Probe_F:

SEQ ID NO: 56

GTACGAGGTCTCA*GAAATGACAAATATAGATGGCAAAAGCCATCCCTTTA GTGAGGGTTAAT

SK302_Probe_R:

SEQ ID NO: 57

CATCGTGAGTCACTCGTCACAGATAGGCATGGTGTCAAAGTCATCTATAGT GTCACCTAAAT3'

Figure 4:
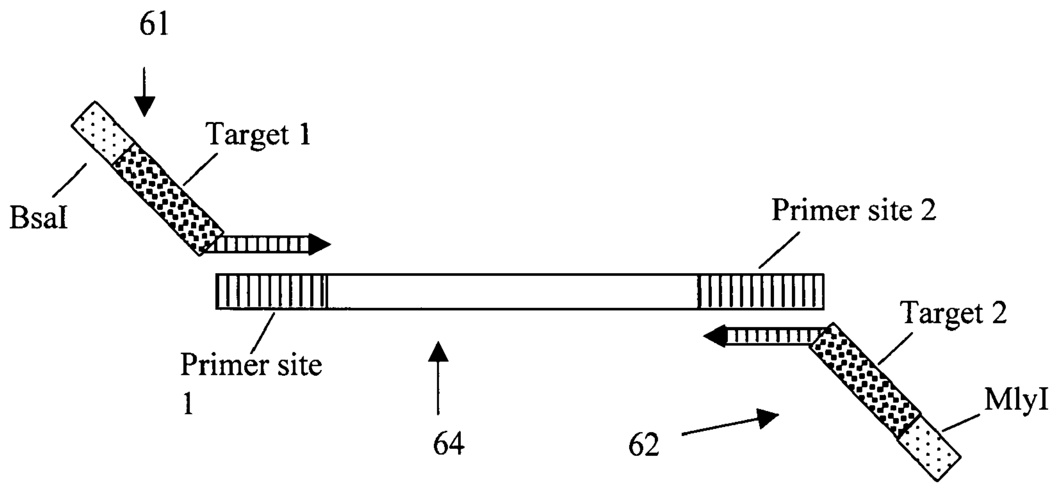
FIG. 4 is a diagram showing a probe having a spacer backbone and adapter sequences.
Figure 4:
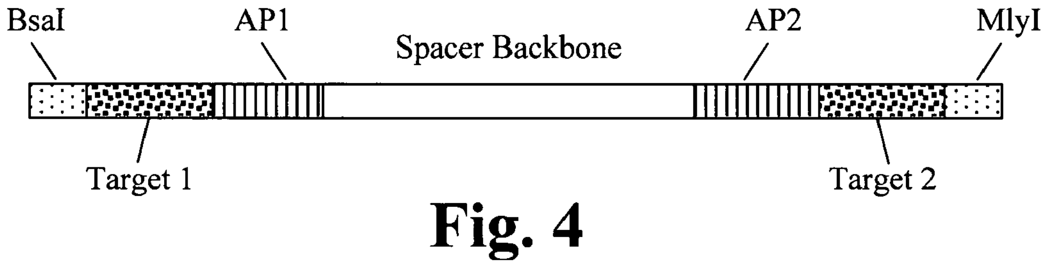

These adaptor sequences are analogous to those shown at 40 and 42 in FIG. 3, but used in a second amplification as shown in FIG. 4. The bold residues adjacent the * will represent the final 5' end and will be seen in the amplified sequence below. The 5' sequence TAC and reverse probe sequence CAT are in shaded text to show the correlation between the target and the probe.

```
                                   Target 2
BsaI                                                SEQ ID NO: 58
GTACGAGGTCTCA*GAAATGACAAATATAGATGGCAAAAGCCATCCCTTTAGTGAGGGTTA
CATGCTCCAGAGTCTTT*ACTGTTTATATCTACCGTTTTCGGTAGGGAAATCACTCCCAAT

ATAGTACGCTTACTTCCGCGAAACGTCAGCGGAAGCACCACTATCTGGCGATCAAAAGGA
TATCATGCGAATGAAGGCGCTTTGCAGTCGCCTTCGTGGTGATAGACCGCTAGTTTTCCT

TGGTCATCGGTCACGGTGACAGTACGGGTACCTGACGGCCAGTCCACACTGCTTTCACGC
ACCAGTAGCCAGTGCCACTGTCATGCCCATGGACTGCCGGTCAGGTGTGACGAAAGTGCG

TGGCGCGGAAAAGCCGCGCTCGCCGCCTTTACAATGTCCCCGACGATTTTTTCCGCCCTC
ACCGCGCCTTTTCGGCGCGAGCGGCGGAAATGTTACAGGGGCTGCTAAAAAAGGCGGGAG

AGCGTACCGTTTATCGTACAGTTTTCAGCTATCGTCACATTAATTTAGGTGACACTATAG
TCGCATGGCAAATAGCATGTCAAAAGTCGATAGCAGTGTAATTAAATCCACTGTGATATC

ATGACTTTGACACCATGCCTATCTGTGA**CGAGTGACTCACGATG 3'
TACTGAAACTGTGGTACGGATAGACACT**GCTCACTGAGTGCTAC 5'
```

As can be seen in the amplified sequence above, the final 5' end is bolded to the right of the *. The bolded region to the left of the * can be seen to be complementary to the bolded sequence of probe R, with the final, added pairs of residues indicated by shading. The ** indicates where the final 3' end will be.

2.5 µl PCRII 10× buffer (ABI)
2.5 µl 25 mM MgCl$_2$
2.5 µl 1.25 mM dNTP
1.25 µl 5 µM SK302_Probe_F
1.25 µl 5 µM SK302_Probe_R
2.5 µl 1:10,000 dil of Step 1 PCR
12.5 µl dH$_2$O
1.25 units amplitaq Gold (ABI)

TABLE 5

| PCR conditions | |
|---|---|
| Hold: | 94° C. 10 mins |
| Cycle Touch down in 0.5° C. decrements 14 cycles. | 94° C. 20 secs, 64° C. 30 sec 72° C. 30 sec. |
| Cycle 25 cycles | 94° C. 20 sec, 56° C. 30 sec 72° C. 30 sec |
| Hold | 72° C. 5 mins |
| Hold | 4° C. o/n |

STEP 3: Digestion With BsaI

The first digestion with BsaI cuts 1 base inward from the recognition site on the top strand, and 5 bases inward on the lower strand. This creates a molecule with a recessed 3' end and a protruding 5' end. The 5' end (G in the sequence GAA adjacent *) now has a phosphate group. The sequence is shown at SEQ ID NO: 58, where the asterisks indicate cut sites.

Procedure:
Clean up the PCR product on a Micro Biospin P-30 column (Bio-Rad).
Spin the column at 1000 g for 2 min.
Add 50 µl PCR product (approx 200 ng) and spin 1000 g 4 min.
Use 45 µl of eluate for BsaI digestion Add 5 ul NEB3 buffer and 3 µl BsaI (New England Biolabs)
Incubate at 50° C. for 2 hrs followed by 65° C. heat inactivation.

STEP 4: Dephosphorylation

The phosphate group on the 5' overhang of this molecule (G in the sequence GAA) is then cleaved with a phosphatase making it resistant to lambda exonuclease cleavage.

Add 3 µl Shrimp Alkaline Phosphatase (1 unit/ul United States Biochemical)
Incubate 37° C. for 60 min followed by heat inactivation at 80° C. 15 min STEP 5: Digestion With MlyI The molecule is then digested with the enzyme MlyI that cuts 5 bases inward from the recognition site, and generates a blunt-end molecule that has a phosphate group at the 5' end. The reaction was cleaned up as in Step 3 on the Micro Bio-Spin P-30 columns as described above:

To 45 µl of the eluate add 5 µl NEB buffer I and 3 µl MlyI (NEB).
Incubate at 37° C. for 60 min followed by heat inactivation for 15 min at 65° C.

After this step, the molecule has the sequence shown in SEQ ID NO: 58, with the portions 5' of the * and 3' of the ** (with reference to the top strand) removed.

STEP 6: Digestion with Lambda Exonuclease

This enzyme preferentially cleaves the phosphorylated strand, and generates the desired single-stranded molecule. The resulting sequence is the top strand of STEP 5.

To achieve this, we added 0.2 units Lambda Exonuclease (NEB) to the MlyI digested DNA. Incubate at 37° C. for 15 min followed by heat inactivation for 15 min at 80° C.

STEP 7: Phosphorylation of 5' End:

Use 10 μl of the exonuclease digested DNA, 5 μl T4DNA ligase buffer (NEB), 1 μl T4 Polynucleotide kinase. Incubate 37° C. 60 min followed by heat inactivation for 15 min at 65° C.

Example 5

Spacer Multiplex Amplification ReacTion (SMART) using the above ssDNA Probe

Dilute kinased probe to 10 fmole/μl. Use this as the stock. Make a fresh 1:200 dilution to make a 50 amol/μl working solution.

TABLE 6

| Hybridization of Probe to Target DNA | |
|---|---|
| Probe | 2 μl |
| Human Genomic DNA | 2 μl (500 ng) |
| Water | 3 μl |
| 10× Ampligase buffer (Epicenter Technologies) | 0.7 μl |
| Mix well by pipetting. | |

Hold at 95° C. for 5 mins.

Gradually decrease temperature by 1° C. decrements to 58° holding at 1 min at each temperature. Hold overnight at 58° C. The target DNA is TLR10 (toll like receptor) of human genomic DNA2. Extension of hybridized probe and ligation Place tubes on a cold metal block on ice.

After 2 mins add a 6.5 μl of a master mix containing 0.8 μl 10× Ampligase buffer 5 units Ampligase Epicenter)

0.5 units Stoffel fragment of Taq polymerase (Applied Biosystems)

5.2 μl dH2O

Incubate 58° C. for 2 mins.

Place on ice block

Add 1.5 μl of Cold dNTP mix (1.25 mM)

Mix well by pipetting.

Incubate 58° C. for 15 mins and hold at 37° C.

2. Exonuclease Digestion of Linear Probes/template:

Add 10 units Exonuclease I (Ecpicenter Technologies) and 10 units Exonuclease III (Ecpicenter Technologies). Incubate at 37° C. for 15 mins and heat inactivate at 80° C. for 15 mins.

3. PCR using Common Primers on Released Probes

5 μl PCRII 10× buffer (ABI)

5 μl 25 mM $MgCl_2$

5 μl 1.25 mM dNTP

5 μl 1 μM Amplification Primer 1

5 μl 1 μM Amplification Primer 2

5 μl 10 ng/μl extension and Ligation mix

20 μl $dH_2O$ 2 units amplitaq Gold (ABI)

PCR conditions

95° C. 10 min.

Cycle 40 times 94° C. 30 sec

63° C. 30 sec

72° C. 30 sec

72° C. 5 mins hold 4° C.

The PCR step described above is carried out after the probe made by exonuclease digestion (i.e. after STEP 7) is hybridized to a target sequence, e.g., human genomic DNA. The hybridized DNA is detected and amplified by the PCR reaction described immediately above. The target sequence that is amplified after extension from the annealed probe is shown below,

SEQ ID NO: 59

ATGACTTTGACACCATGCCTATCTGTGA*GGAAGCTGGCAACATGTCACA
CCTGGAAATCCTAGGTTTGAGTGGGGCAAAAATACAAAAATCAGATTTCC
AGAAAATTGCTCATCTGCATCTAAATACTGTCTTCTTAGGATTCAGAACT
CTTCCTCATTATGAAGAAGGTAGCCTGCCCATCTTAAACACAACAAAACT
GCACATTGTTTTACCAATGGACACAAATTTCTGGGTTCTTTTGCGTGATG
GAATCAAGACTTCAAAAATATTA***GAAATGACAAATATAGATGGCAAAAG
CCA**

In the above representation, the bold sequences can be seen to correspond to those underlined in SEQ ID NO: 58 (amplified sequence) and the remainder of the sequence is that which is filled in. The human DNA sequence is based on *Homo sapiens* toll-like receptor 10 (TLR10), transcript, which can be found in GenBank as, e.g. NM_001017388. In the sequences below, the target sequences are also shown in bold.

Example 6

Multiplex PCR Amplification

In this example, 3 different probes were mixed in the same tube to amplify products that are of three different lengths in the same tube. The present example includes three probes that bound to human genomic DNA. To prepare the probes we used 3 sets of primers. Each primer is identified with reference to the probe for which it is used, e.g. SK302-Probe_F is the forward primer for what will be the SK302 probe.

Probe 1—Extends 328 Bases

SK302_Probe_F:

SEQ ID NO: 56

GTACGAGGTCTCA*GAAATGACAAATATAGATGGCAAAAGCCATCCCTTT
AGTGAGGGTTAAT

It can be seen that the bolded bases of Probe F correspond to the bolded residues at the 3' end of SEQ ID NO: 59.

SK302_Probe_R: This sequence is given above as SEQ ID NO: 57. Probe SK302 is also disclosed in Step 2 of Example 4.

The Target genomic sequence is as given in Example 5, SEQ ID NO: 59.

Probe 2—Extends 244 Bases

SK298_Probe_F and SK298_Probe_R sequences are given in Example 4

Their target genomic sequence 2 is

```
                                          SEQ ID NO: 60
TTCTAGACATGCCCTTCATGTGATTCTTATG*AGAAAAAACCACCCAAAG

AATTCCTAGAAAGATTCAAATCACTTCTCCAAAAGGTATCTACCTTAAGT

TTCATTTGATTTTCTGCTTTATCTTTACCTATCCAGATTTGCTTCTTAGT

TACTCACGGTATACTATTTCCACAGATGATTCATCAGCATCTGTCCTCTA

GAACACACGGAAGTGAAGATTCCTGAGGATCTAACTTGCAGTTGGACACT

ATGTTACATACTCTAATATAGTAGTGAAAGTCATTTCTTTGTATTCCAAG

TGGAGGAGTACAATATATTAGCGATGGGAAAAAAAAACTCATAAGTGTGC

AAAGTCAGGA**TTATTTCCCCATAATCACTATACAATAGTCT
```

This target sequence is from the human IL21 gene

SK298_Probe_F bolded residues can be seen to be the reverse complement of the 5' end of Target genomic sequence 2 and can be visually matched at the asterisk. Similarly, for SK298_Probe_R, the bolded sequence can be found at the double asterisk in genomic sequence 2.

Probe 3 Extends 251 Bases

```
SK303_Probe_F:
                                          SEQ ID NO: 61
CATCGTGAGTCACTCG*TAGGCATGGTGTCAAAGTCATTAAAAGAAAGAC
TATAGTGTCACCTAAAT

SK303_Probe_R:
                                          SEQ ID NO: 62
GTACGAGGTCTCA**GAAATGACAAATATAGATGGCAAAAGCCAATTTCC
CTTTAGTGAGGGTTAAT
```

Target Genomic Sequence 3, also from TLR10

```
                                          SEQ ID NO: 63
TCTTTCTTTTAATGACTTTGACACCATGCCTA*TCTGTGAGGAAGCTGGC

AACATGTCACACCTGGAAATCCTAGGTTTGAGTGGGGCAAAAATACAAAA

ATCAGATTTCCAGAAAATTGCTCATCTGCATCTAAATACTGTCTTCTTAG

GATTCAGAACTCTTCCTCATTATGAAGAAGGTAGCCTGCCCATCTTAAAC

ACAACAAAACTGCACATTGTTTTACCAATGGACACAAATTTCTGGGTTCT

TTTGCGTGATGGAATCAAGACTTCAAAAATATTA**GAAATGACAAATAT

AGATGGCAAAAGCCAATT
```

These three sets of primers (SK302 Probe F, SK302 Probe R; SK298 Probe F, SK298 ProbeR; and SK303 ProbeF and SK303 ProbeR) were used in each of three PCR amplifications with the template used in STEP 2 of the example where we describe preparation of the double stranded PCR product prior to digestion with MlyI (Example 2). All subsequent steps were performed exactly as in the example. After the single-stranded probes were phosphorylated using T4 polynucleotide kinase, the three single stranded probes were then mixed together such that their final concentration was 100 attomoles/μl. 2 μl of the mixed probe set was used in the SMART reaction exactly as described in the example. After amplification using the common PCR primers, we were able to identify the 3 discrete products that were the result of the three extensions and circularization of the three probes.

This example demonstrates that we can perform a multiplex PCR using the SMART probes.

Example 7

Multiplex PCR Amplification using Over 500 Different Probes, which are Described in Accompanying CD We designed probes to amplify exons from human genomic DNA in a multiplex fashion. To achieve this goal, we identified targets in the introns adjacent to the exons. For each exon, we designed two targets, one on each side of the exon, in the flanking intronic sequence. The distance between the targets varied based on the size of the exon. To connect the two targets we made a spacer backbone (see FIG. 4) from lambda DNA that was common to all the probes. To construct each exon probe, we designed a pair of primers (FIG. 4, 61, 62) that amplified a double-stranded PCR product using the backbone template. One primer for each exon had a BsaI site, a target sequence for the exon, followed by a region of homology to the backbone DNA (shown by vertical stripes in FIG. 4). The other primer for the exon probe had an MlyI site, the second target exon, followed by the homology to the backbone. The double-stranded probes for each exon were then converted into single-stranded probes. It should be noted that exons are about 150 to 400 nt long, so that the probes must obtain such information (gap filling) for the sequencing purpose described here. That is, one will obtain on the order of $10^6$ amplified probes containing the exon sequence (30-40 PCR cycles), which is sufficient to determine the exon sequence in the gap. Another aspect of the present multiplex methodology is the high number of probes which can be amplified simultaneously, without artifacts. Aspects enabling this are the use of common amplification primers, and the use of a relatively low level of amplification primer (on the order of 100 attomoles).

Step 1. Preparation of the Backbone

The template used was Lambda DNA, shown at 64, FIG. 4, and at 30 in FIG. 2. Primers (52 and 54 in FIG. 3, 61, 62, FIG. 4) were prepared by the addition of Amplification 1 (AP1) and Amplification 2 (AP2) sequences to backbone from bacteriophage lambda. The Primer SK618 has Amplification primer 1 shown below in bold italics, and the primer SK619 has Amplification primer 2 shown in bold italics. The PCR reaction was performed in 50 mM Potassium Chloride, 10 mM Tris-HCl (pH8.5), 2.5 mM Magnesium Chloride, 2 units Amplitaq gold. The cycling conditions were 10 min heat inactivation at 950 C followed by 25 cycles of 94° C. for 30 sec, 63° C. for 30 sec, and 72° C. for 30 sec per cycle.

```
Primer 1 (SK618 has AP1)
                                          SEQ ID NO: 64
GGGGCGCGCCCTATAGTGTCACCTAAATTAATGTGACGATAGCTG

Primer 2 (SK619 has AP2seq)
                                          SEQ ID NO: 65
CCATCGATCCCTTTAGTGAGGGTTAATAGTACGCTTACTTCCGCG
```

The sequence after amplification (see FIG. 4B) is

SEQ ID NO: 66

*5'GGGGCGCGCCCTATAGTGTCACCTAAAT*TAATGTGACGATAGCTGAAAACTGTACG
ATAAACGGTACGCTGAGGGCGGAAAAAATCGTCGGGGACATTGTAAAGGCGGCGA
GCGCGGCTTTTCCGCGCCAGCGTGAAAGCAGTGTGGACTGGCCGTCAGGTACCCGTA
CTGTCACCGTGACCGATGACCATCCTTTTGATCGCCAGATAGTGGTGCTTCCGCTGA
CGTTTCGCGGAAGTAAGCGTACT*ATTAACCCTCACTAAAGGGATCGATGG*

For the convenience of the reader, three corresponding nucleotides are shaded to show correspondence between primer 2 and the amplified sequence.

Preparation of Single Stranded Probes

For each probe, two primers were used with this backbone as the template for a PCR reaction. One primer had a target sequence to genomic DNA with a BsaI adaptor, and the second primer had the target with a MlyI adaptor. These primers were used in a PCR reaction with the backbone DNA as template analogous to that shown in FIG. 4.

As an example:

Primer 292361_Bsa

SEQ ID NO: 67

GTACGAGGTCTCActgtaagccctgcaatttccccCCATCGATTCCCTTT
AG

Primer 292361_Mly

SEQ ID NO: 68

CATCGTGAGTCACTCGtcatggggtaagacgatcatagaGGGGCGCGCCC
TATAGTGT

The sequence of the double-stranded probe after amplification is shown below.

```
BsaI
                                               SEQ ID NO: 69
5' GTACGAGGTCTCA*ctgtaagccctgcaatttccccCCATCGATTCCCTTTAGGGTTAATA
CATGCTCCAGAGTGACAT*TCGGGACGTTAAAGGGGGGTAGCTAAGGGAAATCCCAATTAT

GTACGCTTACTTCCGCGAAACGTCAGCGGAAGCACCACTATCTGGCGATCAAAAGGATGG
CATGCGAATGAAGGCGCTTTGCAGTCGCCTTCGTGGTGATAGACCGCTAGTTTTCCTACC

TCATCGGTCACGGTGACAGTACGGGTACCTGACGGCCAGTCCACACTGCTTTCACGCTGG
AGTAGCCAGTGCCACTGTCATGCCCATGGACTGCCGGTCAGGTGTGACGAAAGTGCGACC

CGCGGAAAAGCCGCGCTCGCCGCCTTTACAATGTCCCCGACGATTTTTTCCGCCCTCAGC
GCGCCTTTTCGGCGCGAGCGGCGGAAATGTTACAGGGGCTGCTAAAAAAGGCGGGAGTCG

GTACCGTTTATCGTACAGTTTTCAGCTATCGTCACATTAATTTAGGTGACACTATAGGGC
CATGGCAAATAGCATGTCAAAAGTCGATAGCAGTGTAATTAAATCCACTGTGATATCCCG

GCGCCCCtctatgatcgtcttaccccatga**CGAGTGACTCACGATG 3'
CGCGGGGAGATACTAGCAGAATGGGGTACT**GCTCACTGAGTGCTAC MlyI
```

It will be apparent that the "tga" at the 3' end adjacent the ** corresponds to the reverse complement of the "tca" at the beginning of Primer 292361_Mly shown in bold. The target sequences that hybridize to genomic DNA are shown in lower case and underlined. The restriction cut sites for BsaI and MlyI are shown with an asterisk. As can be seen in the amplified sequence above, the final 5' end is bolded to the right of the *.

After the double-stranded probe was amplified, the PCR products were digested with 10 units of BsaI in NEB4 (New England Biolabs) at 50° C., followed by digestion with 3 units Shrimp Alkaline Phosphatase (United States Biochemicals) at 37° C. in the same buffer for 60 min. The reaction volume was increased to 100 μl, and the MlyI digestion was carried out in NEB buffer 4 at 37° C. using 20 units MlyI (New England Biolabs). 20 ul of this reaction was digested with 0.5 units of Lambda Exonuclease (NEB) at 37° C. for 10 mins. The reaction products were phosphorylated using 5 units of Polynucleotide Kinase in T4DNA ligase buffer (NEB).

Hybridization of Probes, Extension, Multiplex PCR 100 attomoles of each probe was hybridized to 500 ng of human genomic DNA in 7 μl of 1× ampligase buffer containing 20 mM tris-Hcl (pH8.3), 25 mM Kcl, and 10 mM magnesium chloride. The hybridization was carried out in a single tube in a thermal cycler by raising the temperature of the mix to 98° C. for 2 min, and gradually bringing the temperature to 58° C. by decreasing the temperature by 1° C. per minute. The reaction was held at 58° C. overnight. The extension reaction was carried out by adding 1.6 μl of 5×GC buffer (NEB) that was supplied with Phusion™ High-Fidelity DNA Polymerase, 100 nM dNTP, 0.4 units Phusion™ High-Fidelity DNA Polymerase (NEB), and 0.5 units ampligase (Epicenter). The reaction was incubated for 20 min at 58° C. and 10 min at 72° C. The excess probe and genomic DMA was digested with 1 unit Exonuclease I and 0.2 units Exonuclease III for 310 min at 37° C. followed by heat inactivation for 20 min at 80° C. The reaction volume was raised to 50 μl and the PCR reaction was carried out in 1×GC buffer (NEB), 200 mM dNTP, and 0.2 units Phusion™ High-Fidelity DNA Polymerase after addition of the two amplification primers AP1 and AP2. The reactions were cycled 40 times at 98° C. for 30 sec, 62° C. 30 sec, and 72° C. 30 sec per cycle.

Determining Success of Multiplex PCR 1.5 micrograms of the PCR products were digested with 0.04 units DnaseI (NEB) for 5 min. After a column cleanup on a Biorad P-30 chromatography column, the products were end-labeled with followed by end-labeling at 37° C. for 10 min with 1 nmole of Bio-N6-ddATP in 1× NEBuffer 4 (NEB) supplemented with 2.5 mM cobalt chloride using 1 unit Terminal Transferase (NEB).

The labeled products were hybridized to a DNA microarray chip containing tiling probes to all the exon targets under interrogation. Tiling probes are complementary to various subsequences within a DNA sequence set (here, the human genome). They are further described in European Patent EP1479782. The success of the multiplex PCR was determined by whether a sequence for each exon could be determined by analyzing the re-sequencing array.

TABLE 7

Success of multiplex PCR

| Size of | Percent GC 35-50% | | Percent GC >50% | | |
|---|---|---|---|---|---|
| amplicon(bp) | Success | Failures | Success | FAILURES | Total |
| 150-200 | 78 | 1 | 27 | 7 | 113 |
| 200-300 | 187 | 2 | 67 | 46 | 302 |
| 300-400 | 57 | 0 | 25 | 14 | 96 |
| 400-500 | 9 | 0 | 5 | 8 | 22 |
| Total | 331 | 3 | 124 | 75 | 533 |

The above results show that overall, 331 probes out of 533 were amplified in the multiplex reaction, as evidenced by sufficient quantity of probe to show a signal when the amplicon, containing the target sequence, was hybridized to a DNA microarray containing human gene sequences. If the probes are designed to contain less than 50% GC content in the amplicon and target and primer sequences, the failure rate is 3/331 or less than 1%.

purposes of exemplification of a large scale multiplex reaction with relatively large gaps filled in and amplified using the present SMART probes.

Conclusion: Other Embodiments

The present specific description is meant to exemplify and illustrate the invention and should in no way be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but would be understood by workers in the field Such patents or publications are hereby incorporated by reference to the same extent as if each was specifically and individually incorporated by reference for the purpose of describing and enabling the method or material referred to.

Alternative embodiments may be carried out, given the present teachings. For example, US PGPUB 2005/0053990 to Roberts et al., published Mar. 10, 2005 entitled "Cleavage of RNA by restriction endonucleases," hereby incorporated by reference, teaches that a number of restriction endonucleases have been shown to be capable of cleaving RNA in RNA/DNA duplexes although this property is not inherent in the universe of restriction endonucleases. It is taught there that restriction endonuclease cleavage of RNA/DNA duplexes have precise ends corresponding to the cleavage site of the restriction endonuclease. RNA is expected to be size limited only at the lower end of the range, typically 2-8 nucleotides longer than the length of the recognition sequence of the restriction enzyme. Given this teaching, one may prepare cDNA-RNA duplexes from RNA using reverse transcriptase and prepare ssDNA probes from cDNA according to the present teachings.

REFERENCES

1. Cho R J, Mindrinos M N, Richards D R, Sapolsky R J, Anderson M, Drenkard E, Dewdney J, Reuber T L, Stammers M, Federspiel N, Theologis A, Yang W H, Hubbell E, Lashkari D, Lemieux B, Dean C, Lipshutz R J, Ausubel F M, Davis R W and Oefner P J. Genome-Wide Mapping with Biallelic Markers in *Arabidopsis thaliana. Nature Genetics,* 1999, 23:203-207.

LENGTHY TABLES

The patent contains a lengthy table section. A copy of the table is available in electronic form from the USPTO web site (http://seqdata.uspto.gov/?pageRequest=docDetail&DocID=US07897747B2). An electronic copy of the table will also be available from the USPTO upon request and payment of the fee set forth in 37 CFR 1.19(b)(3).

A Lengthy Table is submitted herewith on CD describing all 500 probes, SEQ ID NOs 70-601. Each entry on the CD ROM is organized as follows: an arbitrary probe ID NO (e.g. 29190), SEQ ID NO; the size of the amplified sequence in bp (e.g. 235), including the target sequence, and the actual sequence filled in and amplified with the target sequences set off by slashes. These sequences represent human gene exon sequences obtained with the probes and are presented for 2. Crothers et al., Amplification of DNA to produce single-stranded product of defined sequence and length U.S. Pat. No. 6,815,167 (Nov. 9, 2004).

3. Hardenbol P, Baner J, Jain M, Nilsson M, Namsaraev E A, Karlin-Neumann G A, Fakhrai-Rad H, Ronaghi M, Willis T D, Landegren U, Davis R W. Multiplexed genotyping with sequence-tagged molecular inversion probes. *Nat. Biotechnol.* (2003) June; 21(6):673-8.

4. Higuchi, R and Ochman, H. Production of single-stranded DNA templates by exonuclease digestion following the polymerase chain reaction. *Nucleic Acids Research*, Vol 17, No. 14, 5865 (1989).
5. Landegren et al., Rolling circle replication of padlock probes U.S. Pat. No. 6,558,928 (May 6, 2003).
6. Landegren et al., Nucleic acid detecting reagent U.S. Pat. No. 6,235,472 (May 22, 2001).
7. Li M, Diehl F, Dressman D, Vogelstein B, Kinzler K. BEAMing up for detection and quantification of rare sequence variants. *Nature Methods* 3, 95-97 (2006).
8. Lizardi. Rolling Circle reporter Systems. U.S. Pat. No. 5,854,033. (1998).
9. Multiplex amplification enabled by selective circularization of large sets of genomic DNA fragments Fredrik Dahl, Mats Gullberg, Johan Stenberg, Ulf Landegren and Mats Nilsson *Nucleic Acids Research* (2005) 33(8):e71.
10. Nikiforov et al., U.S. Pat. No. 5,518,900 Method for generating single-stranded DNA molecules (May 1996).
11. Nilsson, M., et al., "Padlock Probes: Circularizing Oligonucleotides for Localized DNA Detection," *Science,* 285: 2085-2088 (1994).
12. Willis et al., Direct multiplex characterization of genomic DNA U.S. Pat. No. 6,858,412, (February 2005).

What is claimed is:

1. A polynucleic acid probe, having a defined sequence, for hybridization to a target polynucleic acid sequence, comprising the following sub-sequences:

(a) a first target sequence, at one end of the probe, complementary to a first target region of the target polynucleic acid, for specifically binding thereto;

(b) a second target sequence, at an opposite end of the probe, complementary to a second target region of the target polynucleic acid for specifically binding thereto, where said first and second target regions are separated on the target polynucleic acid, when hybridized thereto, by a gap of at least 250 nt of target sequence, said gap adapted to be filled by at least 250 nt of added gap filling nucleotides;

(c) at least one amplification primer site, on the probe, adjacent the target sequence, and connected to a spacer backbone sequence, for specifically binding a PCR primer, said primer oriented in a direction for amplification of target sequences and gap filling nucleotides only when nucleotides are joined to the target sequences as complementary to the target polynucleic acid and further oriented to not amplify the backbone sequence; and (d) said spacer backbone sequence, of at least 125 nt, chosen to be non-complementary to the target polynucleic acid, and being a random nucleic acid sequence having a length permitting a length of said gap of at least 250 nt, said spacer backbone sequence having a length of at least 50% of the length of said gap.

2. The probe of claim 1 wherein the polynucleic acid molecule is DNA.

3. The probe of claim 1 comprising two amplification primer sites, one adjacent the first target sequence and one adjacent the second target sequence, oriented towards each other for amplification of a sequence comprising a sequence complementary to the gap sequence.

4. The probe of claim 1 which has been circularized with at least 25 nt complementary to said target polynucleic acid.

5. The probe of claim 1 wherein the spacer backbone sequence is from a non-human organism and the target sequences hybridize to human genetic sequences.

6. The probe of claim 1 wherein the target sequences are sequences which hybridize, respectively, adjacent to a 5' end and adjacent to a 3' end of an exon of a eukaryotic gene.

7. The probe of claim 1 wherein the target sequences are separated on the target polynucleic acid by between 250 and 1000 nt.

8. A pre-probe for making a probe for hybridization to a target polynucleic acid sequence, comprising a polynucleic acid molecule comprising the following sequences:

(a) a first target sequence, at a 5' end of the probe, complementary to a first region of the target polynucleic acid, for specifically binding thereto, (b) a second target sequence, at a 3' end of the probe, complementary to a second region of target polynucleic acid for specifically binding thereto, said first and second regions of target polynucleic acid separated on the target polynucleic acid by a gap, said gap having a length of at least 250 nt, (c) at least one amplification primer site, adjacent a target sequence, and connected to a spacer backbone sequence, for specifically binding PCR primers, said primers oriented in a direction for amplification of target sequences only when nucleic acids are joined to the target sequences as complementary to the target polynucleic acid and further oriented to not amplify the spacer backbone sequence;

(d) said spacer backbone sequence being of at least 250 nt. wherein said backbone sequence is a random nucleic acid sequence chosen to be non-complementary to any target polynucleic acid, said spacer backbone sequence having a length of at least 50% of the length of said gap; and (e) restriction endonuclease recognition sites 5' of the desired 5' target sequence and 3' of the desired 3' target sequence, further defining cut sites at the desired final 5' nucleotide and desired final 3' nucleotide, said restriction endonuclease recognition sites being comprised in a sequence extending 5' of said desired final 5' nucleotide and in a sequence extending 3' of said desired final 3' nucleotide.

9. A method for preparing a single stranded DNA molecule according to claim 1, of defined sequence and length, having a predefined 5' end and 3' end, using a portion of a first strand of a double stranded precursor molecule, comprising the steps of:

(a) amplifying the double stranded precursor with primers containing a sequence homologous to the desired 5'and 3' ends, said primers further containing restriction enzyme cleavage sites to obtain an amplified double stranded molecule having cleavage sites at the desired 3' and 5' ends;

(b) cleaving the amplified double stranded molecule with a restriction enzyme which leaves a 5' overhang or blunt end on the first strand at the desired 5' end;

(c) removing a 5' terminal phosphate on the first strand;

(d) cleaving the amplified double stranded molecule at the desired 3' end to create a 3' blunt end or no 5' overhang; and (e) digesting the second strand to leave the single stranded DNA molecule of defined sequence and length.

10. The method of claim 9 wherein the cleaving is done with a type IIs restriction enzyme.

11. The method of claim 9 further comprising the steps of digesting with Bsal to generate a 5' overhang outside of BsaI's recognition site.

12. The method of claim 9 wherein multiple probes, having different sequences, are prepared using single cleaving, removing and digesting steps.

13. A collection of probes according to claim 1, wherein each probe comprises a different first and second target sequence, and similar amplification sites for simultaneous amplification of individual probes, each individual probe comprising two amplification sites.

14. The collection of probes of claim 13 wherein the probes are targeted to human genomic DNA.

15. The collection of probes of claim 13 comprising at least 500 probes.

16. A method for specifically detecting a target polynucleic acid sequence, comprising:

(a) hybridizing the target polynucleic acid sequence with a probe comprising the following sequences:

(i) a first target sequence, at one end of the probe, complementary to a first region of the target polynucleic acid, for specifically binding thereto, (ii) a second target sequence. at an opposite end of the probe, complementary to a second region of target polynucleic acid for specifically binding thereto, said first and second regions of target polynucleic acid separated on the target polynucleic acid by a gap, said gap having a length of at least 250 nt, (iii) at least one amplification primer site, adjacent the target sequence, and connected to a backbone sequence, for specifically binding PCR primers, said primers oriented in a direction for amplification of target sequences only when nucleic acids are joined to the target sequences as complementary to the target polynucleic acid and further oriented to not amplify the backbone sequence; and (iv) a backbone sequence which is at least 125 nt long to permit hybridization of the first target sequence and the second target sequence with said gap, said spacer backbone sequence being at least 50% of the length of said gap and wherein said spacer backbone sequence is a random nucleic acid sequence from a nonhuman organism and does not hybridize to target sequences;

(b) filling in said gap of at least 250 nt with gap filling nucleotides to form a circular probe; and (c) amplifying said circular probe without cleaving the probe using said amplification primer site, whereby amplification only occurs if said first target sequence and said second target sequence hybridize to the target polynucleotide, and said gap is filled.

* * * * *

UNITED STATES PATENT AND TRADEMARK OFFICE

CERTIFICATE OF CORRECTION

PATENT NO. : 7,897,747 B2
APPLICATION NO. : 11/805676
DATED : March 1, 2011
INVENTOR(S) : Mindrinos et al.

It is certified that error appears in the above-identified patent and that said Letters Patent is hereby corrected as shown below:

In the specification

Please replace Column 1, lines 12-16 with:

--STATEMENT OF GOVERNMENT SUPPORT

This invention was made with Government support under contracts GM062119 and HG000205 awarded by the National Institutes of Health. The Government has certain rights in the invention.--

Signed and Sealed this
Twelfth Day of July, 2016

Michelle K. Lee
*Director of the United States Patent and Trademark Office*

SEQUENCE LISTING

```
<160> NUMBER OF SEQ ID NOS: 607

<210> SEQ ID NO 1
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

cctcagc                                                                  7


<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

gaattc                                                                   6


<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 3

gccnnnnngg c                                                            11


<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

ctgaag                                                                   6


<210> SEQ ID NO 5
```

-continued

<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 5
cgannnnnnt gc 12

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 ggtctc 6

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, g, t, unknown or other

<400> SEQUENCE: 7
ggtctcnnnn nn 12

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, g, t, unknown or other

<400> SEQUENCE: 8
nnnnnnnnnn gagacc 16

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(14)
<223> OTHER INFORMATION: a, c, g, t, unknown or other

<400> SEQUENCE: 9
gagtcnnnnn nnnn 14

-continued

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(9)
<223> OTHER INFORMATION: a, c, g, t, unknown or other

<400> SEQUENCE: 10
nnnnnnnnnc actc 14

<210> SEQ ID NO 11
<211> LENGTH: 7
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11 cacctgc 7

<210> SEQ ID NO 12
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12 acctgc 6

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13 cagctc 6

<210> SEQ ID NO 14
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14 ggatc 5

<210> SEQ ID NO 15
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15

-continued gtctc 5

<210> SEQ ID NO 16
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16 gaagac 6

<210> SEQ ID NO 17
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17 gcagc 5

<210> SEQ ID NO 18
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18 gaagac 6

<210> SEQ ID NO 19
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19 acggc 5

<210> SEQ ID NO 20
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20 gaagac 6

<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21

-continued ggtctc 6

<210> SEQ ID NO 22
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22 cgtctc 6

<210> SEQ ID NO 23
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23 gggac 5

<210> SEQ ID NO 24
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24 cccgc 5

<210> SEQ ID NO 25
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25 ggatg 5

<210> SEQ ID NO 26
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26 gacgc 5

<210> SEQ ID NO 27
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27 gcatc 5

-continued

<210> SEQ ID NO 28
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28 gagtc 5

<210> SEQ ID NO 29
<211> LENGTH: 7
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29 gctcttc 7

<210> SEQ ID NO 30
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30 ctgaag 6

<210> SEQ ID NO 31
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31 ggtga 5

<210> SEQ ID NO 32
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32 gtatcc 6

<210> SEQ ID NO 33
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33 actggg 6

-continued

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34 ctggag 6

<210> SEQ ID NO 35
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35 gcaatg 6

<210> SEQ ID NO 36
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36 ggatg 5

<210> SEQ ID NO 37
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37 ctcag 5

<210> SEQ ID NO 38
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38 gaggag 6

<210> SEQ ID NO 39
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39 gcaatg 6

-continued

<210> SEQ ID NO 40
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40 ggatg 5

<210> SEQ ID NO 41
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41 ggcgga 6

<210> SEQ ID NO 42
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42 ctgaag 6

<210> SEQ ID NO 43
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43 ctgrag 6

<210> SEQ ID NO 44
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44 tccrac 6

<210> SEQ ID NO 45
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45 cccaca 6

<210> SEQ ID NO 46

-continued

<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46 atgaa 5

<210> SEQ ID NO 47
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47 caarca 6

<210> SEQ ID NO 48
<211> LENGTH: 298
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 48
ttgttttctc cgtcgccgta tccctttagt gagggttaat agtacgctta cttccgcgaa 60
acgtcagcgg aagcaccact atctggcgat caaaaggatg gtcatcggtc acggtgacag 120
tacgggtacc tgacggccag tccacactgc tttcacgctg gcgcggaaaa gccgcgctcg 180
ccgcctttac aatgtccccg acgatttttt ccgccctcag cgtaccgttt atcgtacagt 240
tttcagctat cgtcacatta tttaggtgac actatagcca caaatcaaga tccgaatt 298

<210> SEQ ID NO 49
<211> LENGTH: 298
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 49
ttgttttctc cgtcgccgta tccctttagt gagggttaat agtacgctta cttccgcgaa 60
acgtcagcgg aagcaccact atctggcgat caaaaggatg gtcatcggtc acggtgacag 120
tacgggtacc tgacggccag tccacactgc tttcacgctg gcgcggaaaa gccgcgctcg 180
ccgcctttac aatgtccccg acgatttttt ccgccctcag cgtaccgttt atcgtacagt 240
tttcagctat cgtcacatta tttaggtgac actatagcca caaatcaaga tccgaatt 298

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
catcgtgagt cactcgaatt cggatcttga tttgtgg 37

-continued

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
gtacgaggtc tcacttgttt tctccgtcgc cgta 34

<210> SEQ ID NO 52
<211> LENGTH: 326
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 52
gtacgaggtc tcattgtttt ctccgtcgcc gtatcccttt agtgagggtt aatagtacgc 60
ttacttccgc gaaacgtcag cggaagcacc actatctggc gatcaaaagg atggtcatcg 120
gtcacggtga cagtacgggt acctgacggc cagtccacac tgctttcacg ctggcgcgga 180
aaagccgcgc tcgccgcctt tacaatgtcc ccgacgattt tttccgccct cagcgtaccg 240
tttatcgtac agttttcagc tatcgtcaca ttatttaggt gacactatag ccacaaatca 300
agatccgaat tgagtgactc acgatg 326

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
tgtctatagt gtcacctaaa ttaatgtgac gatagctg 38

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
tgtcccttta gtgagggtta atagtacgct tacttccgcg 40

<210> SEQ ID NO 55
<211> LENGTH: 263
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 55
tgtctatagt gtcacctaaa ttaatgtgac gatagctgaa aactgtacga taaacggtac 60
gctgagggcg gaaaaaatcg tcggggacat tgtaaaggcg gcgagcgcgg cttttccgcg 120
ccagcgtgaa agcagtgtgg actggccgtc aggtacccgt actgtcaccg tgaccgatga 180

-continued ccatcctttt gatcgccaga tagtggtgct tccgctgacg tttcgcggaa gtaagcgtac 240
tattaaccct cactaaaggg aca 263

<210> SEQ ID NO 56
<211> LENGTH: 62
<212> TYPE: DNA
<213> ORGANISM: Artificial Sequence
<220> FEATURE:
<223> OTHER INFORMATION: Description of Artificial Sequence: Synthetic
probe

<400> SEQUENCE: 56
gtacgaggtc tcagaaatga caaatataga tggcaaaagc catcccttta gtgagggtta 60
at 62

<210> SEQ ID NO 57
<211> LENGTH: 62
<212> TYPE: DNA
<213> ORGANISM: Artificial Sequence
<220> FEATURE:
<223> OTHER INFORMATION: Description of Artificial Sequence: Synthetic
probe

<400> SEQUENCE: 57
catcgtgagt cactcgtcac agataggcat ggtgtcaaag tcatctatag tgtcacctaa 60
at 62

<210> SEQ ID NO 58
<211> LENGTH: 344
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 58
catcgtgagt cactcgtcac agataggcat ggtgtcaaag tcatctatag tgtcacctaa 60
attaatgtga cgatagctga aaactgtacg ataaacggta cgctgagggc ggaaaaaatc 120
gtcggggaca ttgtaaaggc ggcgagcgcg gcttttccgc gccagcgtga aagcagtgtg 180
gactggccgt caggtacccg tactgtcacc gtgaccgatg accatccttt tgatcgccag 240
atagtggtgc ttccgctgac gtttcgcgga agtaagcgta ctattaaccc tcactaaagg 300
gatggctttt gccatctata tttgtcattt ctgagacctc gtac 344

<210> SEQ ID NO 59
<211> LENGTH: 301
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 59
atgactttga caccatgcct atctgtgagg aagctggcaa catgtcacac ctggaaatcc 60
taggtttgag tggggcaaaa atacaaaaat cagatttcca gaaaattgct catctgcatc 120
taaatactgt cttcttagga ttcagaactc ttcctcatta tgaagaaggt agcctgccca 180
tcttaaacac aacaaaactg cacattgttt taccaatgga cacaaatttc tgggttcttt 240
tgcgtgatgg aatcaagact tcaaaaatat tagaaatgac aaatatagat ggcaaaagcc 300
a 301

<210> SEQ ID NO 60
<211> LENGTH: 390
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 60
ttctagacat gcccttcatg tgattcttat gagaaaaaac cacccaaaga attcctagaa 60
agattcaaat cacttctcca aaaggtatct accttaagtt tcatttgatt ttctgcttta 120
tctttaccta tccagatttg cttcttagtt actcacggta tactatttcc acagatgatt 180
catcagcatc tgtcctctag aacacacgga agtgaagatt cctgaggatc taacttgcag 240
ttggacacta tgttacatac tctaatatag tagtgaaagt catttctttg tattccaagt 300
ggaggagtac aatatattag cgatgggaaa aaaaaactca taagtgtgca aagtcaggat 360
tatttcccca taatcactat acaatagtct 390

<210> SEQ ID NO 61
<211> LENGTH: 66
<212> TYPE: DNA
<213> ORGANISM: Artificial Sequence
<220> FEATURE:
<223> OTHER INFORMATION: Description of Artificial Sequence: Synthetic probe

<400> SEQUENCE: 61
catcgtgagt cactcgtagg catggtgtca aagtcattaa aagaaagact atagtgtcac 60
ctaaat 66

<210> SEQ ID NO 62
<211> LENGTH: 65
<212> TYPE: DNA
<213> ORGANISM: Artificial Sequence
<220> FEATURE:
<223> OTHER INFORMATION: Description of Artificial Sequence: Synthetic probe

<400> SEQUENCE: 62
gtacgaggtc tcagaaatga caaatataga tggcaaaagc caatttccct ttagtgaggg 60
ttaat 65

<210> SEQ ID NO 63
<211> LENGTH: 315
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 63
tctttctttt aatgactttg acaccatgcc tatctgtgag gaagctggca acatgtcaca 60
cctggaaatc ctaggtttga gtggggcaaa aatacaaaaa tcagatttcc agaaaattgc 120
tcatctgcat ctaaatactg tcttcttagg attcagaact cttcctcatt atgaagaagg 180
tagcctgccc atcttaaaca caacaaaact gcacattgtt ttaccaatgg acacaaattt 240
ctgggttctt ttgcgtgatg gaatcaagac ttcaaaaata ttagaaatga caaatataga 300
tggcaaaagc caatt 315

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
ggggcgcgcc ctatagtgtc acctaaatta atgtgacgat agctg 45

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
ccatcgatcc ctttagtgag ggttaatagt acgcttactt ccgcg 45

<210> SEQ ID NO 66
<211> LENGTH: 275
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 66
ggggcgcgcc ctatagtgtc acctaaatta atgtgacgat agctgaaaac tgtacgataa 60
acggtacgct gagggcggaa aaaatcgtcg gggacattgt aaaggcggcg agcgcggctt 120
ttccgcgcca gcgtgaaagc agtgtggact ggccgtcagg tacccgtact gtcaccgtga 180
ccgatgacca tccttttgat cgccagatag tggtgcttcc gctgacgttt cgcggaagta 240
agcgtactat taaccctcac taaagggatc gatgg 275

<210> SEQ ID NO 67
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
gtacgaggtc tcactgtaag ccctgcaatt tccccccatc gattcccttt ag 52

<210> SEQ ID NO 68
<211> LENGTH: 58
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
catcgtgagt cactcgtcat ggggtaagac gatcatagag gggcgcgccc tatagtgt 58

<210> SEQ ID NO 69
<211> LENGTH: 346
<212> TYPE: DNA
<213> ORGANISM: Artificial Sequence
<220> FEATURE:

-continued

<223> OTHER INFORMATION: Description of Artificial Sequence: Synthetic
nucleotide construct

<400> SEQUENCE: 69
gtacgaggtc tcactgtaag ccctgcaatt tccccccatc gattcccttt agggttaata 60
gtacgcttac ttccgcgaaa cgtcagcgga agcaccacta tctggcgatc aaaaggatgg 120
tcatcggtca cggtgacagt acgggtacct gacggccagt ccacactgct ttcacgctgg 180
cgcggaaaag ccgcgctcgc cgcctttaca atgtccccga cgattttttc cgccctcagc 240
gtaccgttta tcgtacagtt ttcagctatc gtcacattaa tttaggtgac actatagggc 300
gcgcccctct atgatcgtct taccccatga cgagtgactc acgatg 346

<210> SEQ ID NO 70
<211> LENGTH: 235
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 70
atctttttgc aggtcatcat cagatttgaa atatttaaag tggatacaaa actatttcag 60
caatgcagac aattaagtgt gttgttgtgg gcgatggtgc tgttggtaaa acatgtctcc 120
tgatatccta cacaacaaac aaatttccat cggaatatgt accgactgta agtataaagg 180
cttccttctg ttagtaaaat gttgtaaaat ttgatatcct tttgaaaacg ctttc 235

<210> SEQ ID NO 71
<211> LENGTH: 287
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 71
aaaacgcttt ctctatgtgt actgaatttt tttctgttgt ctgcctttgt ttcctgtttt 60
taaagatctt gacttctcat gggtaaatta tatacacttt aaacagctga aaaatcagtg 120
gaaagtcaga aggggtgaca cagggtttgc aagaagtgct gggaggcaaa actccagtag 180
acaagattct aacgagtggt ggtctcaatt tggtgaagta tgccctacat cttggaatga 240
ggtgactttt tttttttttt ttttgatatt ttggccaatt attgatc 287

<210> SEQ ID NO 72
<211> LENGTH: 177
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 72
tttaactctc tccttgcaca ctaacagtgt tgtatttttt tgtttttagg tttttgacaa 60
ctatgcagtc acagttatga ttggtggaga accatatact cttggacttt ttgatactgc 120
aggtgaaaac ttaatgtctt ttatactgtt ttgatcttta acagttgcta gttgtct 177

<210> SEQ ID NO 73
<211> LENGTH: 209
<212> TYPE: DNA
<213> ORGANISM: Artificial Sequence -continued
<220> FEATURE:
<223> OTHER INFORMATION: Description of Artificial Sequence: Synthetic
nucleotide construct

<400> SEQUENCE: 73
tgaggacacc aagattcagt tgctgaattc tctccaatat ttttcttttt tctagggcaa 60
gaggattatg acagattacg accgctgagt tatccacaaa cagatgtatt tctagtctgt 120
ttttcagtgg tctctccatc ttcatttgaa aacgtgaaag aaaaggtaag ctgatcagat 180
actcttgccc taagaagatc atctcagaa 209

<210> SEQ ID NO 74
<211> LENGTH: 186
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 74
ctaatcctct aacctggctg ctattctctc tcctcccctc tgtcttgtag agaggtctga 60
agaatgtgtt tgatgaggct atcctagctg ccctcgagcc tccggaaact caacccaaaa 120
ggaagtgctg tatattctaa actgttttct ccttcccttc tttgctgctg cttcctgtcc 180
cactac 186

<210> SEQ ID NO 75
<211> LENGTH: 184
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 75
actgaaaatc agaccgccca ttttttcttt ctacccettt tcagaaaggc ctaaagaatg 60
tatttgacga agcaatattg gctgccctgg agcctccaga accgaagaag agccgcaggt 120
gtgtgctgct atgaacatct ctccagagcc ctttctgcac agctggtgtc ggcatcatac 180
taaa 184

<210> SEQ ID NO 76
<211> LENGTH: 425
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 76
cgattcctac cccctcgcct tccccggcg ccgacggcca caccgccgga cgatgcgcgc 60
ccgcggccgc ccgggaggct gagcccagct tcccgctccg ccttccccgc gcagctgccc 120
ccatggcttt gcggggcgcc gcgggagcga ccgacacccc ggtgtcctcg gccgggggag 180
cccccggcgg ctcagcgtcc tcgtcgtcca cctcctcggg cggctcggcc tcggcgggcg 240
cggggctgtg ggccgcgctc tatgactacg aggctcgcgg cgaggacgag ctgagcctgc 300
ggcgcggcca gctggtggag gtgctgtcgc aggacgccgc cgtgtcgggc gacgagggct 360
ggtgggcagg ccaggtgcag cggcgcctcg gcatcttccc cgccaactac gtggctccct 420
gccgc 425

-continued

<210> SEQ ID NO 77
<211> LENGTH: 278
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 77
ttgtgacaga aaaattaaaa gaatatgcaa atgtctcact tttgattttt ctttagtttt 60
gctacttgag aagatagaac atgatgacat ctgcaataaa actttgaaga ttacagattt 120
tgggttggcg agggaatggc acaggaccac caaaatgagc acagcaggca cctatgcctg 180
gatggccccc gaagtgatca agtcttcctt gttttctaag ggaagcgaca tctggaggtg 240
agcctttcct tttgcaaaca tcggcagaaa ctgcttgc 278

<210> SEQ ID NO 78
<211> LENGTH: 232
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 78
acactgttta gcccattgag catatgaaat ccttgctttc tagctatgga gtgctgctgt 60
gggaactgct caccggagaa gtcccctatc ggggcattga tggcctcgcc gtggcttatg 120
gggtagcagt caataaactc actttgccca ttccatccac ctgccctgag ccgtttgcca 180
agctcatgaa aggtattgtg tgtgtgtgtg tgtgtctttg tgggggcaag aa 232

<210> SEQ ID NO 79
<211> LENGTH: 285
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 79
tctaaactgc gttgagagat ggtattaatg tgatttttgt ttattttaga atgctggcaa 60
caagaccctc atattcgtcc atcgtttgcc ttaattctcg aacagttgac tgctattgaa 120
ggggcagtga tgactgagat gcctcaagaa tcttttcatt ccatgcaaga tgactggaaa 180
ctagaaattc aacaaatgtt tgatgagttg agaacaaagg aaaaggtgag agaaattttt 240
aaacagcata atgtactcaa atttatgaaa actatggaaa atatg 285

<210> SEQ ID NO 80
<211> LENGTH: 344
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 80
ccttcttcct gctgggaatg attccggtgg gtgtgaatct gtgtcgcagg agctgcgatc 60
ccgggaagag gagctgactc gggcggctct gcagcagaag tctcaggagg agctgctaaa 120
gcggcgtgag cagcagctgg cagagcgcga gatcgacgtg ctggagcggg aacttaacat 180
tctgatattc cagctaaacc aggagaagcc caaggtaaag aagaggaagg gcaagtttaa 240

-continued

```
gagaagtcgt ttaaagctca aagatggaca tcgaatcagt ttaccttcag gtatgatctt    300

gtttttatgt ttttgaaaga tttttgtgtg tcctcctttt aatc                     344
```

<210> SEQ ID NO 81
<211> LENGTH: 216
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 81

```
taaaggaaaa ccatgaaata ccagttctcc ctttttgcct ccaacagatt tccagcacaa     60

gataaccgtg caggcctctc ccaacttgga caaacggcgg agcctgaaca gcagcagttc    120

cagtcccccg agcagcccca caatgatgcc ccgactccga gccatacagt gtgagctttc    180

tgcactgcca cgggggctcc tgtgttgact tctctc                              216
```

<210> SEQ ID NO 82
<211> LENGTH: 252
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 82

```
atattggtta atatgattgt tgtggttaat atggttaata atgttctttt tagtgacttc     60

agatgaaagc aataaaactt ggggaaggaa cacagtcttt cgacaagaag aatttgagga    120

tgtaaaaagg aattttaaga aaaaaggttg tacctgggga ccaaattcca ttcaaatgaa    180

agatagaaca gattgcaaag aaaggtacgt gtgtggtatc tggtggtatt cattgtgtaa    240

tatgacaaat cc                                                        252
```

<210> SEQ ID NO 83
<211> LENGTH: 197
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 83

```
ctaattggtg tgttgtgtgc ttctatctta tgaaaagaaa cattttttctc ttgtaggata     60

agacctctct ccgatggcaa cagtccttgg tcaactatct taataaaaaa tcagaaaacc    120

atgcccttgg cttcattgtt tgtggaccag ccaggtaaat gtgtttcagg aggtaggatt    180

tgcttgagca gtccttg                                                   197
```

<210> SEQ ID NO 84
<211> LENGTH: 355
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 84

```
caatcttgtt taaatgactt ttgctgtaaa atgatactac agtgtatgta cttatacctt     60

tatttagggt cctgtgaaga gccaaaactt tcccctgatg gattagaaca cagaaaacca    120
```

-continued

```
aaacaaataa aattgcctag tcaggcctac attgatctac ctcttgggaa agatgctcag    180

agagagaatc ctgcagaagc tgaaagctgg gaggaggcag cctctgcgaa tgctgccaca    240

gtctccattg agatgactcc tacgaatagt ctgagtagat ccccccagag aaagaaaacg    300

gagtcagctc tgtatgggtg caccgtcctt ctggcatcgg tggctctggg actgg         355


<210> SEQ ID NO 85
<211> LENGTH: 336
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 85

tctttctcca caaagtgcct gctgcagatg gacagtgaag atccactggt ggacagtgca     60

cctgtcactt gtgactctga gatgctcact ccggattttt gtcccactgc cccaggaagt    120

ggtcgtgagc cagccctcat gccaagactt gacactgatt gtagtgtatc aagaaacttg    180

ccgtcttcct tcctacagca gacatgtggg aatgtacctt actgtgcttc ttcaaaacat    240

agaccgtcac atcacagacg gaccatgtct gatggaaatc cgaccccaag taggttgcat    300

taattaggta aaagcataaa acactgctgt agagat                              336


<210> SEQ ID NO 86
<211> LENGTH: 286
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 86

tttagaactc attttctttc taactgcata ctgttttggc tttctcaacc agctggtgca     60

actattatct cagccactgg agcctctgca ctgccactct gcccctcacc tgctcctcac    120

agtcatctgc caagggaggt ctcacccaag aagcacagca ctgtccacat cgtgcctcag    180

cgtcgccctg cctccctgag aagccgctca gatctgcctc aggcttaccc acagacagca    240

gtgtctcagc tggcacagac tgcctgtgta gtgggtcgcc caggac                   286


<210> SEQ ID NO 87
<211> LENGTH: 307
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 87

ctgcctcagg cttacccaca gacagcagtg tctcagctgg cacagactgc ctgtgtagtg     60

ggtcgcccag gaccacatcc cacccaattc ctcgctgcca aggagagaac taaatcccat    120

gtgccttcat tactggatgc tgacgtggaa ggtcagagca gggactacac tgtgccactg    180

tgcagaatga ggagcaaaac cagccggcca tctatatatg aactggagaa agaattcctg    240

tcttaaacta agtgccttac tgttgtttaa gcattttttt aaggtgaaca aatgaacaca    300

atgtatc                                                              307


<210> SEQ ID NO 88
<211> LENGTH: 224
<212> TYPE: DNA
```

-continued

<213> ORGANISM: Artificial Sequence
<220> FEATURE:
<223> OTHER INFORMATION: Description of Artificial Sequence: Synthetic
      nucleotide construct

<400> SEQUENCE: 88
tacaaaaatt accacttgta ctagtatgcc ttaagaaaaa agtacaaatt gtatttacat 60
aattacacac tttgtctttg acttcttttt cttcttttta ccatctttgc tcatcttttc 120
tttatgtttt cgaatttctc gaactaatgt atagaaggca tcatcaacac cctgaaatac 180
ataaaaagta ttaaaatgtg aatatatacg atggcttcat gtgt 224

<210> SEQ ID NO 89
<211> LENGTH: 225
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 89
aaaagacatc tgctttctgc caaaattaat gtgctgaact taaacttacc agattacatt 60
ataatgcatt ttttaatttt cacacagcca ggagtctttt cttctttgct gatttttttc 120
aatctgtatt gtcggatctc cctcaccaat gtataaaaag catcctccac tctctgcatt 180
gtaaaacaca acttctttaa agtctgttgc attggtaaga gtaat 225

<210> SEQ ID NO 90
<211> LENGTH: 356
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 90
gccctctcaa gagacaaaaa catttactaa atattgtttt atttcctagt atagcataat 60
tgagagaaaa actgatatat taaatgacat aacagttatg attttgcaga aaacagatct 120
gtatttattt cagtgttact tacctgtctt gtctttgctg atgtttcaat aaaaggaatt 180
ccataacttc ttgctaagtc ctgagcctgt tttgtgtcta ctgttctaga aggcaaatca 240
catttatttc ctactaggac cataggtaca tcttcagagt ccttaactct tttaatttgt 300
tctctgggaa agaaaaaaaa gttatagcac agtcattagt aacacaaata tctttc 356

<210> SEQ ID NO 91
<211> LENGTH: 231
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 91
caaagaatgg tcctgcacca gtaatatgca tattaaaaca agatttacct ctattgttgg 60
atcatattcg tccacaaaat gattctgaat tagctgtatc gtcaaggcac tcttgcctac 120
gccaccagct ccaactacca caagtttata ttcagtcatt ttcagcaggc cttataataa 180
aaataatgaa aatgtgacta tattagaaca tgtcacacat aaggttaata c 231

<210> SEQ ID NO 92
<211> LENGTH: 225

-continued

<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 92
ccttctgcag ggttcccagg cccccgctcc agggccgggc tgacccgact cgctggcgct 60
tcatggagaa cttccaaaag gtggaaaaga tcggagaggg cacgtacgga gttgtgtaca 120
aagccagaaa caagttgacg ggagaggtgg tggcgcttaa gaaaatccgc ctggacacgt 180
gagtggcctc tgtacccggg actcctaact ggggacctcc ttgat 225

<210> SEQ ID NO 93
<211> LENGTH: 405
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 93
ggaatatttg taaccatatt cccatctctg ctttcccaac ctctccaagt gagactgagg 60
gtgtgcccag tactgccatc cgagagatct ctctgcttaa ggagcttaac catcctaata 120
ttgtcaagta agtatgcgtc tgagaggtga tccagctgga aaggaggata agttctgtct 180
gtacagtgtg ggcatttctc tctctcacac acctccattt cctcaaactt tccttctcta 240
ggctgctgga tgtcattcac acagaaaata aactctacct ggtttttgaa tttctgcacc 300
aagatctcaa gaaattcatg gatgcctctg ctctcactgg cattcctctt cccctcatca 360
aggtaatgct tctcatcagc tcctctcatc atgggcatgt cttgg 405

<210> SEQ ID NO 94
<211> LENGTH: 266
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 94
gtctgctcac tgtaatggag aaacacagtc ctctctttct cctttgtcag agctatctgt 60
tccagctgct ccagggccta gctttctgcc attctcatcg ggtcctccac cgagacctta 120
aacctcagaa tctgcttatt aacacagagg gggccatcaa gctagcagac tttggactag 180
ccagagcttt tggagtccct gttcgtactt acacccatga ggtgagtccc tttatgtctt 240
ttttctctga gcttcccaag aggtgt 266

<210> SEQ ID NO 95
<211> LENGTH: 205
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 95
ccatacccta taaaccaccc cgcccctccc tattcccgtc cctcaggtgg tgaccctgtg 60
gtaccgagct cctgaaatcc tcctgggctg caaatattat tccacagctg tggacatctg 120
gagcctgggc tgcatctttg ctgagatggt atggaggctt gcccaagttc cacccagccc 180

-continued cctccctctc ctccccacat ccaag 205

<210> SEQ ID NO 96
<211> LENGTH: 294
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 96
gactgacgtc aacgtgggtc ttggtatttc ctctttcccc attttcaggt gactcgccgg 60
gccctattcc ctggagattc tgagattgac cagctcttcc ggatctttcg gactctgggg 120
accccagatg aggtggtgtg gccaggagtt acttctatgc ctgattacaa gccaagtttc 180
cccaagtggg cccggcaaga ttttagtaaa gttgtacctc ccctggatga agatggacgg 240
agcttgttat cggtgagagt gggcacctgt tttccctcat tcatttctcc cagg 294

<210> SEQ ID NO 97
<211> LENGTH: 205
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 97
gctgcccatt tagtccacta tcacatcatt gaagtcaaca tgcatctctc cctctagcaa 60
atgctgcact acgaccctaa caagcggatt tcggccaagg cagccctggc tcaccctttc 120
ttccaggatg tgaccaagcc agtaccccat cttcgactct gatagccttc ttgaagcccc 180
cagccctaat ctcaccctct cctcc 205

<210> SEQ ID NO 98
<211> LENGTH: 244
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 98
tgagaatttg tgtccagccc tcagccactc ttccctctgc tttgaacagt gtgtcctggg 60
actctgaatg gcctgagtgt gaccggcgat gctgagaacc aataccagac actgtacaag 120
ctctacgaga ggtgtgaggt ggtgatgggg aaccttgaga ttgtgctcac gggacacaat 180
gccgacctct ccttcctgca ggttagtgag cccaccctcc ttcctcaacc tgctcctctt 240
tatt 244

<210> SEQ ID NO 99
<211> LENGTH: 276
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 99
attattttgc cctgttgtct ctctcattta cataatctgc tctgtcacag tggattcgag 60
aagtgacagg ctatgtcctc gtggccatga atgaattctc tactctacca ttgcccaacc 120
tccgcgtggt gcgagggacc caggtctacg atgggaagtt tgccatcttc gtcatgttga 180

-continued actataacac caactccagc cacgctctgc gccagctccg cttgactcag ctcaccggtc 240
agttcccgat ggttccttct ggcctcaccc ctcagc 276

<210> SEQ ID NO 100
<211> LENGTH: 236
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 100
atgggtggag aggtaaggaa gaggcgttcc gctgcggccc ttaaccctgt cacttctttc 60
cctacctcag agattctgtc agggggtgtt tatattgaga agaacgataa gctttgtcac 120
atggacacaa ttgactggag ggacatcgtg agggaccgag atgctgagat agtggtgaag 180
gacaatggca gaagctgtaa gtggccgtga tcaagattgc tccccagtcc caccaa 236

<210> SEQ ID NO 101
<211> LENGTH: 165
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 101
caagcctttc ttagccctga tggccccttg tgttgccttc cttcccaacc aggtcccccc 60
tgtcatgagg tttgcaaggg gcgatgctgg ggtcctggat cagaagactg ccagacatgt 120
gggtttgaaa ttccctccaa aaacttcact catacgcttt catat 165

<210> SEQ ID NO 102
<211> LENGTH: 206
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 102
cagtcctagg agccctaaca gccatgcttt ctctccttcc atagtgacca agaccatctg 60
tgctcctcag tgtaatggtc actgctttgg gcccaacccc aaccagtgct gccatgatga 120
gtgtgccggg ggctgctcag gccctcagga cacagactgc tttgtatgta ccctttccat 180
tgcctgggtt ctgaaattgg gatgtg 206

<210> SEQ ID NO 103
<211> LENGTH: 265
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 103
ggaggaggta ggggtacaca cgtaacataa atctgatgag cctccttttt tcccaggcct 60
gccggcactt caatgacagt ggagcctgtg tacctcgctg tccacagcct cttgtctaca 120
acaagctaac tttccagctg gaacccaatc cccacaccaa gtatcagtat ggaggagttt 180
gtgtagccag ctgtccccgt aagtgtctga ggggaaggaa caatgatcaa caatagtaga 240

-continued

```
tccaagattt tagacaaaat tgtgg                                         265


<210> SEQ ID NO 104
<211> LENGTH: 412
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 104

gatgttcctc cctcatctct aatggtgtcc tcctcctctt ccctagataa ctttgtggtg     60

gatcaaacat cctgtgtcag ggcctgtcct cctgacaaga tggaagtaga taaaaatggg    120

ctcaagatgt gtgagccttg tgggggacta tgtcccaaag gtgggtagga gatggtaaga    180

agttgtaaag agacagcctt tcctctgagc ctgcgcagac cacccccact gaacctctct    240

tacatttgca gcctgtgagg gaacaggctc tgggagccgc ttccagactg tggactcgag    300

caacattgat ggatttgtga actgcaccaa gatcctgggc aacctggact ttctgatcac    360

cggcctcaat gggttagaga tcctgccttc cctccttaga ccccagccca cg            412


<210> SEQ ID NO 105
<211> LENGTH: 433
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 105

gctcattgcc attgagttat acctttacct tattgactgg tttctactgt tctattcaga     60

gacccctggc acaagatccc tgccctggac ccagagaagc tcaatgtctt ccggacagta    120

cgggagatca caggtgagtg gcagagagtt tgccctttct agaagaatag gtgaaccact    180

ggcataaatt gcggtataac tacttgagaa aatcacgtcc caagttatag gggaggagcc    240

aggagaaccc aagaaagaag aaggctccct gcccatatgc ctctctccaa cccctcaggt    300

tacctgaaca tccagtcctg gccgccccac atgcacaact tcagtgtttt ttccaatttg    360

acaaccattg gaggcagaag cctctacaag tgagtaaagg gtatggagga aatggcatct    420

tcaggcaatg aag                                                       433


<210> SEQ ID NO 106
<211> LENGTH: 256
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 106

gaagagaggg cttgctggga gtcctcagac tcctctccta acccacccct tcctttccag     60

tggcagaggg caaagtgtgt gacccactgt gctcctctgg gggatgctgg ggcccaggcc    120

ctggtcagtg cttgtcctgt cgaaattata gccgaggagg tgtctgtgtg acccactgca    180

actttctgaa tgggtacagt aaggggagcc agtcaaggat gggtgggggt ggggccctgc    240

aatggaactg ttcagg                                                    256


<210> SEQ ID NO 107
<211> LENGTH: 183
<212> TYPE: DNA
```

-continued

<213> ORGANISM: Artificial Sequence
<220> FEATURE:
<223> OTHER INFORMATION: Description of Artificial Sequence: Synthetic
nucleotide construct

<400> SEQUENCE: 107
ggtcaggact tggaagtgac cccccctcc ctttattccc cactacaggg agcctcgaga 60
atttgcccat gaggccgaat gcttctcctg ccacccggaa tgccaaccca tggagggcac 120
tgccacatgc aatggctcgg tatactagta gcaccaggat ctccaaggga gacagagaag 180
ggg 183

<210> SEQ ID NO 108
<211> LENGTH: 245
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 108
gaattgacct tgggatctga ttcttcctga ccttctctct tccactcagg gctctgatac 60
ttgtgctcaa tgtgcccatt ttcgagatgg gccccactgt gtgagcagct gcccccatgg 120
agtcctaggt gccaagggcc caatctacaa gtacccagat gttcagaatg aatgtcggcc 180
ctgccatgag aactgcaccc aggggtcagt gatgggataa taaggagagg gggtcaggtg 240
gaagg 245

<210> SEQ ID NO 109
<211> LENGTH: 165
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 109
gcctctgctg tccaagctct catttaaggt ggtgactttc ttccctaggt gtaaaggacc 60
agagcttcaa gactgtttag gacaaacact ggtgctgatc gggtatgatg gggttggaga 120
ttctggaaac tggggatatt tgggagttgg gagagaggtg gttac 165

<210> SEQ ID NO 110
<211> LENGTH: 244
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 110
agatgcaaac ccaggataat gttgggtttc tatatatccc atagcaaaac ccatctgaca 60
atggctttga cagtgatagc aggattggta gtgattttca tgatgctggg cggcactttt 120
ctctactggc gtgggcgccg gattcagaat aaaagggcta tgaggcgata cttggaacgg 180
ggtgaggtga gtacttagct tacttttgtt ttttcttttc tttttttgca tgtcctggaa 240
gtct 244

<210> SEQ ID NO 111
<211> LENGTH: 205
<212> TYPE: DNA
<213> ORGANISM: Artificial Sequence -continued
<220> FEATURE:
<223> OTHER INFORMATION: Description of Artificial Sequence: Synthetic
      nucleotide construct

<400> SEQUENCE: 111
gggaatggcc tttcctgagt aactccttcc catttgctcc tcagagcata gagcctctgg     60
accccagtga gaaggctaac aaagtcttgg ccagaatctt caaagagaca gagctaagga    120
agcttaaagt gcttggctcg ggtgtctttg gaactgtgca caaagtgagt gacccatagg    180
aattctggag aggtggggaa ggcat                                          205

<210> SEQ ID NO 112
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 112
ctagggagaa tgaccttatg ccaactcctg ccccaaactt cccagggagt gtggatccct     60
gagggtgaat caatcaagat tccagtctgc attaaagtca ttgaggacaa gagtggacgg    120
cagagttttc aagctgtgac agatgtaagt gaaggaaatt ctgtatgccg ctaggagaga    180
ggacaa                                                               186

<210> SEQ ID NO 113
<211> LENGTH: 284
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 113
gtatgtgaac ctgttggttt cctagataat accttttgtg tctcttagca tatgctggcc     60
attggcagcc tggaccatgc ccacattgta aggctgctgg gactatgccc agggtcatct    120
ctgcagcttg tcactcaata tttgcctctg ggttctctgc tggatcatgt gagacaacac    180
cggggggcac tggggccaca gctgctgctc aactggggag tacaaattgc caaggtgaga    240
gaagcctgga ggaattctgt gataagaact gcttgtctgg gggc                     284

<210> SEQ ID NO 114
<211> LENGTH: 250
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 114
actgattccc ccaaccttaa gaatactttc ttcccctata cctacaggga atgtactacc     60
ttgaggaaca tggtatggtg catagaaacc tggctgcccg aaacgtgcta ctcaagtcac    120
ccagtcaggt tcaggtggca gattttggtg tggctgacct gctgcctcct gatgataagc    180
agctgctata cagtgaggcc aaggtgagga gacacaaagg gtaaggaggc gggggtggag    240
tgaagcatgg                                                           250

<210> SEQ ID NO 115
<211> LENGTH: 170
<212> TYPE: DNA

-continued

<213> ORGANISM: Artificial Sequence
<220> FEATURE:
<223> OTHER INFORMATION: Description of Artificial Sequence: Synthetic
nucleotide construct

<400> SEQUENCE: 115
ctaagaaaat ttgtggaaat aaacttgtga tacctctatc tttaatccgc agactccaat 60
taagtggatg gcccttgaga gtatccactt tgggaaatac acacaccaga gtgatgtctg 120
gagctatggt cagtgcatct ggatgccctc tctaccatca ctggccccag 170

<210> SEQ ID NO 116
<211> LENGTH: 194
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 116
ccatggaatg tattctcttt tatgtctcta cctcctacat cttatctcca ggttggatga 60
ttgatgagaa cattcgccca acctttaaag aactagccaa tgagttcacc aggatggccc 120
gagacccacc acggtatctg gtcataaagg tgagtaggga gtaggaggtg ctaaggaaat 180
ttagaaaaag gagg 194

<210> SEQ ID NO 117
<211> LENGTH: 245
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 117
ctatcgatat agagagagag tgggcctgga atagcccctg ggccagagcc ccatggtctg 60
acaaacaaga agctagagga agtagagctg gagccagaac tagacctaga cctagacttg 120
gaagcagagg aggacaacct ggcaaccacc acactgggct ccgccctcag cctaccagtt 180
ggaacactta atcggccacg tggggtaaga caacttctaa ttacccaaca ctttgcaccc 240
tgagc 245

<210> SEQ ID NO 118
<211> LENGTH: 162
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 118
gtagatttct cccttcatct taaccttttc cttatttttt catcctagag ccagagcctt 60
ttaagtccat catctggata catgcccatg aaccagggta atcttgggga gtcttgccag 120
gtaagttctg ttgctgagag gctgggtttt aggatcagat tg 162

<210> SEQ ID NO 119
<211> LENGTH: 425
<212> TYPE: DNA
<213> ORGANISM: Artificial Sequence
<220> FEATURE:
<223> OTHER INFORMATION: Description of Artificial Sequence: Synthetic
nucleotide construct -continued

<400> SEQUENCE: 119
taaacaaatc tctcttcttt cctcatcatg taaatttcct tgcattattt tctgtttatt 60
ttcttcctta ggagtctgca gtttctggga gcagtgaacg gtgcccccgt ccagtctctc 120
tacacccaat gccacgggga tgcctggcat cagagtcatc agaggggcat gtaacaggct 180
ctgaggctga gctccaggag aaagtgtcaa tgtgtaggag ccggagcagg agccggagcc 240
cacggccacg cggagatagc gcctaccatt cccagcgcca cagtctgctg actcctgtta 300
ccccactctc cccacccggg ttagaggaag aggatgtcaa cggttatgtc atgccagata 360
cacacctcaa aggtgcctga ctcttcctag ggctttcctc aatttttcct cgaattcttt 420
ccccg 425

<210> SEQ ID NO 120
<211> LENGTH: 356
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 120
ctaccctcat gaagttcttc acatacctag cctttcttct caaccccccag gtactccctc 60 ctcccgggaa ggcacccttt cttcagtggg tctcagttct gtcctgggta ctgaagaaga 120
agatgaagat gaggagtatg aatacatgaa ccggaggaga aggcacagtc cacctcatcc 180
ccctaggcca agttcccttg aggagctggg ttatgagtac atggatgtgg ggtcagacct 240
cagtgcctct ctgggcagca cacagagttg cccactccac cctgtaccca tcatgcccac 300
tgcaggcaca actccagatg aagactatga atatatgaat cggcaacgag atggag 356

<210> SEQ ID NO 121
<211> LENGTH: 344
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 121
ctccaccctg tacccatcat gcccactgca ggcacaactc cagatgaaga ctatgaatat 60
atgaatcggc aacgagatgg aggtggtcct gggggtgatt atgcagccat gggggcctgc 120
ccagcatctg agcaagggta tgaagagatg agagcttttc aggggcctgg acatcaggcc 180
ccccatgtcc attatgcccg cctaaaaact ctacgtagct tagaggctac agactctgcc 240
tttgataacc ctgattactg gcatagcagg cttttcccca aggctaatgc ccagagaacg 300
taactcctgc tccctgtggc actcagggag catttaatgg cagc 344

<210> SEQ ID NO 122
<211> LENGTH: 186
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 122
agaagggaaa tggcagcttt tcttccttcc atggcagcca ctccattgct cactccggat 60
taccttcatc cttatgtaga taagagtgct gcagagctcg aaaggcagag attcgcttgt 120

-continued

```
gtgggttaaa agtcagcatt tcctgagggg agaggcaaag gtcagaaaac catgaagaaa    180

acagac                                                               186


<210> SEQ ID NO 123
<211> LENGTH: 417
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 123

ttccccagtc tctatttctt tccctgtgcc cacagccatc tccagtacca gcagcagctg     60

tgctcccgac tcctccatct caggtaccac cgactgcact gggcggggcc ctctgggggg    120

aaaggctcca cggggcaggg atacatctcg aggccagtca tcctctggag gcagcccaat    180

caggctgtgg gggacaggag aactctggtc aggagggtcc tccagttccc atccccatgg    240

gcagagccag ttgccatcct gggttcagca gaaagaggac tcagaataga aaatcttttt    300

ctcccatgtt ggtcacttac tcaaagattt tgcccaactg gtcggcttca gagtttccac    360

agaagagagg cctaaggtga gaagggatat aaggtagcag tcattttcaa agatatc       417


<210> SEQ ID NO 124
<211> LENGTH: 223
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 124

aagcgatttg gggaattcaa ggtagtccag ggtatgtggg tcccatactt tcgacgaaac     60

atctctgcaa agatacagcc aacactccac atgtccacag gtgttgcata tgtggactgc    120

agaagaactt cgggagctcg gtaccagagt gtaacaacct aaagggaata ggaagaatgg    180

atggggaccc catgggttac catgaaacac aacttgcttg act                      223


<210> SEQ ID NO 125
<211> LENGTH: 263
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 125

ctcctactcc caaccagaac ccattttggt accatctttc tactgaccac gggtgtaagt     60

gccatctggt agctgtagat tctggccagg ccaaagtcag ccagcttgac tgttccacca    120

cttgtcacca gaatgttctc tggcttcaga tctcggtgaa cgatgcaatt ggcatgaagg    180

aaatctaggc ctcttagaaa ctggcgcatc agatcctagt ttcaaagggg aggtacagat    240

gcactggaaa ctaggcacca tac                                            263


<210> SEQ ID NO 126
<211> LENGTH: 225
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 126
```

-continued

```
acaaaggtcc caatccacct ctcaatgcct accaacccca ctcaccttga tcgtttcggc     60

tggcaagcct ggtgggggtg ccttgtccag atatgtcctt aggtcctggt ctacatgctc    120

aaacaccagg gttaccttga tctcccggtc agttcgggat gtggcacaga cgtccatcag    180

cctgaccaga gtaaatgctc acttttcaat cccctttaac ccaac                    225
```

<210> SEQ ID NO 127
<211> LENGTH: 346
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 127

```
gtttcctggg ggtataaata cacatgtgct tctagaaata aggcttcgtg tcaaactcta     60

gatgggtggg gtggagtaca ggaccaccga gttgtagtct gggggcgggg agcagcacgc    120

gattttcctt tccagctcag cgtggtcgta ggtgaacctg cgcttgcctt cgctgacgtg    180

cccacagctg gaatggcaga aactgggcct gctgacatca gacagccccg actccttact    240

tttactggtt actctcaagc taaagaaaga aaggaaagaa atcaaatatt caaaattggt    300

tttttagaaa acaaagacac taaaatctac tctttctgag tgggtc                   346
```

<210> SEQ ID NO 128
<211> LENGTH: 183
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 128

```
tacccctcca tcaactgatc acagaaaaga tacccaattc ttactcaatc ttgagcgagg     60

ccttgggttt gctgtcagtc caggtgaagc gcttcagcat gggagaggcc aacagagtgc    120

tgctgtcgcc ctggtagtcc tagggggaga aggagaaagg ttatactctt gcctggccca    180

gcg                                                                  183
```

<210> SEQ ID NO 129
<211> LENGTH: 175
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 129

```
gggtctatcg gggtgcacta ggtaccttaa cttcacgact tacatcaaac atggaggtgg     60

cattcggtaa aagttcttca aaggttttga ttctttccag gctcatgaac ttgaaagcat    120

ttacgtatct aatgaagaaa cagaaagaat tatcaagaca ggaaaaggca tccag         175
```

<210> SEQ ID NO 130
<211> LENGTH: 236
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 130

-continued

```
cttttttttg ttggaaaatt ctgtgatata aagtttgaga aagaaatctt acctgacatc     60

atcagagctt cctgaattaa acttcggagc tgaaatactt tccttgaaga agtcctcaga    120

gaaggcagga gttgagtatg taaacccact atttcctgtc agtatggcat tgattgggat    180

gtagtcttta ccatcctaaa ataccaaagg tagagctctc gttgcaccaa ttctga        236


<210> SEQ ID NO 131
<211> LENGTH: 204
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 131

gccccccctga cgtacattca aaggcatttt gatgtaaata aatttagttt tacctgttgt     60

acatttgctt gaagcaaatc acctagtttt tccacaagtt ctgcaaatct tggcctttct    120

tttgggtctc tgtgccagca gtccagcatg atctgatagc tggtggggaa aacagcaaca    180

gaaatagttg gagagcagtg atca                                           204


<210> SEQ ID NO 132
<211> LENGTH: 195
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 132

gaaaagcgag ctgtcagatg gggagcagag ggcaccaagg gctcacattt caggagtaga     60

gtactcagga gctctcatcc tcatgccttc cctcaggcga ctgcaaaagt cctcatccat    120

ttgtactcct gggtatggag acccacctgc gggagacaat gtggaaaaca cagggcctgt    180

tatggcttaa gggta                                                     195


<210> SEQ ID NO 133
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 133

agacatttat ttctgggctg tttgatttct tccttctccc aaatttacct aaggagaaga     60

tttcccacag caatactccg taagaccaca cgtcgctctt ggtgctgtag attttgtcaa    120

agatagattc aggagccatc catttcagag gaagtcgagt ctagaagagg gcaagggggc    180

cttgagcaga agggcatgaa aacaaag                                        207


<210> SEQ ID NO 134
<211> LENGTH: 197
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 134

ccagccctgg cagagaagaa aaacagtaaa cagcaagact gacctttctg gaagacagga     60

actccatgcc tctggccact tgaaaactgt aagaaatcag atcttccata gtgatgggct    120
```

-continued ccttgtagaa accgtcagaa tctggaaagc attagaaccg taactgtttg taatggctct 180
tgttatccca ccaaatc 197

<210> SEQ ID NO 135
<211> LENGTH: 243
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 135
gtaaaaatat ctcagcgcgt aggacaggaa ggaattaata cctaccctcc tcttcctcaa 60
catcactcag acttttatct tcctgaaagc cggagctcgc aaagctttcg ctgctggtga 120
cgctatctag tcttggtttc ttgccttgtt ccaggcctgg ctccattttt tctttcttag 180
gctccatgtg tagtgctgca tcctttgaag agaccgaaaa ggacccaggt gaaaaggagc 240
tcc 243

<210> SEQ ID NO 136
<211> LENGTH: 184
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 136
aaatgaaaac tcattgctat ctttaaaaac ctccaacttt tgaaatcctt accttgttga 60
gaaaaaataa gtcacgtttg ctcttgaggt agttggagag atttccatat ttgcagtatt 120
caacaatcac catcagaggc cctgcagcca aaacagcaca tgctcatgct cagccacacc 180
aagc 184

<210> SEQ ID NO 137
<211> LENGTH: 194
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 137
aaaatggtga tgggtcagtt gaaagccaaa ctacagcata catacctttc agcattttca 60
cagccacagt ccggcacgta ggtgatttct taatgccaaa tgctgatgct tgaaccactt 120
ttccaaaagc ccctcttcca agtgatttgc ctgtaatgaa gagaagacac tggtttgttt 180
gccgaggcaa tagg 194

<210> SEQ ID NO 138
<211> LENGTH: 236
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 138
gtttttcatg taatatgtgc tcagtatagg tttatgaatc tgttgaacaa atatcttacc 60
cagtttaagt ctctcccggg caaactccca cttgctggca tcataaggga gccgctcaca 120

-continued ctgctcatcc aaaggaactt catctgggtc cattataatt gataggtagt cagtctttat 180
ttcagaagaa gactgagaaa taaagagatc tcaaagtcat cgagaagaaa acaact 236

<210> SEQ ID NO 139
<211> LENGTH: 226
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 139
ctagacatca gatcgggctt tttagaatat atgtaaaaag gagcatagaa catcacctat 60
gttcttaccc ttttcatttt tcggataaag agggttaata ggagccagaa gagagtcgca 120
gccacacagg tgcatgttag agtgatcagc tccagattag acttgtccga ggttcctgga 180
gagaaaaaaa atcacaatag tggtgcaaca aagaaattcc caaact 226

<210> SEQ ID NO 140
<211> LENGTH: 225
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 140
aatagatgtc tgaccaattt cttgttgctt tcttaagcag ctgtttacct tgaacagtga 60
ggtatgctga actttccaca gagcccttct ggttggtggc tttgcagtga tagacacctt 120
catcctcttc tgtgactctt tcaataaaca gcgtgctgct tcctggtcct aaaataattc 180
ctgaggggtg agagatgttt agattagtgg gcctggatga caaac 225

<210> SEQ ID NO 141
<211> LENGTH: 250
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 141 gggggctga tgaaagatga gaaataataa atggaagaaa aaaaagtctc ttaccaggct 60
cttgttgtat tttgtggttg tttttaaacc aagtgatctg aggctcgggg acaccattag 120
catgacagtc taaagtggtg gaactgctga tggccactgt gtgatcactg aggtttcgca 180
ggaggtatgg tgcttcctga tctagtgaag aaagaaaggg agctgtgatt actcgtcaac 240
tttattcttg 250

<210> SEQ ID NO 142
<211> LENGTH: 417
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 142
tgtgctttta aatttggaga tccgagagaa aacagccttt ttgttgcagt gctcacctct 60
gattgtaatt tctttcttct ggaggatttc ttcccctgtg tatacattcc tggctctgca 120
ggcataggtg cctgaatctt gcagggaaac attcatgatg gtaagattaa gagtgatgga 180

-continued

```
gtgctcctta gtgatggcca ttttttgctt gctaatactg tagtgcattg ttctgttatt    240

aactgtccgc agtaaaatcc aagtaacgtc tctgtataag aacttgttaa ctgtgcaaga    300

cagtttcagg tcctctcctt ccgtcggcat tttttccaag ttaacatgaa acccatttgg    360

cacatctata aaataagaat aaagaacttc agttcacaga aaaatcagtg tcttttta      417


<210> SEQ ID NO 143
<211> LENGTH: 217
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 143

gaatgaagtc accaggctgt ctctggttat aggatgtgtg gcttacctgt gatataaaag     60

cttatgtttc ttcccacagt cccaacttta ttggaagcta tgcaaatgta gattccagaa    120

attctagagt cagccacaac caaggtgcta gccatctgca aaagaaaagg aaactttagc    180

tagcaacagg acaaataact aattgaacac cccaagc                             217


<210> SEQ ID NO 144
<211> LENGTH: 227
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 144

gaattgggag ctgagagtgt atttgtggaa taaatatccc agtgcgcatt tttacaaaca     60

ataccttatt ctttccttct attattgcca tgcgctgagt gatgctctca attctgtttc    120

ccatgttgct gtcagcatcc aggataaagg actcttcatt attggaacaa aagtcacacc    180

tattaaaaaa aaaagttgtc acaatgtggc tttacagcat ggttcag                  227


<210> SEQ ID NO 145
<211> LENGTH: 265
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 145

aaaatcttaa ttccaggtgt caaaaagtat ttgaaagtta gtaaaaaaac tgactgtccc     60

taccttgctt cggaatgatt atggttacag gggtgccaga accacttgat tgtaggttga    120

gggataccat atgcggtaca agtcaggatt tgtctgctgc ccagtgggta gagagccggg    180

tctggaaacg atgacacggc cttttcgtaa atctggggtt tcactggaaa ggagatgaag    240

aacgggacag aagtcaagag cagtt                                          265


<210> SEQ ID NO 146
<211> LENGTH: 266
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 146
```

-continued

```
ctaatttgtt gcctaccaga accagaagaa agtatgaaca gcaaacttac cattgacaat     60

tagagtggca gtgaggtttt taaacacatt tgactgtttt atgctcagca agattgtata    120

attccctgca tcctcttcag ttacgtcctt gataattaac gagtagccac gagtcaaata    180

gcgagcagat ttctcagtcg caggtaaccc atcttttaac ctgtggttaa aaacatgatc    240

agtaagtcat ttcacacggc ctctca                                         266
```

<210> SEQ ID NO 147
<211> LENGTH: 237
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 147

```
gcagcttccc acttacaaag tatgtcttaa actgttatgg aaataaggat ggtcctacca     60

tacaacttcc ggcgagggaa atgccttcac tttcatagag agccggtaag accgcttgcc    120

agctacggtt tcaagcacct gctgttttcg atgtttcaca gtgatgaatg ctttatcttt    180

gaaaggagaa gtgatacata cattagaaaa gaataatttc cataaacaaa accttag       237
```

<210> SEQ ID NO 148
<211> LENGTH: 277
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 148

```
caatgattag aaagcatagc atgagttggc aacgctgaac tatgcttacc atatatatgc     60

actgaggtgt taacagattt gaatgatggt ccactcctta cacgacaagt ataaagtcct    120

ttgtctttgt tctgcatttt gtcaatagta agaacactgt agaatatgtt ggcatgggaa    180

ttgctttggt caattcgtcg ccttacggaa gctctcttat ttttctagaa agaaaatgta    240

taacaaatgt agaaggagtg agtgttcatg cttaaag                              277
```

<210> SEQ ID NO 149
<211> LENGTH: 267
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 149

```
atttcacttg cttaaaatac tgtcctgcag aagaaataga aaaatgggtc actcacttca     60

tcagggtaac tccaggtcat ttgaactctc gtgttcaagg gagtggtagc agtacaattg    120

aggacaagag tatggcctct aagtaatttg actgggcgtg gtgtgcttat ttggacatct    180

atgattgtat tggctgcaag cataagagag aaattttta aaattaagat ttcattacac     240

agataaaaat acagagcact tcggctt                                        267
```

<210> SEQ ID NO 150
<211> LENGTH: 256
<212> TYPE: DNA
<213> ORGANISM: Artificial Sequence
<220> FEATURE:
<223> OTHER INFORMATION: Description of Artificial Sequence: Synthetic nucleotide construct -continued

<400> SEQUENCE: 150
acagagcact tcggcttatg ttcatgcctt tgaagcatca cttactttgt cgatgtgtga 60
gatagtttgt cttatacaaa tgcccattga ctgttgcttc acaggtcaga agccctattt 120
ctttgtacgt tgcatttgat atgatgaagc cctttctact gtcccagatt atgcgttttc 180
catcagggat caaagtgtca agtggaaact gaaaaggaag aggcatgcat taacaaggtc 240
ctattagcac tggttg 256

<210> SEQ ID NO 151
<211> LENGTH: 229
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 151
cttatttgca gtgaaagtat gctgagaata gcggtgttca aatttacctt ttttaaagta 60
acagtgatgt taggtgacgt aacccggcag ggaatgacga gctcccttcc ttcagtcatg 120
tgtataattt cggggatttc actgtacatc tctacgaaag gtctacctgt atctgaatga 180
gaagaaaatg aaaaaaatat atacataaat gattgacatg caagcatct 229

<210> SEQ ID NO 152
<211> LENGTH: 323
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 152
atttgcaaag caaaagcaaa cagaatgtag aaaatggaag tcttaccact aataaatata 60
tagattgcag attctgtttc cttcttcttt gaagtaggta cagctagata tttgcagctg 120
tagaagccag tgtggtttgc ttgagctgtg ttcaaggtta aagtactgca gaattgtttg 180
ccatttcttc cacaggcaga tttagttatg ctcagccttt cgctttcctt actcaccatt 240
tcaggcaaag accatttatg ggctgcttcc cccctgcaat cacagataag aaaacaaaac 300
atatttatgg ctgggcccta ggc 323

<210> SEQ ID NO 153
<211> LENGTH: 226
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 153
cttaggcatg gcaactagat tattcccaaa ccaacacagc cacttacctg cattggagat 60
gcagtgtctg gcctgcttgc atgatgtgct gggtgccttt taaactcagt tcaggatctt 120
ttaattttga acctgaacta gatcctgaaa aacaaatttt taaaatgtat tatttgtaaa 180
ttgtcttctt accttttttt aagttatctt tccatgaagg tgagtt 226

<210> SEQ ID NO 154
<211> LENGTH: 259
<212> TYPE: DNA
<213> ORGANISM: Artificial Sequence -continued
<220> FEATURE:
<223> OTHER INFORMATION: Description of Artificial Sequence: Synthetic
nucleotide construct

<400> SEQUENCE: 154
ggctacagcc tcgtctcccc gcgtgcaccc cgccctggcc tcggaggctc tgccctccgg 60
ccgccccatc gcagcccgcc tcaggccccg gcccccagcc gcgcctcacc tgtgagaagc 120
agacagctga gcagcgcgca cagcaggacc ccggtgtccc agtagctgac catggtgagc 180
gcgacgcggc ctgctcgccc ggtgcccgcg ctccccgcgg ccaacgaccc ggccgccaga 240
gtccgtcctc tcgttcgcc 259

<210> SEQ ID NO 155
<211> LENGTH: 195
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 155
ctccatccct ccaagctatc gtccagcgca gtccaccgcc gcctcaggcc gtgccgctgg 60
ccgagtagga gaactggggg aagtggggcc tgcgctcgct gtccacacac tccatgctgt 120
catctgtggg tgtagacagc tcagaccccg gtgccccacc tccctgccac ctccacccac 180
ccacagctcc agtag 195

<210> SEQ ID NO 156
<211> LENGTH: 201
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 156
tgagtgtgga gagaaaaggg agtgggcggg ggcaggcagt ggcccctcac cttggtcagg 60
tggtgtgatg gtgatcatct gggccgtgaa ctcctcatca aaatacctgg tgtcagtctc 120
cgacgtgacc tggggcttga agggtgggct gagctgcaga ggtgggcaga cgggacagtc 180
atgagcttcg ctccccactc c 201

<210> SEQ ID NO 157
<211> LENGTH: 234
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 157
atgcgtgagt gtggatatgt ggggagcatg cgtgcgcgtg aatatgcggg gagcagccgc 60
accttcttct cgtacacgtg ctgccacacg ataccggcaa agaagcgatg ctgcatgatc 120
tccttggcgt cctcggagcc cccgccaagc ctgcaggcag gaaacaaggc cacagtgtcg 180
gtaccgccac ctgcccaggc cctgggttca ggccccttcc tcctgtgatg tagg 234

<210> SEQ ID NO 158
<211> LENGTH: 262
<212> TYPE: DNA
<213> ORGANISM: Artificial Sequence
<220> FEATURE:

-continued

<223> OTHER INFORMATION: Description of Artificial Sequence: Synthetic
      nucleotide construct

<400> SEQUENCE: 158
ccgtctggtg ccatggagag tagccgaggc tccgggaagg accggcccca ccatgggcgg 60
cccacaggcc gcgaagtcca tcccccgcag ccccagcccc tacctcgccc ccgttggcgt 120
actccatgac aaagcagagg cggtcgtggg tctggaaaga gtacttcagg gcctgcaagg 180
aaggggagct ggaactgcgg ccccacaggc aggacggcag ccccgcacca cgctgcccga 240
caccacgctg cttgatacca cg 262

<210> SEQ ID NO 159
<211> LENGTH: 252
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 159
ccctccacag tccaaggcag ccccaggcac aggcagaagt ggggacaggc ctcaccacgc 60
ggtgcttggg cttggccagg gacacctcca tctcttcagc ccctgagttg tcactgggtg 120
agcccgaccg gaagtccatc tcctcctcct cctgcttctt gaggccgtca gccacagtct 180
ggatggcggt tgtccactcc tccctgcagg aggtcaggtg aggctgcagg cctgtaccag 240
atcaggagct cc 252

<210> SEQ ID NO 160
<211> LENGTH: 289
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 160
ccatccccgt gtccctccta agcgctgggg ctgcccaagt gcctggcctg gccgccacag 60
cccacgtacc gctcctcagg agtctccaca tggaaggtgc gttcgatgac agtggtccac 120
tgcaggcagc ggatgatgaa ggtgttgggc cggggccgct ccgtcttcat cagctggcac 180
tctgcgggca ggcagagcct ctgtctgcgt gcatcccccct gcccctccca gggccctcac 240
cacagccccc gctgcaccag ccagctcccc ttgcatacca cccaccagg 289

<210> SEQ ID NO 161
<211> LENGTH: 212
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 161
ccccccaaat ctgaatcccg agaggccaag ggatacttta cgcgccacag agaagttgtt 60
gaggggagcc tcacgttggt ccacatcctg cggccgctcc ttgtagccaa tgaaggtgcc 120
atcattcttg aggaggaagt agcgtggccg ccaggtcttg atgtactccc ctacagacgt 180
gcgggtggtg agagccacgc acactctacc cg 212

<210> SEQ ID NO 162
<211> LENGTH: 235

-continued

<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 162
ggaggaagcg agaggtgctg ccctcccccc ggagttggaa gcgcgttacc cgggtccaaa 60
atgcccaaga agaagccgac gcccatccag ctgaacccgg cccccgacgg ctctgcagtt 120
aacgggacca gctctgcgga gtaagtatgg ggcgggcggt gaacctcggg gcccggctgg 180
ggaggcccga gccggggagc aggagcgcgc gccaggctcc gatctggttt gtcac 235

<210> SEQ ID NO 163
<211> LENGTH: 314
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 163
ctttgggttg acttctctgg tgacagtatt gacttgtgct ccccactttg gaacaggacc 60
aacttggagg ccttgcagaa gaagctggag gagctagagc ttgatgagca gcagcgaaag 120
cgccttgagg cctttcttac ccagaagcag aaggtgggag aactgaagga tgacgacttt 180
gagaagatca gtgagctggg ggctggcaat ggcggtgtgg tgttcaaggt ctcccacaag 240
ccttctggcc tggtcatggc cagaaaggtg agtttgcctt gattaacagg taattggatt 300
atttctcagg gtac 314

<210> SEQ ID NO 164
<211> LENGTH: 248
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 164
ctttcatccc ttcctccctc tttctttcat aaaacctctc tttcttccac ctttctccag 60
ctaattcatc tggagatcaa acccgcaatc cggaaccaga tcataaggga gctgcaggtt 120
ctgcatgagt gcaactctcc gtacatcgtg ggcttctatg gtgcgttcta cagcgatggc 180
gagatcagta tctgcatgga gcacatggta tgtgacaccc tctcagcctc tggagcaatg 240
gccttaag 248

<210> SEQ ID NO 165
<211> LENGTH: 186
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 165
tcacttgaaa gaatagttag aacattgtca ctaactggtc tggtattctc gatcttagga 60
tggaggttct ctggatcaag tcctgaagaa agctggaaga attcctgaac aaattttagg 120
aaaagttagc attgctgtga gtatgttatg aagtttttct tctaagttcc tcattgataa 180
gttaat 186

-continued

<210> SEQ ID NO 166
<211> LENGTH: 158
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 166
gtatttttct tatcaccagt attttctttt cttttacatt ccctttcctc taggtaataa 60
aaggcctgac atatctgagg gagaagcaca agatcatgca cagaggtaag aagttatttg 120
ctagttattt tgctttgaat tttagatata atccaaag 158

<210> SEQ ID NO 167
<211> LENGTH: 213
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 167
ctacctgtgt cagttccctc cttttctatt ttctcttccc tgcagatgtc aagccctcca 60
acatcctagt caactcccgt ggggagatca agctctgtga ctttggggtc agcgggcagc 120
tcatcgactc catggccaac tccttcgtgg gcacaaggtc ctacatgtcg gtatgaacag 180
aagtttccat tgcttgagct tcttgtacgg tca 213

<210> SEQ ID NO 168
<211> LENGTH: 294
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 168
ccaggggtcc aagttaggtt aggtgattat cactgtctgt ctctcctgca gccagaaaga 60
ctccagggga ctcattactc tgtgcagtca gacatctgga gcatgggact gtctctggta 120
gagatggcgg ttgggaggta tcccatccct cctccagatg ccaaggagct ggagctgatg 180
tttgggtgcc aggtggaagg agatgcggct gagaccccac ccaggccaag gacccccggg 240
aggcccctta gctgtgagta gcctggtgtg tccccatctt ggactgttgg aggg 294

<210> SEQ ID NO 169
<211> LENGTH: 176
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 169
cttgcctcat attaacaagt aatctgtttc tgagaagtat tttttctttt tataaaattt 60
gtagcatacg gaatggacag ccgacctccc atggcaattt ttgagttgtt ggattacata 120
gtcaacgagg taagtactgc ctggtttcct tcaccttgga atttacttgc tcatct 176

<210> SEQ ID NO 170
<211> LENGTH: 164
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 170
gagcaaggag ccaggcattt ttcttatctc aacatgtgtt tgcagcctcc tccaaaactg      60
cccagtggag tgttcagtct ggaatttcaa gattttgtga ataaatggta agttggctcc     120
ttgttctctg gaagcgtata ctctggattt gtcaggctcc ccac                      164

<210> SEQ ID NO 171
<211> LENGTH: 165
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 171
ccagtgccag gcaacagctc ttaccttgtc tttcttcctt taagcttaat aaaaaacccc      60
gcagagagag cagatttgaa gcaactcatg gtgagtctat ttattccgga ttcttacagt    120
acctgtttat tcatttgttc ttctctgtca gtcatctgtg cagta                    165

<210> SEQ ID NO 172
<211> LENGTH: 224
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 172
tttttttgtt tcttttaac accacgtcct ctcgtttcct tacatgcagg ttcatgcttt       60
tatcaagaga tctgatgctg aggaagtgga ttttgcaggt tggctctgct ccaccatcgg    120
ccttaaccag cccagcacac caacccatgc tgctggcgtc taagtgtttg ggaagcaaca    180
aagagcgagt cccctgcccg gtggtttgcc atgtcgcttt tggg                     224

<210> SEQ ID NO 173
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 173
gacttgtttc ctttcatttc ctttttttct tttcttttct ttttttttt tttttttttt      60 tttgagaaag gggaatttca tcccaaataa aaggaatgaa gtctggctcc ggaggagggt    120
ccccgacctc gctgtggggg ctcctgtttc tctccgccgc gctctcgctc tggccgacga    180
gtggagaaag tgagtatgtg cccgccgccc gcggccactg cgggaacttt tcctcc        236

<210> SEQ ID NO 174
<211> LENGTH: 357
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 174
taaaaattat ttccttctaa ctgagacgtt taccctcttg tctcccttca gtctgcgggc      60

-continued

```
caggcatcga catccgcaac gactatcagc agctgaagcg cctggagaac tgcacggtga    120

tcgagggcta cctccacatc ctgctcatct ccaaggccga ggactaccgc agctaccgct    180

tccccaagct cacggtcatt accgagtact tgctgctgtt ccgagtggct ggcctcgaga    240

gcctcggaga cctcttcccc aacctcacgg tcatccgcgg ctggaaactc ttctacaact    300

acgccctggt catcttcgag atgaccaatc tcaaggatat tgggctttac aacctga       357
```

<210> SEQ ID NO 175
<211> LENGTH: 352
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 175

```
cttctacaac tacgccctgg tcatcttcga gatgaccaat ctcaaggata ttgggcttta     60

caacctgagg aacattactc ggggggccat caggattgag aaaaatgctg acctctgtta    120

cctctccact gtggactggt ccctgatcct ggatgcggtg tccaataact acattgtggg    180

gaataagccc ccaaaggaat gtggggacct gtgtccaggg accatggagg agaagccgat    240

gtgtgagaag accaccatca acaatgagta caactaccgc tgctggacca caaaccgctg    300

ccagaaaagt aagaatgatg ctgactgctg ctttctctct gcctctctct ct            352
```

<210> SEQ ID NO 176
<211> LENGTH: 245
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 176

```
cttacaccaa gtgagcacac agtgacacaa tccccctttca atgtagataa cattgcttca     60

gagctggaga acttcatggg gctcatcgag gtggtgacgg gctacgtgaa gatccgccat    120

tctcatgcct tggtctcctt gtccttccta aaaaaccttc gcctcatcct aggagaggag    180

cagctagaag ggtaagtgcc ccaaatttca tgagctgacg ttctattaca aaataagcag    240

cgtgc                                                                245
```

<210> SEQ ID NO 177
<211> LENGTH: 215
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 177

```
agagacacat gaatctctgt cactcacgga tgtactcttt gccccaggtg aaagtgacgt     60

cctgcatttc acctccacca ccacgtcgaa gaatcgcatc atcataacct ggcaccggta    120

ccggccccct gactacaggg atctcatcag cttcaccgtt tactacaagg aagcgtgagt    180

ttctgctttg ggtgatgcca ttctgttgac agggc                               215
```

<210> SEQ ID NO 178
<211> LENGTH: 324
<212> TYPE: DNA
<213> ORGANISM: Artificial Sequence -continued
<220> FEATURE:
<223> OTHER INFORMATION: Description of Artificial Sequence: Synthetic
      nucleotide construct

<400> SEQUENCE: 178
gatgtcagag ccccgaactt tctctgaact taattgtctt tcagaccctt taagaatgtc     60
acagagtatg atgggcagga tgcctgcggc tccaacagct ggaacatggt ggacgtggac    120
ctcccgccca acaaggacgt ggagcccggc atcttactac atgggctgaa gccctggact    180
cagtacgccg tttacgtcaa ggctgtgacc ctcaccatgg tggagaacga ccatatccgt    240
ggggccaaga gtgagatctt gtacattcgc accaatgctt caggtatcca tgcctagaca    300
agcccccagc atccacactt cttc                                           324

<210> SEQ ID NO 179
<211> LENGTH: 294
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 179
aacggctttc attcccactc ttgttttggc ttttcttttc cgagaagaca aaatccccat     60
caggaagtat gccgacggca ccatcgacat tgaggaggtc acagagaacc ccaagactga    120
ggtgtgtggt ggggagaaag ggccttgctg cgcctgcccc aaaactgaag ccgagaagca    180
ggccgagaag gaggaggctg aataccgcaa agtctttgag aatttcctgc acaactccat    240
cttcgtgccc aggtacccag ctcatgtgaa atttcagttg gcaaaaccca ctgc          294

<210> SEQ ID NO 180
<211> LENGTH: 259
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 180
agacaaaaga ggtaaaagta cttaaaagcc acatttctct cctccttgca gacctgaaag     60
gaagcggaga gatgtcatgc aagtggccaa caccaccatg tccagccgaa gcaggaacac    120
cacggccgca gacacctaca acatcaccga cccggaagag ctggagacag agtacccttt    180
ctttgagagc agagtggata acaaggagag aactgtcatt tctaaccttc ggcctttcac    240
attgtaccgc atcgatatc                                                 259

<210> SEQ ID NO 181
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 181
gcatcgatat ccacagctgc aaccacgagg ctgagaagct gggctgcagc gcctccaact     60
tcgtctttgc aaggactatg cccgcaggta tggtatgatc cagctggccc cattgccacc    120
ttcctcacaa cctagtggag aagatgtgtt ttatggacac agggtc                   166

<210> SEQ ID NO 182

-continued

<211> LENGTH: 223
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 182
cctgggaacc caaatccaac tttgtcacct gtttaaattg tacagaagga gcagatgaca 60
ttcctgggcc agtgacctgg gagccaaggc ctgaaaactc catcttttta aagtggccgg 120
aacctgagaa tcccaatgga ttgattctaa tgtatgaaat aaaatacgga tcacaagttg 180
aggtaggact ggggcagtgg cccgtgcctg catgtacttc cat 223

<210> SEQ ID NO 183
<211> LENGTH: 255
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 183
cctgcattca tgggaaattg acatgtatgt tttatttccc caggatcagc gagaatgtgt 60
gtccagacag gaatacagga agtatggagg ggccaagcta aaccggctaa acccggggaa 120
ctacacagcc cggattcagg ccacatctct ctctgggaat gggtcgtgga cagatcctgt 180
gttcttctat gtccaggcca aaagtaaggc ttgtggaggg agaagaaacg tggtaaaact 240
gaaagcaggg tggtc 255

<210> SEQ ID NO 184
<211> LENGTH: 217
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 184
gtgaagaaat gaaatgagca aattgttcac ctggtgatat tttatcattt cctcctcttt 60
gctgcagcag gatatgaaaa cttcatccat ctgatcatcg ctctgcccgt cgctgtcctg 120
ttgatcgtgg gagggttggt gattatgctg tacgtcttcc atagaaagag gtcagtgatg 180
tgcaaagtta tgacactttc tgtggctgag tggtttg 217

<210> SEQ ID NO 185
<211> LENGTH: 172
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 185
gaatgtatgg aggtggggtt ttgttaacgt gaatttaatc tttttgacag aaataacagc 60
aggctgggga atggagtgct gtatgcctct gtgaacccgg agtacttcag cgctgctgat 120
ggtaagagtc cgggccacca gcactgccag cgtgcagggc aggtagatcg gg 172

<210> SEQ ID NO 186
<211> LENGTH: 316
<212> TYPE: DNA
<213> ORGANISM: Artificial Sequence -continued
<220> FEATURE:
<223> OTHER INFORMATION: Description of Artificial Sequence: Synthetic
      nucleotide construct

<400> SEQUENCE: 186
ctaagggctt gtttctgtac ctgctttaat tacggtttct tctccagtgt acgttcctga     60
tgagtgggag gtggctcggg agaagatcac catgagccgg gaacttgggc aggggtcgtt    120
tgggatggtc tatgaaggag ttgccaaggg tgtggtgaaa gatgaacctg aaaccagagt    180
ggccattaaa acagtgaacg aggccgcaag catgcgtgag aggattgagt ttctcaacga    240
agcttctgtg atgaaggagt tcaattgtca ccatgtggta agagaaagtt cctgaaaagc    300
caaaatgcag cacagg                                                    316

<210> SEQ ID NO 187
<211> LENGTH: 200
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 187
aagggccacc tgaccctctg agtctttctc tttttgattc ctcccaggtg cgattgctgg     60
gtgtggtgtc ccaaggccag ccaacactgg tcatcatgga actgatgaca cggggcgatc    120
tcaaaagtta tctccggtct ctgaggccag aaatggaggt cagttttcat ttccaccggt    180
attgcatgtt gcctggcctg                                                200

<210> SEQ ID NO 188
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 188
ctcgaaagaa attggcatgg aaaaaaaaaa tccaaaattc tcatgtgaat ttttttaaat     60
ctccaacaga ataatccagt cctagcacct ccaagcctga gcaagatgat tcagatggcc    120
ggagagattg cagacggcat ggcatacctc aacgccaata agttcgtcca cagagacctt    180
gctgcccgga attgcatggt agccgaagat ttcacagtca aaatcggagg tgtgtcctta    240
gctttccagg tctgggcaag aactaaactc aggtgt                              276

<210> SEQ ID NO 189
<211> LENGTH: 226
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 189
ttcagtccat ccctttccaa gctcctcaca gtttttttct ccctgtaggt ccttcggggt     60
cgtcctctgg gagatcgcca cactggccga gcagccctac cagggcttgt ccaacgagca    120
agtccttcgc ttcgtcatgg agggcggcct tctggacaag ccagacaact gtcctgacat    180
gctgtacgta cttcctgggc cctccgtgct cttctgagtt ctcttc                   226

<210> SEQ ID NO 190

-continued

<211> LENGTH: 326
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 190
tacgcttgta tgcgggaaac cactgcaggc ggcccatgaa gcctcctggc catgtgcgcc 60
ctcccggttt ggaccccctc ccgtgtgtct tggctgcagg tttgaactga tgcgcatgtg 120
ctggcagtat aaccccaaga tgaggccttc cttcctggag atcatcagca gcatcaaaga 180
ggagatggag cctggcttcc gggaggtctc cttctactac agcgaggaga acaagctgcc 240
cgagccggag gagctggacc tggagccaga gaacatggag agcgtccccc tggacccctc 300
ggcctcctcg tcctccctgc cactgc 326

<210> SEQ ID NO 191
<211> LENGTH: 272
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 191
ctggacctgg agccagagaa catggagagc gtccccctgg acccctcggc ctcctcgtcc 60
tccctgccac tgcccgacag acactcagga cacaaggccg agaacggccc cggccctggg 120
gtgctggtcc tccgcgccag cttcgacgag agacagcctt acgcccacat gaacgggggc 180
cgcaagaacg agcgggcctt gccgctgccc cagtcttcga cctgctgatc cttggatcct 240
gaatctgtgc aaacagtaac gtgtgcgcac gc 272

<210> SEQ ID NO 192
<211> LENGTH: 320
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 192
tgtgaagctg agattcccct ccattgggac cggagaaacc aggggagccc cccgggcagc 60
cgcgcgcccc ttcccacggg gccctttact gcgccgcgcg cccggccccc acccctcgca 120
gcaccccgcg ccccgcgccc tcccagccgg gtccagccgg agccatgggg ccggagccgc 180
agtgagcacc atggagctgg cggccttgtg ccgctggggg ctcctcctcg ccctcttgcc 240
ccccggagcc gcgagcaccc aaggtgggtc tggtgtgggg aggggacgga gcagcggcgg 300
gaccctgccc tgtggatgcc 320

<210> SEQ ID NO 193
<211> LENGTH: 280
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 193
ggccaggtct gagaaggtcc cccgccagtg tcctctgacc catctgctct ctcctgccag 60
tgtgcaccgg cacagacatg aagctgcggc tccctgccag tcccgagacc cacctggaca 120

-continued

```
tgctccgcca cctctaccag ggctgccagg tggtgcaggg aaacctggaa ctcacctacc    180

tgcccaccaa tgccagcctg tccttcctgc aggtgaggcc cgtgggcaac ccagccaggc    240

cctgcctcca gctgggctga gccctctgtt tacaggtggg                          280


<210> SEQ ID NO 194
<211> LENGTH: 306
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 194

gtggcagtgt tcctatttca gccccactct gcttccccct cccaggatat ccaggaggtg     60

cagggctacg tgctcatcgc tcacaaccaa gtgaggcagg tcccactgca gaggctgcgg    120

attgtgcgag gcacccagct ctttgaggac aactatgccc tggccgtgct agacaatgga    180

gacccgctga acaataccac ccctgtcaca ggggcctccc caggaggcct gcgggagctg    240

cagcttcgaa gcctcacagg tggccttcac cgtcattgaa accttctctt ggttattcag    300

agctga                                                               306


<210> SEQ ID NO 195
<211> LENGTH: 222
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 195

gtgacagaag ggaaagggt cctctgatca ttgctcaccc cacagagatc ttgaaaggag      60

gggtcttgat ccagcggaac ccccagctct gctaccagga cacgattttg tggaaggaca    120

tcttccacaa gaacaaccag ctggctctca cactgataga caccaaccgc tctcgggcct    180

gtaagccatg cccctccctg ctgcctcttc tctcagacag cc                       222


<210> SEQ ID NO 196
<211> LENGTH: 230
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 196

tagaaggtga tgctgatgag ggtctggtgc ccagggcgcc actcagccct catcctgccc     60

tttgcccaac agtgacgcgc actgtctgtg ccggtggctg tgcccgctgc aaggggccac    120

tgcccactga ctgctgccat gagcagtgtg ctgccggctg cacgggcccc aagcactctg    180

actgcctggt atgtgcctct gctttgtgcc caatgtgctc taccccccag               230


<210> SEQ ID NO 197
<211> LENGTH: 234
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 197
```

-continued

```
caccagggca aaacagcaca gtgaaagcca gccacctgtc cccccaggcc tgcctccact     60

tcaaccacag tggcatctgt gagctgcact gcccagccct ggtcacctac aacacagaca    120

cgtttgagtc catgcccaat cccgagggcc ggtatacatt cggcgccagc tgtgtgactg    180

cctgtccctg tgagtgccag ggagaaacac agttttctca ttttggtggg gagg          234


<210> SEQ ID NO 198
<211> LENGTH: 237
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 198

ggtaatgctg ctcatggtgg tgcacgaagg gccagggtat gtggctacat gttcctgatc     60

tccttagaca actacctttc tacggacgtg ggatcctgca ccctcgtctg ccccctgcac    120

aaccaagagg tgacagcaga ggatggaaca cagcggtgtg agaagtgcag caagccctgt    180

gcccgaggta cccactcact gcccccgagg ccagctgcag ttcctgtccc tctgcgc       237


<210> SEQ ID NO 199
<211> LENGTH: 313
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 199

gaatagcctt tgctgaccgg gaaggggtcc gtggtaaggt gcccaccttt ctcccatagt     60

ggcgcctact cgctgaccct gcaagggctg ggcatcagct ggctggggct gcgctcactg    120

agggaactgg gcagtggact ggccctcatc caccataaca cccacctctg cttcgtgcac    180

acggtgccct gggaccagct ctttcggaac ccgcaccaag ctctgctcca cactgccaac    240

cggccagagg acgagtgtgg taagacaggg agcccagtgt gcgcactccc catctgccag    300

cacacagcag tgc                                                       313


<210> SEQ ID NO 200
<211> LENGTH: 445
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 200

ggcctcccct aaaagtcccc tgcggtccct tcctcctcac tgcagtgggc gagggcctgg     60

cctgccacca gctgtgcgcc cgagggcact gctggggtcc agggcccacc cagtgtgtca    120

actgcagcca gttccttcgg ggccaggagt gcgtggagga atgccgagta ctgcaggggt    180

atgaggggcg gaggagaggg tggctggagg ggtgcatggg gctcctctca gaccccctca    240

ccactgtccc ttctctcagg ctccccaggg agtatgtgaa tgccaggcac tgtttgccgt    300

gccaccctga gtgtcagccc cagaatggct cagtgacctg ttttggaccg gtgagctgct    360

ggcgggctca gagctgggtg gagggggggca gcgaggggga ttgccaggga cttggcagga    420

tggcgagatg cagtagggtg tgcta                                          445


<210> SEQ ID NO 201
```

-continued

<211> LENGTH: 277
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 201
ctaagggcct gatcctactg ccctgggggt gtcagtgcca gccccccaca aatcttttct 60 gccccccccca ggaggctgac cagtgtgtgg cctgtgccca ctataaggac cctcccttct 120
gcgtggcccg ctgccccagc ggtgtgaaac ctgacctctc ctacatgccc atctggaagt 180
ttccagatga ggagggcgca tgccagcctt gccccatcaa ctgcacccac tcgtgagtcc 240
aacggtcttt tctgcagaaa ggaggacttt cctttca 277

<210> SEQ ID NO 202
<211> LENGTH: 164
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 202
ttgttgtgag gctggaaagg tggttcccaa gagggtggtt cccagaattg ttgatgagac 60
tgtttctcct gcagctgtgt ggacctggat gacaagggct gccccgccga gcagagagcc 120
aggttggcct ggaccccagg atgtaccctt cattgccctt cact 164

<210> SEQ ID NO 203
<211> LENGTH: 295
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 203
caccccaaac tagccctcaa tccctgaccc tggcttccgc ccccagccct ctgacgtcca 60
tcatctctgc ggtggttggc attctgctgg tcgtggtctt gggggtggtc tttgggatcc 120
tcatcaagcg acggcagcag aagatccgga agtacacgat gcggagactg ctgcaggaaa 180
cggaggtgag gcggggtgaa gtcctcccag cccgcgtggg gtctgcaccg gcccccggca 240
ctgacccacc accccctcac cccagctggt ggagccgctg acacctagcg gagcg 295

<210> SEQ ID NO 204
<211> LENGTH: 299
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 204
gctgcaggaa acggaggtga ggcggggtga agtcctccca gcccgcgtgg ggtctgcacc 60
ggcccccggc actgacccac cacccctca ccccagctgg tggagccgct gacacctagc 120
ggagcgatgc ccaaccaggc gcagatgcgg atcctgaaag agacggagct gaggaaggtg 180
aaggtgcttg gatctggcgc ttttggcaca gtctacaagg tcagggccag gtcctggggt 240
gggcggcccc agaggatggg ggcggtgcct ggaggggtgt ggtcggcagt tctgatggg 299

-continued

<210> SEQ ID NO 205
<211> LENGTH: 192
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 205
ccagcccacg ctcttctcac tcatatcctc ctctttctgc ccagggcatc tggatccctg 60
atggggagaa tgtgaaaatt ccagtggcca tcaaagtgtt gagggaaaac acatccccca 120
aagccaacaa agaaatctta gacgtaagcc cctccaccct ctcctgctag gaggacagga 180
aggaccccat gg 192

<210> SEQ ID NO 206
<211> LENGTH: 242
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 206
cccaggccct cccagaaggt ctacatgggt gcttcccatt ccaggggatg agctacctgg 60
aggatgtgcg gctcgtacac agggacttgg ccgctcggaa cgtgctggtc aagagtccca 120
accatgtcaa aattacagac ttcgggctgg ctcggctgct ggacattgac gagacagagt 180
accatgcaga tgggggcaag gttaggtgaa ggaccaagga gcagaggagg ctgggtggag 240
tg 242

<210> SEQ ID NO 207
<211> LENGTH: 191
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 207
ccacctcccc acaacacaca gttggaggac ttcctcttct gccctcccag gtgcccatca 60
agtggatggc gctggagtcc attctccgcc ggcggttcac ccaccagagt gatgtgtgga 120
gttatggtgt gtgatggggg gtgttgggag gggtgggtga ggagccatgg ctggagggag 180
gatgagagct g 191

<210> SEQ ID NO 208
<211> LENGTH: 252
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 208
cagtacacta aagctccctc tggccctccc actcctgacc ctgtctctgc cttaggtgtg 60
actgtgtggg agctgatgac ttttggggcc aaaccttacg atgggatccc agcccgggag 120
atccctgacc tgctggaaaa gggggagcgg ctgccccagc cccccatctg caccattgat 180
gtctacatga tcatggtcaa atgtgcgtgg ctgagctgtg ctggctgcct ggaggagggt 240
gggaggtcct gg 252

-continued

<210> SEQ ID NO 209
<211> LENGTH: 185
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 209
cacagggcct gggactagca tgctgacctc cctcctgccc caggttggat gattgactct 60
gaatgtcggc caagattccg ggagttggtg tctgaattct cccgcatggc cagggacccc 120
cagcgctttg tggtcatcca ggtactgggc ctctgtgccc catccctgcc tgtggctaag 180
agcac 185

<210> SEQ ID NO 210
<211> LENGTH: 298
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 210
cccctcacgg aaggctgcat gctgggctgg ggaggggcca ccatcctgcc tctccttcct 60
ccacagaatg aggacttggg cccagccagt cccttggaca gcaccttcta ccgctcactg 120
ctggaggacg atgacatggg ggacctggtg gatgctgagg agtatctggt accccagcag 180
ggcttcttct gtccagaccc tgccccgggc gctgggggca tggtccacca caggcaccgc 240
agctcatcta ccagggtcag tgccctcggt cacactgtgt ggctgtctgc ttacctcc 298

<210> SEQ ID NO 211
<211> LENGTH: 342
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 211
cccagatccg tgagtgaccc ccatcatgac tttctttctt gtccccagag tggcggtggg 60
gacctgacac tagggctgga gccctctgaa gaggaggccc ccaggtctcc actggcaccc 120
tccgaagggg ctggctccga tgtatttgat ggtgacctgg gaatgggggc agccaagggg 180
ctgcaaagcc tccccacaca tgaccccagc cctctacagc ggtacagtga ggaccccaca 240
gtacccctgc cctctgagac tgatggctac gttgcccccc tgacctgcag cccccagcct 300
ggtatggagt ccagtctaag cagagagact gatgggcagg gg 342

<210> SEQ ID NO 212
<211> LENGTH: 296
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 212
agagacaccg gggttccttc ccctaatggg tcaccttctc ttgacctttc agaatatgtg 60
aaccagccag atgttcggcc ccagcccccct tcgccccgag agggccctct gcctgctgcc 120
cgacctgctg gtgccactct ggaaaggccc aagactctct ccccagggaa gaatggggtc 180

-continued

```
gtcaaagacg tttttgcctt tgggggtgcc gtggagaacc ccgagtactt gacaccccag    240

ggaggagctg cccctcagcc ccaccctcct cctgccttca gcccagcctt cgacaa        296


<210> SEQ ID NO 213
<211> LENGTH: 399
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 213

gacgtttttg cctttggggg tgccgtggag aaccccgagt acttgacacc ccagggagga     60

gctgcccctc agccccaccc tcctcctgcc ttcagcccag ccttcgacaa cctctattac    120

tgggaccagg acccaccaga gcggggggct ccacccagca ccttcaaagg gacacctacg    180

gcagagaacc cagagtacct gggtctggac gtgccagtgt gaaccagaag gccaagtccg    240

cagaagccct gatgtgtcct cagggagcag ggaaggcctg acttctgctg gcatcaagag    300

gtgggagggc cctccgacca cttccagggg aacctgccat gccaggaacc tgtcctaagg    360

aaccttcctt cctgcttgag ttcccagatg gctggaagg                           399


<210> SEQ ID NO 214
<211> LENGTH: 174
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 214

ccagcagcct tatttcctgg ggcctgggtg gcagcctgca ccctcccggt cccagaaccc     60

gctggcatca ctcactgtga gcatcttcag gtccgcccgc tccgctgggt tcttgatgag    120

gctgggggtt ccaagaggca ggaccgggag gcggtggagg agacaagaca gggc          174


<210> SEQ ID NO 215
<211> LENGTH: 176
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 215

ggaaggagtg gcacatctgg gtcccggcca ggggtgtggg cagcccggct ccacctacca     60

tttattgaca aactcctgga agtcgggggt gaacacaccg ttgggcagct taggaggtgg    120

ctgtggagga gaacagaggg tggggtcagc cctgggcatc gtcagggacc ctcggc        176


<210> SEQ ID NO 216
<211> LENGTH: 177
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 216

aagaagaaag aaaaggaaaa gaaaagccaa aaggcatcaa gcacaaacct cgttcacaat     60

atagtccagg agttcaaaga tggccatggc aggccggcta tccatcccgt gacctgcaca    120
```

-continued gggagagaga tggaggtgag atgggccgat ggccacctca cttctgctgg gggttgg 177

<210> SEQ ID NO 217
<211> LENGTH: 403
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 217
ggaggcagct gctgaccctg gcacagcagg ccccgcgcag ggcactgcgc gtccagaccg 60
gaagttgcag attcaggccg taccgctgac ggggcgcccg gggggcctcg gccgaggcga 120
gatgctgtga ggctctcctt cttccccgtc gaccacgggc cggccaaaga tggcctccag 180
ctctttggcg tcgggcgggg ggatggggta ccttccgacg gccagctcca ccagggacag 240
gcccatgctc cagatgtccg actgcaccga gtaatgtgtg ccctgcaacc gctccggctg 300
cagcagagcc agggaggaaa gagcccagag gggcgaggat ggcagctgga acccgggagg 360
cttgccccgt tacagccccc gtcaccctct ccatggctaa tga 403

<210> SEQ ID NO 218
<211> LENGTH: 442
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 218
ggagacatgg gggtgagagc tgagggggag agctggctgg cagagctggg tggggagagc 60
ttgggggaga gcagcaggga ggagagctgg aggggagagc cagcggggac tcacagccat 120
gtaggagcgc gtgcccacga aggagttggc catggagtcg atgagctggc cgctcacccc 180
gaagtcacac agcttgatct cccctctaga gttcacgagg atgttggagg gcttcacatc 240
tggaggcggc aggctgcggg tgaggggcgc ccaacagttg cctgccggcc cccggggctc 300
tggggagggc gggctgggcc ttacctcggt gcatgatctg gtgcttctct cggaggtacg 360
ccaagccccg gagaacctgc aggggagcgc ggagggagtc acgggacaag gccaccaggg 420
cttagctcct gaccgagccc gg 442

<210> SEQ ID NO 219
<211> LENGTH: 304
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 219
gtggaagagg tccgtgcaga gtgcggtggg ggcgcgatgt gggtctgcgg tggactcacc 60
gcgatgctga ctttccccag gatctcctcg ggaatcctct tggcctcttt cagcacctgg 120
tccagggagc cgccgtccta gagggcacac aaggagtgag tgcaggctct gcgcaggtgg 180
ccgggaagcc acggatgcgt ccccccactc ccggcgaggg ggtggtctgc ctcctgacgg 240
gaagcagggg ccggagccca actccaccca cgggccaagg gcagggcgtc ttctgacagt 300
tctg 304

<210> SEQ ID NO 220

-continued

<211> LENGTH: 266
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 220
ccaacatgct ctgttccgtg gaggccctgc ccctgcccct gccccggacg cactcaccat 60
gtgttccatg caaatgctga tctccccgtc actgtagaag gccccgtaga agcccacgat 120
gtacggcgag ttgcattcgt gcaggacctg cagctcgcgg atgatctggt tccggatggc 180
cggcttgatc tcaaggtgga tcagctgcaa ggggagaggg gcgagactgg cttgggggt 240 gcccgaaaac gggatgaagg catttg 266

<210> SEQ ID NO 221
<211> LENGTH: 243
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 221
ctcgtgcact cctcgcgaac ccccgtcccc tcgccccgtc cttccccgag ggctccctgc 60
cccgtgcacc ccaagcctcc ggctgacccc tgcccactca ctcggaggcg ccctcgctgg 120
taggggatgg gccctcggcg atggtagggt tgatggtgag cgccggcagc accggcttcc 180
tccgggccag catcggggct ccgcgggccg gcggcggcgg cgcctctagc cggggcccat 240
agg 243

<210> SEQ ID NO 222
<211> LENGTH: 237
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 222
gttattccca aatgaatgaa tgaatgagtg agtgaatgga tgcattcctc tcattttaca 60
gatgagtaac ccgaagcccc tagaggagtg gtcacctgcc tgagggcact tctgtcccac 120
cagcatcaga ccaggtgtgt gcaggtgtgt gcgactccag ggcccaggcc cggggcagct 180
ggggtggggc cttagggggg agcaggacct gggcccctcc tcccacaggc actgtgg 237

<210> SEQ ID NO 223
<211> LENGTH: 353
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 223
agagacatgg gcaggctctc actcacccac cgtgattccc tcccgcaggc cgcaccgagt 60
ccccggcacc atgtttggga agaggaagaa gcgggtggag atctccgcgc cgtccaactt 120
cgagcaccgc gtgcacacgg gcttcgacca gcacgagcag aagttcacgg ggctgccccg 180
ccagtggcag agcctgatcg aggagtcggc tcgccggccc aagcccctcg tcgaccccgc 240
ctgcatcacc tccatccagc ccggggcccc caaggtatgt ggcacccacc accacctccc 300

-continued ccagcccacc ccaacccccg agtggccctg gccctcaacc ccacactcga ccc 353

<210> SEQ ID NO 224
<211> LENGTH: 337
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 224
tgtgtgcccc actccttgct gggcccccac ccaccattgc ctgggacccc agaccatcgt 60
gcggggcagc aaaggtgcca aagatggggc cctcacgctg ctgctggacg agtttgagaa 120
catgtcggtg acacgctcca actccctgcg gagagacagc ccgccgccgc ccgcccgtgc 180
ccgccaggaa aatgggatgc cagaggagcc ggccaccacg gccagagggg gcccagggaa 240
ggcaggcagc cgaggccggt tcgccggtca cagcgaggcg ggtggcggca gtggtgacag 300
gcgacgggcg gggccagaga agaggcccaa gtcttcc 337

<210> SEQ ID NO 225
<211> LENGTH: 428
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 225
ggaaaatggg atgccagagg agccggccac cacggccaga gggggcccag ggaaggcagg 60
cagccgaggc cggttcgccg gtcacagcga ggcgggtggc ggcagtggtg acaggcgacg 120
ggcggggcca gagaagaggc ccaagtcttc cagggagggc tcagggggtc cccaggagtc 180
ctcccgggac aaacgccccc tctccgggcc tgatgtcggc aaccccccagc ctgctggtct 240 ggccagtggg gcgaaactgg cagctggccg gccctttaac acctacccga gggctgacac 300
ggaccaccca tcccggggtg cccaggtaac ccatccccccg ccccagggcc cccactgtcc 360
cctgcccgtt gctcctctgt ccccaccttc cagccccgcc ccaccaccgt gcatctcatc 420
ctgaccac 428

<210> SEQ ID NO 226
<211> LENGTH: 292
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 226
ccctggcacc catcactgac agctacctct cttctgtttc agggggagcc tcatgacgtg 60
gcccctaacg ggccatcagc ggggggcctg gccatccccc agtcctcctc ctcctcctcc 120
cggcctccca cccgagcccg aggtgccccc agccctggag tgctgggacc ccacgcctca 180
gagccccagc tggcccctcc agcctgcacc cccgccgccc ctgctgttcc tgggccccct 240
ggcccccgct caccacagcg ggagccacag cgagtatccc atgagcagtt cc 292

<210> SEQ ID NO 227
<211> LENGTH: 504
<212> TYPE: DNA
<213> ORGANISM: Artificial Sequence -continued
<220> FEATURE:
<223> OTHER INFORMATION: Description of Artificial Sequence: Synthetic
      nucleotide construct

<400> SEQUENCE: 227
cccctaacgg gccatcagcg gggggcctgg ccatccccca gtcctcctcc tcctcctccc     60
ggcctcccac ccgagcccga ggtgccccca gccctggagt gctgggaccc cacgcctcag    120
agccccagct ggcccctcca gcctgcaccc ccgccgcccc tgctgttcct gggccccctg    180
gcccccgctc accacagcgg gagccacagc gagtatccca tgagcagttc cgggctgccc    240
tgcagctggt ggtggaccca ggcgaccccc gctcctacct ggacaacttc atcaagattg    300
gcgagggctc cacgggcatc gtgtgcatcg ccaccgtgcg cagctcgggc aagctggtgg    360
ccgtcaagaa gatggacctg cgcaagcagc agaggcgcga gctgctcttc aacgaggtgc    420
gggcgctgct gccctgccgc cctgctggtc ctcccacccc tccctcccac cctccctccc    480
ctcctccctc ctctccctgc actc                                           504

<210> SEQ ID NO 228
<211> LENGTH: 256
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 228
cggtggctgg gtctggcact ggcagccctc ccgcctccct ccaccactga cccagcccct     60
gcacaggtgg taatcatgag ggactaccag cacgagaatg tggtggagat gtacaacagc    120
tacctggtgg gggacgagct ctgggtggtc atggagttcc tggaaggagg cgccctcacc    180
gacatcgtca cccacaccag gtatttctgg ggcctcagac ccctcctgtg acacgaccaa    240
gtcccctcca gaccac                                                    256

<210> SEQ ID NO 229
<211> LENGTH: 287
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 229
cattgtgtct gaagccaagg aatgacgcag gcagacgccc ctgctcgccc tcctgctgtg     60
ccagctcctc tgaccccact gcctctgccc tgtcccaggt gaagctgtca gactttgggt    120
tctgcgccca ggtgagcaag gaagtgcccc gaaggaagtc gctggtcggc acgccctact    180
ggatggcccc agagctcatc tcccgccttc cctacgggcc agaggtgagc cccggggtgg    240
cttggttgtc ccgccgtgga cagcgtacgc tgccattttc cagctgc                  287

<210> SEQ ID NO 230
<211> LENGTH: 343
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 230
ccaccatccc ccaacagctc agccctgctg tcccttctcc cgccccaggt agacatctgg     60

-continued tcgctgggga taatggtgat tgagatggtg gacggagagc ccccctactt caacgagcca 120
cccctcaaag ccatgaagat gattcgggac aacctgccac cccgactgaa gaacctgcac 180
aaggtaggcc cctccctggc tgggaaactg tgcgccagct ggcgggtggc agggctccag 240
gtggagcatg ggtgtggat gggatgggga caatgatggc gcctgggatg gcgcttactg 300
tgtgctgggc cccccacccc cgggcctcat gtgtctgtgc aga 343

<210> SEQ ID NO 231
<211> LENGTH: 295
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 231
cactgcagcc ctacagcaaa tgaacagtgg ggagcctcgc cccctgaccc tcccctcctt 60
ctcgacaggt gtcgccatcc ctgaagggct tcctggaccg cctgctggtg cgagaccctg 120
cccagcgggc cacggcagcc gagctgctga agcacccatt cctggccaag gcagggccgc 180
ctgccagcat cgtgcccctc atgcgccaga accgcaccag atgaggccca gcgcccttcc 240
cctcaaccaa agagcccccc gggtcacccc cgccccactg aggccagtag ggggc 295

<210> SEQ ID NO 232
<211> LENGTH: 246
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 232
gagcgacaga gacatttatt gttatttgtt ttttggtggc aaaaagggaa aatggcgaac 60
gactcccctg caaaaagtct ggtggacatc gacctctcct ccctgcgggt gagtgggccc 120
gcgagcgggc gcgcggggag cgggcagccg gcagccggca gccggggccg cgcccaggtc 180
ggccgggcgc tcgggcgccg ccgtgggcag agccgcgggg cgcggcggcc cctttgtctt 240
cctgtg 246

<210> SEQ ID NO 233
<211> LENGTH: 166
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 233
caaaaaaatt ggtgctgatt tttgatctat tttttctgtt tttcagggtc gacatgttaa 60
aacgggtcag ttggcagcca tcaaagttat ggatgtcact gaggtaagat tgagtcacac 120
acatttttaa ataatgttag atggaagaca aagattcccc caacaa 166

<210> SEQ ID NO 234
<211> LENGTH: 215
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 234

-continued ttcacatcgt tcagtagcca cacattttat ttttattttt tcataaggat gaagaggaag 60
aaatcaaact ggagataaat atgctaaaga aatactctca tcacagaaac attgcaacat 120
attatggtgc tttcatcaaa aagagccctc caggacatga tgaccaactc tgggtaggtg 180
gatgtttcct gagcatttgt gggcattcca tttgc 215

<210> SEQ ID NO 235
<211> LENGTH: 203
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 235
aatttctcca agatatgttg ctcaccttgt gtcttgtctg ccctatagct tgttatggag 60
ttctgtgggg ctgggtccat tacagacctt gtgaagaaca ccaaagggaa cacactcaaa 120
gaagactgga tcgcttacat ctccagagaa atcctgaggg taaggaaagt gggtggctac 180
agtgctccaa ctcatgatcc tgt 203

<210> SEQ ID NO 236
<211> LENGTH: 193
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 236
cctggctgtt tacttatagt cacagaaaac taaaattcag gtctgtcttt cctattcagg 60
gactggcaca tcttcacatt catcatgtga ttcaccggga tatcaagggc cagaatgtgt 120
tgctgactga gaatgcagag gtgaaacttg gtatgtaatg gatgtgcggc gtgatctcat 180
aattgcacct ggc 193

<210> SEQ ID NO 237
<211> LENGTH: 244
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 237
atctggtttg tagttgtgtt tatctttctt tatctgcctt tttcttcctc ccacagttga 60
ctttggtgtg agtgctcagc tggacaggac tgtggggcgg agaaatacgt tcataggcac 120
tccctactgg atggctcctg aggtcatcgc ctgtgatgag aacccagatg ccacctatga 180
ttacagagta agaggcacct gctccgtagg cctttgcagg gccactggca tacccgaggg 240
atgg 244

<210> SEQ ID NO 238
<211> LENGTH: 176
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 238

-continued

```
tgtaagttag tggctttgta tctactccag tatctgtaac gtactgtttt atttttgcag     60

agtgatcttt ggtcttgtgg cattacagcc attgagatgg cagaaggtgc tccccgtaag    120

taactttctt ttctttttag ctcacttgtt acatgtgact taaacccctc ccaaga        176
```

<210> SEQ ID NO 239
<211> LENGTH: 204
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 239

```
gaatgagtga aataagtgcc atactgacac gaccgtctcc tctccccagc tctctgtgac     60

atgcatccaa tgagagcact gtttctcatt cccagaaacc ctcctccccg gctgaagtca    120

aaaaaatggt aagctatata tggttttttg ttgttctttt cccttttttt taaattgctt    180

ctttttagtt atactttcct ctga                                           204
```

<210> SEQ ID NO 240
<211> LENGTH: 284
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 240

```
tttactcttt gtggtggaaa tttgatgatc tttttcactt cttacaggtc gaagaagttt     60

tttagtttta tagaagggtg cctggtgaag aattacatgc agcggccctc tacagagcag    120

cttttgaaac atccttttat aagggatcag ccaaatgaaa ggcaagttag aatccagctt    180

aaggatcata tagatcgtac caggaagaag agaggcgaga aaggtactaa gcctgttttt    240

gttttcatcc tttaaaattt ttatgtttag tttcttgcca acta                     284
```

<210> SEQ ID NO 241
<211> LENGTH: 172
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 241

```
gtgtcaggac ttgtgaactg tcccatttat cttgtccttt tcttcataga tgaaactgag     60

tatgagtaca gtgggagtga ggaagaagag gaggaagtgc ctgaacagga aggagagcca    120

aggtaaccac aaagccactg ttcagtatcc tgctttatga agggattaag tt            172
```

<210> SEQ ID NO 242
<211> LENGTH: 317
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 242

```
cttataggac agtgtgatcg gtgcacaccc ctgaaagccc tgctttttcc aacagttcca     60

ttgtgaacgt gcctggtgag tctactcttc gccgagattt cctgagactg cagcaggaga    120

acaaggaacg ttccgaggct cttcggagac aacagttact acaggagcaa cagctccggg    180
```

-continued agcaggaaga atataaaagg caactgctgg cagagagaca gaagcggatt gagcagcaga 240
aagaacagag gcgacggcta gaagaggtag caaaaggaaa atgtccaagt tggttggtct 300
tttctctttc tgcattt 317

<210> SEQ ID NO 243
<211> LENGTH: 249
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 243
ggcgggaaga tccctggtaa ttatacattt ttacttacgt agcaacaaag gagagagcgg 60
gaagctagaa ggcagcagga acgtgaacag cgaaggagag aacaagaaga aaagaggcgt 120
ctagaggagt tggagagaag gcgcaaagaa gaagaggaga ggagacgggc agaagaagaa 180
aagaggagag ttgaaagaga acaggttagt tcacagataa catagcaggc atacacttgt 240
gaagtttgt 249

<210> SEQ ID NO 244
<211> LENGTH: 175
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 244
cttttctttg ggataatttg attgctgggt gatttctgtg tgacaggagt atatcaggcg 60
acagctagaa gaggagcagc ggcacttgga agtccttcag cagcagctgc tccaggagca 120
ggccatgtta ctggtaaagc cccgcctctg tttcattctg tagcatcagg gctcc 175

<210> SEQ ID NO 245
<211> LENGTH: 315
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 245
cgagctctcc agtgtcccat agatttagtg ttatcctctc cctctccaag gagtgccgat 60
ggcgggagat ggaggagcac cggcaggcag agaggctcca gaggcagttg caacaagaac 120
aagcatatct cctgtctcta cagcatgacc ataggaggcc gcacccgcag cactcgcagc 180
agccgccacc accgcagcag gaaaggagca agccaagctt ccatgctccc gagcccaaag 240
cccactacga gcctgctgac cgagcgcgag aggtatcctc tttcctttgt cacttagaca 300
ttgccctgga aagtc 315

<210> SEQ ID NO 246
<211> LENGTH: 378
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 246

-continued tttatgcaga acgcattgaa tgttttgtgt tttgttttct tgtaaggtac agtggtccca 60
cctggcatct ctcaagaaca atgtttcccc tgtctcgcga tcccattcct tcagtgaccc 120
ttctcccaaa tttgcacacc accatcttcg ttctcaggac ccatgtccac cttcccgcag 180
tgaggtgctc agtcagagct ctgactctaa gtcagaggcg cctgacccta cccaaaaggc 240
ttggtctaga tcagacagtg acgaggtgcc tccaagggta aggagcagaa agacagatgt 300
gtgctgcttt tttcctttt gttatttttt tttaaagatt atttatttta attatgggta 360
tgcaacttga ccaaattt 378

<210> SEQ ID NO 247
<211> LENGTH: 207
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 247 tttttttcc ttttcatgtt ttcaataatt taattgctat attttctact taaaggttcc 60
tgtgagaaca acatctcgct cccctgttct gtcccgtcga gattccccac tgcagggcag 120
tgggcagcag aatagccagg caggacagag aaactccacc aggtaaaaga caagtgagca 180
ctgagaacag gccttctgtg cagtcta 207

<210> SEQ ID NO 248
<211> LENGTH: 245
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 248
gcatctagag atgacacatt agctgttctc tcttcttctt ttctaacagc agtattgagc 60
ccaggcttct gtgggagaga gtggagaagc tggtgcccag acctggcagt ggcagctcct 120
cagggtccag caactcagga tcccagcccg ggtctcaccc tgggtctcag agtggctccg 180
gggaacgctt cagagtgaga tgtaagctgc ctttcctttc ctttttccct gctaatgttt 240
tgagc 245

<210> SEQ ID NO 249
<211> LENGTH: 205
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 249
catatgttga tatgtgtctg tccatcttgt cccttttgaa cccaacagca tcatccaagt 60
ctgaaggctc tccatctcag cgcctggaaa atgcagtgaa aaaacctgaa gataaaaagg 120
aagttttcag acccctcaag cctgctgtaa ggattgtgca ggatcagttt tacttatttc 180
agacttgaat gagatctttc tatta 205

<210> SEQ ID NO 250
<211> LENGTH: 285
<212> TYPE: DNA
<213> ORGANISM: Artificial Sequence
<220> FEATURE:

-continued

<223> OTHER INFORMATION: Description of Artificial Sequence: Synthetic nucleotide construct

<400> SEQUENCE: 250
gtccctgctc ctgcttgcct tactctctct tttctgtcct ttgctttagg atctgaccgc 60
actggccaaa gagcttcgag cagtggaaga tgtacggcca cctcacaaag taacggacta 120
ctcctcatcc agtgaggagt cggggacgac ggatgaggag gacgacgatg tggagcagga 180
aggggctgac gagtccacct caggaccaga ggacaccaga gcagcgtcag tccccggtct 240
cttttagagc ggatgagagt attctctcag agcctgcttt ccact 285

<210> SEQ ID NO 251
<211> LENGTH: 244
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 251
agaagtgaat tgaaatgtgt atttttaatg ttcattttta aaatgccagt tgtattaata 60
acattgaaat ttacattgca gactcagtcc gctagtagca cactccagaa acacaaatct 120
tcctcctcct ttacaccttt tatagacccc agattactac agatttctcc atctagcgga 180
acaacagtga catctgtggg taagtacagt agcaacaaga aagcagctga caaatgggac 240
ttta 244

<210> SEQ ID NO 252
<211> LENGTH: 275
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 252
ggaggcaggc atagtgtgtg tgtgtacaga aaataatttc aaatatattg tgtttcagtg 60
ggattttcct gtgatgggat gagaccagaa gccataaggc aagatcctac ccggaaaggc 120
tcagtggtca atgtgaatcc taccaacact aggccacaga gtgacacccc ggagattcgt 180
aaatacaaga agaggtttaa ctctgagatt ctgtgtgctg ccttatgggg taggtgtcta 240
gccactactc caacactttc atttttgttc tgagt 275

<210> SEQ ID NO 253
<211> LENGTH: 235
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 253
gccaagcaca gcataaaatt gaggcctttc tgtgtccctg aaacaggagt gaatttgcta 60
gtgggtacag agagtggcct gatgctgctg gacagaagtg gccaagggaa ggtctatcct 120
cttatcaacc gaagacgatt tcaacaaatg gacgtacttg agggcttgaa tgtcttggtg 180
acaatatctg gtgagtgttt gttttgtaaa ccagaatatg tgacaccatc ttaac 235

<210> SEQ ID NO 254
<211> LENGTH: 195

-continued

<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 254
tactgacctg tgcttctctt gcttttttat ttgctgcttt tcagtaaaat atgaaagaat 60
caaatttctg gtgattgctt tgaagagttc tgtggaagtc tatgcgtggg caccaaagcc 120
atatcacaaa tttatggcct ttaaggtaac aacatcaagt gaatttaaaa gtagtattgg 180
ccattcaagc tgcaa 195

<210> SEQ ID NO 255
<211> LENGTH: 277
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 255
aaaaaaaaat gttctccttc atcttctcac ttctcttatg gcttctttgc agtcatttgg 60
agaattggta cataagccat tactggtgga tctcactgtt gaggaaggcc agaggttgaa 120
agtgatctat ggatcctgtg ctggattcca tgctgttgat gtggattcag gatcagtcta 180
tgacatttat ctaccaacac atgtaagaaa gaacccacac tctatggttg gttgactggc 240
ttcattttgt tttgactttc ttctttactc tgcttag 277

<210> SEQ ID NO 256
<211> LENGTH: 247
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 256
aataaccaca gacgttcttc cctgtacttt gttcctgttc tctagatcca gtgtagcatc 60
aaaccccatg caatcatcat cctccccaat acagatggaa tggagcttct ggtgtgctat 120
gaagatgagg gggtttatgt aaacacatat ggaaggatca ccaaggatgt agttctacag 180
tggggagaga tgcctacatc agtaggtatg gagaacttgg ggaaaggcag catttgtgaa 240
aatggag 247

<210> SEQ ID NO 257
<211> LENGTH: 245
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 257
gggctgtttc ctcatcttta acggtttgca atttttccct ccccaaaagc atatattcga 60
tccaatcaga caatgggctg gggagagaag gccatagaga tccgatctgt ggaaactggt 120
cacttggatg gtgtgttcat gcacaaaagg gctcaaagac taaaattctt gtgtgaacgc 180
aatgacaagg taatagttcc cttatggatt ctttttagtt gctctatctt ttaataatgg 240
cttgt 245

-continued

<210> SEQ ID NO 258
<211> LENGTH: 398
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 258
ggaaacctgg cgtactggct gtggcttctc tagcgggact cggcatgagg ctggcgcggc 60
tgcttcgcgg agccgccttg gccggcccgg gcccggggct gcgcgccgcc ggcttcagcc 120
gcagcttcag ctcggactcg ggctccagcc cggcgtccga gcgcggcgtt ccgggccagg 180
tggacttcta cgcgcgcttc tcgccgtccc cgctctccat gaagcagttc ctggacttcg 240
gtgagtgcgg cccgggacct tgggcctttt tgcgcggtcc cgggcgggga gctgcggccg 300
ctgccccagg ccgggtcggc gccggccagc tctcgcctga ggcgcacccc tcctcctcag 360
cgtttccgcc cccagcgcct taggtgcttc cttcctcc 398

<210> SEQ ID NO 259
<211> LENGTH: 237
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 259
gtttccttat ggcttttact tactgcttta cccatcatgt ttggtttcag gatcagtgaa 60
tgcttgtgaa aagacctcat ttatgtttct gcggcaagag ttgcctgtca gactggcaaa 120
tataatgaaa gaaataagtc tccttccaga taatcttctc aggacaccat ccgttcaatt 180
ggtacaaagc tggtaagatt ctcatcttgt gtttgcaatt tgatggagtt gtggact 237

<210> SEQ ID NO 260
<211> LENGTH: 188
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 260
atattgaact ttcagaatat aaaagaacaa acttatccta ttgatctgca ttttaggtat 60
atccagagtc ttcaggagct tcttgatttt aaggacaaaa gtgctgagga tgctaaagct 120
atttatgagt aagttcacta ttttgaccct attcttaaac ctattattag gtcacttggg 180
ggaaattg 188

<210> SEQ ID NO 261
<211> LENGTH: 192
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 261
aagtttactt gtcaaaatat ttggctgttt tgacagatgg gtttgtttag ctttacagat 60
actgtgatac ggatcagaaa ccgacacaat gatgtcattc ccacaatggc ccagggtgtg 120
attgaataca aggagagctt tggggtggat cctgtcacca gccagaatgt tcagtacttt 180

-continued ttggatcgat tc 192

<210> SEQ ID NO 262
<211> LENGTH: 265
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 262
agagcattag gtggtttagc ttattttgtt ggttttttc ctttttggat agctttattg 60
tttggtggaa aaggcaaagg aagtccatct catcgaaaac acattggaag cataaatcca 120
aactgcaatg tacttgaagt tattaaaggt aaatactgac atttctcctt gcaaaaaaag 180
atacaaaaat caaaattatt gttatttctt actattaaaa catctatttg tatcatgaga 240
taaaatggta ggcacaaatg catgg 265

<210> SEQ ID NO 263
<211> LENGTH: 215
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 263
taccattgcc atcttaatgc gtgaaagaga agtatattta ttaaatcctt ttttgttttg 60
ttttgattca cactagatgg ctatgaaaat gctaggcgtc tgtgtgattt gtattatatt 120
aactctcccg aactagaact tgaagaacta aatggtaagc ctgatgttgt ctttttctca 180
ataattagtg ctttgattac ttgataaggg ataag 215

<210> SEQ ID NO 264
<211> LENGTH: 184
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 264
gctttaagca catctctctg tactttcata tttttctctt ctgctctgta gcaaaatcac 60
caggacagcc aatacaagtg gtttatgtac catcccatct ctatcacatg gtgtttgaac 120
ttttcaaggt ttgtaaaata gtattacata acctttacca gtacttttct gaggttagga 180
atct 184

<210> SEQ ID NO 265
<211> LENGTH: 287
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 265
gattctttgg catatttcca tcaaatttta aaacttcaaa tagtgcatat gtacttgaaa 60
attacacttt ctcttttcta aaaagctgta tttttaatac aaccctaatg tatttcagaa 120
tgcaatgaga gccactatgg aacaccatgc caacagaggt gtttaccccc ctattcaagt 180

-continued

```
tcatgtcacg ctgggtaatg aggatttgac tgtgaaggta aatgtgttta atggtttgtt    240

ttcttttttt ttttttgta attgatgaac agacatgcaa aggtaac                    287


<210> SEQ ID NO 266
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 266

gttttgagga tttgggcata gagcacgatc cttttcttac cttagatgag tgaccgagga     60

ggtggcgttc ctttgaggaa aattgacaga cttttcaact acatgtattc aactgcacca    120

agacctcgtg ttgagacctc ccgcgcagtg cctctggtat gttatcaaga aataatgaag    180

tgtgtttctg tgaattgcct tccacat                                         207


<210> SEQ ID NO 267
<211> LENGTH: 233
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 267

agaaaagtat ttcagtgtgt gtctttctga atagaatttt gtttttctca tcaaacaggc     60

tggttttggt tatggattgc ccatatcacg tctttacgca caatacttcc aaggagacct    120

gaagctgtat tccctagagg gttacgggac agatgcagtt atctacatta aggtaatagc    180

tgtagtcttc ttgatttaat atttcttttg atgataagaa cagatgtcca tac           233


<210> SEQ ID NO 268
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 268

ctttttgcca ttgtctattt tctcaaataa tgaattctaa aaaatgccag acttaatagg     60

tcttaggttt ttctttttca ggctctgtca acagactcaa tagaaagact cccagtgtat    120

aacaaagctg cctggaagca ttacaacacc aaccacgagg ctgatgactg gtgcgtcccc    180

agcagagaac ccaaagacat gacgacgttc cgcagtgcct agacacactt gggacatcgg    240

aaaatccaaa tgtggctttt gtattaaatt tggaag                              276


<210> SEQ ID NO 269
<211> LENGTH: 305
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 269

aaattggagc aggtgtgtct ctccacctaa aaaaccacaa ctgagcttac accacagtat     60

tccggtgtct gtaaggtgga ggcggcagca cagtgcctgg cttcagggag aactcagaga    120

ggtattcagg attctctgcc acaataggcc ggatccgccc attctgttta taaaaatatt    180
```

ttgtgctgta ctcctgcagg tagtctgggt gctgaagggt gctccgaggt ggcaggctgt 240
ggttccagta gtcagggttg tcaaacgctt tcttggcctt ctctggcatt gacagtatgt 300
tgttc 305

<210> SEQ ID NO 270
<211> LENGTH: 306
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 270
gctgtggttc cagtagtcag ggttgtcaaa cgctttcttg gccttctctg gcattgacag 60
tatgttgttc ttcaggtact cagcttttcc caaggtgttg gcaaaggtgt tgaggtacag 120
tggctcattc acatactcat cctcggcctt gggtggacca ttggatgcat tgtgatattc 180
gggattatcc aatgcttgaa ggtctccatt ttttctccga gaaacaaaag ggttctcctc 240
cactggattc aggtattcta aaggaataaa aaaatatcag ctaacctcta gtttctggaa 300
aatatt 306

<210> SEQ ID NO 271
<211> LENGTH: 387
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 271
ggaagtgaac ttcgaatggc gatcgtttct gaataatcag ttcatacctt gtttgggttt 60
gtctcgcata ggagtcatgt aaccttcctc atccagctct cctcgtgggc tccgttctgg 120
ggcaaacacg gtggggtcag cactgtacct ctgggtgcta ctgtcctctt ggacatgggg 180
tgccactggc ttgcgtaggg tgccattaca gcaggagtca tcaaaaatct cagcagtagc 240
accctgtgcc acaggagctt ctggaattgt gctagttggg gctctgtagg gcacagacac 300
tccttgttca gcagcaaaac ctccatctcg gtatacaaac tggttctgtt aataagagaa 360
acatatgtgg agagaaggcg ttgttag 387

<210> SEQ ID NO 272
<211> LENGTH: 158
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 272
ggaaacatgg taagcaaaga ccgaaaatcc taaaagatga aggttgattg tgaaatactt 60
actcctgaca tgggggtgta ggcaggagga gggctgtgtc caatttcact ctaataggaa 120
agaaaaatgg aatgatggat ataataagag gcaatatg 158

<210> SEQ ID NO 273
<211> LENGTH: 196
<212> TYPE: DNA
<213> ORGANISM: Artificial Sequence
<220> FEATURE:
<223> OTHER INFORMATION: Description of Artificial Sequence: Synthetic -continued nucleotide construct

<400> SEQUENCE: 273
gtttgccatt ggcctagtct taaaggcata agtcaaatgt actcacctga ataactaggt 60
atctttgagg gtctcgagcc atccttgaaa actcagcagc cagttcctta aatttaggtc 120
tactgtcagc atcaatcatc caacctggaa atttacacag tgaaaatgtc actatattcg 180
taactagaaa ggagtt 196

<210> SEQ ID NO 274
<211> LENGTH: 271
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 274
ctattacttt actaagaatg atgatggtga taacattatt ttgcagtctt acatttgacc 60
atgaccatgt aaacgtcaat agtgcagatg ggaggctgag gcaaacgttc tcctttctct 120
aataaatcag ggatttctcg cgttggaatt ccatcatagg gttttcctcc aaaggtcatc 180
agttcccata tagtaactcc tatattggag aaaaaattct tacttaagca tattaacaac 240
atatgttgaa caaaccagca ctataccagt a 271

<210> SEQ ID NO 275
<211> LENGTH: 306
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 275
ctaagcttca ggcttattgg tttcttgtat aaaatataag gagataaaag gatattatac 60
tatattttca agcaagattg ctctcaaaaa gatacccacc tttcctccat cagcattgta 120
ctctttttca tctccttcca agagtctggc tagcccaaaa tctgtgattt tcacatggtt 180
tggagatttc actaagacat tacgggctgc caaatcccga tgaacgagtc gtctttcttc 240
caggtacatc attccctgaa aaatatcaag ttccttaatg atattcagtt aatgcccagg 300
ttttcc 306

<210> SEQ ID NO 276
<211> LENGTH: 308
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 276
aatatgaaaa ctgttccagg ttaggaaata ttaacctaaa aatgtaattt ccatagaaat 60
tgacaggcac ttaccttagc tatctggaca caccagttaa gcagcagttg tgatccaatg 120
ttatccttgt gctcgtggac atactccaac aggcagccat ggggcataag ttgagtaacc 180
agctggatgg ttgggctcag acacacaccc agcaaccgga ctaggtgtgg atgatccata 240
cttgccatga tcagagcttc ctgtaagaaa aaaatgcaat accatgattt caactcaaat 300
tttcttag 308

-continued

<210> SEQ ID NO 277
<211> LENGTH: 275
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 277
gcaggctatt tgataatgga gaaaaatgtg attgcctggg tgtctgtact tacatccatg 60
aactccacat ttgccttggg accagttgtc tcattaagaa tcttaatagc cacaggaatc 120
ttcacagttt ctccttcagg tacccaaata ccctttgggg aaaaaaattt acattaaata 180
tgacatctca acctattaag ttcttacaaa gtaacttaga agtttgatat tataacattc 240
aatcaacaaa tgtttattta gcacctgtta catgt 275

<210> SEQ ID NO 278
<211> LENGTH: 244
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 278
aactccattg gctattattt tctaaacatc taaaacaaaa cttaactaac gatatgcgtt 60 gtttttttact tactttataa accgttccaa aagcacctga gccaaggact tttaccctct 120
tcagctcagt ttctttcaaa atacgaagtt gagcttgatt gggtgctgtg ccactgggag 180
ttaatggttc caccaactgc aaagcggaaa gaagaaggtt atactttcag tccgatagtc 240
agtc 244

<210> SEQ ID NO 279
<211> LENGTH: 246
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 279
cctgatgaaa atccccaaac acatgaagag gagaaagaaa tacctcacct ctgtttccaa 60
gaatcttctc aaggctcttt tctttttgat gctcttcctt ctaacataaa cagcaaatgt 120
cagacccaca atgaccagaa tgaagagccc accaattact ccagctgcaa tcaggggagt 180
tctgacaacc agaatgagaa aaaaaaaaat aaaaagtatg aagagagaga agacagagga 240
agagaa 246

<210> SEQ ID NO 280
<211> LENGTH: 415
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 280
ggaaaggatt tgagcgacaa aatggaaaca tggtagatgt tacctagcat gttgtggtaa 60
agtggaatgg cccgtccatg ggtagtaaat gcagtcatga ctagtgggac cgttacacct 120
gcaggcaatt acagaacaga aaacatcatt ctccatccac agtgacatgc acacacatgc 180

-continued accagtgctc acacatggag ccttggagga agaacatggg aagcaagcac accaagtacc 240
tatccatcag gccgatgcag tcttcaatac ttgagcctat gcacctgcag aaaatgcaaa 300
tttaaaaaaa tacaagggga aaaaattagt catttaaaaa atcagtaaaa taaatattga 360
ttgtctcgaa ttcttataac tattagacta ttttggaaca caatgaattt caagc 415

<210> SEQ ID NO 281
<211> LENGTH: 255
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 281
gataacacat accaggtgag cccttggcca gcaagaatgc ttacccttgg gtgcagtttg 60
gatggcatgg gtggcactcc cgatctggat cagcatactt gaaaatgaaa ctgtttgccc 120
cctgtaagcc atctggacat ttttccacac agtttgggcc atctttaaaa tgagagcact 180
ttgtacagtt gtcaggaccc tgaaatgtga aaacgaaaaa aaaagaaaaa agaaaagtgg 240
tgtcatttcc tctgg 255

<210> SEQ ID NO 282
<211> LENGTH: 191
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 282
catacatgat actaaataag ccaacacacc acagatgtct tcaggcttac cggtccatgg 60
catgtgagga ggccatcttc catcttctca cactgggggt cacactccac acagatggag 120
ccattctcaa actcccgaaa ttcactgtga aaacatcagc cacatgagga ggtgtaagca 180
aacaagcgtc a 191

<210> SEQ ID NO 283
<211> LENGTH: 223
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 283
ccttcaaagc tcatgaggtg aaggcaaccc tagaagaagc cttacccatc atagaggtta 60
caagactcta tgcagatcct tcctctactg aagcggcgac acgacagaca ttggtctggc 120
ccaggtcccc aacagccatc actggaacac agatggttgc acaccattcc ttcagcagct 180
gtgaaacacc aaaatcaagg ggaaataaaa cagaggattg tgt 223

<210> SEQ ID NO 284
<211> LENGTH: 313
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 284

-continued

```
tgtttggtcc aaagaagaat gggaaaaaat ttaagtttct atgttttaaa tgtctgagta      60

atgtacttac tacaattttc agcttttctg ttgtcccgga ttactattct ctggttgatt     120

gtgctgaaga gtgttgtcca gttaatggta tgataataac acaggttgct gttgtcagta     180

atatagatgt ttcctgcgct gatttccttc agggactgga actgtagaga ggtgatgccc     240

tgttgcttga ggataagcaa ggacaggcca ctaaggaggg ggaagtgaga aaacggaacc     300

atgaaacgca ttc                                                        313


<210> SEQ ID NO 285
<211> LENGTH: 200
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 285

tcttgaaatc tgtgagccct gcagctttaa acatatccac ttacctatag agtactcttc      60

caccaatggt caccaggtta gaaaaaacac tgaagtcagt catgtttggt ggccatgact     120

gtatgttcag gaaacctaca agtgaagagt agaaaaaata aatcagaata tcattgtctt     180

agtattagtg ctgatttttc                                                 200


<210> SEQ ID NO 286
<211> LENGTH: 197
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 286

ttaaaaaaat tatattgttc atagcgcaac agttgcagtt taaaaaatta cctgttatct      60

ctctgactgt ccgaaagacg ttcagtttct ctgggtctat ggcttcaatt gcattgtaag     120

ggtccctaga aaatcaagaa gagatgtagc caaatttaaa ttttactaaa ggattgaaaa     180

tatgagaaat gtgacaa                                                    197


<210> SEQ ID NO 287
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 287

gaatctcttc agttttgtct acactttgta aaataacttg cacaaaaatt taatactgac      60

ccatgaatac cagtgactag aaagatcaaa ttcccattga tcttggtaca gtttatgaat     120

ttgtcaatgt tactggaatc cacagtctga gctgacatca atgatcctgt gccaatgcca     180

tcacaagctg tagaaacaag actcagagtt aggggattga gaaacttatt tttggc         236


<210> SEQ ID NO 288
<211> LENGTH: 237
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 288
```

-continued

```
taaaaacctt gttatatagg cccagttcta actaaataat ctgagctacc actcaccttt     60

tgggcaaatg tcagtgcaag gtttacacat tttaatccca ttttcttcta cttccatctt    120

ggaactaggg caggcacgca cacaagaact ggaatctacc acaaagttat ctgattaaaa    180

aaaaaaaaaa ggtaaaataa gcattaatgt taacattcag caaacaagct caaaaca       237


<210> SEQ ID NO 289
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 289

aaaattcttt tgatttcaaa taatgaccta attaatttgg ttattcttat tctgttactt     60

acgtggacat ttcttgacac agaatgctcc atatgtgtac tttgcattga aattgtgctc    120

cagttgaaag gtggttggat tgtagacaaa ggtttgggga cactgagtaa cacatgctcc    180

actgtcattg aaattcatgc aggcctgcaa cacagcaaat attactttca tttacaaata    240

aactcataat acttgttaat gaaacgctgc caaaac                              276


<210> SEQ ID NO 290
<211> LENGTH: 215
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 290

gaaggaaagg agagcaggat aataaaagag agaaatcaca gacatacaaa gcagtctgtg     60

tccttaggtc ctgagcagcc tccagcacat tctcgatggc agcagtcact gacgtaaggt    120

ccgtagcatc tgccgtcaca ttgttctgca cacaccgtcc ttgtcactgc agaagacaga    180

gataggacca tgatcaaagt ctgccaccag gagaa                               215


<210> SEQ ID NO 291
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 291

aattccttga ccacatcaaa cctgtgtgct ctcactgatg aacacttaca agtctggcaa     60

tgattttctg tgggtcccca gcaacggcca gtacaggact tatggcaacg tccacctgca    120

gaacacgaaa agggaaaaag gacatgcacg ttataatctt tcactc                   166


<210> SEQ ID NO 292
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 292

tcatcgccac atagggtaga acattttgag aaattaaaaa gaataattct acttacatcc     60
```

-continued

```
tgaactacca tttgttgaca caagagtcaa gttggaaggc catgggttcc gaacaatatc    120

ttgccaatga atggtgtctg cataacaaag gaatttgttc tggtctacat agactccacc    180

atttaggatt tctgtattaa aaaacaaata aacaaatttt ttgtcaaact gcttgttgat    240

gaaaag                                                               246


<210> SEQ ID NO 293
<211> LENGTH: 162
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 293

tgacagtaac cctacatata caattgcctt atattgataa tgaaagcata tttgccattt     60

tggatatatt ccttacctgt caagttcttt aatccaagtt cttgaagtcc aaagtttcca    120

tcttttctgt agtttaaaaa tattgccaag gcatatcgat cc                       162


<210> SEQ ID NO 294
<211> LENGTH: 158
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 294

catatcgatc ctcataaagt tttgtcccac gaataatgcg taaattctcc agaggcaggt     60

aacgaaactg attaagagcc actaacacgt agcctgtgac ttctcgaaca gactgaaaag    120

acacaaacag ttgcctgtgt tataaaacga atttgtca                           158


<210> SEQ ID NO 295
<211> LENGTH: 263
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 295

gacgccactg tccattcaca aagaagagaa agaaagccac agctttaccc gcaggaagga     60

gaggtcccgg ttgtgctcaa tgctggttat ctccaggttg cccatgacaa cctcacagtt    120

ttcatagtac ttgcgcaagg ctcggtactg ctgttccagg tcagagagag agctcagttt    180

attctccgtt cctgcacaca ctgcaaagac aagaagatac acgtgaaatt acataacctt    240

tatatgatat gcgcaatgat aat                                            263


<210> SEQ ID NO 296
<211> LENGTH: 215
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 296

gggatgggtg aagagggcag gggagccact cgaggcagcc ccgccggcgg ctgcaggttc     60

ggcgaccgga gtgccagaag gaacccacct gactgagaat cgctgggctg gacggtcccc    120

gccgccacga gaaggctcac ccagacccaa agtcctgtcg ccggcttcat tttttggaag    180
```

-continued tctcagatcc cgtgctgaca attacatgtc caaat 215

<210> SEQ ID NO 297
<211> LENGTH: 178
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 297
gaacaagaat ctacaggaat agccacatac agaatgccaa tttcttacct ttataagaca 60
gtcctcttct tgagatgaca gtaaaacatt ctctggcttt aagtcacggt gtataatacc 120
gttttcatga aggtactaca cagaaaggca ggcatgaccc tcagattcat gcagtaga 178

<210> SEQ ID NO 298
<211> LENGTH: 185
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 298
aactaaaaga aaggcagctg tcaaaagaat tgagggcttc ttttacctgc acagccaaga 60
gcatctggta aaaatagagc ttgcaggtag cttctttcag gcgtttattc cccaccactt 120
tgtcaaacag ctctccccct tccatcctga aacacaaagg caaggcaagg ggttcattcc 180
tgggg 185

<210> SEQ ID NO 299
<211> LENGTH: 167
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 299
ataaagcatt tgaatggaaa cagaaatttt taaaaagttt actacttaca attccaaaac 60
aatataataa tcttctgcat caaaaaagtt tttaatcttg atgatgcaag gctaagaaga 120
gggggagaaa aaagggaaag tagtgagaaa ctcccaagag gaaaacc 167

<210> SEQ ID NO 300
<211> LENGTH: 205
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 300
gaaaccacca atcacaaatg tatagtgaaa aaattaagtg catttatata agaaaataat 60
ttaccttcca agagtttttg acatgatgta ttcatctctt aatgccttag gataaactga 120
ctgatcatct acagtcagat caaaaaagac aaaaactaag gaagaaaaga gtagaaatgg 180
gtttcattaa tttattcaca agagg 205

<210> SEQ ID NO 301
<211> LENGTH: 257
<212> TYPE: DNA

-continued

<213> ORGANISM: Artificial Sequence
<220> FEATURE:
<223> OTHER INFORMATION: Description of Artificial Sequence: Synthetic nucleotide construct

<400> SEQUENCE: 301

```
attttcctcc tatgagagag tggaaaaaaa aaattccagt aaccataaga taataatatt     60

acctttattt ctgcttagtg acagtgcaat ttcagaattg ttattcaaag gacggcgttt    120

tcctttccct acaagctctg tatttacaaa ggttccattg ccactgtgat cttctatgta    180

tgcaatgtaa gagtttttag gacccacttc ctaaaataga gaacattttg tttcagactt    240

tgaatagcag agattta                                                   257
```

<210> SEQ ID NO 302
<211> LENGTH: 216
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 302

```
tgaccaaatt accagctctc ctagatacat gggtattcat tacctaccct gaaaatccga     60

aagtgtttct tgctgtatgt tcggtattta tctgttcttt tcagcagtgg ttcatcaaag    120

caatattcac agcttttgtc cctcccaaac cagtagttgt cattcacaca ttctgtaata    180

taaaagcatg catcagaggg ctgttgaatt tcatgt                              216
```

<210> SEQ ID NO 303
<211> LENGTH: 414
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 303

```
aagtgttttt ctgaacaaaa cgtgatacta tacaacaaag ggtcttacca agattggcaa     60

atccatcctg aagggcccat aatcgagccc agggggcagg ggtaggctcc tcaggttctt    120

ggtcctcagg ttcttggtcc tcaggaatag aatagagttc ctgagtggac actgtctcta    180

aggagctcag tgtcccagag ctggagtgag aggactggct ggagtttggc atcgtgctgg    240

tagaggagct ggatatgccc tgggactgtg aggaggagcc ttgggactgg gtaacgctgc    300

catggggctg tgaacaggca ctgctgccat gagactgctg agcctcaaca tccgactccc    360

gagacatcac gacctcaaaa agaaagtgtc caacaacaaa ggtgagtttc aagg          414
```

<210> SEQ ID NO 304
<211> LENGTH: 349
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 304

```
ttggggttag ctcaaggcag ctaagcaggt ccagcccaag aactaagtca agtgggccga     60

ggaggctctg agagtggccg gggccggcgt acattccctg gcatgggtga gaactgcggc    120

tgttctggac gcacattcat ctcatgcgag gtgctggggc ccaagttcat gtaggttgct    180

ggcagctgca cataatggtc cccaagcagt gcagacacta tctgctccac ctcccccact    240
```

-continued

```
agtactctga aggtgggtcg cactgctggg tctgcctccc agcattgctg catcacttgg    300

tacctgttgg gggaaaggga tgtcaggtta aggcaatttc cacccaagg               349
```

<210> SEQ ID NO 305
<211> LENGTH: 250
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 305

```
ggtgccaaag ccatgtggac tgtagggcag gtggggcctc accacatcag acttggtggt     60

aaatctatag gtctgcaggc tctccagcgc catccacttc acaggtaggc gagcgtggcg    120

atgctgttga acactatagt actccctgtc caggatgtcg cgggccaaac caaagtcagc    180

caccttgact gtgaatgact cgtccagcct taggggtagg gagaggatca cacttaggac    240

tggcccttac                                                           250
```

<210> SEQ ID NO 306
<211> LENGTH: 207
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 306

```
catgccctgt ccttttgctt caccccagct actctggact ctcacatgca gttccgcgca     60

gccaggtccc tgtgcacaaa cttctgctct gccaggtact ccatgctgcg ggctacctgc    120

aggccaaagc tgatgaggtc cttcacggtg gggttctggg ggcacaggtg ggttggtggg    180

caagggcaca gcagctcctt ctccagc                                        207
```

<210> SEQ ID NO 307
<211> LENGTH: 295
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 307

```
gggcacagca gctccttctc cagctgctgc ccagccccca acccagagcc agatgaacac     60

tgacccgctg aggtgagcgg atgaactgga gcaggtcacc gtggcacata tagggcagca    120

gcacatgggg caggccctca ggtggcaaca tgataccaat gagagccagc acattcgggt    180

ggttcaggcc acgcatgagc agcccctctc gcaggaaggc ctccacctgc tgcatctctg    240

tgatgcctgc agagcagcgc aagtcaggca cagggcaggg cgtcccttta taagg         295
```

<210> SEQ ID NO 308
<211> LENGTH: 204
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 308

```
ggagcttgta gggacagggg gtggctttag cttctcatgc ctccactatc tcaccaaggc     60
```

-continued

```
cacttctgta gtcagagccc gagtacagaa taggcagggg tgtggctcca gcagtctggt    120

ccagggatgc caggtcattc aggttgggag gaagaactgt ggaaagagaa tccttggtgg    180

cttggctttc caagctccta gggg                                           204
```

<210> SEQ ID NO 309
<211> LENGTH: 276
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 309

```
gttgggggta ggggctgatt aaaggtagga gcagagaact cacctagctg cttcctccgc     60

caccagtagc tgaagaccag tgcagtcgcc agtgcagcca caagcagcag caaaggcagc    120

aggataccaa ggagcgtgct ctgtgggacc ccatctggcc ctggccgcac cactctaccc    180

aggatatgac attcaccatc tacgcagacc tgggggcagg tggcaactca ggcccagcct    240

gtaggccctc tgcccgtgtt tcccagggag gtccag                              276
```

<210> SEQ ID NO 310
<211> LENGTH: 259
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 310

```
cccagcctgt aggccctctg cccgtgtttc ccagggaggt ccagctgggc tgcctacctg     60

caatggggca ccatcctggc caagctgcag ggatgggggc agggggcaga caaccatgtc    120

cccccggaac tcgtgctggc agctctcacc acccacggtc acgttgatac ccacacagtc    180

agccacagcg cccagcccaa tatactgcag agagggtcat gaggaccagc cagtaggctg    240

gcccctactt tcagatccc                                                 259
```

<210> SEQ ID NO 311
<211> LENGTH: 303
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 311

```
gcccctactt tcagatcccc aactgtccct gcccctatcc cttacactta cctcaaactt     60

aatggcatgc tcctcaggct tcagtggaac taggttggca ctgggtggat ggggtggggg    120

taggaagcga aagccaggca gtgtaaagcc agcagctcca tcccctcggg cactcagatt    180

ccctgccacc catccctggg ggtctcggac cacatattca ggaaggcggc acagctgctg    240

ctctggaagc tgcctctcac actgctggga ccaatatgag agtgattagc caggaacccc    300

acc                                                                  303
```

<210> SEQ ID NO 312
<211> LENGTH: 185
<212> TYPE: DNA
<213> ORGANISM: Artificial Sequence
<220> FEATURE:
<223> OTHER INFORMATION: Description of Artificial Sequence: Synthetic nucleotide construct -continued

<400> SEQUENCE: 312
ggaactcatc cagccttcct ccctcctggc cagcactcac tcaccctgct ttccactgcc 60
ctaagcccgt catggaatga cagcactaag tgccatgctg aagttagatg ctggccacag 120
atggtgatgt gggagttgct gtggaagagg gtagggtggt aggctttggg tgttctccaa 180
agctg 185

<210> SEQ ID NO 313
<211> LENGTH: 254
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 313
ggctctctca ttccccagag gccagagtgg gcaaagaggc agtgcttaca tgtagccaca 60
gttggggctg atgcttagca cgacagggtc ttctctgtac tggaaggtcc aggaaccagg 120
tacctgggca ccccccacct gcaggctaag ggggacactg gccaccgtgg ccccaggggg 180
tgtggcacat aaaagctgcc cctcactgac cctacaggaa caagagattg ggctcaaggt 240
taccctcttt gtga 254

<210> SEQ ID NO 314
<211> LENGTH: 235
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 314
ggtccccacc tggatagaac cctgcggcct cccatgcctg cctggtggta cttaccgtgc 60
tagcagacac tcagtcccat tgaccagcac agcccggctg gtgcctacag acagactctg 120
gccttcaaga gtgagacagg tgcctcctgc ccgtgggcca aagaggggtt gcactgctat 180
cagcactggc tcctaagagg acatagaggt ggcttaggca ggtcctccac tccaa 235

<210> SEQ ID NO 315
<211> LENGTH: 275
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 315
cccctccctt cccgtaccat gcactggcca agggcacaga cagggcaagg tagcctcacc 60
atgaaagaga agcctctcag cacggaggtg ccgtctaccc ggaagtgctt gcccggtggc 120
atgttagtca cggtgaggct gacgttggta ggccccactg cctgggtgcc caagggctcc 180
agttcacact caaactcctc tacaaagtct ttccggggca ctggtctggg gcaccagggg 240
aacccctgag gtcagccagg aattacacag gccta 275

<210> SEQ ID NO 316
<211> LENGTH: 291
<212> TYPE: DNA
<213> ORGANISM: Artificial Sequence
<220> FEATURE:
<223> OTHER INFORMATION: Description of Artificial Sequence: Synthetic -continued nucleotide construct

<400> SEQUENCE: 316
ggctgcttgg tttccccctt cagggaaagg gaggggaggg accagattgt acctgagttt 60
tgagctgtcc ttgggcagtg gccggcaggg actttggccc acagtgacct gatgggttcc 120
ctcaggcacc agaccagaag ggtgaaggta gaagttggag ccacacaggg tcagccttgt 180
actgcccctt agaggtccac tgtgggggtg gaactgaaat gggggaaaca gcctgagtcc 240
tcatgtgggg ttgggctctc tcagccccac ctgcttcccc aaagtctcct g 291

<210> SEQ ID NO 317
<211> LENGTH: 222
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 317
gtctgtgatc ccacaaccct ggccccaggc cctgcccctg cccacctcac ctggtcccca 60
gaggcaaaga gtaggtggtc cccaagacga ctgacatccc gctgcacggg ctgcccactg 120
tcacccagtg agaagttgga cacatacagc aagtagttta gtgacctgac cagctccacc 180
taggacaggt cagatgtgag caaaatgggg atggagacaa gg 222

<210> SEQ ID NO 318
<211> LENGTH: 286
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 318
ggatggagac aaggacccag ggctagggga ctgtggggat gaggacccac ctgcaggata 60
cgcccatcca ttgtgcccat gtgtgccact gtgacgttgt caaggcgtgt cacatacaat 120
gcagtgacct gtactggtcc caacagccca ttgaataggt ccacacgtga gaagctgcta 180
ctgaccagca gagggaagtg gcggcagctg gtgttggggc tgagggcttc caggccaggc 240
tgggaaaggt cagggaaggg aaggagtcag ggttcagcct tgtgcc 286

<210> SEQ ID NO 319
<211> LENGTH: 386
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 319
atgtgcatgc agctcacaag taagggcccc ttctttcagc ttaccgggtt ggggcaaaaa 60
ctgggcgact ggaagaagtc gaggcctcgc cggaggcctg gatggactgg ggattcacaa 120
cagcgctcca caccctcatc aattagtgtg tccagcaggt caatggggaa ggcacagacg 180
acagagttgg ggcccacgcc aggaccacca tccttgccag tcacaaagac cccaaatagt 240
acttcctggc cctcggcgat gctcagctca gtggcaagtt gggcacccac tggagcggag 300
tgggccaccc gcagcacagg gtagggctgt ccgccttctg gggccccccg gcgcctgcgt 360
tttggagcaa atctgcagtc gaggac 386

<210> SEQ ID NO 320
<211> LENGTH: 384
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 320
gcagcacagg gtagggctgt ccgccttctg gggcccccg gcgcctgcgt tttggagcaa 60
atctgcagtc gaggaccagc tcccgatagt cacccaactc tggctcagtg gcgctaagcc 120
gtgccaggcg tgtgtgcagg gcactaggat catctgtcac gctggccggc tgtacagtca 180
ggaagtatac gaaggctccc gtgtggaagc tgtgcacgta ttcaatactg taggagacaa 240
gatgcttggg cagcactgac aacgccacaa agcccggtgc gaatcccgag gcgtcagcct 300
tgagacgcct gatagacact gagcgtgggc tgaagctggc agccacggct gcgtccagtg 360
aggatgccac gtagaaatag gagg 384

<210> SEQ ID NO 321
<211> LENGTH: 404
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 321
agacactgag cgtgggctga agctggcagc cacggctgcg tccagtgagg atgccacgta 60
gaaataggag gcctggcctt gctcaaccac agttacacgg gtgcccaatg ggctggccac 120
acagtcgggg cagtcatcgg gccggttatg gtgggctgag aagaggcagg ctggcgctgc 180
cagatgcacg gctgtccctt ggggctctag gtcatgcagg aagcagcggc cctgcaggct 240
ggagccacaa ctgaccagcg caggcagcgc gggatccagc accagcacct ttgtgtctgt 300
gtcaccggga gggccgtggg gtcctgggcc acaggctgca cacgtctggc agccagggtc 360
tccagcaggg cccgtggcca ggctctggac agacttcagg tcag 404

<210> SEQ ID NO 322
<211> LENGTH: 466
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 322
ttgtgtctgt gtcaccggga gggccgtggg gtcctgggcc acaggctgca cacgtctggc 60
agccagggtc tccagcaggg cccgtggcca ggctctggac agacttcagg tcaggcccaa 120
gcacatgcag gcgattgcgt atggctacaa acacagcact ctcatttctg tcgccctcgt 180
aggtcaccat ggcctgtacc aggcctccgg cggagaagct gggcaccacg tacttcacgt 240
caaagtcgcg agaggccgcg tagggggtgc gcgggcactg ccagtcctcg cccgccgcgg 300
gcttggcagg caacagcagc agcaacagga aggactgagg cagcggcggg aggagctcca 360
tcgaggcgag ctgggaccct agaggatccc taccggcctg ggcctggacc tgggcgtggg 420
cctggctggg ggcccgactc gaggtctgga ctgggccaaa tttaag 466

<210> SEQ ID NO 323

-continued

<211> LENGTH: 313
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 323
gcacctctca tgtgatgtcc aggagttggg ggtgtggatg cttcctttta aacaggagga 60
gagctcagtg tggtccccga gtcaggctgg agaatctggg ctgtgctacc ggtttgcact 120
ccaatctcta tcagctttaa aagttctgct tcctcactgg agtacacggt ggtgtctgtg 180
tcatcggagt gatatccgga ctggtagccg cttgtctggt ttgagccttc agatgccaca 240
gactccctgc ttttgctggg caccattcca ctgcagaaga aatggcaaac aaaggagttg 300
gcagagagaa gac 313

<210> SEQ ID NO 324
<211> LENGTH: 213
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 324
ctagctagtg tttcatcctt tgtattattt ctaagactat ttttaaaaga cgtacttaca 60
tctgggatta cttttacttc tggttcttct aacgggatat cttcaaatgt ttttacactc 120
acaggccggc tctttcgctt actgttctgc agatactgac tgcaaaagaa caaatattta 180
tattttagtg gtggtatatt tgactgcaga tcg 213

<210> SEQ ID NO 325
<211> LENGTH: 245
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 325
gccttgaagt caccctcccc cgggggatgt taggccatat acagtacctg attcctgctg 60
tgttgtcata atggaatttg gggtcacata cttcctcctc ctccatacag gaaacaggtg 120
aggtaggcag agagagtcca gaatcctctt ccatgctcaa agtctctgat atcggaagaa 180
caatgtagtc tttgccatcc tgaaacaata aacacagaag actgttgtta tggcttcagt 240
tcttc 245

<210> SEQ ID NO 326
<211> LENGTH: 212
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 326
ccttgacatc taagtactct ttgtaggtgc ttcttggatg gaggtgacaa acctgctgag 60
cattagcttg caagagattt cccaaatgtt ccaccaactc tgaaaacgtg ggtctctgac 120
tgggctcccc gtgccagcag tccagcatgg tctggtacct agagaagcaa aacactgatt 180
tcattaaatg cctctttctt cctgaatgct ga 212

-continued

<210> SEQ ID NO 327
<211> LENGTH: 198
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 327
atttgcgagc aaagaaagag aacacaggaa tacttcttaa agtcttacat ttctggtgta 60
gtataatcag gggccctcat tctagttcct tctttcaatc gcctacaaaa ttcttcatca 120
atctttaccc caggatatgg agaagcacct agaataaaac agggaggaga cattctttga 180
tttgattttc tcttatag 198

<210> SEQ ID NO 328
<211> LENGTH: 207
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 328
atttccaaac ctgtgatctg aaaagatagc tgatttcccc tcaacctttc ttacctttcg 60
cgatgccaag aactccatgc ccttagccac ttggaagctg taacagatga gatgctccaa 120
ggtcaggaag tccttataca gatcttcagg agctgtccaa agaggcagga ggatggagat 180
cagtatttcc atgagttagt gtgatgt 207

<210> SEQ ID NO 329
<211> LENGTH: 266
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 329
acaccctatc accctgtctg ctctgacaag agcatgccat agcatgcagg aagcactagc 60
cagtaccttc ctcttcttct acatcactga gggacttctc ctccacaaat ccagagctgg 120
ctgagctctg gctactggtg atgctgtcca agcgccgttt cagatccaca gggattgctc 180
caacgtagtc tttcccttga cggaatcgtg cccctttggt ctataaaaaa gcaaaggaac 240
aaacaaactc cttgaataca aaatga 266

<210> SEQ ID NO 330
<211> LENGTH: 195
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 330
gtaccatttt gagtttccct tcattttata acatggccag agcaggatta ggagatgaca 60
taccttgtag gggacaaatt catttctctt gctcctcagg taagtggaca ggtttccaaa 120
tttgcagaat tccacaatca ccatgagtgg ccctgcaggc agcatgtcca ggaaggaaaa 180
tgggttttca ctcat 195

-continued

<210> SEQ ID NO 331
<211> LENGTH: 206
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 331
agaggcatgt taaaattggg tgaccaaaac cacccacagt tactcacctc ctggcttggt 60
acaggcacct agaaggttga ccacattgag atggtgacca atatgaatga ggatcttgag 120
ttcagacatg agagctcgat gctcactgtg tgttgctcct tctacaaata cagtacaaag 180
agggaaatca taggtatgga catttc 206

<210> SEQ ID NO 332
<211> LENGTH: 226
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 332
actgatacaa gccttgcaac atatttaaag actagataaa acagaaagat agatcaccac 60
ataattttgc ttttaccttt caacattttg actgctactg tcctgcaagt tgctgtcttg 120
tcaattccaa aggcatctgc ttcaatcact tggccaaagg caccacggcc aagaggctta 180
cctagagtca acaacaacag caacaagaaa acagacttgg attact 226

<210> SEQ ID NO 333
<211> LENGTH: 236
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 333
atggcctggt aaacacaata tcaaattaat agcaattgaa aatgcaccta gcttcagccg 60
gtctctgggg aattcccatt tgctggcatc ataaggcagt cgttcacaat gttcatccaa 120
tgggagttca tctggatcca tgacgatgga caagtagcct gtcttcagtt cccctccatt 180
ggcctggaaa gcatcaatcc ttccagtcat aaacacactg ttgtttggct gttgtt 236

<210> SEQ ID NO 334
<211> LENGTH: 214
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 334
tcattaatca tgaaaaccaa tgtgcatggg cagaagggaa attatttttt tacccgctta 60
acggtccgta ggatgatgac aagaagtagc cagaagaaca tggcaatcac cgccgtgcct 120
actagaataa tgatttccaa gttcgtcttt tcctgggcac ctggaaagac acaattgaat 180
gagtatcaac agttggaaac ttatactttt tgtt 214

<210> SEQ ID NO 335
<211> LENGTH: 246

-continued

<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 335
gctgcatagc attccatggt gtatatgtac cacatttttt tttatcccac tgaccttcta 60
ttatgaaaaa tgcctccact tttgcacagc caagaacact gcatgcctgg caggtgtaga 120
ggccttcgtc ctccttcctc actctgcgga tagtgaggtt ccggttccca tccttcaata 180
caatgcctaa cagaggaaga aaacgatcat tctcatttat gatgatgtag tctgtgaagt 240
ttttca 246

<210> SEQ ID NO 336
<211> LENGTH: 244
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 336
ctgggaaagt tctgcaaccc aagagtgata gccaaattct atttacctga gtcttctaca 60
agggtctcat tatctttaaa ccacatgatc tgtggagggg gattcccaga tgccgtgcat 120
gagacttcga tgctttcccc aatacttgtc gtctgattct ccaggtttcc tgtgatcgtg 180
ggtgccacac gctctagaca cacaaaaaga aaatcacaga acatggaatt ataacttttg 240
aaat 244

<210> SEQ ID NO 337
<211> LENGTH: 247
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 337
cattccaact gcctctgcac aatgatccag aattgtctcc ctacctagga ctgtgagctg 60
cctgaccacg caatgtcttt tcttggtctt cctgtcttga gcaaggcaga catagtctcc 120
ttggtcctgc aaggatgcat tcttaagctc catgatcaaa atgtcatttg tgctattaga 180
gaacatggtg gcattcaatt tccaaagagt atccaagttc ttgcaaacag gtgtgggcaa 240
ctctccc 247

<210> SEQ ID NO 338
<211> LENGTH: 262
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 338
gaacatggtg gcattcaatt tccaaagagt atccaagttc ttgcaaacag gtgtgggcaa 60
ctctcccaca tggattggca gaggctgtgg gccaagcttg taccatgtga ggttctcaaa 120
cgtagatctg tctgcagtgc accacaaaga cacgctctcc tgctcagtgg gctgcatgtc 180
aggttgcaaa gtaatttcag gaccccctaa aatgaagagg ccatagttat tgaatggtga 240

-continued

```
tttaacttgg tacagctcac ta                                           262


<210> SEQ ID NO 339
<211> LENGTH: 194
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 339

ctgtgtgagt gatccaaccc aaacctccag agaagagtac ttactggtca cgtggaagga     60

gatcaccctc tctcctctcc cgactttgtt gaccgcttca catttgtaca aagctgacac    120

atttgccgct tggataacaa gggtacttac agtctgtgcg gggaaaaaac aaatcccagg    180

ccataaacaa cgcg                                                      194


<210> SEQ ID NO 340
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 340

atgcaagatg gcaggaaagc aaagagcatg tggccttact cacctgggct cgttggcgca     60

ctcttcctcc aactgccaat accagtggat gtgatgcggg ggaggaatgg catagaccgt    120

acatgtcagc gtttgagtgg tgccgtactg gtaggaatcc acaggagaga ttagagattt    180

ctcaccaatc tggggtggga ctgaagatgg gaaaaacaac ttttgaattg tcagtcagct    240

ttgaag                                                               246


<210> SEQ ID NO 341
<211> LENGTH: 262
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 341

caatgtatca taataaatct tgggcagaga ggaaaattga atggactcac catacacaac     60

cagagagacc acatggctct gcttctcctt tgaaatggga ttggtaagga tgacagtgta    120

atttcctgtg tctctttcac tcacttccat aatcgtcagt acatgccccg ctttaattgt    180

gtgattggac tcaaggggta ttccattttt atacctatga aaaaaaattc tcaggaatta    240

gtatagtcaa aggatttgct ct                                             262


<210> SEQ ID NO 342
<211> LENGTH: 215
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 342

atttgctctc acacgaaatg atgctttgca tttatttcca gtagttacca ttttatttct     60

gggggtgggt aaccaaggta cttcgcaggg attctgacac gctcccccac cgtggcttcc    120

accagagatt ccatgccact tccaaaagca acaaaaggtt tttctggaag aaaataaaaa    180
```

-continued

```
aaaaaaaagg tcaacttact gtaaatggtc atttg                         215


<210> SEQ ID NO 343
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 343

tttaaattat ctcacttgtc aaggcacaga ataatttcca agaccatagc ttaccatgga     60

ccctgacaaa tgtgctgttc ttcttggtca tcagcccact ggatgctgca caggtgtaca    120

atccttggtc actccgggtt acaccatcta tagttaaggt gctcaaaaat ttcttcatct    180

cactcccaga ctgggttttt aggtctcggt ttacaagttt cttatgctga tgctgaaaaa    240

aagagttgac tgaacttcca aagcacagca tataacatta cccaataa                 288


<210> SEQ ID NO 344
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 344

ctggggctta ttatctaagt atttggaggt ctggctttga atcattagcg ttaccttcga     60

agaagggtat tcccagttga agtcaatccc cacatttagt tcagttcttg ctgtacaatt    120

taagacaagc ttttctccaa cagatagttc aattccatga gacggactca gaaccacatc    180

ataaatccta taccctagag caagtaaatt gaaaaaacag aacatgagag agcaaataag    240

cctata                                                               246


<210> SEQ ID NO 345
<211> LENGTH: 284
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 345

atctccaaga tcttaataca aggatatgtt attaatgata tggaaaggaa atgtcctctt     60

acctacaacg acaactatgt acataataga ctggtaactt tcatcattaa tttttgcttc    120

acagaagacc atgccagcat agctgatcat gtagctggga atagtaaagc ccttcttgct    180

gtcccaggaa attctgttac catcaggaac aaatctcttt tctgggtatc tctgggtaat    240

aaaaagacat atcaaatatt taatccagta ccaaaaatga gagc                     284


<210> SEQ ID NO 346
<211> LENGTH: 297
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 346

tcattgtgaa tattataaac aggttaccca tcttaatatt agcttaaaat tataaaaact     60
```

-continued taagagacga ttggaggaga tgcaacttac tgcacaaagt gacacgttga gatttgaaat 120
ggacccgaga catggaatca ccacagtttt gtttttgttc tcagtaatgt acacgactcc 180
atgttggtca ctaacagaag caataaatgg agatctgtaa tctagaagaa aatttagttt 240
tattaatgag ttaatagtat ttactagaaa agttggtcat ttttcaggtt cctaaac 297

<210> SEQ ID NO 347
<211> LENGTH: 296
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 347
aactggtaaa gagacgtggg aaatgaattt tatttcacca cttaccttga acatagacat 60
aaatgaccga ggccaagtca gtttcccggt agaagcactt gtaggctcca gtgtcatttc 120
cgatcacttt tggaattgtg agtgtcttac agaagaggcc atcgctgcac tcagtcacct 180
ccaccctttg ctcactgcca ctctgattat tgggccaaag ccagtccaag tccctctgtc 240
ccctgaaaaa ttaatttcag ggaggtatta atatgaagtg ccagactgtg aggcta 296

<210> SEQ ID NO 348
<211> LENGTH: 207
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 348
aattatttcc actcaataaa caatcagtta cttaacacaa gaaatctaga tctagaatga 60
atccttacct gcaagtaatt tgaagagttg tattagcctt aattgtaagt atgtcttttt 120
gtatgctgag cctgggcaga tcaagagaaa cactaggcaa acctagaaac aaattaaata 180
aatgaatgta gttgccactg agttaga 207

<210> SEQ ID NO 349
<211> LENGTH: 181
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 349
agatctggct ttcaggtcct ctccgccctc acccgacctg tctgccttcc tcctccagag 60
tgggctcctt acccacagag gcggcccggg tctccacgca gagccacagg gcgacggcca 120
gcagcacctt gctctgcatc ctgcacctcg agccgggcga aatgcccaga actcgggagc 180
c 181

<210> SEQ ID NO 350
<211> LENGTH: 290
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 350
ggcctgaacc cccaagtgct gggggtcttg tccgatgctg cttagtagct gttgtctgtg 60

-continued aagaaagtca cgcgggcaga cggggagcag tggtcctcct cgcttggctc cgacagctcc 120
ccatactcgc tgttgtaaaa cacctggcct cctcgggccc cccgctcagg ccgccgccgc 180
ctcccttggg agtcagggtg tgccctggtc acagccacat tctggccagg tcctttacag 240
ctgccaagac agggaaggtg gtgttagtaa gagaagaagg ctgggtggcg 290

<210> SEQ ID NO 351
<211> LENGTH: 265
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 351
ccttacgaat tcctgacgct gcctcccctg aggcggcccc agccctgagc cgagagcgca 60
gcccccaccc ttcatgtgaa gtaccacaga gcctttgtag gtcgttgggg tcatggggaa 120
ttcctcaaat gtcttcatcc tggaggaacc acgggtctca gcccctctgg ccaggcaccc 180
gggaaaggac acccagttgt aatacctgtg gggagaaatc agaaggtgct gaggaacgcg 240
ctgcagcaac cctcctcgaa cttct 265

<210> SEQ ID NO 352
<211> LENGTH: 245
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 352
acatggcttt ctcccaccct actcctggac ctgcaggaca gctgacctgg cggccaggct 60
gtggcgctgc aggcttggcg ggctgtcctc agcgtcagcc tgggcgatgt gtagggccat 120
ggtggacacc tgcgagaagc tgccctcttc tgagctctga gagctgcgcg gggccatgca 180
gacctcctct tcctcctggc gggaacagga gaggcagcca ggccagaaac caccagccac 240
tgccc 245

<210> SEQ ID NO 353
<211> LENGTH: 212
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 353
ggggccaaag gccatagtag aacagggtgg ggaaggggct cacttgcagg cccctgccct 60
ggagcaggtc ccccaggatc tccaccagct ccgagaatgc aggtctcgcc ttggggtctc 120
cggaccagca gttcagcatg atgcggcgtc tgcaggatca cgtgggctgc tggactgcat 180
gcaccccacc cccgtcccag gaccttcagt gc 212

<210> SEQ ID NO 354
<211> LENGTH: 243
<212> TYPE: DNA
<213> ORGANISM: Artificial Sequence
<220> FEATURE:
<223> OTHER INFORMATION: Description of Artificial Sequence: Synthetic nucleotide construct -continued

<400> SEQUENCE: 354
gacgcttgct gtccccaaaa cctgcagggc catggggagg ctcacatggc gggagtggcc 60
agctccgggg ccctcatcct tgtgccgtct ctcagccgct ggcagaactc ctcattgatc 120
tgcaccccag ggtacgggga ggcccctgac aacaggaagg ggaggtgggt ggggagcaag 180
cctcctgcgg ctcagcccag ccccccaagt caccccatcc tgtcccttcc ccatcaagtc 240
acc 243

<210> SEQ ID NO 355
<211> LENGTH: 293
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 355
ttcagaacga cctggcacac acctccaggt gcccagtccc ttactccagc aggggcggtc 60
atgtaacctg ccgccagtga cctcgcctcc tctccccacc ggcaccccat cctgcactca 120
cccagagaga agatctccca gagaagcacc ccaaaggacc acacgtcact ctgcgtggtg 180
tacaccttgt cgaagatgct ttcaggggcc atccacttca ggggcagccg ggcctgggga 240
gacagaggga agcttgtccc gtggtggatg gggagacgga gggaagcgtg tcc 293

<210> SEQ ID NO 356
<211> LENGTH: 252
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 356
ccaccccttc acctgttccg ccccacgttc cctctcctca atggcctgca ctcacactgc 60
ccttgcggac gtagtcgggg tctttgtaga tgtcccgggc aaggccaaag tcacagatct 120
tcaccacgtc gctttccgac agcagaatgt tccgagcagc caggtctctg tggatgcact 180
ggggtgcggg gaggcggcag gggggctgtc agtgcaggcc cctggggtaa tacccacacc 240
cgaaactcca gg 252

<210> SEQ ID NO 357
<211> LENGTH: 223
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 357
atgcaccctt ttcccgtctg aagggccttc gggggaagct cacctttcgg gaagccagga 60
actccatccc tctggccacc tggaagctgt agcagacaag atcttccatg gtcagcgggc 120
tcagccacag gtcctcagct acacagtgga gccaggtggg ctcaggaggc gcctcctccg 180
cggcctccat ctacccagcc ccagggaaca gctaacaagc atg 223

<210> SEQ ID NO 358
<211> LENGTH: 353
<212> TYPE: DNA
<213> ORGANISM: Artificial Sequence
<220> FEATURE:

-continued

<223> OTHER INFORMATION: Description of Artificial Sequence: Synthetic
      nucleotide construct

<400> SEQUENCE: 358
gcccgtcagg cactaggaaa agggaagagg ccaggctctc accttcttgg tctggagaag     60
cccgcctcgc tccgccctcg gtcttcgaga accgcgcgaa gaggaccctg tcgctgctcc    120
ccggccgcct ccgatccagc ctggcgagct ccaccatggc gcggaagcgt ccgcgctgct    180
cgggagactt ctcctgcgga tgcacgaagc tggctcgagg gcgcccagtc gtccgccgca    240
gaggcgcctc cattcccccg ccgcccgcgg cgccccgcag gccgcccgct caccgcgcag    300
gggctgaagg cgtcccgctt ggcgcgcagg aagttggaga ggttgccgta ctt           353

<210> SEQ ID NO 359
<211> LENGTH: 371
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 359
cggatgcacg aagctggctc gagggcgccc agtcgtccgc cgcagaggcg cctccattcc     60
cccgccgccc gcggcgcccc gcaggccgcc cgctcaccgc gcaggggctg aaggcgtccc    120
gcttggcgcg caggaagttg gagaggttgc cgtacttgca gaactccacg atcaccatga    180
gggggcctgc ggcgggaccg ggcggcggcc gtgcgttcgg aacccggggc gcgctgcggg    240
cgcgctccgc gtttgcaccc gcgccccctc ccgcccgcgg cgccccgcgc ccggggtctc    300
gccgtcccag cgggccgccc gctccgtacc ctgcggcttg gtgcacgccc cgaggaggtt    360
gaccacgttg a                                                         371

<210> SEQ ID NO 360
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 360
gaactccacg atcaccatga gggggcctgc ggcgggaccg ggcggcggcc gtgcgttcgg     60
aacccggggc gcgctgcggg cgcgctccgc gtttgcaccc gcgccccctc ccgcccgcgg    120
cgccccgcgc ccggggtctc gccgtcccag cgggccgccc gctccgtacc ctgcggcttg    180
gtgcacgccc cgaggaggtt gaccacgttg aggtggttgc cgatgtgaat gaggatcttg    240
agctccgaca tcagcgcgcg gtgctcgctg gccgtggcgc cctctggagg ggacacgggc    300
ctcacaccgg ccccgaccct ggcaggtccc cgttccccgc cacccggcgc ttttgggagg    360
gggagggtta ctaag                                                     375

<210> SEQ ID NO 361
<211> LENGTH: 194
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 361
gctgctcctc accagctagg ctgccccttc cgcccgctga ccccacacct ttcagcattt     60

-continued

```
tcacggccac ggtgtcacag ctgctgccct tgtggatgcc gaaagcggag gcttccacca    120

ccttcccgaa ggcgccgtag ccgagcactc tccctgtcgg ggcagggggc cagttgcagg    180

tgagctgtac gggg                                                      194


<210> SEQ ID NO 362
<211> LENGTH: 229
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 362

gggcaggagg tgtgggttgg gcaggctggt gctggcctca cccaggtgca gccgctctcg     60

ggggaattcc cactggctgg catcgtagga caggtattcg cattgctcct ccagaggcac    120

ctccccgggg tccatgatga tggacaggta gcccgtcttg atgtctgcgt gggccggctg    180

cggggagggg acagggagga gtggggcagc tcactgattt ggccatacc                229


<210> SEQ ID NO 363
<211> LENGTH: 228
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 363

ctggggacgg gaagggagtt gaggggtgca gcctgaggcc agaccttcca cggccacgct     60

ggcggaggag ttgacgcagc ccttggcgtt gcacacgctg cacagatagc gtcccgcatc    120

ctcctcgcgc acgcgctgga tgctcagctt ctggttggag tccgccaagt cgactcctgc    180

agggggtggg gtggaggtgc gggtccacct gggtttggga tcgtcggc                 228


<210> SEQ ID NO 364
<211> LENGTH: 263
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 364

gggtccacct gggtttggga tcgtcggcct cgcgggcctc cggacctgcc cttcgccagg     60

gccaccctcc ctaccagact tttcctccag cagcctctcg tctttgtacc acacgatgct    120

gggcgcgtgc gctccggcca ccaagcactg catctccagc gagtcgctca cgttcaccag    180

gaggtcggtc aagttctgcg tgagccgagg ggcttccagg gctgggggca ggggtcgaga    240

gggagctaag tggagctgca ctt                                            263


<210> SEQ ID NO 365
<211> LENGTH: 205
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 365

cccctcctg accctgtacc caggcctccc cgccctggtc tggtcactca ctggtcacat     60
```

-continued agaagtagat gagccgctca tcctggccca ccttgttgga gaccacacac ttgtacatgg 120
cagacacgtt ggcattctgg atcaccagct tgctcacagt ctgggagagc acaggcacaa 180
ggatccattt cctgcccaag ttctc 205

<210> SEQ ID NO 366
<211> LENGTH: 222
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 366
ccttctcctt ctccctgggc actcagcagc gcggctggcc tgtaccttat tctttccctc 60
cacaaactcg gtccaggtgt ccaggctctc gatggggttc acggcatcct gcgtggtcac 120
cgccctccag tcacggcact gtggcatgag gtcttgctgc tgccgccgcc ggctgccagg 180
accagaagag gcaagggcag gtcagggata caggcaggaa gg 222

<210> SEQ ID NO 367
<211> LENGTH: 309
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 367
ttcctcatgg ctgaggctgg gggctgtggc tgtgcagggg acctgaggct ggagctgtac 60
tcacagacta cgctgggcaa acatcttgca gggtgtccag ggccgccagt gccactggat 120
gctgagaggc aggggcaccc cgtaggccgt gcaggtgagg gcctggcggc tgtgacgcga 180
gtagatgctg gggaggaggg cctccttctc atgtatctgg gggggcactg tgggcacaca 240
gatggccggt cagctggcct ccaatgccag gccgcccacc cgtgcgctct cccgtccctg 300
acctaccat 309

<210> SEQ ID NO 368
<211> LENGTH: 294
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 368
cactgtgggc acacagatgg ccggtcagct ggcctccaat gccaggccgc ccacccgtgc 60
gctctcccgt ccctgaccta ccattcacca ccagctccag gctgatgttg cgcctcaggc 120
cagcagcgga gttccacagg gcgagggtgt aggtgcctgt gctggcctct gtcacctcct 180
tgagcaccag ggcatgtgga ctgtggcgcc cggacagtgc ctttccatcc ttgtacctgg 240
ccagggaagg gaggtcaggg cccatacaga tcccaccaca gccccaacct catg 294

<210> SEQ ID NO 369
<211> LENGTH: 215
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 369

-continued ctggacttgg aagggtatcg gcggggtcgg tggggagcca gggctgttac cactggaact 60
cgggcggggg gtacgctgcc agcttcacgg gcagcttcac cagctcgtct cctgccgtgg 120
cctccaggat gggtcctttg agccactcga cgctgatgaa gggattttct gccggacagg 180
agaagtcact gtaaatccag gactgacccg tcgtg 215

<210> SEQ ID NO 370
<211> LENGTH: 384
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 370
ctgagtgctc aagggcaccg tgagctctgg gcccaggccc acagggcaca aggaccctgg 60
tttcccaggc cataccatgc acaatgacct cggtgctctc ccgaaatcgc tggatgccgt 120
tgttggcctt gcacacatac gagcccaggt cgtgctggct gacgttgtgg atggtcagga 180
tgctggagag ttctgtgtgg gtctgctggg agcgtcgctc gggcacccac ttaccccgct 240
ctgcctgccc gcacccaggg aagccccgcg tcagcaggcg ggctcctgca cagctacccc 300
accgaaggca cacctcccag cccagccagc ggtggctccg gaagccctgg acccaggccc 360
tgagttttct ttgggtggaa cact 384

<210> SEQ ID NO 371
<211> LENGTH: 374
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 371
ggtcatccca caccacctcc tgcccgtctg gccacagcac cgagctttgc tggagggaca 60
aggccaccat cattgcccag ctgccccttg ctcctggcca gacaggcggc cgcctttccc 120
aggggtggga tgggagggtc ggatgctggg gttggggtgg ggccgtaccg agcgcagcgt 180
gacattgagg ccggggatgg acaccagaca gggcacccac atggcgtcct tcctgttgac 240
caagagcgtg tcaggcttgt tgatgaatgg ctgctcaaag tctatggaga gggagcaagc 300
tgttggggaa gggacgtggc ggccaggctg ggggagggct ccacggggct gggtggtgct 360
ggtcctgaac cagc 374

<210> SEQ ID NO 372
<211> LENGTH: 451
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 372
gccccgttct ctcctcctgc cagcccaggg tccacaggct gggggcggtg tgggccccag 60
ctgcccggga ccctgctcca gcctggcccg cctccaagtc tcacctctca cgaacacgta 120
ggagctggcg gccgtggtgc cctcgatgcg tgccttgatg tacttgtagt agcagacgta 180
gctgcctgtg tcgttggcat gtacctcgtg cagcagcaac accttgcagt agggcctggc 240
gtctgtgccc tcgcagtctc gcaccacccc cgtgtcctcg ctgtccttgt ctccggtggc 300

-continued

```
tggcgcctcc tgagctcctg gccaagccca ctcgaggggg tgctgtcccc tggcagagga    360

caggagtggt caggtgggcc ccagggcagc ccatggggac tgtccctgag aagcctccct    420

caggccgagc ctcaccaggt ttgtcttacc c                                   451


<210> SEQ ID NO 373
<211> LENGTH: 201
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 373

gggcttgtgc agcctctctg gcctgccagt gggagaggga cccagtacct gcaggagatg     60

gacaggctgt caccggtgtc gatgacgtgt gactcctccg tgatgttcaa ggtcgggggg    120

gtcatggagt agccactcac caggcctggg gtgggagaca gggtcagcgt ggtgctgggc    180

tgtgacttgg cacgacgttg a                                              201


<210> SEQ ID NO 374
<211> LENGTH: 301
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 374

ccccttcctc atcccgaggt cccgcgcccc aagcgccgtg ctcccctcag gcgtccgcgc     60

accagggcca ccgtgtcccc cgcccgtacc cggcggagcg gtctcagcgc ccgccccagg    120

tgcgcggtac cccctccccg gccagcccca cgctcgggcg ggtggcccgt tcgccgcgct    180

caccgtccag gagtcccagg cagagccaca gtcgcaggca cagcgcggcg ccccgctgca    240

tctccggccg ctgcgcgtgg gtccgacccg agcggccgcg gctcggggct gaaagtgtcc    300

g                                                                    301


<210> SEQ ID NO 375
<211> LENGTH: 313
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 375

ccagtattga tcgggagagc cggagcgagc tcttcgggga gcagcgatgc gaccctccgg     60

gacggccggg gcagcgctcc tggcgctgct ggctgcgctc tgcccggcga gtcgggctct    120

ggaggaaaag aaaggtaagg gcgtgtctcg ccggctcccg cgccgccccc ggatcgcgcc    180

ccggaccccg cagcccgccc aaccgcgcac cggcgcaccg gctcggcgcc cgcgcccccg    240

cccgtccttt cctgtttcct tgagatcagc tgcgccgccg accgggaccg cgggaggaac    300

gggacgtttc gtt                                                       313


<210> SEQ ID NO 376
<211> LENGTH: 255
<212> TYPE: DNA
<213> ORGANISM: Artificial Sequence
<220> FEATURE:
<223> OTHER INFORMATION: Description of Artificial Sequence: Synthetic
```

-continued nucleotide construct

<400> SEQUENCE: 376
ttctgcattt ctcagtattt catgtgatat ctgtcttttt cttccagttt gccaaggcac 60
gagtaacaag ctcacgcagt tgggcacttt tgaagatcat tttctcagcc tccagaggat 120
gttcaataac tgtgaggtgg tccttgggaa tttggaaatt acctatgtgc agaggaatta 180
tgatctttcc ttcttaaagg ttggtgactt tgattttcct acacaaataa aattggagaa 240
aatctaagtg gagaa 255

<210> SEQ ID NO 377
<211> LENGTH: 274
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 377
agttcctcaa aagagaaatc acgcatttat gttttctctt cttagaccat ccaggaggtg 60
gctggttatg tcctcattgc cctcaacaca gtggagcgaa ttcctttgga aaacctgcag 120
atcatcagag gaaatatgta ctacgaaaat tcctatgcct tagcagtctt atctaactat 180
gatgcaaata aaaccggact gaaggagctg cccatgagaa atttacaggg tgagaggctg 240
ggatgccaag gctgggggtt cataaatgca gaca 274

<210> SEQ ID NO 378
<211> LENGTH: 225
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 378
taaaggagct ggaaagagtg ctcaccgcag ttccattctc ccgcagaaat cctgcatggc 60
gccgtgcggt tcagcaacaa ccctgccctg tgcaacgtgg agagcatcca gtggcgggac 120
atagtcagca gtgactttct cagcaacatg tcgatggact tccagaacca cctgggcagc 180
tgtaagtgtc gcatacacac tatctctgcc tccagctcct atggg 225

<210> SEQ ID NO 379
<211> LENGTH: 172
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 379
gaaagggcgt catcagtttc tcatcatttc actgagatat gcatctatta cttttacatt 60
tcaggccaaa agtgtgatcc aagctgtccc aatgggagct gctggggtgc aggagaggag 120
aactgccaga aacgtaagtc agtgaacagc ctcagaccca tgtgtgaccg cc 172

<210> SEQ ID NO 380
<211> LENGTH: 241
<212> TYPE: DNA
<213> ORGANISM: Artificial Sequence
<220> FEATURE:
<223> OTHER INFORMATION: Description of Artificial Sequence: Synthetic
nucleotide construct -continued

<400> SEQUENCE: 380
ctaccctcac tcttcagctc acagggaacc tttgctcttt ttcagtgacc aaaatcatct 60
gtgcccagca gtgctccggg cgctgccgtg gcaagtcccc cagtgactgc tgccacaacc 120
agtgtgctgc aggctgcaca ggcccccggg agagcgactg cctggtaaga tgcccctcca 180
gcagcctccc tggagcaggc tggggctgca cccgccccac ccacaccagg acagaagact 240
t 241

<210> SEQ ID NO 381
<211> LENGTH: 235
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 381
gagtgtactt acctcacttg cccagcgtgt cctctctcct ccataggtct gccgcaaatt 60
ccgagacgaa gccacgtgca aggacacctg ccccccactc atgctctaca accccaccac 120
gtaccagatg gatgtgaacc ccgagggcaa atacagcttt ggtgccacct gcgtgaagaa 180
gtgtccccgt gagtcctcct ctgtgggccc tctaactggt caggcatcct tgtcc 235

<210> SEQ ID NO 382
<211> LENGTH: 254
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 382
ttccatcacc cctcaagagg acctggaccg cctgtgtgag gcccgagcac ctggtgccac 60
cgtcatcacc ttcctttcat gctctcttcc ccaggtaatt atgtggtgac agatcacggc 120
tcgtgcgtcc gagcctgtgg ggccgacagc tatgagatgg aggaagacgg cgtccgcaag 180
tgtaagaagt gcgaagggcc ttgccgcaaa ggtaggaagc ccgccggtgt gcggacgagg 240
cttgttctcg gctg 254

<210> SEQ ID NO 383
<211> LENGTH: 397
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 383
ttaatccaac aaatgtgaac ggaatacacg tctctcttat ctctgcagtg tgtaacggaa 60
taggtattgg tgaatttaaa gactcactct ccataaatgc tacgaatatt aaacacttca 120
aaaactgcac ctccatcagt ggcgatctcc acatcctgcc ggtggcattt agggggtgag 180
tcacaggttc agttgcttgt ataaagaaaa acaaaatctg cctttttaac tggtagagat 240
tggtgatcaa taatcaccct gttgtttgtt tcagtgactc cttcacacat actcctcctc 300
tggatccaca ggaactggat attctgaaaa ccgtaaagga aatcacaggt ttgagctgaa 360
ttatcacatg aatataaatg ggaaatcagt gttttag 397

-continued

<210> SEQ ID NO 384
<211> LENGTH: 181
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 384
aactcctacg tggtgtgtgt ctgaagtctt tcatctgcct tacagggttt ttgctgattc 60
aggcttggcc tgaaaacagg acggacctcc atgcctttga gaacctagaa atcatacgcg 120
gcaggaccaa gcaacagtaa gttgaccaca gccaaagcct ggtagattac atttgccttt 180
t 181

<210> SEQ ID NO 385
<211> LENGTH: 304
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 385
acattgtttt tataattttt caccacatga tttttcttct ctccaatgta gtggtcagtt 60
ttctcttgca gtcgtcagcc tgaacataac atccttggga ttacgctccc tcaaggagat 120
aagtgatgga gatgtgataa tttcaggaaa caaaaatttg tgctatgcaa atacaataaa 180
ctggaaaaaa ctgtttggga cctccggtca gaaaaccaaa attataagca acagaggtga 240
aaacagctgc agtaagtcac cgctttctgt ttagtttatg gagttggttc taatgggtcc 300
ttta 304

<210> SEQ ID NO 386
<211> LENGTH: 222
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 386
ccctgctctg tcactgactg ctgtgaccca ctctgtctcc gcagaggcca caggccaggt 60
ctgccatgcc ttgtgctccc ccgagggctg ctggggcccg gagcccaggg actgcgtctc 120
ttgccggaat gtcagccgag gcagggaatg cgtggacaag tgcaaccttc tggaggggta 180
ggaggttatt tctttaatcc ccttgcgttg atcaaaaata ag 222

<210> SEQ ID NO 387
<211> LENGTH: 176
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 387
atgtctcagg ggtgggctga cgggtttcct cttcctcctc tcagtgagcc aagggagttt 60
gtggagaact ctgagtgcat acagtgccac ccagagtgcc tgcctcaggc catgaacatc 120
acctgcacag gacgggtaag agccccttgc tgctatccac gtccatttca tgggaa 176

<210> SEQ ID NO 388

-continued

<211> LENGTH: 256
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 388
gaaaagaaag agacatgcat gaacattttt ctccaccttg gtgcagggac cagacaactg 60
tatccagtgt gcccactaca ttgacggccc ccactgcgtc aagacctgcc cggcaggagt 120
catgggagaa aacaacaccc tggtctggaa gtacgcagac gccggccatg tgtgccacct 180
gtgccatcca aactgcacct acgggtgagt ggaaagtgaa ggagaacaga acatttcctc 240
tcttgcaaat tcagag 256

<210> SEQ ID NO 389
<211> LENGTH: 163
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 389
gtttgccaaa tatagaaaga ggggatttag tcaagattta aattaaaaat gttagtggtc 60
atttttctaa tgtctttcta ttttttccca ggtcctaata aatcttcact gtctgacttt 120
agtctcccac taaaactgca tttcctttct acaatttcaa ttt 163

<210> SEQ ID NO 390
<211> LENGTH: 356
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 390
tgttacacca gggctcccca ggcctctcac atattgaaat gtacttgtcc atctttctcc 60
aggccaggaa atgagagtct caaagccatg ttattctgcc tttttaaact atcatcctgt 120
aatcaaagta atgatggcag cgtgtcccac cagagcggga gcccagctgc tcaggagtca 180
tgcttaggat ggatcccttc tcttctgccg tcagagtttc agctgggttg ggtggatgc 240 agccacctcc atgcctggcc ttctgcatct gtgatcatca cggcctcctc ctgccactga 300
gcctcatgcc ttcacgtgtc tgttcccccc gcttttcctt tctgccaccc ctgcac 356

<210> SEQ ID NO 391
<211> LENGTH: 161
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 391
aaaatctcca aaatatatgc caaagaagta gaatgagaaa aatgtatatt tctctttcac 60
ttcctacaga tgcactgggc caggtcttga aggctgtcca acgaatgggt aagtgttcac 120
agctctgtgt cacatggacc tcgtcaagaa tgaccacact g 161

<210> SEQ ID NO 392
<211> LENGTH: 252

-continued

<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 392
gaatctgtca gcaacctcac ccttccttgt tcctccacct cattccaggc ctaagatccc 60
gtccatcgcc actgggatgg tgggggccct cctcttgctg ctggtggtgg ccctggggat 120
cggcctcttc atgcgaaggc gccacatcgt tcggaagcgc acgctgcgga ggctgctgca 180
ggagagggag gtgagtgcca gtcctgggtg ggctcaggag ccctcgcacc ccgacaggaa 240
caagggccag cc 252

<210> SEQ ID NO 393
<211> LENGTH: 231
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 393
gagggctgag gtgacccttg tctctgtgtt cttgtccccc ccagcttgtg gagcctctta 60
cacccagtgg agaagctccc aaccaagctc tcttgaggat cttgaaggaa actgaattca 120
aaaagatcaa agtgctgggc tccggtgcgt tcggcacggt gtataaggta aggtccctgg 180
cacaggcctc tgggctgggc cgcagggcct ctcatggtct ggtggggagc c 231

<210> SEQ ID NO 394
<211> LENGTH: 203
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 394
cagcatgtgg caccatctca caattgccag ttaacgtctt ccttctctct ctgtcatagg 60
gactctggat cccagaaggt gagaaagtta aaattcccgt cgctatcaag gaattaagag 120
aagcaacatc tccgaaagcc aacaaggaaa tcctcgatgt gagtttctgc tttgctgtgt 180
gggggtccat ggctctgaac ctc 203

<210> SEQ ID NO 395
<211> LENGTH: 305
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 395
gggtccatgt gcccctcctt ctggccacca tgcgaagcca cactgacgtg cctctccctc 60
cctccaggaa gcctacgtga tggccagcgt ggacaacccc cacgtgtgcc gcctgctggg 120
catctgcctc acctccaccg tgcagctcat cacgcagctc atgcccttcg gctgcctcct 180
ggactatgtc cgggaacaca aagacaatat tggctcccag tacctgctca actggtgtgt 240
gcagatcgca aaggtaatca gggaagggag atacggggag gggagataag gagccaggat 300
cctca 305

-continued

<210> SEQ ID NO 396
<211> LENGTH: 246
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 396
ttcccatgat gatctgtccc tcacagcagg gtcttctctg tttcagggca tgaactactt 60
ggaggaccgt cgcttggtgc accgcgacct ggcagccagg aacgtactgg tgaaaacacc 120
gcagcatgtc aagatcacag attttgggct ggccaaactg ctgggtgcgg aagagaaaga 180
ataccatgca gaaggaggca aagtaaggag gtggctttag gtcagccagc attttcctga 240
caccag 246

<210> SEQ ID NO 397
<211> LENGTH: 186
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 397
aactttttcc aacagaggga aactaatagt tgtctcactg cctcatctct caccatccca 60
aggtgcctat caagtggatg gcattggaat caattttaca cagaatctat acccaccaga 120
gtgatgtctg gagctacggt gagtcataat cctgatgcta atgagtttgt actgaggcca 180
agctgg 186

<210> SEQ ID NO 398
<211> LENGTH: 176
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 398
ttgttcattc atgatcccac tgccttcttt tcttgcttca tcctctcagg ggtgactgtt 60
tgggagttga tgacctttgg atccaagcca tatgacggaa tccctgccag cgagatctcc 120
tccatcctgg agaaaggaga acgcctccct cagccaccca tatgtaccat cgatgt 176

<210> SEQ ID NO 399
<211> LENGTH: 165
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 399
ccatcgatgt ctacatgatc atggtcaagt gtgagtgact ggtgggtctg tccacactgc 60
ctagctgagc cttggtggct gctcttagcc aaacagctga ggcctttgca tccctggaga 120
aatgtcatca cattacttaa ggcaggcaca caaatccaga aacat 165

<210> SEQ ID NO 400
<211> LENGTH: 267
<212> TYPE: DNA
<213> ORGANISM: Artificial Sequence -continued
<220> FEATURE:
<223> OTHER INFORMATION: Description of Artificial Sequence: Synthetic
      nucleotide construct

<400> SEQUENCE: 400
gaatagcatc tctacgggcc attctaatag cctcaaaatc tctgcaccag ggggatgaaa 60
gaatgcattt gccaagtcct acagactcca acttctaccg tgccctgatg gatgaagaag 120
acatggacga cgtggtggat gccgacgagt acctcatccc acagcagggc ttcttcagca 180
gcccctccac gtcacggact cccctcctga gctctctggt atgaaatctc tgtctctctc 240
tctctctcaa gctgtgtcta ctcattt 267

<210> SEQ ID NO 401
<211> LENGTH: 164
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 401
cctgcattca ggaaaagtgg atgagatgtg gtacaagcat tccatgggca acttctctgt 60
ttctttttca gagtgcaacc agcaacaatt ccaccgtggc ttgcattgat agaaatgggg 120
tatgtatgaa caccttataa gccagaattt acagctctcc acta 164

<210> SEQ ID NO 402
<211> LENGTH: 193
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 402
ggcagccctg accggagtaa ccttccctca tttcctcctg cagctgcaaa gctgtcccat 60
caaggaagac agcttcttgc agcgatacag ctcagacccc acaggcgcct tgactgagga 120
cagcatagac gacaccttcc tcccagtgcc tggtgagtgg cttgtctgga aacagtcctg 180
ctcctcaacc tcc 193

<210> SEQ ID NO 403
<211> LENGTH: 272
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 403
ggtgctttgc tgattacttc acctctgatt tctttccact ttcagaatac ataaaccagt 60
ccgttcccaa aaggcccgct ggctctgtgc agaatcctgt ctatcacaat cagcctctga 120
accccgcgcc cagcagagac ccacactacc aggaccccca cagcactgca gtgggcaacc 180
ccgagtatct caacactgtc cagcccacct gtgtcaacag cacattcgac agccctgccc 240
actgggccca gaaaggcagc caccaaatta gc 272

<210> SEQ ID NO 404
<211> LENGTH: 275
<212> TYPE: DNA
<213> ORGANISM: Artificial Sequence
<220> FEATURE:

-continued

<223> OTHER INFORMATION: Description of Artificial Sequence: Synthetic
      nucleotide construct

<400> SEQUENCE: 404
ggtgttctcc gcaggatcag cttaaggcgg ctgctgaggc ctcaggctgt attcagctcc     60
gaggtgttct ggctgggcgg caggtgggaa tccaggtttt ctttgcacct ttccaggtcc    120
tggaagtatg ggtgagacag ggcactgtag gcagatattc ttttggctgg gttaaatgtc    180
aaacacttct gtaataaaga aaaaaataat tggttgatat acaatacatc aatgtaaata    240
atgtacttac agagttatcc ctttattcac tgtca                               275

<210> SEQ ID NO 405
<211> LENGTH: 160
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 405
ccatgtggct gtggcatgtg atgcctatag cagctactga actgatattt gtgcccacca     60
cccagtctgg gtagagcagg tgtctcactg gcacagtgca gacgagcttg acatcagaaa    120
aacttaccag aagtaggtct ttgcctagtt catcgatatc                          160

<210> SEQ ID NO 406
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 406
tcatcgatat ctgttacaaa cttctcaatt ggttgggcag attttgaatg aaaagcctgc     60
ctgggaaggg caacatctct aggccagtct tcttctcctg ggagtccaat cacgctacaa    120
aagaaccaca catggacata agcattagct actatgcaga agctgt                   166

<210> SEQ ID NO 407
<211> LENGTH: 173
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 407
taaatgtttt aatgctatgg acactggtgt aaaattataa ttattactta ctccaagatt     60
tttcctagtt gatcaacatc tgaacttcca cgaaaaagag gcctaaaaga ataaagatac    120
attttaaata agaaatgttc tcagattaca tttcaatcat atttgccatt atc          173

<210> SEQ ID NO 408
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 408
gactgtcatt caaaatagga aaaataagtt taataaaagg acagcactct ctcactcacc     60

-continued

```
actgaggtta gagccatctg gaaactatag atgcgggcaa ggccgaagtc agcgagtttt    120

atttgtccgc tgctggtcac cagaatgttc tgtggtttta gatcgcgatg cactactcgg    180

tgtgaatgaa gaaagtccag acctcggaga agctgaaaca tcatatccta ataaaattaa    240

aaaaagaaaa tcagtaaaca ctcaaaacgg aagttg                              276


<210> SEQ ID NO 409
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 409

agactataat agtcgactgc ctgataagac atgaagatga ttcttgatac ctttatggtt     60

tcagtgggca ctccaggctc tggaacttta tccaagtaag tggtcaagtc ttgatcgaca    120

tgttcaaaca ctaaagttag tttggtttct ctgtctgttc gtgacactgt gcacacatca    180

aacaacctag aagaaaaaac aaagaggtta agtaggtggc aataagcaaa gaagta        236


<210> SEQ ID NO 410
<211> LENGTH: 381
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 410

cctttctggg cctgaggatt cccggctcgg ccctccccgc gcgcgcgagg ccccagatgg     60

cgagggcgca gctccctggc tcacctgacc acgttggggt gctcgaaggt ctccaggtgc    120

ctcagcaccg ccacctcgcg gatggtggag agcggcatgc cctcctcgcc ggtctgcacc    180

cgcacgcgct tcaacgccac gaaacggcct ccgttcttca agtcgcgggc cttgaacacc    240

ttcccatagg cgccctcccc gatctccgcc acgcattcgt actgctggtc agcgcggcac    300

aggccgtcct tctccatgcc gcctggacgc cgcccgccgc ggcgccgctg gggcgggcgg    360

ggggtgcgct caactagctg g                                              381


<210> SEQ ID NO 411
<211> LENGTH: 373
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 411

tgaactgctc tcgccttgaa cctgttttgg cagataaacc tctcataatg aaggccccccg    60

ctgtgcttgc acctggcatc ctcgtgctcc tgtttacctt ggtgcagagg agcaatgggg    120

agtgtaaaga ggcactagca aagtccgaga tgaatgtgaa tatgaagtat cagcttccca    180

acttcaccgc ggaaacaccc atccagaatg tcattctaca tgagcatcac attttccttg    240

gtgccactaa ctacatttat gttttaaatg aggaagacct tcagaaggtt gctgagtaca    300

agactgggcc tgtgctggaa cacccagatt gtttcccatg tcaggactgc agcagcaaag    360

ccaatttatc agg                                                       373


<210> SEQ ID NO 412
```

-continued

<211> LENGTH: 377
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 412
cctgtgctgg aacacccaga ttgtttccca tgtcaggact gcagcagcaa agccaattta 60
tcaggaggtg tttggaaaga taacatcaac atggctctag ttgtcgacac ctactatgat 120
gatcaactca ttagctgtgg cagcgtcaac agagggacct gccagcgaca tgtctttccc 180
cacaatcata ctgctgacat acagtcggag gttcactgca tattctcccc acagatagaa 240
gagcccagcc agtgtcctga ctgtgtggtg agcgccctgg gagccaaagt cctttcatct 300
gtaaaggacc ggttcatcaa cttctttgta ggcaatacca taaattcttc ttatttccca 360
gatcatccat tgcattc 377

<210> SEQ ID NO 413
<211> LENGTH: 377
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 413
ggaccggttc atcaacttct ttgtaggcaa taccataaat tcttcttatt tcccagatca 60
tccattgcat tcgatatcag tgagaaggct aaaggaaacg aaagatggtt ttatgttttt 120
gacggaccag tcctacattg atgttttacc tgagttcaga gattcttacc ccattaagta 180
tgtccatgcc tttgaaagca acaattttat ttacttcttg acggtccaaa gggaaactct 240
agatgctcag acttttcaca caagaataat caggttctgt tccataaact ctggattgca 300
ttcctacatg gaaatgcctc tggagtgtat tctcacagaa aagagaaaaa agagatccac 360
aaagaaggaa gtgttta 377

<210> SEQ ID NO 414
<211> LENGTH: 210
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 414
tacatggaaa tgcctctgga gtgtattctc acagaaaaga gaaaaaagag atccacaaag 60
aaggaagtgt ttaatatact tcaggctgcg tatgtcagca agcctggggc ccagcttgct 120
agacaaatag gagccagcct gaatgatgac attcttttcg gggtgttcgc acaaagcaag 180
ccagattctg ccgaaccaat ggatcgatct 210

<210> SEQ ID NO 415
<211> LENGTH: 206
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 415
ggatcgatct gccatgtgtg cattccctat caaatatgtc aacgacttct tcaacaagat 60

-continued

```
cgtcaacaaa aacaatgtga gatgtctcca gcatttttac ggacccaatc atgagcactg    120

ctttaatagg gtaagtcaca tcagttcccc acttataaac tgtgaggtat aaattagaaa    180

taagtatcag tctcaaaaag aatatc                                         206
```

<210> SEQ ID NO 416
<211> LENGTH: 295
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 416

```
ttgttcatgt ctggattcac attaactcta tgaccatatt ttattccaga cacttctgag     60

aaattcatca ggctgtgaag cgcgccgtga tgaatatcga acagagttta ccacagcttt    120

gcagcgcgtt gacttattca tgggtcaatt cagcgaagtc ctcttaacat ctatatccac    180

cttcattaaa ggagacctca ccatagctaa tcttgggaca tcagagggtc gcttcatgca    240

ggtaagtgct ttctgagagt agctgtgtct gttctatctg gtattgtgca attaa         295
```

<210> SEQ ID NO 417
<211> LENGTH: 225
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 417

```
actgagcttg ttggaataag gatgttataa ctttttgct gtttaggttg tggtttctcg     60

atcaggacca tcaacccctc atgtgaattt tctcctggac tcccatccag tgtctccaga    120

agtgattgtg gagcatacat taaaccaaaa tggctacaca ctggttatca ctgggaagaa    180

ggtaagctgt tcccacaggg aatttccata gacgtggttt ttccc                    225
```

<210> SEQ ID NO 418
<211> LENGTH: 262
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 418

```
actagatacc cctctggaag ctctttccac cccttctctt cacagatcac gaagatccca     60

ttgaatggct tgggctgcag acatttccag tcctgcagtc aatgcctctc tgccccaccc    120

tttgttcagt gtggctggtg ccacgacaaa tgtgtgcgat cggaggaatg cctgagcggg    180

acatggactc aacagatctg tctgcctgca atctacaagg taggaatctc taacagctgg    240

catacatgtt tttgtttggt gt                                             262
```

<210> SEQ ID NO 419
<211> LENGTH: 295
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 419

-continued

```
tatacatttt gtttgttcgt tttccatata tgtgaaaaat tataatatat tgggtttttt      60

taaaagttct atgttgtcct tgtaggtttt cccaaatagt gcaccccttg aaggagggac     120

aaggctgacc atatgtggct gggactttgg atttcggagg aataataaat ttgatttaaa     180

gaaaactaga gttctccttg gaaatgagag ctgcaccttg actttaagtg agagcacgat     240

gaatacgtaa ggatcttaaa atgctttgct ggggtgtgct tggaaaatag gtttt          295
```

<210> SEQ ID NO 420
<211> LENGTH: 256
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 420

```
cagaaaattc cttggatttg tcatgtatta aactttgggt tttttttcca gattgaaatg      60

cacagttggt cctgccatga ataagcattt caatatgtcc ataattattt caaatggcca     120

cgggacaaca caatacagta cattctccta tgtggtaagg aagattctat cctatcatgt     180

ttgattttta cttaatctat ttaaattata agatgaacaa gttactttgt tttgttttta     240

tctcccctcc aggatc                                                     256
```

<210> SEQ ID NO 421
<211> LENGTH: 277
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 421

```
aaggaagatt ctatcctatc atgtttgatt tttacttaat ctatttaaat tataagatga      60

acaagttact ttgttttgtt tttatctccc ctccaggatc ctgtaataac aagtatttcg     120

ccgaaatacg gtcctatggc tggtggcact ttacttactt taactggaaa ttacctaaac     180

agtgggaatt ctagacacat ttcaattggt ggaaaaacat gtactttaaa aaggtgttgt     240

aaatttattt tttgttgcat ctgtcaattt gaattaa                              277
```

<210> SEQ ID NO 422
<211> LENGTH: 296
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 422

```
tatatccttt tgatttgtgg atataattct aaaatatgtg tatctctaat agctaaaatt      60

cacttcctta atttttttg ttcagtgtgt caaacagtat tcttgaatgt tataccccag     120

cccaaaccat ttcaactgag tttgctgtta aattgaaaat tgacttagcc aaccgagaga     180

caagcatctt cagttaccgt gaagatccca ttgtctatga aattcatcca accaaatctt     240

ttattaggta agtagaagct tctgatgggt ataagaaaac aatgaataca aggatg         296
```

<210> SEQ ID NO 423
<211> LENGTH: 266
<212> TYPE: DNA
<213> ORGANISM: Artificial Sequence
<220> FEATURE:

-continued

<223> OTHER INFORMATION: Description of Artificial Sequence: Synthetic nucleotide construct

<400> SEQUENCE: 423
gactgtgcct ctgacctgta atcagtgcag gtgattaaat tgaatccctc tcttacagta 60
cttggtggaa agaacctctc aacattgtca gttttctatt ttgctttgcc agtggtggga 120
gcacaataac aggtgttggg aaaaacctga attcagttag tgtcccgaga atggtcataa 180
atgtgcatga agcaggaagg aactttacag tggtaagtcc tttgagcaat ggttctactc 240
agagctctgc atctttgcct ctaacc 266

<210> SEQ ID NO 424
<211> LENGTH: 316
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 424
ttgccaagct gtattctgtt tacagtggat aattgtgtct ttctctaggc atgtcaacat 60
cgctctaatt cagagataat ctgttgtacc actccttccc tgcaacagct gaatctgcaa 120
ctccccctga aaaccaaagc ctttttcatg ttagatggga tcctttccaa atactttgat 180
ctcatttatg tacataatcc tgtgtttaag ccttttgaaa agccagtgat gatctcaatg 240
ggcaatgaaa atgtactgga aattaaggta agaaatgctt taaacactgt cttaaatcat 300
cagctcaaac ttaatt 316

<210> SEQ ID NO 425
<211> LENGTH: 257
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 425
gttagcattc ctgcagaact gtgaagtgtt aacaaccttt tttttttttt ttcctttcag 60
ggaaatgata ttgaccctga agcagttaaa ggtgaagtgt taaaagttgg aaataagagc 120
tgtgagaata tacacttaca ttctgaagcc gttttatgca cggtccccaa tgacctgctg 180
aaattgaaca gcgagctaaa tatagaggtg ggattcctgc attcctctca tgatgtaaat 240
aaggaagcca gtgtaat 257

<210> SEQ ID NO 426
<211> LENGTH: 262
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 426
aatatctatc atggctaaat gctgactttt ctttatttgt catttttagt ggaagcaagc 60
aatttcttca accgtccttg gaaaagtaat agttcaacca gatcagaatt tcacaggatt 120
gattgctggt gttgtctcaa tatcaacagc actgttatta ctacttgggt ttttcctgtg 180
gctgaaaaag agaaagcaaa ttaaaggtgc atttttgtta ctgttcattt ttagaagtta 240
ccttaagaac acagtcatta ca 262

-continued

<210> SEQ ID NO 427
<211> LENGTH: 246
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 427
ccatgatagc cgtctttaac aagctctttc tttctctctg ttttaagatc tgggcagtga 60
attagttcgc tacgatgcaa gagtacacac tcctcatttg gataggcttg taagtgcccg 120
aagtgtaagc ccaactacag aaatggtttc aaatgaatct gtagactacc gagctacttt 180
tccagaaggt atatttcagt ttattgttct gagaaatacc tatacatata cctcagtggg 240
ttgtga 246

<210> SEQ ID NO 428
<211> LENGTH: 335
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 428
cattaaatga ggttttactg ttgttcttta ataattttcc ttcatcttac agatcagttt 60
cctaattcat ctcagaacgg ttcatgccga caagtgcagt atcctctgac agacatgtcc 120
cccatcctaa ctagtgggga ctctgatata tccagtccat tactgcaaaa tactgtccac 180
attgacctca gtgctctaaa tccagagctg gtccaggcag tgcagcatgt agtgattggg 240
cccagtagcc tgattgtgca tttcaatgaa gtcataggaa gaggtaagta tttccactca 300
gctttttgtt aaatacgatt ttccagtaag cattt 335

<210> SEQ ID NO 429
<211> LENGTH: 188
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 429
atttcataat taaatgttac gcagtgctaa ccaagttctt tcttttgcac agggcatttt 60
ggttgtgtat atcatgggac tttgttggac aatgatggca agaaaattca ctgtgctgtg 120
aaatccttga acagtaagtg gcattttatt taaccatgga gtatactttt gtggtttgca 180
acctaata 188

<210> SEQ ID NO 430
<211> LENGTH: 282
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 430
gtattcactg ttccataatg aagttaatgt ctccaccact ggatttctca ggaatcactg 60
acataggaga agtttcccaa tttctgaccg agggaatcat catgaaagat tttagtcatc 120

-continued

```
ccaatgtcct ctcgctcctg ggaatctgcc tgcgaagtga agggtctccg ctggtggtcc    180

taccatacat gaaacatgga gatcttcgaa atttcattcg aaatgagact catgtaagtt    240

gactgccaag cttactaact ggcaaactag ctgtaagcca gc                       282
```

<210> SEQ ID NO 431
<211> LENGTH: 206
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 431

```
attagaacag tagatgctta gtttatgctt ttctaactct ctttgactgc agaatccaac     60

tgtaaaagat cttattggct ttggtcttca agtagccaaa ggcatgaaat atcttgcaag    120

caaaaagttt gtccacagag acttggctgc aagaaactgt atgtaagtat cagaatctct    180

gtgccacaat ccaaattaag tgacaa                                         206
```

<210> SEQ ID NO 432
<211> LENGTH: 265
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 432

```
attattctat ttcagccacg ggtaataatt tttgtccttt ctgtaggctg gatgaaaaat     60

tcacagtcaa ggttgctgat tttggtcttg ccagagacat gtatgataaa gaatactata    120

gtgtacacaa caaaacaggt gcaaagctgc cagtgaagtg gatggctttg gaaagtctgc    180

aaactcaaaa gtttaccacc aagtcagatg tggtaatgta ttggttatct ctgagtttct    240

cctcttttac tttcatatcc aactt                                          265
```

<210> SEQ ID NO 433
<211> LENGTH: 236
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 433

```
atggtcacat ctctcacctc atctgtcctg tttcttgttt tactagtggt cctttggcgt     60

gctcctctgg gagctgatga caagaggagc cccaccttat cctgacgtaa acacctttga    120

tataactgtt tacttgttgc aagggagaag actcctacaa cccgaatact gcccagaccc    180

cttgtaagta gtctttctgt acctcttacg ttctttactt ttacagaaat gcctgc        236
```

<210> SEQ ID NO 434
<211> LENGTH: 328
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 434

```
tttattttcc ttttgttgct actctcctga actctctcac tcatttgttt cagtggacag     60

gaaacgcacc atatccccct gcctggatgg gtgtttttgg agaagcacaa gcatatagac    120
```

-continued

```
taaaatcctc tgtttggaaa ccagcccgat tcaaggaggg ttctgatgca ctgcggtgaa    180

tttttggcaa tgagcgggcc agcagctcaa tagaggcgag aatctacaaa aaaaaaaaga    240

aaaaaaaaag aaaaaaaaag aaaaaagaaa aaaaaagaaa gaaagaaaaa gaaaaaacag    300

aaagaagaat gaaaatctgg gtggtata                                        328
```

<210> SEQ ID NO 435
<211> LENGTH: 267
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 435

```
ctatgaatgt tagtctgttc ttttggatag catgaagctt ttacttactt ggggaaagag     60

tggtctctca tctcttttct ttttgaggca ctctgccatt aatctcttca tggcttttgg    120

acagttactc cgtaccttac tgagatctgg agacaggtat cctcgtccca ccataaaaat    180

tatctggaga gagaaaaaaa agggaaataa ttcaaccttg tagataagtt gaaaaatata    240

cttcacactc attgaaaaca caataag                                         267
```

<210> SEQ ID NO 436
<211> LENGTH: 267
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 436

```
cttattttct acaactggag ccttgtatat agacggtaaa ataaacacca agacgtggta     60

aatatttacc tggtccctgt tgttgatgtt tgaataaggt aactgtccag tcatcaattc    120

atacagaaca attccaaatg catatacatc tgactgaaag ctgtatggat ttttatcttg    180

cattctgatg acttctggtg cctgttagaa catacaaaga aaaatattct tcacttcaat    240

tgaataaaga ctgaaaaaca acctact                                         267
```

<210> SEQ ID NO 437
<211> LENGTH: 226
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 437

```
tcagggccaa aaatttaatc agtggaaaaa tagcctcaat tcttaccatc cacaaaatgg     60

atccagacaa ctgttcaaac tgatgggacc cactccatcg agatttcact gtagctagac    120

caaaatcacc tatttttact gtgaggtctt catgaagaaa tatatctgag gtgtagtaag    180

taaaggaaaa cagtagatct cattttccta tcagagcaag cattat                    226
```

<210> SEQ ID NO 438
<211> LENGTH: 159
<212> TYPE: DNA
<213> ORGANISM: Artificial Sequence
<220> FEATURE:
<223> OTHER INFORMATION: Description of Artificial Sequence: Synthetic nucleotide construct -continued

<400> SEQUENCE: 438
tcaggatgtt ttcaaacttc gcagacaaat ttcaggaagg atactattac tcttgaggtc 60
tctgtggatg attgacttgg cgtgtaagta actgaaaaac aaaacatcat tttaacctga 120
gtagggctaa aggactctgg cctcgaaatc tacagaaca 159

<210> SEQ ID NO 439
<211> LENGTH: 294
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 439
aaaacatcct caatggtctt caaaaataat ttacaagaca tttaacgaat ggaacttact 60
ccatgccctg tgcagtctgt cgtgcaatat ctataagttt gatcatctca aatttggtct 120
caatgatatg gagatggtga tacaagctgg agccctcaca ccactgggta acaatagcca 180
gttgtggctt tgtggaatag cccatgaaga gtaggatatt cacatgtcgt gttttcctgt 240
acaaagaaat gtgacagtaa acattaaatg tcgacaaact ttagcaattc ttac 294

<210> SEQ ID NO 440
<211> LENGTH: 197
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 440
ctgggaacca ggagctaata aaaataactt ctttctctgg aaaagagtaa ttcacacaag 60
ctcacctgag tactcctact tcatttttga aggcttgtaa ctgctgaggt gtaggtgctg 120
tcacattcaa cattttcact gccacatcac ctaaaaggca attgttactc caagtgtcat 180
ttcaattttt aaaattt 197

<210> SEQ ID NO 441
<211> LENGTH: 267
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 441
atgcgaacag tgaatatttc ctttgatgat attttttaca aaataaaagt tgttaaacat 60
atcctattat gacttgtcac aatgtcacca cattacatac ttaccatgcc actttccctt 120
gtagactgtt ccaaatgatc cagatccaat tctttgtccc actgtaatct gcccatcagg 180
aatctcccaa tcatcactcg agtcccgtct accaagtgtt ttcttgataa aaacagtaaa 240
aaagtcaagt caagccaaac agaaaaa 267

<210> SEQ ID NO 442
<211> LENGTH: 242
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 442

-continued gacttctaag aagaaagaat tcagagaaaa aaagatatca tatactctta ccattcgatt 60
cctgtcttct gaggatgaag atgacttcct ttctcgctga ggtcctggag atttctgtaa 120
ggctttcacg ttagttagtg agccaggtaa tgaggcaggg ggggtagcag acaaacctgt 180
ggttgatcct aaattagtga aaagaaaaat gtatacatta aggaggagca agtatgttaa 240
tt 242

<210> SEQ ID NO 443
<211> LENGTH: 162
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 443
tataaaggaa ataagcagca aagcaattgc agtttccttg agtttttaaa aaaacctgaa 60
atcactactt acctccatca ccacgaaatc cttggtctct aatcaagtcc tacaaataaa 120
tagtaatgta tatttattcc aagcaagcat ataatcagag ag 162

<210> SEQ ID NO 444
<211> LENGTH: 333
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 444
ttatagcaga aaaataaaga tacatacttg gttttttttt agttctagca atgctggata 60
cttacatcaa tattgacagg ttctattgtg tttatatgca cattgggagc tgatgaggat 120
cggtctcgtt gcccaaattg atttcgatga tcttcatctg ctggtcggaa gggctgtgga 180
attggaatgg attttgaagg agacggactg gtgagaattt ggggcctgga aaaatgaagt 240
cattggaaga taagattcag agtaacgata taaaggtaat aatatttaaa aaggaagata 300
aaaggatttt cttgttttta tattctcaaa atc 333

<210> SEQ ID NO 445
<211> LENGTH: 206
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 445
gttcaagtag catgtcgccc aagagcagaa gtcaaaccat acccaataga gtccgaggcg 60
ggtgcggaag gggatgatcc agatgttagg gcagtctctg ctaaggacgc ctcttcctgt 120
ggtattgggt ggtgttcaaa gaacttggag acaaacagca aactgtgagg caaaacaaaa 180
caaacctaac ttgtgcaaaa cccaga 206

<210> SEQ ID NO 446
<211> LENGTH: 275
<212> TYPE: DNA
<213> ORGANISM: Artificial Sequence
<220> FEATURE:
<223> OTHER INFORMATION: Description of Artificial Sequence: Synthetic nucleotide construct -continued

<400> SEQUENCE: 446
catcgtagct tcacattaag aaaatttaag tgtaaaatgg taggtagaaa agagatattt 60
ttggattact tactcaagtt ggtcataatt aacacacatc agtggaactt ctgtactaca 120
acgctggtga aatttataac cacatgtttg acagcggaaa ccctggaaaa gcagctttcg 180
acaaaagtca caaaatgcta aggtgaaaaa cgtttttcgt acctgcaaag taaaaaatca 240
cagagatttc aaaaactcac aagaaaactt tctag 275

<210> SEQ ID NO 447
<211> LENGTH: 236
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 447
catatttcac attccctaaa taaaaattca ttcattaaaa tctaaacatt tttgacattt 60
caaaaaaaaa tgtaaagata catacaaagt tgtgtgttgt aagtggaaca ttctccaaca 120
cttccacatg caattcttct ccagtaagcc aggaaatatc agtgtcccaa ccaattggtt 180
tcttctctct gaaaaatgta gacacaagcc tttcttggtt attacaccta aaaata 236

<210> SEQ ID NO 448
<211> LENGTH: 214
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 448
acttcaaagt ttaatgtgtg attttctttt taaacaaaat ttcacgtcac atacaaacca 60
tacccatcct gaattctgta aacagcacag cactctggga ttagacctct catcatcagt 120
gctttcttta gactgtctcg gactgtaact ccacaccttg caggtaccta tggtatcata 180
aatatattga taagaggtaa agggagcaaa ttac 214

<210> SEQ ID NO 449
<211> LENGTH: 363
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 449
ctgtctgaaa aatacaaaga aacagcaaaa tggtgatatt aaaactgact caccactgtc 60
ctctgtttgt tgggcaggaa gactctaacg ataggttttt gtggtgactt ggggttgctc 120
cgtgccacat ctgtgggatt ttgaaaaact gaaagagatg aaggtagcac tgaaaggcta 180
gaagaggaag aagatgtaac ggtatccatt gatgcagagc tagaaacaga aaaatcagtt 240
ccgttcccca gagattccaa taactgttgt tctctttgtt ggagtgcatc tagcttgctg 300
gtgtattctt cataggccta taaaataaag cagacttata ttcaatccgg actttgtcct 360
gac 363

<210> SEQ ID NO 450
<211> LENGTH: 307
<212> TYPE: DNA

<213> ORGANISM: Artificial Sequence
<220> FEATURE:
<223> OTHER INFORMATION: Description of Artificial Sequence: Synthetic
nucleotide construct

<400> SEQUENCE: 450
taatcccacc tcctaaaata atcaagatta tcagtacaaa tgtttttata agttcatttt 60
ttttcttttc aaaattacta gatatgatac tcaaaagctt acctccagat atattgatgg 120
tggattatgc tccccaccaa atttgtccaa tagggcctct atatgttcct gtgtcaactt 180
aatcatttgt ttgatattcc acacctaaaa aatatttcaa aagaatttaa ataaaaatca 240
cttagtatat gaattagaaa tattttaaca tagacaacta catcacagta actgccagtg 300
ttcctca 307

<210> SEQ ID NO 451
<211> LENGTH: 289
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 451
cgccgcctct ttccaaaata aacaccagcc agccgccgag cccggagtcg ggagggcggc 60
agggtggcgc cagcactcac ctcctccgga atggcagggt ccgcagccga agaggccgcg 120
gcgccggcgc cggcgccggc ctcgggctcc atgtccccgt tgaacagagc ctggcccggc 180
tccgcgccgc caccaccgcc accgctcagc gccgccatct tataaccgag agccggggcc 240
cgagcggccg ctgtcgggcg gggaggggga agggaggcgg agagctggg 289

<210> SEQ ID NO 452
<211> LENGTH: 307
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 452
gaacatcttc aaaagagggt agcaagacgt gctcctaggg gaggctcagt gtggtctcgt 60
ctgcccaagc attttcagtc ttgcttggtc aatgacatcg agtaagtttt tggcatccac 120
agccagggcg tgagcagcag tcagcatttg ctttttgtac tcttgctgga ggctggtcat 180
gacatactgc tgggccagtt tcatcttgtt gatgagctca cccaggtcag agttcaatag 240
cttctgtgcc atctcaatct gaaagacaag agataggtca ggagaactgt tttcagtgat 300
ttttttt 307

<210> SEQ ID NO 453
<211> LENGTH: 176
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 453
agtgctgtca cagagggctg caaggggaag attgtgccct acctctcggt gggtgctggc 60
tggtaggagg ggaatggtct catccacagt ggccaataat gtcctcaggg ccaagccgac 120
ttcctaacag acaagaatca caaccaatat tagaacacac acaaaggatt tttatg 176

-continued

<210> SEQ ID NO 454
<211> LENGTH: 245
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 454
ggaaacaaga acatttttgc cagtacacaa aatgactcta ttttaccttc accataggga 60
catactcctc tggtggggct ggctggattt tactggacat ctcgatgaca gctttcacca 120
ggcccgtcac attctcgtac accttatcat tcgaccggtc caggttggca gtaggagggg 180
ggctgatttc ctggggctga agctgacaac acagaagcca gtcatttttc tgctctccag 240
cagat 245

<210> SEQ ID NO 455
<211> LENGTH: 196
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 455
aaatcctgca agcagaaggt gctgcacagg ctcagatgcc caccttgaca ccctcgttgt 60
agctgtcagc agggctgctg aggctggcaa ggcttcccag atgaccggga gctccagggc 120
gaggcggttt ctttggtgga gctgcaggat ctggtgagag agaatgattc ccattaagtc 180
atgtgcgtta agaaag 196

<210> SEQ ID NO 456
<211> LENGTH: 166
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 456
tcaaaacctg ctttcatcaa attaaactaa cttctttccg cccaattctt ttcttcttta 60
cctggtttac ccacaggctg atatatatgt tggtttccaa tctgtgggaa aagaaaagtt 120
cagtcaatgc actggtatat acacttgggc aatgacctct ctcacc 166

<210> SEQ ID NO 457
<211> LENGTH: 175
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 457
cgcacaggag aactggaaat caaatcctgc tgaaaactca ggcttaccgg accctgaaga 60
cttccatcct ccctgtcaat actgcctcga gagagtctca catcaggttt ctgaagaaat 120
taaaacaaaa tcaaaacaat ttcatttttg atttgaaaat ttttgacaga ttctg 175

<210> SEQ ID NO 458
<211> LENGTH: 235
<212> TYPE: DNA

-continued

<213> ORGANISM: Artificial Sequence
<220> FEATURE:
<223> OTHER INFORMATION: Description of Artificial Sequence: Synthetic
      nucleotide construct

<400> SEQUENCE: 458
ctaacagggc ttaaaaagtc aaagaagcct ttcagaaaca caattaccag aaatctttcc 60
tctttttcca gccagcgctg atcttcttcc atttcctgtt gctgtcggat tagacgctct 120
tccatcagat gggttggcaa cacttgccca atccctcgca ggtccaatac tgtagagtcc 180
tggaagaagg gttgaaaaca gcatattcag tctcataagt ctattcctat gctct 235

<210> SEQ ID NO 459
<211> LENGTH: 255
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 459
gcccagcttt gccatgcttt ataagttaac aaactgaagc ccaagacacc cgatttacct 60
ccacattggg ctgccacatt gctatctcct gaggtctatg attccatgaa tctgtttggt 120
ccaaaagaga tgcctgacct ggatagatgc tgccagccat ggctgtgatt ccatgtgaac 180
cagggtagcc agaaacctgt gaatgagtaa ggaggcaagg taatgttcaa ctataacatc 240
tgcacagttc tgctt 255

<210> SEQ ID NO 460
<211> LENGTH: 196
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 460
ctaccccaaa agcgctaaat aataaaataa cacagtttat atctgtaatg actggcatac 60
ctggtaatga ttggtttgta ccatgtgctg tgggctggga taaaatcctt cgctggacct 120
cggactggga taacccggtc tgctgggctg taaaatcaag agagcatcat atgaatgaac 180
cttttgattt tgacaa 196

<210> SEQ ID NO 461
<211> LENGTH: 206
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 461
tcttgaaagt tagtaagagt aaccccaaag ttggggtggg gactgtagct accttgggcg 60
gtgcttcatc agaccctccg gagtcccagg acactgtggc ctgtcttctg gactccatcc 120
tcatgcgctc ttcttgctga gccttctctt cctccaggat tgtgctagag agacaacaca 180
ttgtcttagg ggagctgaca acccag 206

<210> SEQ ID NO 462
<211> LENGTH: 184
<212> TYPE: DNA
<213> ORGANISM: Artificial Sequence -continued
<220> FEATURE:
<223> OTHER INFORMATION: Description of Artificial Sequence: Synthetic
nucleotide construct

<400> SEQUENCE: 462
gcacctgaac aagcaatgga tgttttaaat ataaaaacag aagtattcaa aaggtggcaa 60
aggagtaatt ctctctttcg gggcagggtt gattaggaag ccttcctgaa gcaggtaaca 120
tctgagctgg gttctgaaaa ctgaataaaa gtttataggt ggcaaaggtc aggaaaggga 180
tttc 184

<210> SEQ ID NO 463
<211> LENGTH: 306
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 463
gagaagcagc ataatctgcc cccaccccca ggccctctct cccgccaact cctacctgag 60
ctgagcttta agttcagtaa acctgggccg cctgctgggg tcataggccc agcatttcgt 120
cataaggctg tagagggtag gaggacaatt tggaggcatt ggtaatcttt ccccattttc 180
aattcgaccg attacatcat tgttcttcac tccttgaaaa ggcttcacac catgcatcag 240
tatctcccac atacacacac ctgtcaagtg ggaatgaaaa cacaacagtg agctcagtat 300
gaagaa 306

<210> SEQ ID NO 464
<211> LENGTH: 247
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 464
gaaggcaaat caacctacat attccaaaaa gagataattt ttttttgtat aacatatgaa 60
atataatttt taaagaatac aaaacttttta agagtactca ccaaacatcc atacgtcact 120
agctgaggta aaacgtcgaa aattgattga ctctggagcc atccatttaa taggcaattt 180
tcctttggaa gctagaagat taattttaga aaataaattt tccttgttat ctgcttaaga 240
atctaac 247

<210> SEQ ID NO 465
<211> LENGTH: 218
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 465
aatacgttaa agattccaag cctatttctt aggtactact ctgatttctt acctttgtag 60
taagtactat cttccatata tcgggataat ccaaagtctc ctaattttac acaatcattt 120
gaggacacca gaacattccg agcagcaatg tccctgataa agaagaattt gagacaataa 180
gacttaaaat aagaaaaaca aacatacaag ctcatata 218

<210> SEQ ID NO 466

-continued

<211> LENGTH: 226
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 466
gatcactact tttcagaagg gaacttaaca gctttatgac tgtatcttac ctgtgtacaa 60
atcttttgct ctctagatat gcaagagctg tactaagctg ataggcatac aggatcaaag 120
atgctagatc caaactgtat ttccttactt gcaaaaatga cctcagcttt tggaacaatg 180
accaaaagaa aaaaaaaaaa aaaagaatta gtggcagtga atcgaa 226

<210> SEQ ID NO 467
<211> LENGTH: 185
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 467
tagtctatga gctccatcag ggcagggact gtgtgtgtca tgctcacctc tgcattcctg 60
gggtctgggc agcatcaaca ttaggatcac ttatatatct gcaccaattc cagtgcaaag 120
atgtgtaatg gcctaagtac caaagtataa agtaaatgca catcaatcta cctttacaca 180
taaaa 185

<210> SEQ ID NO 468
<211> LENGTH: 186
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 468
gatttcacag atagaaagtc aaatggagtt ccacagaaat ttctagacac ttacaggctt 60
cttgaagaaa tttctctctc acgctgtccg aagtacagtt tttacatgtt ttaattgcaa 120
ccgccaaagc tggattctcc tgtgttaggg aaattataga atcacacaca catgcaaaaa 180
ggtttg 186

<210> SEQ ID NO 469
<211> LENGTH: 166
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 469
gaggcatctg tcaagtctga gcaagaacaa aatcagaagt ttacttactt gagggcatgg 60
tgtaagtatc ttcttcatct ataatctcag cataatcatc tgtttctgca ggaaaagaaa 120
cagatatgtt gaaagaggtt aaacatctga cctcctggta tttcat 166

<210> SEQ ID NO 470
<211> LENGTH: 156
<212> TYPE: DNA
<213> ORGANISM: Artificial Sequence
<220> FEATURE:
<223> OTHER INFORMATION: Description of Artificial Sequence: Synthetic -continued nucleotide construct

<400> SEQUENCE: 470
tctatgatcg tcttacccca tgagagtgct tttcgaggtc tgctacctag agccccttac 60
ctgacacaga gacggcgtgt gtccgcatgc cttgcttttc gctgttggcc aacctgtgac 120
agacaagagc aaagctgtaa gccctgcaat ttcccc 156

<210> SEQ ID NO 471
<211> LENGTH: 166
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 471
aatttcctta aactttccaa caaaacaaaa taacagtaca aaaaaagcag tacttacttt 60
ggtattgatg gcaaagcccg ttcaccttct gcggggaaaa agaaaagaga tgcataaggc 120
tcttttcact ccttttgaaa agatggtgcc tagaatcagg gaggaa 166

<210> SEQ ID NO 472
<211> LENGTH: 216
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 472
ttggtagaag cgcaattggg aatgctcaga aacagcacct cacctttctg aggtctgatg 60
ataaatgact gcgaggttcc attcaccagc cggcagtacc catctattag gtcagccata 120
ttctccgcaa tggttaggga tggtgccgtc actgtcagag gctaacggag aaaagatcaa 180
gaaaacagac ttcattgttc ttcccagtaa gcaaag 216

<210> SEQ ID NO 473
<211> LENGTH: 246
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 473
acatccctat ttaaccattt tcccttaatg atgaacgtaa cagttcctta cctcgggtgc 60
acctgctatt tttagttgta gcattccttt tctgtccttg tcttcactgt ttgaatactg 120
aatggtttgc acttgagtga agtcagcaag atgtgtgggc tataaaaagg aaaggtaaaa 180
tctttagact acggataaaa aactcatttc acagagtctg taaatgttct gtgaaatcct 240
cgttgt 246

<210> SEQ ID NO 474
<211> LENGTH: 163
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 474
tctttgtgta acgccaagtt cccgaaaggt cagagcagac ttacattgca gcccttgtcc 60

-continued gttaggtaac tgattccttc ttctgggccg attgccagtt ccactgaaat aatccagctt 120
gacttttgaa ggtgaaacaa gtgagaacag aggtggcaga agg 163

<210> SEQ ID NO 475
<211> LENGTH: 246
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 475
agaaaaagta aaatcaaact agcccactat ttcccatatt cccatactta caccaagagc 60
acacttgaag cattccttat caaatctgta gactggagac aggatctcaa agaatttcag 120
aatactttct tctctattaa ggttggcaaa ttgtctaaat gtttgttgga tcagttttct 180
tagtgttttg gcctgcatga caaaattacc aaaacatctt gtaaaaatca gcaatgagta 240
aagacc 246

<210> SEQ ID NO 476
<211> LENGTH: 167
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 476
ctggggaaaa ggtcttggca taattttgtt attttattat gataaaggag actctaatta 60
ccttgacaga atccagtaaa ctcttaggaa aaaatcgctt taaaccaaca tcttttctga 120
aatataaaaa gaagcgtatt aacaaataac accaccaaat caattaa 167

<210> SEQ ID NO 477
<211> LENGTH: 227
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 477
agaaatagca gtgtttcaga atcagtattt aattttaaaa taaactaaga atttagttct 60
gcatatttgc aggtatagat tgtaagtaca atacttactc taatacttca tagttagact 120
tcttttctag tgcattgccc cgcatctccc agtatgatcg cctaaaatca gggaagacat 180
acatttatat gtatatataa ggaatgtttg tgttgttaag tgataaa 227

<210> SEQ ID NO 478
<211> LENGTH: 195
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 478
aaataggatt caaagaaaca aacaaaaaag tatatgaaag cagtctctaa tacctgttga 60
tagaagaaat tcaaagttgg cttatcttca gtaaactggt ttagaaatcc ttttggcaaa 120
taacgaattc tcaattcata tctaaaaata attcacaaaa cagaacaatt agaaatcagt 180

-continued

```
cattttctca attta                                                     195


<210> SEQ ID NO 479
<211> LENGTH: 368
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 479

gttgtaatga caagcagtgt gaaaattaaa catatacatt tgttatcttg tgcatgtttt     60

taaaaagcaa aagaaatcaa gtgtgcatca caccaaagca ggtttgtatc ttacttccac    120

tcctctggtg ggtgagcaag ctcatacttc tccctcacac tggagacgcc catatccacg    180

tgaagccagt gaacctcctc tgaccgcagg tgactgaggc ggaatccata gcaggccaca    240

tgctttactt tgtgactgtc cactatcttc tgaatgatgc cctaaaacat accccccaca    300

agaatgactg ttataaactg aaaaaaaaaa aaaaaaaaaa aaaaaccaaa acaaaacaaa    360

aacaaaac                                                             368


<210> SEQ ID NO 480
<211> LENGTH: 358
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 480

catacatgcc attacatttt aacctaaata aacattaaag atgtctcatg gaaaaacgta     60

cttaccctga catcagtagc atctccatgc ctgataatac tggcccaggt ggttggctca    120

ctattgcttt caaaataatg aaagaccttt aatactcgct ccattgcacc aggagaacgt    180

tccataccag tacccaggtg agtcttagta ctcgaatttg gtgtgtgatt caagttgggg    240

tcaaggtaag cagctgccat tattttgcta gatgctaggt atctgtcata ttctgttaaa    300

agaacaaaat aattttttgt gtataatact tgaaatctac caattacaat gtgatatg      358


<210> SEQ ID NO 481
<211> LENGTH: 193
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 481

cccagctatt cgggaggctg aggcagggca attgcttgaa cctgggaggc agaggttgca     60

gtcagccgag atcatgccac tccactccag cctggcagcc tgggtgacac agcaagactc    120

tgtctcaaaa aaaaacaaaa aaaaaagact aagcattaca taatcatgta gtacaatcac    180

atgccacaca agg                                                       193


<210> SEQ ID NO 482
<211> LENGTH: 325
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 482
```

-continued

```
ccgctgcaca gaaggagccc gcccagcccc cgacccgcgc cccgcgcccg gcgccccgca     60

ctcactcgga ccgcggctcg gcgccgtgaa gcgaaggcag acgacgacgg ggcggcgctg    120

ggcgacagca gccgcgcttc ctcccacgcc tcacgccgcg ggctcacagt ggtccgggac    180

cggcggcggc ggcggcggcg cgggctcgcg ccctcgaggc cgtgctgcgt cggcgcgggc    240

ccgcgcgcgt gcgcggcagc cggctgaggc gcgcgtcctc tctcggcagc gcacgcccga    300

cccggtctca gtccggagtt cccgc                                          325
```

<210> SEQ ID NO 483
<211> LENGTH: 177
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 483

```
gttttctgtt gcagttcgtg ccctcgtgag gctggcatgc aggatggcag gacagcccgg     60

ccacatgccc catggaggga gttccaacaa cctctgccac accctggggc ctgtgcatcc    120

tcctgaccca caggtaagcc ccttaccttt gtctgcagca cactgaagag ttcccaa       177
```

<210> SEQ ID NO 484
<211> LENGTH: 285
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 484

```
ccttagaggg tgctgttggg gtgctgggcc tctaggggtc gtccccaggc ctctgctgca     60

gcctggctgc tcacggaggc cctctgtccc ccgttccaga ggcatcccaa cacgctgtct    120

tttcgctgct cgctggcgga cttccagatc gaaaagaaga taggccgagg acagttcagc    180

gaggtgtaca aggccacctg cctgctggac aggaagacag tggctctgaa gaaggtgcag    240

gtgagctgac aacccgtggg gtcaaacctg catctcggga ggtgg                    285
```

<210> SEQ ID NO 485
<211> LENGTH: 195
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 485

```
cactggacac agattgtaac cactctattt ctctttttcc tcccgcccaa gatctttgag     60

atgatggacg ccaaggcgag gcaggactgt gtcaaggaga tcggcctctt gaaggtgagc    120

accctgggcc gagcgggagc tttgcctcct cggggaggtt ctggggccgc ggctgggcca    180

catcatgtcc atcac                                                     195
```

<210> SEQ ID NO 486
<211> LENGTH: 226
<212> TYPE: DNA
<213> ORGANISM: Artificial Sequence
<220> FEATURE:
<223> OTHER INFORMATION: Description of Artificial Sequence: Synthetic
nucleotide construct -continued

<400> SEQUENCE: 486
gtcccgtctt cacttggtgc ccccttccct ctttccctcc tcatgcagca actgaaccac 60
ccaaatatca tcaagtattt ggactcgttt atcgaagaca acgagctgaa cattgtgctg 120
gagttggctg acgcagggga cctctcgcag atgatcaagg tgagcgcctg gcggggtggg 180
ggtgctgggg gctgcgcaga tctggagcca aaggtggcag tcttcc 226

<210> SEQ ID NO 487
<211> LENGTH: 272
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 487
actggggaaa ggacagaggc agtgccctgt ggccacccac ctccaagccc gctcacccgg 60
gcctatccct ctgcttgtct cccccactgc agtactttaa gaagcagaag cggctcatcc 120
cggagaggac agtatggaag tactttgtgc agctgtgcag cgccgtggag cacatgcatt 180
cacgccgggt gatgcaccga ggtacgtgcc acccgccagg agccgcccgg agccacctgg 240
agcccaggaa gacacttcct catggctcct cc 272

<210> SEQ ID NO 488
<211> LENGTH: 235
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 488
cacctacccc aagcctccta ccccacacca atctccttct cctcgccctg cagacatcaa 60
gcctgccaac gtgttcatca cagccacggg cgtcgtgaag ctcggtgacc ttggtctggg 120
ccgcttcttc agctctgaga ccaccgcagc ccactcccta ggtaaggggg acctgtctgt 180
gccccagcag cccccagcgg tcctggtgac catgcaggga gacgcaaaca ttctc 235

<210> SEQ ID NO 489
<211> LENGTH: 185
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 489
ccctacatgg agcataagca gccccgcccc ttgctgtgtt gcagtgggga cgccctacta 60
catgtcaccg gagaggatcc atgagaacgg ctacaacttc aagtccgaca tctggtccct 120
gggctgtctg ctgtacgagg tgagtctctg tccgtggctc agcagcattt ggtgggacat 180
gcatg 185

<210> SEQ ID NO 490
<211> LENGTH: 233
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 490

-continued

```
cttctgagcc ttgaggccga aagcttatct tcgttgttcc cgtcccttgc agatggcagc     60

cctccagagc cccttctatg gagataagat gaatctcttc tccctgtgcc agaagatcga    120

gcagtgtgac taccccccac tccccgggga gcactactcc gagaaggtga gtttgcagga    180

gccggaggcc tcgccagccc caggaggcca ccgaggctta tgagggccgc tcc           233
```

```
<210> SEQ ID NO 491
<211> LENGTH: 204
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 491

cctcagtaag actgctttct tgagaataac acaccattct ctcccctgca gttacgagaa     60

ctggtcagca tgtgcatctg ccctgacccc caccagagac ctgacatcgg atacgtgcac    120

caggtggcca agcagatgca catctggatg tccagcacct gagcgtggat gcaccgtgcc    180

ttatcaaagc cagcaccact ttgc                                           204
```

```
<210> SEQ ID NO 492
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 492

taggcttggg acctgattgc ttattttaac aaagtcactt tgagagcccc actcaccagc     60

caatatagca ctggcagagg ttttcatggg atgtcgcttg tttgatgagc agctcaactt    120

gcgttggaac atccaaagtg tcatcatgag agaagtcccg acctagcaca ggaggaacaa    180

aaacatttca ctctcttcct ggcaatc                                        207
```

```
<210> SEQ ID NO 493
<211> LENGTH: 176
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 493

gtgtgctcag attttatgtc ccttttaagt aaacacatga cacactcacc agtgagctta     60

tctcgaaccc tgttaataat ctggatagct ttcttattta gggcctctgg tttcaccaaa    120

ccgtctccaa ctggaataca caaaagtaga aataactgta agaatgggag caatac        176
```

```
<210> SEQ ID NO 494
<211> LENGTH: 177
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 494

ttaatgagct agtcactggt gcggttcctc agaggctgaa cttactgaaa gaatgaatag     60

attctggcac tgtggtcccc gttttcttat gggctggctc tccaagttcc acaccgtcca    120
```

-continued

```
aaatttctat gggaaaagaa atcaattaac agaaaattca aacaccaaaa agccact       177


<210> SEQ ID NO 495
<211> LENGTH: 177
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 495

gcacaagggg gagagccttt gcgacctccc gtggatgcac ctaccgactg actggccagc     60

agagtaggaa tccgtcctcg ttcgggatcg cttgttgcct ttggtatttg ctagggagag    120

aaataaagag tattgaaaca tgcttcaaat tttgacttga aagaaacttg gttattt       177


<210> SEQ ID NO 496
<211> LENGTH: 250
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 496

ggattacagg tgtgagccac tgagctcagc tcccaggcac ttgatgatac tcactgtcca     60

tcagcctcca gttcagcaag gggtcataga caaaggcttc cagcacggcc atgacactgt    120

ccttgtgctc tcgcagcacc tccatcactg tgtggcatgt gattctgtag ttgccatcca    180

ggcctgtaac ctagaaatgg gacagagcca ctcaccacag gagttactaa ctctccaccc    240

aaagcaagcc                                                           250


<210> SEQ ID NO 497
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 497

cctgatccca tttggaagca gctcgttccc gatatccact cacctccata gcattggtca     60

acattcttgt tagtctaaat ggaatcttct ctggaaactt ctctcgggtc atagcaacct    120

acagaataat aaatgggaaa agccaaatca atgtttattt tcttta                   166


<210> SEQ ID NO 498
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 498

agtgatcacc cgggaagatg aggttggggt tctagaacat gtgttcacct caaagcagtc     60

cccaaagtca atgtgcagga tcttcccact cagacggtcc agcatcaggt tggatgggtg    120

tctttgagaa acagaagaca gatcagggag ggatcaacag agataa                   166


<210> SEQ ID NO 499
<211> LENGTH: 188
<212> TYPE: DNA
<213> ORGANISM: Artificial Sequence
```

-continued

<220> FEATURE:
<223> OTHER INFORMATION: Description of Artificial Sequence: Synthetic
nucleotide construct

<400> SEQUENCE: 499
cattcaggaa aactacaatg gagaaagaag actaaaaaaa ccaaattaaa ttactcacct 60
atctcccagg cctaaaatat acccaaccat tgacatgacc gctaaagaac gggtataatt 120
ggttcttcgg tcaaaccaca cctagaacac aggagtgcat gtgaactacg gttctggaaa 180
ctttaatt 188

<210> SEQ ID NO 500
<211> LENGTH: 214
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 500
gggttccagg agagcgcagg tctgcagggc ccagtggcct acctcggagc tggggctttt 60
cagccacagc agcttggcca ggtcgtcccc agctgtatta ttgacggcat gctcaaacac 120
ctccaccttc tgcatcagag tcaagtggtc atagtccgga gccatctgca tcaggacaca 180
actgttcagt aagagagcag cctaagacat gtag 214

<210> SEQ ID NO 501
<211> LENGTH: 236
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 501
gccacggaag gggcactagc tctcgtggcc gcatcacata cccgcaacat gatgcgatgc 60
tcgatgttga gaaggatctt cttcttctcc ctgtagtccc ggatgagggc gtgcagtgtg 120
tcacagtggg gaacccagcc aatgaggccc gagttggtcg ataaagggat gacagcgtat 180
ctctggatgc tggcgcccac agaaaagcag ggttagtgta ccgtaaagag agtata 236

<210> SEQ ID NO 502
<211> LENGTH: 266
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 502
acatgactac acgagacaaa tgtaggaaaa aaccagaaga cttctcaaat tgttgccatt 60
tcagggtttc tgaatacctg aggtttttcc gaagagatgt tgggtcattg gccagaaggg 120
tgttaaccag gccgaagagc tgcatcacac gctcatcctg gcgcagatct tcatggcctt 180
ttagaaggaa aacaaactca tgtccgttgc tgcctgtaag gaacagtggg agcggtgagt 240
gtacatcaga ggtcctcagc tcttca 266

<210> SEQ ID NO 503
<211> LENGTH: 266
<212> TYPE: DNA
<213> ORGANISM: Artificial Sequence
<220> FEATURE:

-continued

<223> OTHER INFORMATION: Description of Artificial Sequence: Synthetic nucleotide construct

<400> SEQUENCE: 503
gtgtaggagg gagaagtggg tgacagaagt gcacaatggt ccttacccat aagtgtcaat 60
ttccggggcc tctgcttgga tgtgatgact tgcaaagacg gtgctatgga ctgaatgcga 120
atgattggct ggttggggtc atatgttcct ggcacagcca attcaaggtc ccggcacatc 180
agaagttttg gggaaacata ttgcagctct aaggatgtga gctgtaaata attaccaaag 240
gatttagtgt tctgcctcca gggaag 266

<210> SEQ ID NO 504
<211> LENGTH: 236
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 504
cagaaaggac tataatgaca gttaaccctg ccaggagcct gaagatccta cctgaggcag 60
ctgctttgag attcgtcgga acacatgata atagaggtcc caggcttggg tgaggtcctt 120
gacattccct gatttcatgt acttcctgca ccactcttgg gcctccatta aatctcgacc 180
ataggcctga gagagaaagc aggcacgttt tcaagttatc aaagtctcaa ccaacc 236

<210> SEQ ID NO 505
<211> LENGTH: 282
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 505
tagtggcaga atatttctac agggttatgt cctttcgtgt tttttacccc atacctgatt 60
aaaggatgtt tccttcagag tctgggggcc ccgttccatc atagcatgca agggctccag 120
cacctcaaac atgcctttca cgttcctttc cccaaagtac aaacgagatg cctcttccag 180
gccttcatgc cacatctcat gccagaggat ggccactcgg atcagctcct cgctcacctg 240
aagccaagag aagaaggaga gaagcatcaa gaatcagcta ac 282

<210> SEQ ID NO 506
<211> LENGTH: 216
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 506
aagggaccag ggtctatgaa gccccacagt ggctccgacc caccatcatg gcctgctgga 60
ccagggtgtt gctgtgctca cacatgttct tcagaatctt gttggctgca ttgtgccggg 120
ctgtcgtggt agacttagaa gccactgtca gtgggtagat gagggcctga gggaaaaaca 180
gaagaaacat ctataaagga aatgtgggtt ggggaa 216

<210> SEQ ID NO 507
<211> LENGTH: 215
<212> TYPE: DNA
<213> ORGANISM: Artificial Sequence -continued
<220> FEATURE:
<223> OTHER INFORMATION: Description of Artificial Sequence: Synthetic
      nucleotide construct

<400> SEQUENCE: 507
ggaaaggctg accaccaaac cagtggttag atgagaaact gcccagagtc tccacatacc 60
tgggggtggt accgaccaat gtctgtgaga agctggtgaa tgagacgtcc caccaagggt 120
ctgggcgtat caattcttgc aatgagctga ggtataacct ggtattcaaa aagacacagt 180
atgtagcata tgagacttga aacaactagt tattc 215

<210> SEQ ID NO 508
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 508
agagagactt ggagccacct tcacctgtaa ccaagtatcc tcacctgtag ccaggtatca 60
atctggatgg ctttcacccc ctccactaag gcctcattga catctggcca gtgaccataa 120
tcaaaccata aggtgagaac tctgaaaaag aaatgagaaa gtcacagaaa atttagtttc 180
ccagtt 186

<210> SEQ ID NO 509
<211> LENGTH: 194
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 509
cttgccatta acatggccta ccagagttgc atccttccct tctctgatac ctgagtgtat 60
cctggaggtt gttgcctcgt gacaaggaga tggaacggaa gaagccctgg acggcaggca 120
ccgtgtacat caggagggtt ttggacagat cctgttggaa cacacacgtg ttagcgacac 180
tcttgcctct gctt 194

<210> SEQ ID NO 510
<211> LENGTH: 343
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 510
cctggcacct tggttggttg ttaataagga agaagggaag ggtacctcag tgaccttctt 60
ctgcagcggc gatggggtgg ggctgttctc ggtgctctcg gcctcgctct cactgttgct 120
gccctcggtg ctggcagtgg tggtggcagt ggcggccgtg gtggcggcag tggtggcgtt 180
ggtgatgttg gccccgctgg catgacgcag tttcttcttc tcatcgcggg cttggttctg 240
atgtttgtag tgtagcacag cttcgaagtt catcactgcc cacgcatgcc aggcctggtt 300
ggggagaaag gcaaggacag acactggagc tgtgaccaac agc 343

<210> SEQ ID NO 511
<211> LENGTH: 194
<212> TYPE: DNA

-continued

<213> ORGANISM: Artificial Sequence
<220> FEATURE:
<223> OTHER INFORMATION: Description of Artificial Sequence: Synthetic nucleotide construct

<400> SEQUENCE: 511
gacagggctg gaatatgact tgccccaggt cagtggggac ctcaccgggc catgagcttg 60
tgcagttcct gcttatgctg ctggtcctca gtagcgatgg catgctgggc ctgttgctgc 120
atggtctgga caaaatgctg catgtgctgg aaggcatcga tctgtaacag gacaaaggca 180
cagagagcca cttg 194

<210> SEQ ID NO 512
<211> LENGTH: 157
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 512
gctgcatggt ctggacaaaa tgctgcatgt gctggaaggc atcgatctgt aacaggacaa 60
aggcacagag agccacttgg cttgtggccc agcttcagag gaagggagct accgttcatc 120
tgataggcat gagtcaaccc ctctccaaac agaatac 157

<210> SEQ ID NO 513
<211> LENGTH: 225
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 513
cattctggag aaggtggtct gttctggatg cattgggata cagaccttgc gggcactctt 60
ccacatgttt ttcatgtagg cataggtcac ctgagggtga actgttggca gaggatggtc 120
aagttgccga gacggatcaa ctcccaggag caacactaaa gttttatgag caagagcctt 180
aaaaataaga gaaactgggt tatagacaga actggacagc ccagg 225

<210> SEQ ID NO 514
<211> LENGTH: 235
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 514
ggacaccatg gggccctacc tgcccatgtg ggtgggtggt tgtcactcac cagcctgcca 60
ctcttgccgc acaggcttgc atacttgagc caggttctca tgtcttcatg agggctgacc 120
acaagggacc gcaccataag gattttctgc cagtcctcta cgatacgctg gcagccctgg 180
aacattcaga agtgaagatt agatatgtct tctgatacat tgtttttgtg gcaga 235

<210> SEQ ID NO 515
<211> LENGTH: 195
<212> TYPE: DNA
<213> ORGANISM: Artificial Sequence
<220> FEATURE:
<223> OTHER INFORMATION: Description of Artificial Sequence: Synthetic nucleotide construct -continued

<400> SEQUENCE: 515
ggtaggggta ggtgggtgaa ctggggcttt ctaccaagct cacctgcagt ctctcccacc 60
agatctggcg gatgatctct cgtcgctcgg ggacaagttt gtactggata acctcctcca 120
gctcggacag catgtggcaa gaaaccatgg cctgatggaa gcaaatcgca ttccaaacta 180
attactgcac gaaca 195

<210> SEQ ID NO 516
<211> LENGTH: 165
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 516
ggaaataagc ctcaaaaatg acaatgtgca gaatagttga cacttacccc atatgcccga 60
ctgtaactct ctcctgccat cgcagttaat tcagcatcca gcaggtccct ggccttgtca 120
atgcactaga agagaaacaa cccttgggac tgagctctgg acttg 165

<210> SEQ ID NO 517
<211> LENGTH: 211
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 517
gaagcactac aatcttttcc tcactgagag atctgggtgc atgtaggttt ttacctgttg 60
tgccaaggag aagaggtcct gatgcagtgc cagcacagct ctataaaatg ccccatcatg 120
ggtgtcccga gggatcatac aggtgtattc ttccatgctg tcccactgac ctatacacac 180
acacatagac agaaagcatc aagggggttg g 211

<210> SEQ ID NO 518
<211> LENGTH: 204
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 518
ctcactcacc ccatccttca cagggtgcct gtgagggaag ctttacctaa accccatgca 60
gctgcagcag ccatccgggc catcttggct tgggtctcat cattaaccag ggtccacttt 120
tcacagcact gctggtggag ttgacccctg aagaaaatga attatatagt cagattaatc 180
caaatctcct taaactacca atct 204

<210> SEQ ID NO 519
<211> LENGTH: 235
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 519
aagagacgaa gtctcttgca gccacacatg ccatcattct aggaagctca ccattccccc 60
aaggcctcga ggcagcgcat gcggcccagc atcagctctg ggtcgtcctt gttggtgtcc 120

-continued

```
attttcttgt cataggccac aagggcatcc tcccactcgt gcagtttctc ataccaggta    180

gcctggatct cctgttacat gggaaagaaa gactgctgtg aggtacacag aagaa         235
```

<210> SEQ ID NO 520
<211> LENGTH: 175
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 520

```
ctagccaagt ctctacctcc tgcttttcca aaaagaatga ggtgcttacc agctctccaa     60

agtgtttcat ggcatattct aacactccgg ccgctgcctc cggctgctgt agcttattat    120

taatgctgag aaaacaaagg gaaaaggtag ttacactcaa caggtctgag ggtag         175
```

<210> SEQ ID NO 521
<211> LENGTH: 241
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 521

```
aagagaggtc attttgcatg aaggcagcaa ttaaaaaggg tttatggcct acctgatgag     60

agattctaga atggcagggg tggggccttt ctggaactcc agttctttgt agtgtagtgc    120

tttggcatat gctcggcact tggcagctct ctcacccagc agaacaatgc cattgtcatc    180

tctcagtggc agggggccct ggagaagagc aaaacctcac agcacaggaa aatggcagat    240

g                                                                    241
```

<210> SEQ ID NO 522
<211> LENGTH: 234
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 522

```
cgttttctat gtgctgatct tctccacccg ccctgacaca ctatacctgg ccatcgggtt     60

gtaggcctgt gccagggccc agcaggagcg cagggagggc gatgatgagt ccttcagcag    120

ctccaggctc agccgtctca gccattccag ccagtcatct ttggagaccc tcctggcagc    180

gccccaggcc tgtgatccca caggtgacaa tggaaaacaa tcagtttcaa gggc          234
```

<210> SEQ ID NO 523
<211> LENGTH: 265
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 523

```
gttaaaagtt ttgagtaagt gagaagagca gagctctcct ttcccagtca cctgaaacaa     60

tggacttgcc ttttggaggt tgatggtgct gacgtgcagt ttcttcatgg gtcctgtttc    120

cactggtcca ctagccaatg catccccttg gccactccta agcatccgat gctggtaaat    180
```

-continued

```
caaaggatcc tcctcttcat cagcaagtgt gtatccctac aaccaaagat ttataggaaa    240

cacctataac tctactagat gcttc                                          265
```

<210> SEQ ID NO 524
<211> LENGTH: 193
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 524

```
gtagtaaaga caacagggac ttcagaacag aaaagaagta tagttcacct tgacaattct     60

gcagatgagc acatcatagc gctgatgatt gattcggtgt cgcaccagaa ctttattcac    120

cattggaatg aaaatttggt actaaaacag gagggggaag agatgagaaa ctatcatttt    180

ggagagtgga gaa                                                       193
```

<210> SEQ ID NO 525
<211> LENGTH: 267
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 525

```
aaataaggca gaagagcacc tgtctgtcca gactcccatc ttaccttctt ccccagctga     60

aaaacaagtg aagacagcgt gtccatggct gtggagcgca gttctgggct ctggtccagt    120

gttcgaacaa tagggtgaat gatccgggag gcatagtcag tgaaatccag ggactccgtc    180

aggcggtcca cagtctctag cgctgcccta caacaatcac taacatacag taactgctaa    240

catacaatct ccaaggaaga gacgtga                                        267
```

<210> SEQ ID NO 526
<211> LENGTH: 228
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 526

```
aaatgaacat tttcaacaaa acattaaagc ttaaagattg ctagtcccaa agaggaggtg     60

ctcactttcg agatggcagt ggagcttcag gggcatcaaa caacttaaca ataggaggca    120

gcagtaaatg caggtagtca tccaggttgg cgccaaacag ctggattgca gccagtaact    180

gcaaaaggga gcaaaagcat ggtgatgaat agtcaggtcc caagtatc                 228
```

<210> SEQ ID NO 527
<211> LENGTH: 185
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 527

```
cttccttgac ccaaacatgg aagaggccaa agcattaact tctactcact ctcatgaggg     60

tgactatttc atccatataa ggtctgatgt ggctcttcac aaaggacacc aacattccca    120

gctgctggaa caaaaactga aatggacaag aggtcaacca gctggtatca tgaaggacat    180
```

-continued tgaac 185

<210> SEQ ID NO 528
<211> LENGTH: 346
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 528
tgtggtgcag aggagaaaga gaaggattgg ggtttgaggt acttacttcc cggatggccc 60
catcacagac tcgaatgacg ttaaggaacg tgggcatgac ctggggcagg aactgcacac 120
atttgagtcc cagggacttg aagatgaagg tgatggcctg gacaaccatg gtgtgatgat 180
gagagagtga ctggtctcgg aagatccgca tcagggccac catggacaca gctgggtaga 240
actcatccag aggcaagttt cccatgttga ccagcatttc actagtgcta tagtcagcta 300
ggacaaaaca acagagagtg ttagagctac acatggcatg acgtga 346

<210> SEQ ID NO 529
<211> LENGTH: 232
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 529
gctctgtgag tgagaacttg gcaagtcttt catggctacc cccaacttac aggaatcctg 60
acttgacttg gattctgaca ggctgacagc agaggcatcc cgggactggt ctatcatgcc 120
aatgttcact ttgtgcttgt aaggatccaa agcccctaaa agccctaaca cacggatggc 180
ctgcgtggga aaggggaggg aaaaaagaaa acattcatca caacatgatt ac 232

<210> SEQ ID NO 530
<211> LENGTH: 227
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 530
gccatcgtcc cagcaaagtc tttaaagacc aagtttgcca cgtcccctac ctctctgcgt 60
gtaccctggt tctgctcagt cttcagaaaa ttcagtagca cctcaagcaa agtagggtac 120
ttcctgtagg gctctactac atagccagtg ctggccacca actgtcccag ggtccacaga 180
gccacctgga taggcacaag aacacgattc aatgagccag tacgaga 227

<210> SEQ ID NO 531
<211> LENGTH: 225
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 531
gatgacaacg cacagagaaa gcaccagcct ctcggtttgt gttaccttca gaataggctc 60
catgtagggg cggatgagtc ggggggcatt ggagaccagg tgccccagca tgcgggcact 120

-continued ctgctctttg attcttccaa tcccactgtg ctccaactct gtcaaaatct gtagggaaga 180
aaggctcata tgttctctat ggcagaagac attctagaga gagac 225

<210> SEQ ID NO 532
<211> LENGTH: 315
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 532
ttgtcctaag ctccttaact cccctagatt ccttctgtct ggcaagcctt accaggatct 60
gttatcccaa ctacgagcag tttgctaagc acatctgcca ccacttgcac tgcggtctgg 120
ctaaccacat gagcatggcc actgatgagg tggatggagg gtgtgagcag gcgggagcag 180
gtgcgggcag cctccatgcg gatctccttg tgctcactgt tcaggaaatg atccgcacag 240
tggcgaacaa attgggtcag agagtggcct ggatagaaag gcagagagaa aacagaataa 300
acactgctgc tgtag 315

<210> SEQ ID NO 533
<211> LENGTH: 335
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 533
ttccagcatc tctcactatc ttggcaagag ccgttgtaat ttcttacctt caaattcaaa 60
gctgccaagc gttcggaggg caagagtgat gctgcccaca tcgctggcct cagggagggt 120
cgtgaggcca ggagaggcca gctgatgggc caggcccttg ggcatgcctg ggtggcgaag 180
gggtttgtgc ataaggacca gggacagcat tttcagtagc ccatcttgaa tgtccttctt 240
tagctgtgga atctgacggc tcaggtcgta gagcactgca gtgagggcag ggctgagggg 300
aaggaaacaa gtcacataag ggctgggcac atgac 335

<210> SEQ ID NO 534
<211> LENGTH: 224
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 534
ccaagcctca cgctgataca gggcaagctc aggtttctga cacccacctt agtcccactg 60
ccagcatggg ctccagcagc tccttgatat cctgctggat gcctggcccc attgctcgag 120
ccagcatgct gatgcaagtg aagactgtgg catccacctg cattgccttc tgcctcctgt 180
agagaaatgg agagtggcta gttgagacat aatgacattc ttta 224

<210> SEQ ID NO 535
<211> LENGTH: 277
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 535

-continued ccaaccaaat ggagtggaag gtgaaatcat aacagaggtg cttacttatg ggcgaagtcc 60
tttgggggca gggccgctcg gatgatgtcc agcacgcgag gcaaatagac cttaaactca 120
gacctcacag ccacagaaag tagccccagg gcttggaagg ccgctgtacg ttccttctcc 180
ttcttgacac agcttaggac atggttcatg gtatcttgga gatactgggt atctgagcac 240
agaaaagaca aagtagatag ctccaggtca gggttag 277

<210> SEQ ID NO 536
<211> LENGTH: 196
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 536
tgtttaccct gagatgggta atgatgtctt ccatggacat cctcacctgt gaaggcagaa 60
ggtcggaatg cagccaagcg gggcaacaaa ttaaggattg tcatttggat cagcgagttc 120
ttgctattcc tgcatttcag cacccactgg cacacctgag agaggaagga taaagggttg 180
gcaggggaaa agtgag 196

<210> SEQ ID NO 537
<211> LENGTH: 373
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 537
gtgtggagct taggaaaaga gggaaagggc ctctcaccac ttacctgatc aaatttctcc 60
tccatcaagt ctctgcaaca ccggctctcc accagggtgg acttagctgg actgggggag 120
gtcccaaatc ccatgaggcc ttggtgagag ctgtacccca gcagccccac caaggcattt 180
gactgctggg gctgtacagc ctggaaactg gtgaaggggg taatgtgacg aggttttgtt 240
ccgaagccca tgagatcttt gcagtacttg tcgtgtacca gctgctgctg tgtgatttct 300
tccatttctt ctctcagacg ctatatatat gaggaggaaa aaaatcatct ttacttatga 360
ctggcattca aac 373

<210> SEQ ID NO 538
<211> LENGTH: 224
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 538
ggtacacggg gagcctggac tcccctctgc cgtggcttct cacctctccc tccatgctgc 60
tgattcggac cagctcgtta aggatcaaca aggctccatg gatccgatca tcccgattca 120
tgcccttctc tttggccaag gtctcatcaa atcccttctc tgcttcttca aatgtgtgct 180
atgtagagag acagggtgcc ttcattagag acagagtaca aacc 224

<210> SEQ ID NO 539
<211> LENGTH: 295
<212> TYPE: DNA
<213> ORGANISM: Artificial Sequence -continued
<220> FEATURE:
<223> OTHER INFORMATION: Description of Artificial Sequence: Synthetic
nucleotide construct

<400> SEQUENCE: 539
gcagatgtgc tttgctagtg gtgggaatgg agccatctcc ttaccctgta ccactgaggc 60
ttctgcatct ccttcggctc acgctgggtt gtgagaatca gacaggcacg aagggcggct 120
acagctccct cacggatggc ctgtttgggg tcccacacgg ccacaaaaat gttgtcaaag 180
aagggttgca cttgctggaa gaagaaggta gggacgctga tggccagctc acggagaacc 240
aggacctgga gaaaaaagca aaccgagaac tctcattggt accagagttt tgttc 295

<210> SEQ ID NO 540
<211> LENGTH: 332
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 540
ccccatgaca ccatcgttcc ccaagcctgg ctgtgctcct ccctgtagac actcacagct 60
gcatgtctcc ggccctcatt gcggtcagca cccagccatt ccagggctcg cttcacctca 120
aattccacgt actcagcggt aaaagtgtcc cctgccatgg caagacggcc aatggccttg 180
gatgccattt ccatgacaac tgggtcattg gaggggagga ggttccgaag atagttggca 240
aatctgccaa ttcgggtggc attcccacct tccactccta tgaggctagc tgcaaaagag 300
aggaaggcaa aaggtgatga tggggcgtat gc 332

<210> SEQ ID NO 541
<211> LENGTH: 216
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 541
cacaaaggtg agtgtgttgt ttttgtgacc agagactctg tccttaccta tggccaagat 60
gccacctttc ctctcattgg catctgagct ggaaaccaat tcaaaaatgt gatggttcag 120
ttggtcatag aagcgagtag actcctcttg actcatctgc aaaagaagat ataatcagaa 180
caatttctaa taattctcta actgtggtgg tgggag 216

<210> SEQ ID NO 542
<211> LENGTH: 255
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 542
gcccacacat cccacaatga ctggccccag atcccagaag cacctctcgg agttccatgg 60
tgacatagtg ctggagctcc ttggcggctt tggccctggt ttcctcattc cggctcttta 120
ggccactggc aaactgctgc aggacgctca cattgctaga tgtggtggca gcggtggtgg 180
cggcggcagg tccggttcca agcatcttgc cctgaggttc tttagagaga agtttccttt 240
aatattctgg ataag 255

-continued

<210> SEQ ID NO 543
<211> LENGTH: 296
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 543
gcacgtttat aactgttcat gcttccaaag ctcaaacatt cactagttta caagtatgtt 60
gccgcagtca gctgatacca tttaaccgtc tctttgctca agttgaaatc tttcaaaggc 120
agggttactc cacccaagaa aaaattctcc cgcagagatt ctgcactgag tacacttagt 180
tgaagttctc gctgtcttag ggtttctttg ctatatccac tgtatacaag ctacaacaaa 240
ggaaaaaaga acagtaaatc acaaattaaa gtttgtttgg tttcttggaa catttc 296

<210> SEQ ID NO 544
<211> LENGTH: 446
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 544
gcacgtcaga acttaaaaat gaaaattaaa aaaataataa accaaggaaa cttctagaaa 60
tgattttaac ttaccatttc attgaatgtc ggattcctcg tttttcgtga aattttggtt 120
ttacgtttgg atgttttgtg gttatctgga agtaggtatg ttttgacata tggatttggg 180
tcagctccat cttcagtaac ctaaaaagaa aagcagtccc ttaatagtaa tgcttcctac 240
caaggtaagg gtttcctcta caaccatcat tctttgtaat cactcacaag atctttgata 300
tgcatcacca tgatgaaaag agtaccattt cggtaagaga tggataattt cacagctcct 360
cctatttggc ctggagtagg actgaaggaa cctgcatctg aaaatacaaa tattttcatc 420
tttatttact ggttgtagtg gttcaa 446

<210> SEQ ID NO 545
<211> LENGTH: 377
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 545
gacttgcaga tcatgagtta ccaataaaga gaaaaaaaat aatctcacct gcagacctag 60
ctatcccttc agctttctca tcacgaagta aagggtggaa gaaagtacaa acaagatcac 120
actaagaata aagagaaagc aattcattag tttaaatatt atgtaacaca aaaggtataa 180
gatgttatta cttctcattt agtaaggtta cctctgctac atccgttgaa gcattcatca 240
aactctgtaa gtaactgttt aactcaattt tccttttggc tgctacatct tttatgtgtg 300
ttcttcctag aaccatccta ttaggaaagc tacaaaagaa aaacaaaaac aagtgggatt 360
taaataagta caatatt 377

<210> SEQ ID NO 546
<211> LENGTH: 239
<212> TYPE: DNA
<213> ORGANISM: Artificial Sequence
<220> FEATURE:

-continued

<223> OTHER INFORMATION: Description of Artificial Sequence: Synthetic
      nucleotide construct

<400> SEQUENCE: 546
ataacaagtt gtttcctaca aaaaggatta atgtacaagg atgaatacat accctggtaa 60
cttccaaagt ggaaaaataa tactgagctt attgtgaagt tcctgaaatt cgtcaaatgt 120
tcggaagaca aatgatggtt caatctgtcc ttccctcaaa attcggacta cataaatctg 180
aaaagaaatc acaccacaaa cacataaaat ttatatttaa aaccttcttt ccaggccgg 239

<210> SEQ ID NO 547
<211> LENGTH: 336
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 547
gaatcagcaa aggaagtaga aaggacaaca ataatacatg catgattgtt tatgaatatt 60
gaaatcaaac ttacataatg tttatctggg ttgtatttct tatgatatgt aaaaacagag 120
acttccttga ttcgaccatc ttgtctaaag gagtatgttt taggtgaaaa tgaaaggatg 180
ggctcatcat tagaaggaag accagaaaaa cgaagctgag caaggttgtg aatgaagaag 240
ttaaactttg tggcaatgct tcccaaactt gattcaataa gcctacaaaa taatcagaaa 300
attcgttaac agtaaatgag aacacatggt aaattc 336

<210> SEQ ID NO 548
<211> LENGTH: 234
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 548
tcaaagcaat attttatgtt ccttctgcaa tatacttaaa tatgctttac ctagtaaaga 60
aaattgtagc ttctgcgtct gtagtttggg gttgaagtgc atctctaacg tatttcaaat 120
cttgaatact tgtaagttct ggtaaccctg aaggaatcat ctgtagaaga aaacaaaaag 180
ttctgtgagt taaatttttt aaaacatttg ttcctcactc cttcctgtgg gctg 234

<210> SEQ ID NO 549
<211> LENGTH: 321
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 549
taaagcaaat tttattccaa aatcacaaaa taatcttttt taagtattga aacatagatg 60
cattaatata aaactaatta agtgcttata aagaatagtt accagtgaaa ggaggttaag 120
aaaaaggttt gtctgctttc ttatcaagtt gtaggcctga cagcagaggt ccacaaacaa 180
ctgaaaacga atggtgggct tttcaccccc attaatgaca tatgccatat cagaggtcag 240
cacaaaagga gcccgatccc tatttaaaat gaaagtacat acaaaatatt atttacagaa 300
gatactccaa tagtgctatt a 321

-continued

<210> SEQ ID NO 550
<211> LENGTH: 276
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 550
aacaggaagt gcctcatttc tttggcaaca gcaataacat tataccttt gaagctgcca 60 aacatctgtg catgtcccaa aaactttcca aagtcaatgt gaaacatgtg tcccgtgctt 120
cgaagcatta tattgtcatt gtgtcgatca cagatgccta aaacataggt ggctacacag 180
catccagcac aggaatagat aaagttctct gaagcctata aaaaacatac acaattattt 240
tagaaaatga attattttta aaagaggcag agttta 276

<210> SEQ ID NO 551
<211> LENGTH: 241
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 551
cctctgtaac acatttttga caaagctttt tagaatgagg agacatgcta attacctttt 60
catattcttc ttcagaggga ttgtatttcc ttagccactc tgcaagtggt ttatctttaa 120
aggatcctgt cacaccatat tccacttgga ttttcctgag ggtatcggaa gcaggaacca 180
gctccaccat gcctttaatg ataaaatatt aagctatgta aaactgtctc tccaaagtaa 240
g 241

<210> SEQ ID NO 552
<211> LENGTH: 240
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 552
gtacacttta agctaagttc aaggaaaaaa ataagacatc aagacacagc taataaactt 60
acctcgatct ctgccagttg agagacattt gaaaattacc atcctcagat ctagtccttc 120
tttaagccag atcttatcca taatctttat catctgtaaa gctaacatat cttgccgaag 180
atcttcacca accttgaaat caaggaaaca aaatgaaact tgtacatctc caaaagactt 240

<210> SEQ ID NO 553
<211> LENGTH: 228
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 553
caaaatcacc tttgcaattt tgggaaagta atttgataaa aaaatttcta aattgccatt 60
aaaaaacagt aacattattt actcacctta aacatgacat taatttcttc tcccataggg 120
tcagcattca ccattgtgac ttttaggggg acagcattag aactgaagaa ggaacacgac 180
tgcaaataca acatgttaag cattagaaag ataaatgaaa atggattt 228

-continued

<210> SEQ ID NO 554
<211> LENGTH: 246
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 554
ccatttgcct tcttcctatt attttcaaat gtaatatgaa cttataagta ttttatgtgt 60
caccttaata tttaattctt ttgccactag acttggcttg agagggagac ggcatttatt 120
tttctgaaaa aaggactgta ctcgttccat acttctttgg agaacaacct atagaaagag 180
atgtgatact gtaagtacat aatgaaaatg aagatctatt tttcagacaa gttatgctgt 240
ggatac 246

<210> SEQ ID NO 555
<211> LENGTH: 317
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 555
cataaagatc cttcctttaa cattaacaca tttatattac cttttatggg tacatacctg 60
tctggctgat ccactagcct gccttacttt ttctgctact cctcctaaaa gctgtacaag 120
tttcgtctgt tttagaagtt cttctctaag tcgttttcct cctactgaca ggagagcacc 180
caaaacatgt tcgtatcggg tactaaactg tacatcatgc agggcatctt tgagaagcct 240
aatacagcaa aatatttatg ttagtcacgt cttggttttt tttttttttt tttttttttg 300
agacggagcc tcactcg 317

<210> SEQ ID NO 556
<211> LENGTH: 207
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 556
ctataaattc taggaatgga aatacggtaa tcaataaaat ttaaatctta ccaatataaa 60
ttgtgtgcta tctggatatt tcccaatgcc ctggacaaaa ggaattgcac taatgaacta 120
ttcaagtaaa tttcatattt caaagcctac agtaaaagaa aataagaatt attagtggtc 180
taacccatac taaattgttc caataaa 207

<210> SEQ ID NO 557
<211> LENGTH: 215
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 557
gggatccctt agcaagttcc cataaaaaac tagagtgaaa gtataaaggg aggtaatcta 60
gtaaaaaact cacttgtaca aactgtggaa gaagatctgt tagctcatca tcactaatgg 120
cctcaatcca ggtcacagct agggatctta cttcctgatc agcaaatcta gaagattacc 180

-continued ataaaaccaa gattggacag tgatttcttt ccagt 215

<210> SEQ ID NO 558
<211> LENGTH: 354
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 558
tactggaaaa actgacaata aaacaagagc aaataaatgt atttgactta ctttgaatca 60
agaagttcca atgcaattag tgggtacaat gcaggccact ggtgaagcaa tgagtaagtt 120
ttggcaagat taacccattt ccagtttggg gcgcttgcta atattttagg aagacaattt 180
gggtgtttga agcaataata acgtttctcc cataaaaaag ctttatcttc tttagaaagt 240
ctgcatatat aatagaatta aattacttct cagtgataac ataatgatat aatctcaatg 300
attaaaaata caaagaagaa atttatttat ttgggacagc tacttcttca taaa 354

<210> SEQ ID NO 559
<211> LENGTH: 258
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 559
tttacattac aggagatact tagcccaaaa cagaataaac agaacatacc caagtgatga 60
gtctttatga agaatatcaa gaagtttccc ttttatatca ttctctagtg tttctaagtt 120
atgttgctgt ataatgcttc tgtcaacttg aggagttgta taaataatat caaatgcagg 180
agaaggaaaa tcaaccttta aaatttaaca gaaattgatc aaattacagt ctacgtattt 240
gccacattaa cctctttg 258

<210> SEQ ID NO 560
<211> LENGTH: 257
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 560
tcatggtata cacacacaca ttttatgaag aaatttaaat gtacacctct ctacatgtca 60
agaagtacca ttacctgtag cactattctt tccatgacat atccttttttt ggtaactgtt 120 ccaggaacag aatttgtatg tgatgaagtc caaagatata gaagtttagt tccacatgtt 180
aaaaaccttc acggatgtaa aaataataat gtgattttca ttttaaaaat caattcaaaa 240
tttacaacac atgtaat 257

<210> SEQ ID NO 561
<211> LENGTH: 267
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 561

-continued gtaaacaaca ggacacactg aaagaataaa aagccagaaa tttcacttac agttcatccc 60
atttaataag atagaagaaa ttcttgtaag tgccaacctt ctttgattga ataggtttaa 120
aaagatcctt tccattgtga gacagtgaac atatcaagta gtatttttca taactgagaa 180
aagaaagttt aacttgattt ctatcatgat aatacaaatt agttaactaa tacaaataca 240
ttagcagttc ttcctccaaa gagacta 267

<210> SEQ ID NO 562
<211> LENGTH: 311
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 562
gattacaggt gcaagccacc atgcctggct gcttaaacag ttacttactt tgatacccaa 60
ttacttgaaa ttccatgagc agcaaaaata gtaaactgga gctgctctgt tgtagtccat 120
gcttccttga cactcttgct actttgggca cagtctgtag gactcctacc agaatttgca 180
tggagtctga gaagatcata aattgctgca gttaattggt ttatgcttac ttgaacagga 240
ttttcaggat taagtgagcc tagattaaag aaaaaaaaag ttaatagatt ctctgaaaag 300
gcgatgatta t 311

<210> SEQ ID NO 563
<211> LENGTH: 158
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 563
agattctctg aaaaggcgat gattattgct aaaatttaaa gatttaaaca cataccccta 60
gttgaactcc tgctagtgtc ttctcctcca aacaaagaag tcacctacac atgcacacac 120
acacacaata gtcagaaaac tgcctatgac ataatata 158

<210> SEQ ID NO 564
<211> LENGTH: 254
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 564
atctcctgtt taagtacata tttgcatgta ataaaatcct agttaccaaa aatactcaca 60
tcagcagttt tactccttgg aagattaact gctctcttta gcttctttac tgattctgta 120
atggcaagag tctcgacacc atctaaagca ctacagattt ttcttacagc tttaattact 180
tgatctactg ctcggtgttg gttctttaaa aataaaaaat aaaataaaaa taggtaggtg 240
aaatttaaag gacc 254

<210> SEQ ID NO 565
<211> LENGTH: 376
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 565
aagaagcagc aagaatcttt aagtcattat gccaaaatgt gaattaagac ttacttcaat 60
ttgaagagcc agttctactt ggttgtgata agaatctaag agttcttcaa cagggtgtct 120
gaaagaaaca acagttattg tggctgaagg atgctacaca caaaatgatt gttttcatca 180
ccaaaataag tgtatttgca tccaaaaaca aagtctgaaa acctgcaatt aatgctttag 240
atgatatacc tcgtcatggc ttctttgcaa ggtttttcta tttgatacag gtgtttgttt 300
aaatccacgg gtgtttcatc atcttctgcc taaacaaaca catatacaca aaaaaatcac 360
atccactctt tggtct 376

<210> SEQ ID NO 566
<211> LENGTH: 235
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 566
gaattattca gattcaaaca aatggaattc agttatgagg tacacactta ctgttcgggc 60
cagattttga cacattgcac tgaaggtcaa gagttgtagt ctaatttctg tgtcccattt 120
tcgacagttt tgaatatgct catgacttcc aaggcaatga ttactgttaa gatatattaa 180
ttattcacta ttctattcaa attagaaatt ataaaggtga gggtaaaatt taaat 235

<210> SEQ ID NO 567
<211> LENGTH: 223
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 567
ttaaaaatga aatttccaag gatgttgctc agtagttaaa taaacttact tctgcagcac 60
ttcctcttga ccacaaactt ttagaacata gctgccaaca tctacttgat tcaagtcatc 120
atgtacccag caaagggctt gcattataat gatttctaca gtagaactca ctgtaaaaga 180
gttagtcatt attttcactt tgctcattta tatttattca aga 223

<210> SEQ ID NO 568
<211> LENGTH: 265
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 568
ccccctaaca gagcaaaacg agaggcttga ggaaccataa acctaccatc acacgtaaaa 60
gtaactggta gctgaaatcc ttcaatgtca atggagacct tcacactagc attttctccg 120
catatgtttc tttgtgctgt gactggactt aacaaatagc ctgggtttgt gcggtgattg 180
gtatatggaa atttggtctt caatctgttc acaagaaaga agaaattaaa ttcttttttta 240 aaaaaacttc atttgagggc tctga 265

<210> SEQ ID NO 569
<211> LENGTH: 213

<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 569

| | | | | | |
|---|---|---|---|---|---|
| aactggtttt | caagtgaatt | tttcaaatga | acatttataa | agaaaaattc | cttactttgt | 60 |
| aatggatcga | caaaaagctg | ccatctcctc | attctgtact | tcaacttctt | gaagaagaga | 120 |
| acttccagtt | ggcaaactac | tggtcccatt | tgggtctttc | tgtaattaaa | aaagtgtttt | 180 |
| tattttaaaa | gtggaagatc | cacaaaatgc | tac | | | 213 |

<210> SEQ ID NO 570
<211> LENGTH: 355
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 570

| | | | | | |
|---|---|---|---|---|---|
| attatccacc | ttaggcttac | ttagaggatc | caagtctaac | cagtcaaatt | tactgatatc | 60 |
| ctcagacttt | ggagatacct | gtagattgct | gacttttgaa | tctgttatct | ccaaatcagt | 120 |
| ccttgctttc | ccattttta | aaaattctga | tgtactagct | attttgtcaa | atagttttgc | 180 |
| catgtcagta | ctgactactg | gacgatagat | aggtaagctt | ccttgtggat | gaaagggtgt | 240 |
| ggcaggtgtc | aaaggatatg | agaaatatgg | agattgtccc | ggaagactta | aatatatagg | 300 |
| ttctgtagat | ggaaaagtgg | gcattcttgg | attgaagcca | ttttggaatg | cagcc | 355 |

<210> SEQ ID NO 571
<211> LENGTH: 367
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 571

| | | | | | |
|---|---|---|---|---|---|
| ggagattgtc | ccggaagact | taaatatata | ggttctgtag | atggaaaagt | gggcattctt | 60 |
| ggattgaagc | cattttggaa | tgcagcctgt | ttactgtaag | tagaaggata | aatagaaggt | 120 |
| aaagcataag | tggaaggccc | aggtaatcca | ggtggccact | gtcctctctg | aatagtaggt | 180 |
| ctaaaataga | gctgtgctga | aaaggaaggg | ctcagaatag | gagtaactgg | taatacaggt | 240 |
| gtttttttag | tctcgaaact | gtcatccagc | aatagtttct | caagttcagc | ttgggtgagc | 300 |
| ttttctacat | caatatctaa | tgctctttttt | tgggaatctg | attcaggaaa | caccatgaga | 360 |
| tcataat | | | | | | 367 |

<210> SEQ ID NO 572
<211> LENGTH: 366
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 572

| | | | | | |
|---|---|---|---|---|---|
| tcagcttggg | tgagcttttc | tacatcaata | tctaatgctc | ttttttggga | atctgattca | 60 |
| ggaaacacca | tgagatcata | atcctgcttg | ttataaacct | gtgctttttt | tctggtgctg | 120 |

-continued

```
cttgacaact caaagcctct ctgattgtca gtcacttgtc tatccttttg cagttttgct    180

aaagcctctg cttccatctg taatgcttct tctttgtcca catcttttgc tcttgttggt    240

tccggatgtg aagatggaca ttctttaaat ccgctgttgc tagatatctg agccatgtcc    300

actaaaaaga ccaaaccttc cttcctctat ttttttcttg tagcttccaa aatagcaagg    360

cctata                                                               366
```

<210> SEQ ID NO 573
<211> LENGTH: 409
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 573

```
gccctgcctg ttccagtgtc ttctctctct cctgccagga ccatgggtag caacaagagc     60

aagcccaagg atgccagcca gcggcgccgc agcctggagc ccgccgagaa cgtgcacggc    120

gctggcgggg gcgctttccc cgcctcgcag acccccagca agccagcctc ggccgacggc    180

caccgcggcc ccagcgcggc cttcgccccc gcggccgccg agcccaagct gttcggaggc    240

ttcaactcct cggacaccgt cacctccccg cagagggcgg gcccgctggc cggtcagtgc    300

gcgggcggcg cggggtcctc gcccacctgg ggccacggcg gggaggcggc ggggctgtgt    360

gcccggggtc gccccctctg cgcaggccct tcctctcgcc aggggtagc                409
```

<210> SEQ ID NO 574
<211> LENGTH: 242
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 574

```
ccactcctcc tgggtacagg gccatcctgc ccatgccttc cctggctgtg gccccactgt     60

tctgacacac cccacccctc tctgcaggtg gagtgaccac ctttgtggcc ctctatgact    120

atgagtctag gacggagaca gacctgtcct tcaagaaagg cgagcggctc cagattgtca    180

acaacacgtg agtgcccccct tccctattgc ccctcagggc tgggtggtgg gacttcaaag    240

cg                                                                   242
```

<210> SEQ ID NO 575
<211> LENGTH: 193
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 575

```
gctgacggct cccttctcct ttcctccctc cttctgtccc tgctcagaga gggagactgg     60

tggctggccc actcgctcag cacaggacag acaggctaca tccccagcaa ctacgtggcg    120

ccctccgact ccatccaggc tgaggagtga gtaccgtctc tggctgcctc tacccgtcgt    180

ccctggacac tgc                                                       193
```

<210> SEQ ID NO 576
<211> LENGTH: 290
<212> TYPE: DNA

-continued

<213> ORGANISM: Artificial Sequence
<220> FEATURE:
<223> OTHER INFORMATION: Description of Artificial Sequence: Synthetic
nucleotide construct

<400> SEQUENCE: 576
gggcagaaga cccgcctaac tgctcctcct gcctcctcct cagaacacgc cgatggcctg 60
tgccaccgcc tcaccaccgt gtgccccacg tccaagccgc agactcaggg cctggccaag 120
gatgcctggg agatccctcg ggagtcgctg cggctggagg tcaagctggg ccagggctgc 180
tttggcgagg tgtggatggg taaggcctgg ccccctgccct cgggagaggc atccaccccc 240
caccccgtgt ggcagctccg ggctcccttg gtccctttgc ctttagctgc 290

<210> SEQ ID NO 577
<211> LENGTH: 312
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 577
ggatccctgt gtggtaggag ttggggggct ccactgagtc agcctgcatc cctcctcaac 60
agggacctgg aacggtacca ccagggtggc catcaaaacc ctgaagcctg gcacgatgtc 120
tccagaggcc ttcctgcagg aggcccaggt catgaagaag ctgaggcatg agaagctggt 180
gcagttgtat gctgtggttt cagaggagcc catttacatc gtcacggagt acatgagcaa 240
gggtgagtcc tgggcggccg gggcaggggg caggggcact ccggacaggg cagggagcat 300
gagcctcatt tc 312

<210> SEQ ID NO 578
<211> LENGTH: 186
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 578
ggaatcactg catcctggca gagggacagg gcaggagctg gagctgggtc tctctctgcc 60
cagggagttt gctggacttt ctcaaggggg agacaggcaa gtacctgcgg ctgcctcagc 120
tggtggacat ggctgctcag gtgagtcagc ccctcccgcc tccccacacc cttggtcctc 180
aagcac 186

<210> SEQ ID NO 579
<211> LENGTH: 322
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 579
ccagagtgct ctgtggccct gggagggcat gggtggcacc tgagccaggc tcccacggtt 60
ccgcctgcag atcgcctcag gcatggcgta cgtggagcgg atgaactacg tccaccggga 120
ccttcgtgca gccaacatcc tggtgggaga gaacctggtg tgcaaagtgg cggactttgg 180
gctggctcgg ctcattgaag acaatgagta cacggcgcgg caaggtgggc aggggctgtg 240
tggtatgtcg cgcttggcct gggacaggtc acgtcccgct ctgagcccca gttttttcct 300

-continued cagctgtcat tcctcatggt gc 322

<210> SEQ ID NO 580
<211> LENGTH: 224
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 580
cggtcatgac aggaggtcag agctgccctg acctttctcg ttcctgcagg tgccaaattc 60
cccatcaagt ggacggctcc agaagctgcc ctctatggcc gcttcaccat caagtcggac 120
gtgtggtcct tcgggatcct gctgactgag ctcaccacaa agggacgggt gccctaccct 180
ggtaagaagg tcctcatggc ctgtctgtgg tccctgaatc cctc 224

<210> SEQ ID NO 581
<211> LENGTH: 372
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 581
cttatctatg gtcactccca acctgtccta ggcaggaagc cctcgctgcc ctccccatca 60
gcttccccca ccccactttc ctcaccggag ccgggctccc catgcctcgc tctgcccaca 120
gggatggtga accgcgaggt gctggaccag gtggagcggg gctaccggat gccctgcccg 180
ccggagtgtc ccgagtccct gcacgacctc atgtgccagt gctggcggaa ggagcctgag 240
gagcggccca ccttcgagta cctgcaggcc ttcctggagg actacttcac gtccaccgag 300
ccccagtacc agcccgggga gaacctctag gcacaggcgg gcccagaccg gcttctcggc 360
ttggatcctg gg 372

<210> SEQ ID NO 582
<211> LENGTH: 287
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 582
cacagattca taccaaatgc attactttta gattattaac atattctttt acataatttc 60
atttcacata tatggagtcc aaccaagata catctggcat agtaagtttt catcagtagc 120
ttcctgtata aggtaatgca catgtccttc aatagataac ggcagtcctg tcactctatt 180
tcgagtcttg attacacctt gtagtcgctg ctcaatgtca agaacatggg tcttggccta 240
aaaagaagaa acataaaacc aaaaacagat gttaataatt tggaatt 287

<210> SEQ ID NO 583
<211> LENGTH: 203
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 583

-continued

```
tgtagagatg aggactacag cccatatcaa gctatacctt ctactaacct tttcattgac     60

aacttctcca gtttcattca gtggcgcttt ggaatgccct ttcactggtt tactccattc    120

cacaagagga tcatgtagaa aagtctttaa gacactaaaa ttgaaacaaa tattatggta    180

tgatgttatc tttgcaagaa gaa                                            203
```

<210> SEQ ID NO 584
<211> LENGTH: 294
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 584

```
taggggccaa taattatatt cgaggttact gttaaattat ttacaaagta taggtgatta     60

cctcattaaa ggctctcgct gatcacgcat cagcctcatt gtaacttcac atgctcttcg    120

aaaaagaccc tctgttccca taggacccat tccattaacc atattatgag tcaggcgaaa    180

tggcacaatt tctggaactt caaaggtttc tcccttagaa acaatacatt ttattacaaa    240

ctaacaatgt tagaatttaa aaatctttac tcaaagaact tcatgtccag attc          294
```

<210> SEQ ID NO 585
<211> LENGTH: 306
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 585

```
gagaaaagga aattgagaga aaacacaatt agtaagagta actcatatca cataccttat     60

tgaaaagaca attgaaatct acatgtacgc attcaccagt caaagaatca aagagaatat    120

tttcaccatg acggtctcca agccccagaa tataaccaac cattgacatt actgcagtgg    180

aacggcagta agctgatcta ctactgtacc taaaagaaac acaatgccta tgaaatatcc    240

atatacatat gaggccaata taaatctaaa atattaaaaa taaacattca accataacaa    300

cgtatt                                                               306
```

<210> SEQ ID NO 586
<211> LENGTH: 257
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 586

```
taaaaataaa cattcaacca taacaacgta ttatattctt ggtaacttac catgatgtag     60

gatcagggaa tgttctcaga aaccactcat gaaaaatagg aggatgcctg ggcaggagaa    120

attctcggaa tactttgagt ttttcagata aagctgctga ctttggtagc atacactggc    180

gaagttcttt tcctgtcata tacactcctg caaggaagag tgatatccat taatcacatc    240

agccaaatga aaaaagg                                                   257
```

<210> SEQ ID NO 587
<211> LENGTH: 416
<212> TYPE: DNA
<213> ORGANISM: Artificial Sequence
<220> FEATURE:

-continued

<223> OTHER INFORMATION: Description of Artificial Sequence: Synthetic
      nucleotide construct

<400> SEQUENCE: 587
ggaaggaagg gatggaaaca cttaagtgtt tctgtatata aaatctagaa atttcactat 60
agcttatatc aaaaaacata tgctagcata tattaatacc aattataccc atattatata 120
acttagtacc cacactgtat atgtataaga attaatttta gtacccttt ctttatatag 180 tttggtcaga ataggtctca aaccagcagt gttgttcacc cattcaataa tcccacattc 240
atcatttagt ggaataactg catatgttcg aatatgaagt tctcttctac gagactctgc 300
atcttttctt aagcactgtt aaaaaataca cataaattta aaaacaagat agaactcaaa 360
atttctaaat gttatatcaa atatatttaa agattgttca tttcataacc aaagaa 416

<210> SEQ ID NO 588
<211> LENGTH: 277
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 588
aataaaagca atctggtttt ataatagtca aaaatttttt taaaataaaa aataaataaa 60
taaaataaaa gcaaactatc tcccaacctt attaatcaag gaattgaatt ccattagtct 120
acaatccttt ctcaggtcat cttttggctt acacatcatg atgtagaact ttccatctga 180 gcctttttaaa gaaatcttct ttggtttctg aagagaagca agaatttcca cctaaaagat 240
gatgagttat atatgaatta gggccaaaaa tttctgt 277

<210> SEQ ID NO 589
<211> LENGTH: 357
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 589
tcacgtagat tttgtgaaat acacttttta tcttaatttg aagtttttaa caactaaatt 60
ttaaaatcat agtcatataa aactgaagtt taccatatca tcaaaccctg caatataggc 120
ccaatgtcca ggaaatggtt catggctagc atggttagca tgggtaccca gaattgatgg 180
aagtgtaggt atcatgactg attgtagagg aatgaggatt tcactaaatg ttgcttcttc 240
taccagcttt ttaagcattt taaaatgagt gctcatgctt aatgtggaac tacttccatc 300
aacctgaaaa aataaatagt gcattttaat ttgtttttac cttaaattcc actataa 357

<210> SEQ ID NO 590
<211> LENGTH: 457
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 590
tattaaaaac tgctttatta agacaaatca tacataatta aaatatacat tttgatatat 60
gtgtacacct atagttagaa ttttaattta attaatcaaa tgaaaaaatc tgctcaaatt 120
atatacataa ttacccaaca tcagtttata agcactaaga ttatgatagt accggtttat 180
tgcacaattc tagaagctta tctgttaggc gagttgcatc tccaacaaac ttctctaagg 240 atttttttcat atgaatagct ttattgagga tttccttgca tctgttcaca cgcatgggat 300
aagatgactg tcataaaaaa gagttaaatg tcataaaaaa gagtttatac aggattttta 360
aaagataaat tttttgcttg acaaaaaact taaaaagtat tcatgatgag agtttatatg 420
atacaaattt tctgaaaatt tatttggcaa tgctatc 457

<210> SEQ ID NO 591
<211> LENGTH: 386
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 591
agacgccctg gaacttgtat ctacatatta gtattacata atcaagttca tataaaatgg 60
taaaagatct tttcatataa aaaggtaaaa gaccctttta cctttgacac agctgtcatc 120
atccacattg cttgttgagg ataggctaga aatactttgg ctattatttc catcaagaca 180
acaaaaactt catcgtgaga atgacaaatt cgagagatca attgtgaaaa agcagtcaaa 240
aattgatatg gagctaaata gtttgtatgc tctgtgataa ccttgtttat tttacccaaa 300
tcattcctca tttgtacacg atcggagcgg ccagctgggg gaagaaataa gtttaaaaaa 360
caataaagga aagagaaaaa tcagta 386

<210> SEQ ID NO 592
<211> LENGTH: 228
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 592
attagactgt ccagccaaat ctgactttat accaaagtta taattcctag tcctttaaaa 60
cttttacgtg aagagttata cctttttccc attcatatgc ctttgtacca taatcaagcc 120
atagagttaa cattcgtggc attgactgat atatgaactg atttccatat tgtagagatc 180
tgcaattata tagacaagaa acactattag catagctgtc atttttat 228

<210> SEQ ID NO 593
<211> LENGTH: 306
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 593
gaatcagtca taagccagaa aatacctaga atatgctaag acatgtgata acagtttcaa 60
tattaatagt catccttaca tatttaatct gcaaacatgc agttctcata ctcacctgcc 120
aaaatgaaga actatatacc ggatgagatc accttgcttt tccattttgt tgtctgtgac 180
catgggcatc aatttgtcat agtacttggc aaggtaaaaa tgcccatcct cccattctgg 240
caggcacgcg gtcacatcct ataaaaaaga acataggata cctacctaag gaaatcccac 300
gctatg 306

-continued

<210> SEQ ID NO 594
<211> LENGTH: 362
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 594
gacttaagtc attttacgta gtcaacagag ttaactgaaa ctgcattata catatacttg 60
ccttatattt tttcataatt gcattgcttt caaagttagc tgtttcttcc ataaatcggc 120
ccactagtag catagctcga ccatggatta acatgttctt accctcaggt ggggtttcat 180
tttcaggaaa acataattca acaccttttt gaagaacaat tagtgcctgg tgaacatcac 240
cctaaaagaa aaaaggcaac aataagcctt ttaatttaaa aacatacttc tattttctgc 300
aaaagtatta gttcattatg tttttgtaca aatccatttg taatttcatg tttatctttt 360
ac 362

<210> SEQ ID NO 595
<211> LENGTH: 368
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 595
atatccaaat accaaattca agataagtga catttttaaa aaaagtagtg tgagaaacct 60
tttgttgagg cttagtaaag ccctccggag agccaggata ggctccttgg ctctgtagga 120
attctgggtc atttctagtc gagctaccca gtttagagaa tcttcttgag aactgtcacc 180
tggagaatgc tggaaaagtg gtttgatgct atgctccaac tcacataaca tgtgcaatct 240
gaagatagat agagcctatg ttaaaatgtt atcatattca gccttattaa tctcatatat 300
aaagcaagta ctttaaatca gaaataaaga atttaaaata cacagttgtc tttggtagaa 360
ctttaata 368

<210> SEQ ID NO 596
<211> LENGTH: 276
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 596
ctgtcaggtg acatttatag gccagaaata taaaaatgga aattccaaaa tacctcacaa 60
tatattcata tcctcgttgg taggagcctc tttcaaagct tgcagctgaa agaggtacaa 120
tttgttctgc tctcactagt ttcagtgagt cataaaaagc tgtgatatct cttttttttgg 180 ctgataataa tagctgtccc agtctgacac tccatgttgt agattttcca tctgaaaaac 240
aaatgaagag tcaagaaatg tcacggtagc tgggtc 276

<210> SEQ ID NO 597
<211> LENGTH: 205
<212> TYPE: DNA
<213> ORGANISM: Artificial Sequence
<220> FEATURE:
<223> OTHER INFORMATION: Description of Artificial Sequence: Synthetic nucleotide construct -continued

<400> SEQUENCE: 597
ccgcacccat cctaaaactg cttatatttt aagaagtaat tttacctgct gccaaatagt 60
tttccaccaa atcccactgt gacaatttcc aagctgcttc cactctgtac gtgtttaatt 120
catctgtcca ctcggaccta ttaaaagaaa cccatatcaa ctaaacttta atttatttaa 180
ggtgacattc agagattttt cattg 205

<210> SEQ ID NO 598
<211> LENGTH: 205
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 598
ttctccattc agatgcaata acaaaagaaa atcattttat aaaatattac ctgttagcat 60
gcactccatt cacctgagtg ataacagtag acagctgacc aagacctaac atggacttta 120
ctacaccatg ataatgaatg atctagaaat ttaaaaatat ttaaaatagc aattatcact 180
tcaataatag cttggggacc aaaaa 205

<210> SEQ ID NO 599
<211> LENGTH: 285
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 599
ctattcaggg ctattttcat tacagttgcc tttcaattat tatcttacct ggtctggttc 60
tagctgaata gccctgtcat aacaagcagt ggcatccctc agcaagccaa ggctttcatg 120
ttcaaggatc tgttctttta gagatggttc tgcctttcta attgcactga ctccggccac 180
tccatcaggt tcatgcatag cagcatacaa tttctttgtt caatgattaa aaaacaatca 240
aaaacaagaa aaaaacacaa ctggaaataa aactataaaa ccacc 285

<210> SEQ ID NO 600
<211> LENGTH: 392
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 600
ataaaagact ggccacatta attttcatta ttaaattcac tatattaact tcagacctgt 60
aaaaatccaa gatgttcctg aatattttgc ttcttttctg taataaatga ttcaaagtgc 120
attacagctc gtgtgtatgc tttggagcga aaggaagcta ctgccagagt atcctggggt 180
atgaggtcta gaaaacgggt tacactctga tagtcttcat aatccacagt agatactaga 240
tcataaaaaa agttgagtaa ttaaagactt ataagataaa atttaaaagt gtcaatttaa 300
gtatttaagt tcaatttatt tcactaaaca aattaatctg aatatattag gatatcatat 360
ttagaatgta actaacaaca gaacaattgt tc 392

<210> SEQ ID NO 601
<211> LENGTH: 367
<212> TYPE: DNA

-continued

<213> ORGANISM: Artificial Sequence
<220> FEATURE:
<223> OTHER INFORMATION: Description of Artificial Sequence: Synthetic
nucleotide construct

<400> SEQUENCE: 601
taaagggaag agctaattgg tgaatagcta aaaaaaaaaa aaaaaaagaa acagaagtga 60
taactcaccc attgagtcta ccttatttct gtttgatttg ctgtgtggac atttctcagc 120
tttcagtgcc tgaaatttgt gccttgccca ctgtgtgaga tggtcaagca tggagaacac 180
agtctgtgta ctgagttgac acagatcaga tgcaatgtct tgggtattta tggtatgctg 240
atcgtcatgc tttagaactg ccataatttc tgcataaacc tatgagaatc atttataatt 300
aataataata tctatataat accatttaac tattatatga catctaaagc taaccattct 360
aaggcaa 367

<210> SEQ ID NO 602
<211> LENGTH: 265
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 602
agaaagtaag tttcacatgt tcaaaaacca agtaagatga tttatctcac ctcctgctga 60
tcttcttgat tacaacccag taagacatac accagaatat gtggaagaag atagatggtc 120
actttgaaat catgcttcat cataatgcta cagcaggtga aaattttact ggcaagatca 180
tgtcgaacct gtaaatgcaa aatgtgtaga cagtaacaca ctttcacata ttgattaaat 240
gtcaaagagt agcatgtgag ataat 265

<210> SEQ ID NO 603
<211> LENGTH: 11
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(5)
<223> OTHER INFORMATION: a, c, g, t, unknown or other

<400> SEQUENCE: 603
nnnnngagac c 11

<210> SEQ ID NO 604
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (6)..(10)
<223> OTHER INFORMATION: a, c, g, t, unknown or other

<400> SEQUENCE: 604 gagtcnnnnn 10

<210> SEQ ID NO 605
<211> LENGTH: 10

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, g, t, unknown or other

<400> SEQUENCE: 605

nnnnncactc                                                          10


<210> SEQ ID NO 606
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606

cgtcacatta tttaggtgac actatag                                       27


<210> SEQ ID NO 607
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607

gcgtactatt aaccctcact aaagg                                         25
```